US012766239B2

(12) United States Patent
Erbey et al.

(10) Patent No.: US 12,766,239 B2
(45) Date of Patent: Oct. 20, 2026

(54) NEGATIVE PRESSURE THERAPY DEVICES, SYSTEMS, AND TREATMENT METHODS WITH INDWELLING URINARY CATHETERS

(71) Applicant: 3IVE Labs, LLC, Roswell, GA (US)

(72) Inventors: John R Erbey, Milton, GA (US); Jacob L. Upperco, Atlanta, GA (US); Bryan J. Tucker, Chapel Hill, NC (US); Lance Michael Black, Pearland, TX (US)

(73) Assignee: 3IVE Labs, LLC, Roswell, GA (US)

( * ) Notice: Subject to any disclaimer, the term of this patent is extended or adjusted under 35 U.S.C. 154(b) by 546 days.

(21) Appl. No.: 18/467,122

(22) Filed: Sep. 14, 2023

(65) Prior Publication Data

US 2024/0091428 A1 Mar. 21, 2024

Related U.S. Application Data

(60) Provisional application No. 63/406,891, filed on Sep. 15, 2022.

(51) Int. Cl.
*A61M 1/00* (2006.01)
*A61M 25/00* (2006.01)

(52) U.S. Cl.
CPC .......... *A61M 1/80* (2021.05); *A61M 25/0017* (2013.01); *A61M 25/0023* (2013.01)

(58) Field of Classification Search
CPC ...... A61M 1/80; A61M 25/0017; A61M 1/71; A61M 27/008; A61M 2210/1082; A61M 2210/1085
See application file for complete search history.

(56) References Cited

U.S. PATENT DOCUMENTS

| | | | |
|---|---|---|---|
| 1,870,942 | A | 8/1932 | Beatty |
| 2,285,980 | A | 6/1942 | Charles |
| 2,649,092 | A | 8/1953 | Wallace |

(Continued)

FOREIGN PATENT DOCUMENTS

| | | | |
|---|---|---|---|
| AU | 2013332448 | A1 | 4/2015 |
| CA | 1243581 | A | 10/1988 |

(Continued)

OTHER PUBLICATIONS

Bart et al.; "Ultrafiltration in Decompensated Heart Failure with Cardiorenal Syndrome"; N Engl J Med; 2012; p. 2296-2304; vol. 367.

(Continued)

*Primary Examiner* — Bradley J Osinski
(74) *Attorney, Agent, or Firm* — The Webb Law Firm

(57) ABSTRACT

A negative pressure therapy device for inducing negative pressure in a urinary tract includes an inflow member and an outflow member. The inflow member includes (i) a proximal portion, (ii) a retention portion configured to be deployed within a renal pelvis of the urinary tract comprising a drainage hole leading to the inflow lumen, and (iii) an intermediate portion between the proximal portion and the retention portion. The intermediate portion is configured to extend through a portion of the kidney to the renal pelvis. The outflow member includes (i) a proximal portion, (ii) a distal end configured to be positioned in the ureter or bladder, and (iii) at least one intermediate portion extending from the proximal portion to the distal end.

15 Claims, 59 Drawing Sheets

(56) References Cited

U.S. PATENT DOCUMENTS

| | | | |
|---|---|---|---|
| 3,108,595 | A | 10/1963 | Overment |
| 3,397,699 | A | 8/1968 | Kohl |
| 3,561,431 | A | 2/1971 | Pannier, Jr. |
| 3,707,967 | A | 1/1973 | Kitrilakis |
| 3,875,941 | A | 4/1975 | Adair |
| 3,938,529 | A | 2/1976 | Gibbons |
| 3,938,530 | A | 2/1976 | Santomieri |
| 3,943,929 | A | 3/1976 | Patel |
| 4,265,243 | A | 5/1981 | Taylor |
| 4,306,557 | A | 12/1981 | North |
| 4,324,663 | A | 4/1982 | Hirel |
| 4,349,029 | A | 9/1982 | Mott |
| 4,425,124 | A | 1/1984 | Womack |
| 4,437,856 | A | 3/1984 | Valli |
| 4,531,933 | A | 7/1985 | Norton |
| 4,568,338 | A | 2/1986 | Todd |
| 4,571,241 | A | 2/1986 | Christopher |
| 4,575,371 | A | 3/1986 | Nordqvist |
| 4,629,015 | A | 12/1986 | Fried |
| 4,681,564 | A | 7/1987 | Landreneau |
| 4,710,169 | A | 12/1987 | Christopher |
| 4,738,667 | A | 4/1988 | Galloway |
| 4,813,935 | A | 3/1989 | Haber |
| 4,834,724 | A | 5/1989 | Geiss |
| 4,932,938 | A | 6/1990 | Goldberg |
| 4,935,004 | A | 6/1990 | Cruz |
| 4,945,895 | A | 8/1990 | Takai |
| 4,950,228 | A | 8/1990 | Knapp, Jr. |
| 4,957,479 | A | 9/1990 | Roemer |
| 5,009,639 | A | 4/1991 | Keymling |
| 5,011,488 | A | 4/1991 | Ginsburg |
| 5,041,093 | A | 8/1991 | Chu |
| 5,044,902 | A | 9/1991 | Malbec |
| 5,059,169 | A | 10/1991 | Zilber |
| 5,078,684 | A | 1/1992 | Yasuda |
| 5,098,440 | A | 3/1992 | Hillstead |
| 5,116,309 | A | 5/1992 | Coll |
| 5,141,502 | A | 8/1992 | Macaluso, Jr. |
| 5,193,533 | A | 3/1993 | Body |
| 5,256,146 | A | 10/1993 | Ensminger |
| 5,370,690 | A | 12/1994 | Barrett |
| 5,401,257 | A | 3/1995 | Chevalier, Jr. |
| 5,451,215 | A | 9/1995 | Wolter |
| 5,451,218 | A | 9/1995 | Moore |
| 5,505,717 | A | 4/1996 | Moore |
| 5,514,112 | A | 5/1996 | Chu |
| 5,523,092 | A | 6/1996 | Hanson |
| 5,536,274 | A | 7/1996 | Neuss |
| 5,540,701 | A | 7/1996 | Sharkey |
| 5,554,144 | A | 9/1996 | Roe |
| 5,562,622 | A | 10/1996 | Tihon |
| 5,599,291 | A | 2/1997 | Balbierz |
| 5,647,843 | A | 7/1997 | Mesrobian |
| 5,662,713 | A | 9/1997 | Andersen |
| 5,709,874 | A | 1/1998 | Hanson |
| 5,727,555 | A | 3/1998 | Chait |
| 5,762,599 | A | 6/1998 | Sohn |
| 5,769,821 | A | 6/1998 | Abrahamson |
| 5,785,641 | A | 7/1998 | Davis |
| 5,795,319 | A | 8/1998 | Ali |
| 5,865,764 | A | 2/1999 | Moorhead |
| 5,873,865 | A | 2/1999 | Horzewski |
| 5,895,398 | A | 4/1999 | Wensel |
| 5,902,336 | A | 5/1999 | Mishkin |
| 5,915,386 | A | 6/1999 | Lloyd |
| 5,957,867 | A | 9/1999 | Lloyd |
| 5,972,019 | A | 10/1999 | Engelson |
| 5,989,207 | A | 11/1999 | Hughes |
| 6,066,113 | A | 5/2000 | Overtoom |
| 6,090,069 | A | 7/2000 | Walker |
| 6,111,520 | A | 8/2000 | Allen |
| 6,200,485 | B1 | 3/2001 | Kitaevich |
| 6,214,037 | B1 | 4/2001 | Mitchell |
| 6,283,940 | B1 | 9/2001 | Mulholland |
| 6,332,892 | B1 | 12/2001 | Desmond, III |
| 6,364,868 | B1 | 4/2002 | Ikeguchi |
| 6,402,736 | B1 | 6/2002 | Brown |
| 6,442,415 | B1 | 8/2002 | Bis |
| 6,461,346 | B1 | 10/2002 | Buelna |
| 6,463,326 | B1 | 10/2002 | Hartley et al. |
| 6,478,778 | B1 | 11/2002 | Jacobsen |
| 6,482,222 | B1 | 11/2002 | Bruckheimer |
| 6,500,158 | B1 | 12/2002 | Ikeguchi |
| 6,558,350 | B1 | 5/2003 | Hart |
| 6,569,150 | B2 | 5/2003 | Teague |
| 6,620,202 | B2 | 9/2003 | Bottcher |
| 6,648,863 | B2 | 11/2003 | Reever |
| 6,676,623 | B2 | 1/2004 | Whitmore, III |
| 6,685,744 | B2 | 2/2004 | Gellman |
| 6,699,216 | B2 | 3/2004 | Ikeguchi |
| 6,702,834 | B1 | 3/2004 | Boylan |
| 6,764,519 | B2 | 7/2004 | Whitmore, III |
| 6,780,322 | B1 | 8/2004 | Bissler |
| 6,837,868 | B1 | 1/2005 | Fajnsztajn |
| 7,025,753 | B2 | 4/2006 | Reever |
| 7,037,345 | B2 | 5/2006 | Bottcher |
| 7,044,981 | B2 | 5/2006 | Liu |
| 7,316,663 | B2 | 1/2008 | Whitmore, III |
| 7,329,226 | B1 | 2/2008 | Ni |
| 7,396,366 | B2 | 7/2008 | Ward |
| 7,507,218 | B2 | 3/2009 | Aliski |
| 7,550,978 | B2 | 6/2009 | Joy |
| 7,603,170 | B2 | 10/2009 | Hatlestad |
| 7,682,401 | B2 | 3/2010 | Deal |
| 7,722,677 | B2 | 5/2010 | Ward |
| 7,727,222 | B2 | 6/2010 | Da Silva |
| 7,736,354 | B2 | 6/2010 | Gelfand |
| 7,758,562 | B2 | 7/2010 | Gelfand |
| 7,758,563 | B2 | 7/2010 | Gelfand |
| 7,766,961 | B2 | 8/2010 | Patel |
| 7,837,667 | B2 | 11/2010 | Gelfand |
| 7,850,704 | B2 | 12/2010 | Burnett |
| 7,857,803 | B1 | 12/2010 | Salinas |
| 7,879,020 | B1 | 2/2011 | Salinas |
| 7,938,817 | B2 | 5/2011 | Gelfand |
| 7,972,292 | B2 | 7/2011 | Behl |
| 8,007,460 | B2 | 8/2011 | Gelfand |
| 8,021,307 | B2 | 9/2011 | White |
| 8,075,513 | B2 | 12/2011 | Rudko |
| 8,088,170 | B2 | 1/2012 | Whitmore, III |
| 8,105,317 | B2 | 1/2012 | Reever |
| 8,152,786 | B2 | 4/2012 | Shapland |
| 8,157,785 | B2 | 4/2012 | Salinas |
| 8,177,741 | B2 | 5/2012 | Hammack |
| 8,252,065 | B2 | 8/2012 | Ward |
| 8,328,877 | B2 | 12/2012 | Gellman |
| 8,444,623 | B2 | 5/2013 | Gelfand |
| 8,486,010 | B2 | 7/2013 | Nomura |
| 8,512,795 | B2 | 8/2013 | Dias |
| 8,568,387 | B2 | 10/2013 | Paz |
| 8,585,675 | B2 | 11/2013 | Salinas |
| 8,597,260 | B2 | 12/2013 | Tucker |
| 8,597,273 | B2 | 12/2013 | Salinas |
| 8,747,388 | B2 | 6/2014 | Pandey |
| 8,795,305 | B2 | 8/2014 | Martin |
| 8,827,924 | B2 | 9/2014 | Paz |
| 8,852,289 | B2 | 10/2014 | Whitmore, III |
| 8,865,063 | B2 | 10/2014 | Burnett |
| 8,932,320 | B1 | 1/2015 | Janardhan |
| 9,014,815 | B2 | 4/2015 | Yang |
| 9,060,888 | B2 | 6/2015 | Gellman |
| 9,308,348 | B2 | 4/2016 | Mulvihill |
| 9,339,636 | B1 | 5/2016 | Khan |
| 9,682,220 | B2 | 6/2017 | Schertiger |
| 9,744,331 | B2 | 8/2017 | Erbey |
| 9,750,634 | B2 | 9/2017 | Bar-Am |
| 9,788,928 | B2 | 10/2017 | Forsell |
| 9,849,224 | B2 | 12/2017 | Angwin |
| 9,980,663 | B2 | 5/2018 | Wabel |
| 10,182,747 | B2 | 1/2019 | Charlez |
| 10,226,606 | B2 | 3/2019 | Wan |
| 10,307,564 | B2 | 6/2019 | Erbey |
| 10,307,566 | B2 | 6/2019 | Bishawi |
| 10,449,329 | B2 | 10/2019 | Foley |

(56) References Cited

U.S. PATENT DOCUMENTS

| | | | |
|---|---|---|---|
| 11,040,180 | B2 | 6/2021 | Erbey |
| 2001/0053936 | A1 | 12/2001 | Whitmore |
| 2001/0056273 | A1 | 12/2001 | C. |
| 2002/0052576 | A1 | 5/2002 | Massengale |
| 2002/0062148 | A1 | 5/2002 | Hart |
| 2002/0068093 | A1 | 6/2002 | Trogolo |
| 2002/0082547 | A1 | 6/2002 | Deniega |
| 2002/0085951 | A1 | 7/2002 | Gelfand |
| 2002/0143292 | A1 | 10/2002 | Flinchbaugh |
| 2002/0143389 | A1 | 10/2002 | St. Pierre |
| 2002/0177902 | A1 | 11/2002 | Rioux |
| 2002/0183852 | A1 | 12/2002 | McWeeney |
| 2002/0183853 | A1 | 12/2002 | Mitchell |
| 2002/0188246 | A1 | 12/2002 | Hayner |
| 2002/0193667 | A1 | 12/2002 | McNair |
| 2003/0009132 | A1 | 1/2003 | Schwartz |
| 2003/0018291 | A1 | 1/2003 | Hill |
| 2003/0060806 | A1 | 3/2003 | Ikeguchi |
| 2003/0069534 | A1 | 4/2003 | Work |
| 2003/0074082 | A1 | 4/2003 | Bottcher |
| 2003/0109930 | A1 | 6/2003 | Bluni |
| 2003/0120261 | A1 | 6/2003 | Gellman |
| 2003/0135147 | A1 | 7/2003 | Rosenberg |
| 2003/0135195 | A1 | 7/2003 | Jimenez |
| 2003/0144623 | A1 | 7/2003 | Heath |
| 2003/0153970 | A1 | 8/2003 | Rao |
| 2003/0171708 | A1 | 9/2003 | Segura |
| 2003/0176831 | A1 | 9/2003 | Gellman |
| 2003/0181842 | A1 | 9/2003 | Gellman |
| 2003/0181887 | A1 | 9/2003 | Castillo Deniega |
| 2003/0191452 | A1 | 10/2003 | Meglin |
| 2003/0195456 | A1 | 10/2003 | Robertson |
| 2003/0195537 | A1 | 10/2003 | Dubrul |
| 2003/0199805 | A1 | 10/2003 | McWeeney |
| 2003/0216710 | A1 | 11/2003 | Hurt |
| 2003/0224033 | A1 | 12/2003 | Li |
| 2004/0019358 | A1 | 1/2004 | Kear |
| 2004/0054315 | A1 | 3/2004 | Levin |
| 2004/0054351 | A1 | 3/2004 | Deniega |
| 2004/0057037 | A1 | 3/2004 | Ohishi |
| 2004/0073194 | A1 | 4/2004 | Olsen |
| 2004/0097891 | A1 | 5/2004 | Bolmsjo |
| 2004/0129616 | A1 | 7/2004 | Mori |
| 2004/0143209 | A1 | 7/2004 | Liu |
| 2004/0147871 | A1 | 7/2004 | Burnett |
| 2004/0167415 | A1 | 8/2004 | Gelfand |
| 2004/0167634 | A1 | 8/2004 | Atala |
| 2004/0193098 | A1 | 9/2004 | Wentling |
| 2005/0042240 | A1 | 2/2005 | Utterberg |
| 2005/0049575 | A1 | 3/2005 | Snell |
| 2005/0049577 | A1 | 3/2005 | Snell |
| 2005/0101941 | A1 | 5/2005 | Hakky |
| 2005/0107736 | A1 | 5/2005 | Landman |
| 2005/0124969 | A1 | 6/2005 | Fitzgerald |
| 2005/0124978 | A1 | 6/2005 | Kim |
| 2005/0177102 | A1 | 8/2005 | Hart |
| 2005/0187564 | A1 | 8/2005 | Jayaraman |
| 2005/0240141 | A1 | 10/2005 | Aliski |
| 2005/0240280 | A1 | 10/2005 | Aliski |
| 2005/0256441 | A1 | 11/2005 | Lotan |
| 2005/0256447 | A1 | 11/2005 | Richardson |
| 2005/0288722 | A1 | 12/2005 | Eigler |
| 2006/0015015 | A1 | 1/2006 | Kawamoto |
| 2006/0015089 | A1 | 1/2006 | Meglin |
| 2006/0052879 | A1 | 3/2006 | Kolb |
| 2006/0074388 | A1 | 4/2006 | Dextradeur |
| 2006/0074409 | A1 | 4/2006 | Schuermann |
| 2006/0229553 | A1 | 10/2006 | Hammack |
| 2006/0229573 | A1 | 10/2006 | Lamborne |
| 2006/0259151 | A1 | 11/2006 | Ward |
| 2006/0271019 | A1 | 11/2006 | Stoller |
| 2007/0010797 | A1 | 1/2007 | Nishtala |
| 2007/0010798 | A1 | 1/2007 | Stoller |
| 2007/0055198 | A1 | 3/2007 | O'Mahony et al. |
| 2007/0073271 | A1 | 3/2007 | Brucker |
| 2007/0088333 | A1 | 4/2007 | Levin |
| 2007/0112302 | A1 | 5/2007 | Yu |
| 2007/0197957 | A1 | 8/2007 | Hunter |
| 2007/0208291 | A1 | 9/2007 | Patel |
| 2007/0213655 | A1 | 9/2007 | Prusmack |
| 2007/0219488 | A1 | 9/2007 | Francescatti |
| 2007/0255230 | A1 | 11/2007 | Gross |
| 2008/0051678 | A1 | 2/2008 | Lindahl |
| 2008/0051691 | A1 | 2/2008 | Dragoon |
| 2008/0058650 | A1 | 3/2008 | Saadat |
| 2008/0097463 | A1 | 4/2008 | House |
| 2008/0119907 | A1 | 5/2008 | Stahmann |
| 2008/0142023 | A1 | 6/2008 | Schmid |
| 2008/0183299 | A1 | 7/2008 | Monga |
| 2008/0215247 | A1 | 9/2008 | Tonelli |
| 2008/0243091 | A1 | 10/2008 | Humphreys |
| 2008/0255550 | A1 | 10/2008 | Bell |
| 2008/0281291 | A1 | 11/2008 | Tihon |
| 2008/0288082 | A1 | 11/2008 | Deal |
| 2008/0312550 | A1 | 12/2008 | Nishtala |
| 2009/0024091 | A1 | 1/2009 | Li |
| 2009/0030370 | A1 | 1/2009 | Nishtala |
| 2009/0030435 | A1 | 1/2009 | Burnett |
| 2009/0043229 | A1 | 2/2009 | Dunn |
| 2009/0088677 | A1 | 4/2009 | Cohen |
| 2009/0093748 | A1 | 4/2009 | Patterson |
| 2009/0105719 | A1 | 4/2009 | Honey |
| 2009/0143713 | A1 | 6/2009 | Van Dam |
| 2009/0162530 | A1 | 6/2009 | Nesbitt |
| 2009/0171137 | A1 | 7/2009 | Farnan |
| 2009/0171241 | A1 | 7/2009 | Garcia |
| 2009/0281507 | A1 | 11/2009 | Humphreys |
| 2009/0318844 | A1 | 12/2009 | Burnett |
| 2010/0057000 | A1 | 3/2010 | Melsheimer |
| 2010/0081148 | A1 | 4/2010 | Singbartl |
| 2010/0086580 | A1 | 4/2010 | Nyman |
| 2010/0121159 | A1 | 5/2010 | Burnett |
| 2010/0191183 | A1 | 7/2010 | Tanghoej |
| 2010/0204682 | A1 | 8/2010 | Tanghoj |
| 2010/0241240 | A1 | 9/2010 | Willard |
| 2010/0261985 | A1 | 10/2010 | Cohen-Solal |
| 2010/0298857 | A1 | 11/2010 | Zook |
| 2010/0312163 | A1 | 12/2010 | Forsell |
| 2010/0312164 | A1 | 12/2010 | Forsell |
| 2011/0009799 | A1 | 1/2011 | Mullick |
| 2011/0009831 | A1 | 1/2011 | Burkholz |
| 2011/0015558 | A1 | 1/2011 | Kaye |
| 2011/0077605 | A1 | 3/2011 | Karpowicz |
| 2011/0089111 | A1 | 4/2011 | Mori |
| 2011/0098683 | A1 | 4/2011 | Wiita |
| 2011/0118537 | A1 | 5/2011 | Wampler |
| 2011/0132838 | A1 | 6/2011 | Curtis |
| 2011/0208319 | A1 | 8/2011 | Laster |
| 2011/0230950 | A1 | 9/2011 | Knapp |
| 2011/0238163 | A1 | 9/2011 | Andrews |
| 2011/0269167 | A1 | 11/2011 | Bene |
| 2011/0276024 | A1 | 11/2011 | Randolph |
| 2011/0282264 | A1 | 11/2011 | Hurt |
| 2011/0301553 | A1 | 12/2011 | Goral |
| 2011/0301662 | A1 | 12/2011 | Bar-Yoseph |
| 2011/0320008 | A1 | 12/2011 | Teague |
| 2012/0029937 | A1 | 2/2012 | Neftel |
| 2012/0042427 | A1 | 2/2012 | Messier |
| 2012/0053700 | A1 | 3/2012 | Rickner |
| 2012/0078226 | A1 | 3/2012 | Jean-Pierre |
| 2012/0083899 | A1 | 4/2012 | Whitmore, III |
| 2012/0107420 | A1 | 5/2012 | Breit |
| 2012/0136343 | A1 | 5/2012 | Burnett |
| 2012/0154264 | A1 | 6/2012 | Wang |
| 2012/0165641 | A1 | 6/2012 | Burnett |
| 2012/0179144 | A1 | 7/2012 | Carleo |
| 2012/0179145 | A1 | 7/2012 | Nishtala |
| 2012/0220926 | A1 | 8/2012 | Soykan |
| 2012/0238802 | A1 | 9/2012 | Knight |
| 2012/0265020 | A1 | 10/2012 | Pandey |
| 2012/0277155 | A1 | 11/2012 | VanAntwerp |
| 2012/0316656 | A1 | 12/2012 | Deal |
| 2013/0030262 | A1 | 1/2013 | Burnett |
| 2013/0066166 | A1 | 3/2013 | Burnett |

(56) References Cited

U.S. PATENT DOCUMENTS

| | | | |
|---|---|---|---|
| 2013/0085468 | A1 | 4/2013 | Buydenok |
| 2013/0090648 | A1 | 4/2013 | Nagale |
| 2013/0131621 | A1 | 5/2013 | Van Holten |
| 2013/0138077 | A1 | 5/2013 | O'Day |
| 2013/0150828 | A1 | 6/2013 | Conway |
| 2013/0172807 | A1 | 7/2013 | Cruz |
| 2013/0172881 | A1 | 7/2013 | Hill |
| 2013/0184545 | A1 | 7/2013 | Blomqvist |
| 2013/0187563 | A1 | 7/2013 | Sasai |
| 2013/0197471 | A1 | 8/2013 | Williams |
| 2013/0199998 | A1 | 8/2013 | Kelly |
| 2013/0218135 | A1 | 8/2013 | Dein |
| 2013/0231640 | A1 | 9/2013 | Terry |
| 2013/0231752 | A1 | 9/2013 | Rosenbaum |
| 2013/0253409 | A1 | 9/2013 | Burnett |
| 2013/0267845 | A1 | 10/2013 | Howle |
| 2013/0274644 | A1 | 10/2013 | Hertz |
| 2013/0274783 | A1 | 10/2013 | Wynberg |
| 2013/0303865 | A1 | 11/2013 | Rebec |
| 2013/0303961 | A1 | 11/2013 | Wolff |
| 2013/0304082 | A1 | 11/2013 | Aklog |
| 2013/0317322 | A1 | 11/2013 | Andrijauskas |
| 2013/0331824 | A1 | 12/2013 | Kim |
| 2013/0338580 | A1 | 12/2013 | Yamatani |
| 2013/0345670 | A1 | 12/2013 | Rajagopalan |
| 2014/0031773 | A1 | 1/2014 | Mikkaichi |
| 2014/0031787 | A1 | 1/2014 | Burnes |
| 2014/0039375 | A1 | 2/2014 | Jimenez |
| 2014/0073926 | A1 | 3/2014 | Rajendran |
| 2014/0074144 | A1 | 3/2014 | Shrivastava |
| 2014/0135941 | A1 | 5/2014 | Smouse |
| 2014/0142539 | A1 | 5/2014 | Salinas |
| 2014/0148648 | A1 | 5/2014 | Tycast |
| 2014/0148754 | A1 | 5/2014 | Soykan |
| 2014/0155818 | A1 | 6/2014 | Salinas |
| 2014/0188248 | A1 | 7/2014 | Gandhi |
| 2014/0188249 | A1 | 7/2014 | Pendleton et al. |
| 2014/0214009 | A1 | 7/2014 | Reyes |
| 2014/0228801 | A1 | 8/2014 | Keeling |
| 2014/0275984 | A1 | 9/2014 | Hermann |
| 2014/0276341 | A1 | 9/2014 | Ludin |
| 2014/0276628 | A1 | 9/2014 | Gandras |
| 2014/0343515 | A1 | 11/2014 | Sylvester |
| 2014/0364820 | A1 | 12/2014 | Solazzo |
| 2015/0011855 | A1 | 1/2015 | Burnett |
| 2015/0011928 | A1 | 1/2015 | Burnett |
| 2015/0017682 | A1 | 1/2015 | Adam |
| 2015/0065783 | A1 | 3/2015 | Buelna |
| 2015/0080844 | A1 | 3/2015 | Donovan |
| 2015/0094548 | A1 | 4/2015 | Sabatini |
| 2015/0094644 | A1 | 4/2015 | Lenihan |
| 2015/0094696 | A1 | 4/2015 | Adams, Jr. |
| 2015/0100009 | A1 | 4/2015 | Bearss |
| 2015/0134073 | A1 | 5/2015 | Tang |
| 2015/0164370 | A1 | 6/2015 | Wabel |
| 2015/0194052 | A1 | 7/2015 | Sagan |
| 2015/0223953 | A1 | 8/2015 | Pendleton |
| 2015/0224241 | A1 | 8/2015 | Fontanazzi |
| 2015/0273120 | A1 | 10/2015 | Zamarripa |
| 2015/0283362 | A1 | 10/2015 | Shelton |
| 2015/0290411 | A1 | 10/2015 | Warrington |
| 2015/0306364 | A1 | 10/2015 | Shevgoor |
| 2015/0328027 | A1 | 11/2015 | Nishio |
| 2015/0352339 | A1 | 12/2015 | Wang |
| 2016/0045302 | A1 | 2/2016 | Nishio |
| 2016/0051176 | A1 | 2/2016 | Ramos |
| 2016/0058489 | A1 | 3/2016 | Fischell |
| 2016/0183819 | A1 | 6/2016 | Burnett et al. |
| 2016/0213881 | A9 | 7/2016 | Adams, Jr. |
| 2016/0303303 | A1 | 10/2016 | Rovatti |
| 2016/0310711 | A1 | 10/2016 | Luxon |
| 2016/0331294 | A1 | 11/2016 | Imran |
| 2016/0367747 | A1 | 12/2016 | Loske |
| 2017/0020724 | A1 | 1/2017 | Burnett |
| 2017/0021128 | A1 | 1/2017 | Erbey |
| 2017/0095323 | A1 | 4/2017 | Garcia |
| 2017/0095641 | A1 | 4/2017 | Scarpine |
| 2017/0113000 | A1 | 4/2017 | Tobescu |
| 2017/0119519 | A1 | 5/2017 | Sambusseti |
| 2017/0128639 | A1 | 5/2017 | Erbey, II |
| 2017/0128654 | A1 | 5/2017 | Feld |
| 2017/0136222 | A1 | 5/2017 | Hakim |
| 2017/0196576 | A1 | 7/2017 | Long |
| 2017/0197028 | A1 | 7/2017 | Goldsmith |
| 2017/0232153 | A1 | 8/2017 | Babu |
| 2017/0266414 | A1 | 9/2017 | Rocha-Singh |
| 2017/0325927 | A1 | 11/2017 | Gobel |
| 2017/0348507 | A1 | 12/2017 | Erbey, II |
| 2017/0348512 | A1 | 12/2017 | Orr |
| 2017/0367636 | A1 | 12/2017 | Mantinband |
| 2018/0001055 | A1 | 1/2018 | Utas |
| 2018/0116751 | A1 | 5/2018 | Schwartz |
| 2018/0117288 | A1 | 5/2018 | Lindsay |
| 2018/0147330 | A1 | 5/2018 | Peng |
| 2018/0169313 | A1 | 6/2018 | Schwammenthal |
| 2018/0177458 | A1 | 6/2018 | Burnett |
| 2018/0193618 | A1 | 7/2018 | Erbey, II |
| 2018/0207412 | A1 | 7/2018 | Malek |
| 2018/0344250 | A1 | 12/2018 | McKinney |
| 2019/0030303 | A1 | 1/2019 | Holman |
| 2019/0091442 | A1 | 3/2019 | Erbey, II |
| 2019/0105465 | A1 | 4/2019 | Erbey, II |
| 2019/0201662 | A1 | 7/2019 | Lad |
| 2019/0240448 | A1 | 8/2019 | Murdock |
| 2019/0247615 | A1 | 8/2019 | Bishawi |
| 2020/0001045 | A1 | 1/2020 | McIntyre |
| 2020/0094017 | A1 | 3/2020 | Erbey, II |
| 2021/0178133 | A1 | 6/2021 | Walish |
| 2022/0054798 | A1 | 2/2022 | Erbey, II et al. |

FOREIGN PATENT DOCUMENTS

| | | | |
|---|---|---|---|
| CA | 2363001 | C | 9/2000 |
| CA | 2205473 | C | 6/2006 |
| CA | 2992546 | A1 | 1/2017 |
| CA | 2992322 | C | 8/2019 |
| CN | 2175619 | Y | 8/1994 |
| CN | 2562776 | Y | 7/2003 |
| CN | 2588940 | Y | 12/2003 |
| CN | 1479596 | A | 3/2004 |
| CN | 2753382 | Y | 1/2006 |
| CN | 2928043 | Y | 8/2007 |
| CN | 101224148 | A | 7/2008 |
| CN | 101426540 | A | 5/2009 |
| CN | 201814968 | U | 5/2011 |
| CN | 102176928 | A | 9/2011 |
| CN | 202459720 | U | 10/2012 |
| CN | 202526754 | U | 11/2012 |
| CN | 202802478 | U | 3/2013 |
| CN | 103096964 | A | 5/2013 |
| CN | 103203062 | A | 7/2013 |
| CN | 203139180 | U | 8/2013 |
| CN | 103841905 | A | 6/2014 |
| CN | 203777060 | U | 8/2014 |
| CN | 203842151 | U | 9/2014 |
| CN | 204158867 | U | 2/2015 |
| CN | 104520857 | A | 4/2015 |
| CN | 204246651 | U | 4/2015 |
| CN | 204446944 | U | 7/2015 |
| CN | 205126495 | U | 4/2016 |
| CN | 106237417 | A | 12/2016 |
| CN | 106456841 | A | 2/2017 |
| CN | 106473847 | A | 3/2017 |
| CN | 106693092 | A | 5/2017 |
| CN | 10726194 | A | 10/2017 |
| CN | 108136163 | A | 6/2018 |
| DE | 29606509 | U1 | 8/1996 |
| EP | 873760 | A1 | 10/1998 |
| EP | 1011803 | B1 | 1/2004 |
| EP | 1980292 | A2 | 10/2008 |
| EP | 3325076 | A2 | 5/2018 |
| EP | 3470107 | A1 | 4/2019 |
| EP | 3488897 | A1 | 5/2019 |
| EP | 3970775 | A1 | 3/2022 |

(56) References Cited

FOREIGN PATENT DOCUMENTS

| | | | |
|---|---|---|---|
| FR | 3052671 | A1 | 12/2017 |
| JP | 59111748 | A | 6/1984 |
| JP | H42361 | A | 1/1992 |
| JP | 10504469 | A | 5/1998 |
| JP | 2002510536 | A | 4/2002 |
| JP | 2002291879 | A | 10/2002 |
| JP | 2002537893 | A | 11/2002 |
| JP | 2002538888 | A | 11/2002 |
| JP | 2003530165 | A | 10/2003 |
| JP | 2004215787 | A | 8/2004 |
| JP | 2006516214 | A | 6/2006 |
| JP | 2006526464 | A | 11/2006 |
| JP | 2009505802 | A | 2/2009 |
| JP | 2009238520 | A | 10/2009 |
| JP | 2009537256 | A | 10/2009 |
| JP | 2010005282 | A | 1/2010 |
| JP | 2010508984 | A | 3/2010 |
| JP | 2010119737 | A | 6/2010 |
| JP | 2010230618 | A | 10/2010 |
| JP | 2012505022 | A | 3/2012 |
| JP | 2013149498 | A | 8/2013 |
| JP | 2014136116 | A | 7/2014 |
| JP | 2014176689 | A | 9/2014 |
| JP | 2018527061 | A | 9/2018 |
| JP | 2018527974 | A | 9/2018 |
| JP | 2018196754 | A | 12/2018 |
| RU | 2113245 | C1 | 6/1998 |
| RU | 2300399 | C1 | 6/2007 |
| RU | 149161 | U1 | 12/2014 |
| TW | M540625 | U | 5/2017 |
| WO | 9529716 | A1 | 11/1995 |
| WO | 9716218 | A1 | 5/1997 |
| WO | 9816171 | A1 | 4/1998 |
| WO | 9850088 | A1 | 11/1998 |
| WO | 54701 | A1 | 9/2000 |
| WO | 0160260 | A1 | 8/2001 |
| WO | 197896 | A1 | 12/2001 |
| WO | 03017870 | A1 | 3/2003 |
| WO | 2004064681 | A1 | 8/2004 |
| WO | 2006017439 | A2 | 2/2006 |
| WO | 2006023589 | A2 | 3/2006 |
| WO | 2006044621 | A2 | 4/2006 |
| WO | 2007001978 | A2 | 1/2007 |
| WO | 2007027830 | A1 | 3/2007 |
| WO | 2008066625 | A1 | 6/2008 |
| WO | 2010082197 | A2 | 7/2010 |
| WO | 2011109570 | A2 | 9/2011 |
| WO | 2011139498 | A1 | 11/2011 |
| WO | 2013022005 | A1 | 2/2013 |
| WO | 2013029622 | A1 | 3/2013 |
| WO | 2014025367 | A1 | 2/2014 |
| WO | 2014043650 | A2 | 3/2014 |
| WO | 2014062225 | A1 | 4/2014 |
| WO | 2015105916 | A1 | 7/2015 |
| WO | 2015157467 | A1 | 10/2015 |
| WO | 2015198333 | A1 | 12/2015 |
| WO | 2016049654 | A1 | 3/2016 |
| WO | 2016103256 | A1 | 6/2016 |
| WO | 2017015345 | A2 | 1/2017 |
| WO | 2017015351 | A2 | 1/2017 |
| WO | 2017019974 | A1 | 2/2017 |
| WO | 2017087182 | A1 | 5/2017 |
| WO | 2018136603 | A1 | 7/2018 |
| WO | 2018186781 | A1 | 10/2018 |
| WO | 2018200050 | A1 | 11/2018 |
| WO | 2019038730 | A1 | 2/2019 |
| WO | 2020217214 | A1 | 10/2020 |
| WO | 2020236748 | A1 | 11/2020 |

OTHER PUBLICATIONS

Burr et al.; "Urinary catheter blockage depends on urine pH, calcium and rate of flow"; Spinal Cord; 1997; p. 521-525; vol. 35.

Clinical Practice Guidelines for Chronic Kidney Disease: Evaluation, Classification and Stratification; National Kidney Foundation; Am. J. Kidney Dis.; 2002; pg. S1-S266; Suppl. 1.

"The Criteria Committee of the New York Heart Association", (1994), Nomenclature and Criteria for Diagnosis of Diseases of the Heart and Great Vessels, (9th ed.), Boston: Little, Brown & Co. pg. 253-256 (Abstract).

Damman et al., "Increased Central Venous Pressure Is Associated With Impaired Renal Function and Mortality in a Broad Spectrum of XPatients With Cardiovascular Disease", 2009, Journal of the American College of Cardiology, vol. 53:7, pp. 582-588.

Dixon et al., "The musculature of the human renal calices, pelvis and upper ureter", J, Anat., 1982, vol. 135, pp. 129-137.

Gregersen et al., "Regional Differences Exist in Elastic Wall Properties in the Ureter", SJUN, 1996, vol. 30, pp. 343-348.

Harris et al., "Relationship between patients' outcomes and the changes in serum creatinine and urine output and RIFLE classification in a large critical care cohort database", Kidney International, 2015, p. 369-377, vol. 88.

Jessup et al.; "The Cardiorenal Syndrome—Do We Need a Change of Strategy or a Change of Tactics?"; Journal of the American College of Cardiology; 2009; p. 597-599; vol. 53:7.

Johnson et al., "Clinical Practice Guidelines for Chronic Kidney Disease in Adults: Part I. Definition, Disease Stages, Evaluation, Treatment, and Risk Factors", American Family Physician, Sep. 1, 2004, p. 869-876, vol. 70 Issue 5.

Kiil, "Urinary Flow and Ureteral Peristalsis" in: Lutzeyer W., Melchior H. (Eds.) Urodynamics, 1973 Springer, Berlin, Heidelberg (pp. 57-70).

Kim et al., "Relationship between a perioperative intravenous fluid administration strategy and acute kidney injury following off-pump coronary artery bypass surgery: an observational study", Critical Care, 2015, vol. 19:350, pp. 3-11.

Lala et al.,"Relief and Recurrence of Congestion During and After Hospitalization for Acute Heart Failure: Insights from DOSE-AHF and CARRESS-HF", Circ Heart Fail, 2015, vol. 8:4, pp. 741-748.

Legrand et al. "Association between systemic hemodynamics and septic acute kidney injury in critically ill patients: a retrospective observational study", Critical Care, 2013, vol. 17:R278, pp. 1-8.

Mardis et al., "Comparative Evaluation of Materials Used for Internal Ureteral Stents", Journal of Endourology, 1993, pp. 105-115, vol. 7:2.

Mordi et al., "Renal and Cardiovascular Effects of sodium-glucose cotransporter 2 (SGLT2) inhibition with loop Diuretics in diabetic patents with Chronic Heart Failure (REEDE-CHF): protocol for a randomised controlled double-blind cross-over trail". BJM open, 2017, vol. 7, pp. 1-9.

Mullens et al.; "Importance of Venous Congestion for Worsening of Renal Function in Advanced Decompensated Heart Failure"; Journal of the American College of Cardiology; 2009; p. 589-596; vol. 53:7.

Nohria et al., "Cardiorenal Interactions Insights from the ESCAPE Trial", Heart Failure, 2008, vol. 51:13, pp. 1268-1274.

Peters et al.; "Short and Long-Term Effects of the Angiotensin II Receptor Blocker Irbesartan on Intradialytic Central Hemodynamics: A Randomized Double-Blind Placebo-Controlled One-Year Intervention Trial (the SAFIR Study)"; PLoS ONE; Jun. 1, 2015; p. 1-22.

Quadra-Coil | Olympus America | Medical, Ureteral Stents, https://www.medical.olympusamerica.com/products/quadra-coil (downloaded from the Internet Aug. 31, 2022) 2 pages.

"Standard Specification for Ureteral Stents", ASTM International, 2014, Designation F1828-97, p. 1-6.

Stents≤Urology | Olympus America | Medical. Ureteral Stents, https://www.medical.olympusamerica.com/products/stents-Urology (downloaded from the Internet Aug. 31, 2022) 2 pages.

Ureteral stent—Quadra-Coil—Olympus Medical Europa, https://www.medicalexpo.com/prod/olympus-medical-europa/product-69587-661607.html (downloaded from the Internet Aug. 31, 2022) 5 pages.

Uthoff et al., "Central venous pressure and impaired renal function in patients with acute heart failure", European Journal of Heart Failure, 2011. vol. 13, pp. 432-439.

(56) References Cited

OTHER PUBLICATIONS

Verbrugge et al.; "The kidney in congestive heart failure: are natriuresis, sodium, and diuretics really the good, the bad and the ugly?"; European Journal of Heart Failure; 2014; p. 133-142; vol. 16.
Walker, "Annals of Surgery" 1913, Lippincott Williams & Wilkins, p. 58, Figures 3 and 9.
Webb, "Percutaneous Renal Surgery: A Practical Clinical Handbook", 2016, Springer International Publishing, Switzerland, p. 92.
Wolf, Jr. et al.; "Comparative Ureteral Microanatomy"; Journal of Endourology; 1996; p. 527-531; vol. 10:6.
Woodburne et al., "The Uretal Lumen during Peristalsis", Am. J. Anat., 1972. vol. 133, pp. 255-258.
Zelenko et al.; "Normal Ureter Size on Unenhanced Helical CT"; American Journal of Roentgenology; 2004; p. 1039-1041; vol. 182.

NEGATIVE PRESSURE THERAPY DEVICES, SYSTEMS, AND TREATMENT METHODS WITH INDWELLING URINARY CATHETERS

CROSS REFERENCE TO RELATED APPLICATION

This application claims the benefit of U.S. Provisional Patent Application No. 63/406,891, filed Sep. 15, 2022, entitled "Negative Pressure Therapy Devices, Systems, and Treatment Methods with Indwelling Urinary Catheters," the disclosure of which is hereby incorporated by reference in its entirety.

BACKGROUND

Technical Field

The present disclosure relates to devices and systems for providing negative pressure to the urinary tract of a patient and associated treatment methods and, more particularly, to negative pressure therapy devices, systems, and treatment methods comprising an indwelling urinary catheter for providing negative pressure therapy to a kidney and/or renal pelvis of the urinary tract.

Background

The renal or urinary system includes a pair of kidneys, each kidney being connected by a ureter to the bladder, and a urethra for draining fluid or urine produced by the kidneys from the bladder. The kidneys perform several vital functions for the human body including, for example, filtering the blood to eliminate waste in the form of urine. The kidneys also regulate electrolytes (e.g., sodium, potassium and calcium) and metabolites, blood volume, blood pressure, blood pH, fluid volume, production of red blood cells, and bone metabolism. Adequate understanding of the anatomy and physiology of the kidneys is useful for understanding impacts of altered hemodynamics, as well as other fluid overload conditions have on their function.

In normal anatomy, the two kidneys are located retroperitoneally in the abdominal cavity. The kidneys are bean-shaped encapsulated organs. Urine is formed by nephrons, the functional unit of the kidney, and then flows through a system of converging tubules called collecting ducts. The collecting ducts join together to form minor calyces, then major calyces, which ultimately join near the concave portion of the kidney (renal pelvis). A major function of the renal pelvis is to direct urine flow to the ureter. Urine flows from the renal pelvis into the ureter, a tube-like structure that carries the urine from the kidneys into the bladder. The outer layer of the kidney is called the cortex, and is a rigid fibrous encapsulation. The interior of the kidney is called the medulla. The medulla structures are arranged in pyramids.

Each kidney is made up of approximately one million nephrons. Each nephron includes the glomerulus, Bowman's capsule, and tubules. The tubules include the proximal convoluted tubule, the loop of Henle, the distal convoluted tubule, and the collecting duct. The nephrons contained in the cortex layer of the kidney are distinct from the anatomy of those contained in the medulla. The principal difference is the length of the loop of Henle. Medullary nephrons contain a longer loop of Henle, which, under normal circumstances, allows greater regulation of water and sodium reabsorption than in the cortex nephrons.

The glomerulus is the beginning of the nephron, and is responsible for the initial filtration of blood. Afferent arterioles pass blood into the glomerular capillaries, where hydrostatic pressure pushes water and solutes into Bowman's capsule. Net filtration pressure is expressed as the hydrostatic pressure in the afferent arteriole minus the hydrostatic pressure in Bowman's space minus the osmotic pressure in the efferent arteriole.

Net Filtration Pressure=Hydrostatic Pressure (Afferent Arteriole)−Hydrostatic Pressure (Bowman's Space)−Osmotic Pressure (Efferent Arteriole) (Equation 1)

The magnitude of this net filtration pressure defined by Equation 1 determines how much ultra-filtrate is formed in Bowman's space and delivered to the tubules. The remaining blood exits the glomerulus via the efferent arteriole. Normal glomerular filtration, or delivery of ultra-filtrate into the tubules, is about 1 ml/min/1.73 $m^2$.

The glomerulus has a three-layer filtration structure, which includes the vascular endothelium, a glomerular basement membrane, and podocytes. Normally, large proteins such as albumin and red blood cells, are not filtered into Bowman's space. However, elevated glomerular pressures and mesangial expansion create surface area changes on the basement membrane and larger fenestrations between the podocytes allowing larger proteins to pass into Bowman's space.

Ultra-filtrate collected in Bowman's space is delivered first to the proximal convoluted tubule. Re-absorption and secretion of water and solutes in the tubules is performed by a mix of active transport channels and passive pressure gradients. The proximal convoluted tubules normally reabsorb a majority of the sodium chloride and water, and nearly all glucose and amino acids that were filtered by the glomerulus. The loop of Henle has two components that are designed to concentrate wastes in the urine. The descending limb is highly water permeable and reabsorbs most of the remaining water. The ascending limb reabsorbs 25% of the remaining sodium chloride, creating a concentrated urine, for example, in terms of urea and creatinine. The distal convoluted tubule normally reabsorbs a small proportion of sodium chloride, and the osmotic gradient creates conditions for the water to follow.

Under normal conditions, there is a net filtration of approximately 14 mm Hg. The impact of venous congestion can be a significant decrease in net filtration, down to approximately 4 mm Hg. See Jessup M., *The cardiorenal syndrome: Do we need a change of strategy or a change of tactics?, JACC* 53(7):597-600, 2009 (hereinafter "Jessup"). Venous congestion is a common complication of renal insufficiency, heart failure, traumatic injuries and surgery. Prolonged elevated venous pressure can result in distention, edema, stasis, ischemia and/or cellular death. Venous congestion can be determined by observation of symptoms, such as edema, or direct or indirect measurement, as is well known to those skilled in the art. For example, the central venous pressure, which is a measure of pressure in the vena cava, can be measured using a central venous catheter advanced via the internal jugular vein and placed in the superior vena cava near the right atrium. A normal central venous pressure reading is between 0 to 6 mmHg. This value is altered by volume status and/or venous compliance. Alternatively, venous congestion can be measured by jugular venous distension (JVD). While the patient is lying down on an exam table, with the head of the table at a 45-degree angle and head turned to the side, the doctor measures the highest point at which pulsations can be detected in the internal jugular vein. Alternatively, the Venus Excess Ultrasound (VExUS) score (0-3) can be determined using ultrasound, or the distensibility of the inferior vena cava can be measured via ultrasound. A NT-proB-type Natriuretic Peptide (BNP) blood test can provide an assessment of congestion caused by elevated venous pressures.

The second filtration stage occurs at the proximal tubules. Most of the secretion and absorption from urine occurs in tubules in the medullary nephrons. Active transport of sodium from the tubule into the interstitial space initiates this process. However, the hydrostatic forces dominate the net exchange of solutes and water. Under normal circumstances, it is believed that 75% of the sodium is reabsorbed back into lymphatic or venous circulation. However, because the kidney is encapsulated, it is sensitive to changes in hydrostatic pressures from both venous and lymphatic congestion. During venous congestion the retention of sodium and water can exceed 85%, further perpetuating the renal congestion. See Verbrugge, et al., *The kidney in congestive heart failure: Are natriuresis, sodium, and diuretics really the good, the bad and the ugly? European Journal of Heart Failure* 2014:16,133-42 (hereinafter "Verbrugge").

Venous congestion can lead to a prerenal form of acute kidney injury (AKI). Prerenal AKI is due to a loss of perfusion (or loss of blood flow) through the kidney. Many clinicians focus on the lack of flow into the kidney due to shock. However, there is also evidence that a lack of blood flow out of the organ due to venous congestion can be a clinically important sustaining injury. See Mullins K, *Importance of venous congestion for worsening renal function in advanced decompensated heart failure, JACC* 17:589-96, 2009.

Prerenal AKI occurs across a wide variety of diagnoses requiring critical care admissions. The most prominent admissions are for sepsis and Acute Decompensated Heart Failure (ADHF). Additional admissions include cardiovascular surgery, general surgery, cirrhosis, trauma, burns, and pancreatitis. While there is wide clinical variability in the presentation of these disease states, a common denominator is an elevated central venous pressure. In the case of ADHF, the elevated central venous pressure caused by heart failure leads to pulmonary edema, and, subsequently, dyspnea in turn precipitating the admission. In the case of sepsis, the elevated central venous pressure is largely a result of aggressive fluid resuscitation. Whether the primary insult was low perfusion due to hypovolemia or sodium and fluid retention, the sustaining injury is the venous congestion resulting in inadequate perfusion.

Hypertension is another widely recognized state that creates perturbations within the active and passive transport systems of the kidney(s). Hypertension directly impacts afferent arteriole pressure and results in a proportional increase in net filtration pressure within the glomerulus. The increased filtration fraction also elevates the peritubular capillary pressure, which stimulates sodium and water re-absorption. See Verbrugge.

Because the kidney is an encapsulated organ, it is sensitive to pressure changes in the medullary pyramids. The elevated renal venous pressure creates congestion that leads to a rise in the interstitial pressures. The elevated interstitial pressures exert forces upon both the glomerulus and tubules. See Verbrugge. In the glomerulus, the elevated interstitial pressures directly oppose filtration. The increased pressures increase the interstitial fluid, thereby increasing the hydrostatic pressures in the interstitial fluid and peritubular capillaries in the medulla of the kidney. In both instances, hypoxia can ensue leading to cellular injury and further loss of perfusion. The net result is a further exacerbation of the sodium and water re-absorption creating a negative feedback. See Verbrugge, 133-42. Fluid overload, particularly in the abdominal cavity is associated with many diseases and conditions, including elevated intra-abdominal pressure, abdominal compartment syndrome, and acute renal failure. Fluid overload can be addressed through renal replacement therapy. See Peters, C. D., Short and *Long-Term Effects of the Angiotensin II Receptor Blocker Irbesartanon Intradialytic Central Hemodynamics: A Randomized Double-Blind Placebo-Controlled One-Year Intervention Trial* (*the SAFIR Study*), *PLoS ONE* (2015) 10(6): e0126882. doi:10.1371/journal.pone.0126882 (hereinafter "Peters"). However, such a clinical strategy provides no improvement in renal function for patients with the cardiorenal syndrome. See Bart B, *Ultrafiltration in decompensated heart failure with cardiorenal syndrome, NEJM* 2012; 367:2296-2304 (hereinafter "Bart").

Even among the best medical centers, nearly half of all patients admitted for congestion due to ADHF are discharged without achieving clinical decongestion, even with administration of high dose intravenous diuretics. *Circ Heart Fail.*, 8(4), 741-748 (2015). The success in achieving decongestion or avoiding major clinical events for patients with any form of diuretic resistance are significantly worse.

Impaired renal sodium excretion secondary to neurohumoral upregulation is the primary abnormality. The body is composed of semipermeable membranes that allow water, but not ions, to move freely. Sodium accumulation, therefore, is required to precipitate volume overload. Presentation with clinical congestion, therefore, underscores the inability of the kidneys to appropriately regulate sodium and water in the body.

Heart failure is a medical condition where the heart is unable to maintain a sufficient blood flow to support the body. The signs and symptoms of heart failure include, but are not limited to, shortness of breath, fatigue, weakness, swelling in the legs, ankles and feet, rapid and/or irregular heartbeat, persistent cough or wheezing, blood tinged phlegm, increased urine output (especially at night), abdominal swelling, fluid retention, loss of appetite and nausea, loss of concentration and alertness, sudden and/or severe shortness of breath and/or chest pain.

One common symptom in heart failure is edema (i.e., fluid buildup in the patient). This occurs when excess fluid is trapped in the tissues of the body. When blood is not pumped properly during heart failure, blood and fluid can back up in the legs, ankles and feet of a patient. It can also result in swelling in the abdomen along with sudden weight gain due to fluid buildup. Pulmonary edema occurs when fluid builds up in the lungs of a patient which contributes to shortness of breath and respiratory symptoms.

SUMMARY

According to an example of the disclosure, a negative pressure therapy device for inducing negative pressure in a portion of a urinary tract comprises an inflow member and an outflow member. The inflow member comprises at least one inflow lumen configured to be in fluid communication with a negative pressure source. The inflow member further comprises (i) a proximal portion, (ii) a retention portion configured to be deployed within a renal pelvis of the urinary tract, the retention portion comprising at least one drainage hole leading to the at least one inflow lumen, and (iii) at least one intermediate portion between the proximal portion and the retention portion. The at least one intermediate portion is configured to extend through at least a portion of the kidney to the renal pelvis. The outflow member comprises at least one outflow lumen configured to be in fluid communication with the negative pressure source. The outflow member further comprises (i) a proximal portion, (ii) a distal end configured to be positioned in the ureter or bladder, and (iii) at least one intermediate portion extending from the proximal portion to the distal end. The negative pressure is induced in the at least one inflow lumen of the inflow member by the negative pressure source to remove fluid from the kidney and/or renal pelvis and discharge the fluid from the at least one outflow lumen of the outflow member to the ureter or bladder.

According to another example of the disclosure, a system for inducing negative pressure in a portion of a urinary tract comprises: a negative pressure source; and a urinary catheter configured to be deployed in the urinary tract. The urinary catheter comprises an inflow member and an outflow member. The inflow member comprises at least one inflow lumen in fluid communication with the negative pressure source. The inflow member further comprises (i) a proximal portion, (ii) a retention portion configured to be deployed within a renal pelvis of the urinary tract, the retention portion comprising at least one drainage hole leading to the at least one inflow lumen, and (iii) at least one intermediate portion between the proximal portion and the retention portion. The at least one intermediate portion is configured to extend through at least a portion of the kidney to the renal pelvis. The outflow member comprises at least one outflow lumen in fluid communication with the negative pressure source. The outflow member further comprises (i) a proximal portion, (ii) a distal end configured to be positioned in the ureter or bladder, and (iii) at least one intermediate portion extending from the proximal portion to the distal end. When negative pressure is applied through the at least one inflow lumen by the negative pressure source, fluid is drawn into the at least one inflow lumen through the at least one drainage hole, and passes through the at least one inflow lumen and the at least one outflow lumen to the ureter and/or bladder.

According to another example of the disclosure, a method for deploying a negative pressure therapy system within a urinary tract comprises: implanting a negative pressure source within a body outside of the urinary tract and inserting an inflow member of a urinary catheter through a kidney to a renal pelvis of the urinary tract. The inflow member comprises at least one inflow lumen fluidly connected to the implanted negative pressure source. The inflow member further comprises (i) a proximal portion fluidly connected to the negative pressure source, (ii) a retention portion configured to be deployed within the renal pelvis, which comprises at least one drainage hole leading to the at least one inflow lumen, and (iii) at least one intermediate portion between the proximal portion and the retention portion. The method further comprises deploying the retention portion of the inflow member within the renal pelvis to maintain patency of fluid flow from the kidney through at least a portion of the inflow lumen; and inserting an outflow member of the urinary catheter through the kidney, the renal pelvis, a ureter, and to a bladder of the urinary tract. The outflow member comprises at least one outflow lumen configured to be in fluid communication with the negative pressure source. The outflow member further comprises (i) a proximal portion, (ii) a distal end configured to be positioned in the bladder, and (iii) at least one intermediate portion extending from the proximal portion to the distal end.

According to another example of the disclosure, a method for increasing urine output rate from a patient comprises applying negative pressure to an inflow member of a urinary catheter to draw urine through at least one inflow lumen of the inflow member to a negative pressure source. The inflow member comprises (i) a proximal portion, (ii) a retention portion deployed within a renal pelvis of the patient, the retention portion comprising at least one drainage hole leading to the at least one inflow lumen, and (iii) at least one intermediate portion between the proximal portion and the retention portion. The at least one intermediate portion is configured to extend through at least a portion of the kidney to the renal pelvis. The method further comprises expelling the urine from the negative pressure source to a bladder of the patient through an outflow member of the urinary catheter at least partially deployed within the bladder of the urinary tract. The outflow member comprises (i) a proximal portion, (ii) a distal end positioned in the bladder, and (iii) at least one intermediate portion extending from the proximal portion to the distal end.

According to another example of the disclosure, a negative pressure therapy device for inducing negative pressure in a portion of a urinary tract comprises a urinary catheter, which comprises an inflow member and an outflow member. The inflow member comprises at least one inflow lumen configured to be in fluid communication with a negative pressure source. The inflow member further comprises: (i) a proximal portion; (ii) a retention portion configured to be deployed within a kidney and/or renal pelvis of the urinary tract including at least one drainage hole leading to the at least one inflow lumen; and (iii) at least one intermediate portion configured to extend through at least portions of the ureter and bladder to the negative pressure source. The outflow member comprises at least one outflow lumen configured to be in fluid communication with the negative pressure source. The outflow member further comprises (i) a proximal portion; (ii) a retention portion configured to be deployed to maintain a distal end of the outflow member within the bladder; and (iii) at least one intermediate portion between the proximal portion and the retention portion of the outflow member. The negative pressure is induced in the at least one inflow lumen of the inflow member by the negative pressure source to remove fluid from the kidney and/or renal pelvis and discharge the fluid from the at least one outflow lumen of the outflow member to the bladder.

According to another example of the disclosure, a negative pressure therapy device for inducing negative pressure in a portion of a urinary tract includes an inflow member including at least one inflow lumen configured to be in fluid communication with a negative pressure source. The inflow member further includes: (i) a distal portion configured to be deployed within a renal pelvis of the urinary tract having at least one drainage hole leading to the at least one inflow lumen; (ii) a proximal portion configured to extend from the negative pressure source through at least a portion of the kidney to the distal portion of the inflow member; and (iii) at least one flow controller disposed within the at least one inflow lumen configured to control an intensity of negative pressure applied through the at least one drainage hole to the portion of the urinary tract. The urinary catheter further includes an outflow member having at least one outflow lumen configured to be in fluid communication with the negative pressure source. The outflow member includes a distal end configured to be positioned in the ureter or bladder and a proximal portion extending from the distal end toward the negative pressure source. The negative pressure is induced in the at least one inflow lumen of the inflow member by the negative pressure source to remove fluid from the kidney and/or renal pelvis and discharge the fluid from the at least one outflow lumen of the outflow member to the ureter or bladder.

According to another example of the disclosure, a negative pressure therapy device for inducing negative pressure in a portion of a urinary tract includes a urinary catheter including an inflow member including multiple inflow lumens configured to be in fluid communication with a negative pressure source. The inflow member further includes: (i) a distal portion configured to be deployed within a renal pelvis of the urinary tract having at least one drainage hole leading to at least one of the multiple inflow lumens; (ii) a proximal portion configured to extend from the negative pressure source through at least a portion of the kidney to the distal portion; and (iii) a plurality of passive or active valves disposed within the multiple inflow lumens configured to selectively open and close creating different fluid flow paths from the negative pressure source to the at least one drainage hole through the multiple inflow lumens. The negative pressure is induced in the different fluid flow paths through the multiple inflow lumens of the inflow member by the negative pressure source to remove fluid from the kidney and/or renal pelvis.

According to another example of the disclosure, a system for inducing negative pressure in a portion of a urinary tract comprises an implantable negative pressure source configured to be implanted within a body outside of the urinary tract; and a negative pressure therapy device including any of the previously described urinary catheters.

Non-limiting examples of the present invention will now be described in the following numbered clauses:

Clause 1: A negative pressure therapy device for inducing negative pressure in a portion of a urinary tract, the device comprising a urinary catheter comprising: (a) an inflow member comprising at least one inflow lumen configured to be in fluid communication with a negative pressure source, the inflow member comprising (i) a proximal portion, (ii) a retention portion configured to be deployed within a renal pelvis of the urinary tract, the retention portion comprising at least one drainage hole leading to the at least one inflow lumen, and (iii) at least one intermediate portion between the proximal portion and the retention portion, wherein the at least one intermediate portion is configured to extend through at least a portion of the kidney to the renal pelvis; and (b) an outflow member comprising at least one outflow lumen configured to be in fluid communication with the negative pressure source, the outflow member comprising (i) a proximal portion, (ii) a distal end configured to be positioned in the ureter or bladder, and (iii) at least one intermediate portion extending from the proximal portion to the distal end, wherein the negative pressure is induced in the at least one inflow lumen of the inflow member by the negative pressure source to remove fluid from the kidney and/or renal pelvis and discharge the fluid from the at least one outflow lumen of the outflow member to the ureter or bladder.

Clause 2: The negative pressure therapy device of clause 1, wherein the negative pressure source comprises an implanted pump positioned outside of the urinary tract.

Clause 3: The negative pressure therapy device of clause 1 or clause 2, wherein, when negative pressure is applied through the at least one inflow lumen by the negative pressure source, fluid is drawn into the at least one inflow lumen through the at least one drainage hole, and passes through the at least one inflow lumen and the at least one outflow lumen to the ureter and/or the bladder.

Clause 4: The negative pressure therapy device of any of clauses 1-3, wherein the inflow member is fluidly connected to the outflow member, such that fluid passes directly from the at least one inflow lumen to the at least one outflow lumen.

Clause 5: The negative pressure therapy device of any of clauses 1-4, wherein the inflow member is integral with the outflow member forming a continuous tube.

Clause 6: The negative pressure therapy device of any of clauses 1-5, wherein the at least one inflow lumen is contiguous with the at least one outflow lumen.

Clause 7: The negative pressure therapy device of any of clauses 1-6, wherein the proximal portion of the inflow member is configured to connect to an inflow port of the negative pressure source and the proximal portion of the outflow member is configured to connect to an outflow port of the negative pressure source, such that fluid passes from the at least one inflow lumen, through the negative pressure source, to the at least one outflow lumen.

Clause 8: The negative pressure therapy device of any of clauses 1-7, wherein the retention portion of the inflow member is configured to retain at least a distal portion of the inflow member within the kidney and/or renal pelvis.

Clause 9: The negative pressure therapy device of any of clauses 1-8, wherein, when deployed, a maximum outer diameter of the retention portion of the inflow member is greater than a diameter of the at least one inflow lumen of the inflow member.

Clause 10: The negative pressure therapy device of any of clauses 1-9, wherein the inflow member and/or the outflow member comprise elongated tubular members comprising a proximal end, a distal end, and a sidewall extending between the proximal end and the distal end.

Clause 11: The negative pressure therapy device of clause 10, wherein the inflow member comprises at least one radiopaque band on the sidewall, and wherein the at least one radiopaque band is proximate to the retention portion for identifying a location of the retention portion using fluoroscopic imaging.

Clause 12: The negative pressure therapy device of any of clauses 1-11, wherein the inflow member and/or the outflow member comprise one or more of copper, silver, gold, nickel-titanium alloy, stainless steel, titanium, polyurethane, polyvinyl chloride, polytetrafluoroethylene (PTFE), latex, and silicone.

Clause 13: The negative pressure therapy device of any of clauses 1-12, wherein the retention portion of the inflow member, when deployed, defines a three-dimensional shape sized and positioned to maintain patency of fluid flow between the kidney and/or renal pelvis and the proximal portion of the inflow member by inhibiting mucosal tissue from appreciably occluding the at least one drainage hole when the negative pressure is applied through the inflow member.

Clause 14: The negative pressure therapy device of clause 13, wherein, when deployed, the at least one intermediate portion of the outflow member is configured to pass through the three-dimensional shape defined by the retention portion of the inflow member.

Clause 15: The negative pressure therapy device of any of clauses 1-14, wherein the retention portion of the inflow member comprises at least a first coil having a first diameter and at least a second coil having a second diameter, the first diameter being greater than the second diameter.

Clause 16: The negative pressure therapy device of any of clauses 1-15, wherein the retention portion of the inflow member comprises a plurality of coils, and wherein a distal-most coil of the plurality of coils has a smaller diameter than other coils of the plurality of coils.

Clause 17: The negative pressure therapy device of clause 16, wherein, when the inflow member and the outflow member are deployed in the urinary tract, the outflow member extends through one or more of the plurality of coils of the retention portion of the inflow member.

Clause 18: The negative pressure therapy device of clause 16 or clause 17, wherein, when the inflow member and the outflow member are deployed in the urinary tract, the outflow member extends through the distal-most coil of the retention portion of the inflow member.

Clause 19: The negative pressure therapy device of any of clauses 1-18, wherein the retention portion of the inflow member comprises a radially inwardly facing side comprising the at least one drainage hole, and a radially outwardly facing side that is essentially free of drainage holes.

Clause 20: The negative pressure therapy device of any of clauses 1-19, wherein an axial length of the outflow member along a curvilinear axis of the outflow member is longer than an axial length of the inflow member along a curvilinear axis of the inflow member.

Clause 21: The negative pressure therapy device of any of clauses 1-20, wherein the outflow member is free from drainage holes extending through a sidewall of the outflow member.

Clause 22: The negative pressure therapy device of any of clauses 1-21, wherein the distal end of the outflow member is open, such that, when deployed, fluid passes through the open distal end to the ureter and/or bladder.

Clause 23: The negative pressure therapy device of clause 22, wherein the outflow member comprises a retention portion configured to be deployed in the bladder for retaining the distal end of the outflow member in the bladder.

Clause 24: The negative pressure therapy device of clause 23, wherein the retention portion of the outflow member, when deployed, defines a three-dimensional shape sized to restrict a distal end of the outflow member from being pulled out of the bladder into the ureter of the urinary tract.

Clause 25: The negative pressure therapy device of clause 23 or clause 24, wherein, when deployed, the retention portion of the outflow member comprises at least one of a pigtail coil, a helical coil, a funnel, or any combination thereof.

Clause 26: The negative pressure therapy device of any of clauses 23-25, wherein, when deployed, the proximal and intermediate portions of the inflow member and the outflow member are substantially parallel for portions of the members extending from the negative pressure source through the kidney.

Clause 27: The negative pressure therapy device of clause 26, wherein substantially parallel sections of the inflow member and the outflow member are joined together by at least one of a fastener, clip, or adhesive.

Clause 28: The negative pressure therapy device of any of clauses 1-27, wherein the retention portion of the inflow member is configured to be deployed in the kidney and/or renal pelvis of a patient.

Clause 29: The negative pressure therapy device of clause 28, wherein the patient is a human.

Clause 30: The negative pressure therapy device of clause 28 or clause 29, wherein the patient is a dog.

Clause 31: A system for inducing negative pressure in a portion of a urinary tract, the system comprising: a negative pressure source; and a urinary catheter configured to be deployed in the urinary tract, comprising: (a) an inflow member comprising at least one inflow lumen in fluid communication with the negative pressure source, the inflow member comprising (i) a proximal portion, (ii) a retention portion configured to be deployed within a renal pelvis of the urinary tract, the retention portion comprising at least one drainage hole leading to the at least one inflow lumen, and (iii) at least one intermediate portion between the proximal portion and the retention portion, wherein the at least one intermediate portion is configured to extend through at least a portion of the kidney to the renal pelvis; and (b) an outflow member comprising at least one outflow lumen in fluid communication with the negative pressure source, the outflow member comprising (i) a proximal portion, (ii) a distal end configured to be positioned in the ureter or bladder, and (iii) at least one intermediate portion extending from the proximal portion to the distal end, wherein, when negative pressure is applied through the at least one inflow lumen by the negative pressure source, fluid is drawn into the at least one inflow lumen through the at least one drainage hole, and passes through the at least one inflow lumen and the at least one outflow lumen to the ureter and/or bladder.

Clause 32: The system of clause 31, wherein the negative pressure source comprises a pump configured to be implanted in a body outside of the urinary tract of the body.

Clause 33: The system of clause 32, wherein the pump is configured to be positioned posterolateral to the kidney or proximate to an abdominal wall of the body.

Clause 34: The system of clause 32 or clause 33, wherein the pump applies a negative pressure of about 100 mmHg or less to a proximal end of the urinary catheter.

Clause 35: The system of any of clauses 32-34, further comprising a controller configured to regulate positive and/or negative pressure provided by the pump within a pressure range that facilitates increased urine production from the kidney.

Clause 36: The system of any of clauses 32-35, further comprising one or more physiological sensors configured to provide information representative of at least one physical parameter to the controller, and wherein the controller is configured to actuate or cease operation of the pump based on the information representative of the at least one physical parameter.

Clause 37: The system of clause 36, further comprising at least one fluid sensor in fluid communication with the at least one inflow lumen, wherein the controller of the negative pressure source is configured to: receive and process information from the at least one fluid sensor to determine at least one of flow rate and flow volume of the fluid through the at least one inflow lumen; compare the determined flow rate or flow volume to a target value; and adjust the negative pressure source based on the comparison to increase or decrease the at least one of flow rate or flow volume through the at least one inflow lumen.

Clause 38: The system of any of clauses 32-37, wherein the pump comprises: a housing defining at least one fluid inflow port fluidly connected to the at least one inflow lumen and at least one outflow port fluidly connected to the at least one outflow lumen; and a pump chamber at least partially enclosed within the housing fluidly connected to the at least one fluid inflow port and the at least one fluid outflow port, wherein the pump is configured to draw the fluid through the at least one inflow lumen to the pump chamber, thereby exerting the negative pressure to at least a portion of the kidney and/or renal pelvis.

Clause 39: The system of clause 38, wherein the pump is further configured to expel fluid from the pump chamber to the at least one outflow lumen.

Clause 40: The system of any of clauses 31-39, further comprising an external controller positioned outside of the body, the external controller being electrically coupled to the negative pressure source to provide power to the negative pressure source.

Clause 41: The system of clause 40, further comprising at least one electrical cable extending between the external controller and the negative pressure source through at least one percutaneous access opening in the body.

Clause 42: The system of any of clauses 31-41, wherein the negative pressure source comprises a wireless transceiver configured to receive operating instructions from a remote computer device and to provide information about negative pressure treatment from the negative pressure source to the remote computer device.

Clause 43: The system of any of clauses 31-42, wherein the retention portion of the inflow member, when deployed, defines a three-dimensional shape sized and positioned to maintain patency of fluid flow between the kidney and/or renal pelvis and the proximal portion of the inflow member by inhibiting mucosal tissue from appreciably occluding the at least one drainage hole when the negative pressure is applied through the inflow member, and wherein, when the inflow member and the outflow member are deployed in the urinary tract, the outflow member extends through the three-dimensional shape defined by the retention portion of the inflow member.

Clause 44: The system of any of clauses 31-43, wherein the retention portion of the inflow member comprises a plurality of coils, wherein a distal-most coil of the plurality of coils has a smaller diameter than other coils of the plurality of coils, and wherein, when the inflow member and the outflow member are deployed in the urinary tract, the outflow member extends through one or more of the plurality of coils of the retention portion of the urinary catheter.

Clause 45: The system of any of clauses 31-44, wherein a distal portion of the outflow member comprises a retention portion configured to be deployed in the bladder for retaining the distal end of the outflow member in the bladder.

Clause 46: The system of clause 45, wherein the retention portion of the outflow member, when deployed, defines a three-dimensional shape sized to restrict the distal end of the outflow member from being pulled out of the bladder into the ureter of the urinary tract.

Clause 47: The system of clause 45 or clause 36, wherein, when deployed, the retention portion of the outflow member comprises at least one of a pigtail coil, a helical coil, a funnel, or any combination thereof.

Clause 48: The system of any of clauses 45-47, wherein, when deployed, the proximal and intermediate portions of the inflow member and the outflow member are substantially parallel for portions of the members extending from the negative pressure source through the kidney.

Clause 49: A method for deploying a negative pressure therapy system within a urinary tract, the method comprising: implanting a negative pressure source within a body outside of the urinary tract; inserting an inflow member of a urinary catheter through a kidney to a renal pelvis of the urinary tract, wherein the inflow member comprises at least one inflow lumen fluidly connected to the implanted negative pressure source, the inflow member further comprising (i) a proximal portion fluidly connected to the negative pressure source, (ii) a retention portion configured to be deployed within the renal pelvis, the retention portion comprising at least one drainage hole leading to the at least one inflow lumen, and (iii) at least one intermediate portion between the proximal portion and the retention portion; deploying the retention portion of the inflow member within the renal pelvis to maintain patency of fluid flow from the kidney through at least a portion of the inflow lumen; and inserting an outflow member of the urinary catheter through the kidney, the renal pelvis, a ureter, and to a bladder of the urinary tract, wherein the outflow member comprises at least one outflow lumen configured to be in fluid communication with the negative pressure source, the outflow member further comprising (i) a proximal portion, (ii) a distal end configured to be positioned in the bladder, and (iii) at least one intermediate portion extending from the proximal portion to the distal end.

Clause 50: The method of clause 49, further comprising deploying a retention portion of the outflow member in the bladder to retain the distal end of the outflow member in the bladder, such that fluid expelled from the negative pressure source passes through the at least one outflow lumen to the bladder.

Clause 51: The method of clause 50, wherein deploying the retention portion of the outflow member causes the retention portion of the outflow member to adopt a three-dimensional shape sized to restrict a distal end of the outflow member from being pulled out of the bladder into the ureter of the urinary tract.

Clause 52: The method of clause 50 or clause 51, wherein deploying the retention portion of the outflow member causes the retention portion of the outflow member to form at least one of a pigtail coil, a helical coil, a funnel, or any combination thereof.

Clause 53: The method of any of clauses 49-52, wherein the negative pressure source comprises a pump.

Clause 54: The method of any of clauses 49-53, wherein the pump is implanted at a position posterolateral to the kidney or proximate to an abdominal wall of the body.

Clause 55: The method of any of clauses 49-54, wherein inserting the inflow member of the urinary catheter comprises: inserting a needle into a portion of a patient's body to create a percutaneous opening; inserting the needle into the kidney and advancing the needle through the kidney to the renal pelvis; and inserting the inflow member over the needle, such that a distal end of the inflow member advances from the kidney into the renal pelvis.

Clause 56: The method of clause 55, wherein inserting the needle comprises inserting the needle into an abdominal region of the body.

Clause 57: The method of any of clauses 49-56, wherein deploying the retention portion of the inflow member causes the retention portion of the inflow member to adapt a three-dimensional shape sized and positioned to maintain patency of fluid flow between the kidney and/or renal pelvis and a proximal end of the at least one inflow lumen by inhibiting mucosal tissue from appreciably occluding the at least one drainage hole when negative pressure is applied through the inflow member.

Clause 58: The method of clause 57, wherein inserting the outflow member comprises inserting the outflow member through the three-dimensional shape defined by the retention portion of the inflow member.

Clause 59: The method of any of clauses 49-58, wherein deploying the retention portion of the inflow member causes the retention portion to form a plurality of coils, and wherein a distal-most coil of the plurality of coils has a smaller diameter than other coils of the plurality of coils.

Clause 60: The method of clause 59, wherein inserting the outflow member comprises inserting the outflow member through one or more of the plurality of coils of the retention portion of the inflow member.

Clause 61: The method of clause 59 or clause 60, wherein inserting the outflow member comprises inserting the outflow member through the distal-most coil of the plurality of coils of the retention portion of the inflow member.

Clause 62: The method of any of clauses 49-61, further comprising activating the negative pressure source to draw fluid from the renal pelvis and/or kidney through the at least one inflow lumen to the negative pressure source and to expel fluid to the bladder through the at least one outflow lumen.

Clause 63: The method of clause 62, further comprising regulating positive and/or negative pressure provided by the negative pressure source within a pressure range that facilitates increased urine production from the kidney.

Clause 64: A method for increasing urine output rate from a patient, the method comprising: applying negative pressure to an inflow member of a urinary catheter to draw urine through at least one inflow lumen of the inflow member to a negative pressure source, the inflow member comprising (i) a proximal portion, (ii) a retention portion deployed within a renal pelvis of the patient, the retention portion comprising at least one drainage hole leading to the at least one inflow lumen, and (iii) at least one intermediate portion between the proximal portion and the retention portion, wherein the at least one intermediate portion is configured to extend through at least a portion of the kidney to the renal pelvis; and expelling the urine from the negative pressure source to a bladder of the patient through an outflow member of the urinary catheter at least partially deployed within the bladder of the urinary tract, the outflow member comprising (i) a proximal portion, (ii) a distal end positioned in the bladder, and (iii) at least one intermediate portion extending from the proximal portion to the distal end.

Clause 65: The method of clause 64, wherein the outflow member comprises a retention portion deployed in the bladder for retaining the distal end of the outflow member in the bladder.

Clause 66: The method of clause 64 or clause 65, wherein the inflow member extends from the negative pressure source, through the kidney, and to the renal pelvis, and the outflow member extends from the negative pressure source through the kidney, the renal pelvis, the ureter, and to the bladder.

Clause 67: A negative pressure therapy device for inducing negative pressure in a portion of a urinary tract, the device comprising a urinary catheter comprising: (a) an inflow member comprising at least one inflow lumen configured to be in fluid communication with a negative pressure source, the inflow member comprising: (i) a proximal portion; (ii) a retention portion configured to be deployed within a kidney and/or renal pelvis of the urinary tract, the retention portion comprising at least one drainage hole leading to the at least one inflow lumen; and (iii) at least one intermediate portion configured to extend through at least portions of the ureter and bladder to the negative pressure source; and (b) an outflow member comprising at least one outflow lumen configured to be in fluid communication with the negative pressure source, the outflow member comprising (i) a proximal portion; (ii) a retention portion configured to be deployed to maintain a distal end of the outflow member within the bladder; and (iii) at least one intermediate portion between the proximal portion and the retention portion of the outflow member, wherein the negative pressure is induced in the at least one inflow lumen of the inflow member by the negative pressure source to remove fluid from the kidney and/or renal pelvis and discharge the fluid from the at least one outflow lumen of the outflow member to the bladder.

Clause 68: The negative pressure therapy device of clause 67, wherein, when negative pressure is applied through the at least one inflow lumen by the negative pressure source, fluid is drawn into the at least one inflow lumen through the at least one drainage hole, and passes through the at least one inflow lumen and the at least one outflow lumen to the bladder.

Clause 69: The negative pressure therapy device of clause 67 or clause 68, wherein the inflow member is configured to extend from the negative pressure source, through a hole in a wall of the bladder, and through the ureter to the renal pelvis and/or kidney, and wherein the outflow member is configured to extend from the negative pressure source through another hole in the bladder wall to the bladder.

Clause 70: The negative pressure therapy device of any of clauses 67-69, wherein the retention portion of the outflow member, when deployed, defines a three-dimensional shape sized to restrict a distal end of the outflow member from being pulled out of the bladder into the ureter of the urinary tract.

Clause 71: The negative pressure therapy device of any of clauses 67-70, wherein, when deployed, the retention portion of the outflow member comprises at least one of a pigtail coil, a helical coil, a funnel, or any combination thereof.

Clause 72: A system for inducing negative pressure in a portion of a urinary tract, the system comprising: an implantable negative pressure source configured to be implanted within a body outside of the urinary tract; and the negative pressure therapy device comprising the urinary catheter of any of clauses 67-71.

Clause 73: The system of clause 72, wherein the implantable negative pressure source comprises a pump.

Clause 74: The negative pressure therapy device of clause 73, wherein the pump is configured to be positioned posterolateral to a wall of the bladder.

Clause 75: A negative pressure therapy device for inducing negative pressure in a portion of a urinary tract, the device comprising a urinary catheter comprising: (a) an inflow member comprising at least one inflow lumen configured to be in fluid communication with a negative pressure source, the inflow member comprising (i) a distal portion configured to be deployed within a renal pelvis of the urinary tract comprising at least one drainage hole leading to the at least one inflow lumen, (ii) a proximal portion configured to extend from the negative pressure source through at least a portion of the kidney to the distal portion of the inflow member, and (iii) at least one flow controller disposed within the at least one inflow lumen configured to control an intensity of negative pressure applied through the at least one drainage hole to the portion of the urinary tract; and (b) an outflow member comprising at least one outflow lumen configured to be in fluid communication with the negative pressure source, the outflow member comprising a distal end configured to be positioned in the ureter or bladder and a proximal portion extending from the distal end toward the negative pressure source, wherein the negative pressure is induced in the at least one inflow lumen of the inflow member by the negative pressure source to remove fluid from the kidney and/or renal pelvis and discharge the fluid from the at least one outflow lumen of the outflow member to the ureter or bladder.

Clause 76: The negative pressure therapy device of clause 75, wherein the flow controller comprises at least one of a one-way valve, two-way valve, three-way valve, solenoid valve, impeller, flow restrictor, or flow straightener.

Clause 77: The negative pressure therapy device of clause 75 or clause 76, wherein the at least one flow controller is activated in response to at least one of a user input or a negative pressure intensity detected by at least one sensor.

Clause 78: A negative pressure therapy device for inducing negative pressure in a portion of a urinary tract, the device comprising a urinary catheter comprising: an inflow member comprising multiple inflow lumens configured to be in fluid communication with a negative pressure source, the inflow member comprising (i) a distal portion configured to be deployed within a renal pelvis of the urinary tract comprising at least one drainage hole leading to at least one of the multiple inflow lumens, (ii) a proximal portion configured to extend from the negative pressure source through at least a portion of the kidney to the distal portion, and (iii) a plurality of passive or active valves disposed within the multiple inflow lumens configured to selectively open and close creating different fluid flow paths from the negative pressure source to the at least one drainage hole through the multiple inflow lumens, wherein the negative pressure is induced in the different fluid flow paths through the multiple inflow lumens of the inflow member by the negative pressure source to remove fluid from the kidney and/or renal pelvis.

Clause 79: The negative pressure therapy device of clause 78, wherein the plurality of passive or active valves comprise at least one of a one-way check valve (e.g., a duckbill valve, swing check valve, or lift check valve), two-way valve, three-way valve, and/or solenoid valve.

Clause 80: The negative pressure therapy device of clause 78 or clause 79, wherein the inflow member further comprises at least one of a flow straightener or a flow restrictor disposed in one of the multiple lumens for controlling negative pressure applied through the inflow member.

BRIEF DESCRIPTION OF THE DRAWINGS

These and other features and characteristics of the present disclosure, as well as the methods of operation, use, and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which.

DETAILED DESCRIPTION

Figure 1A:
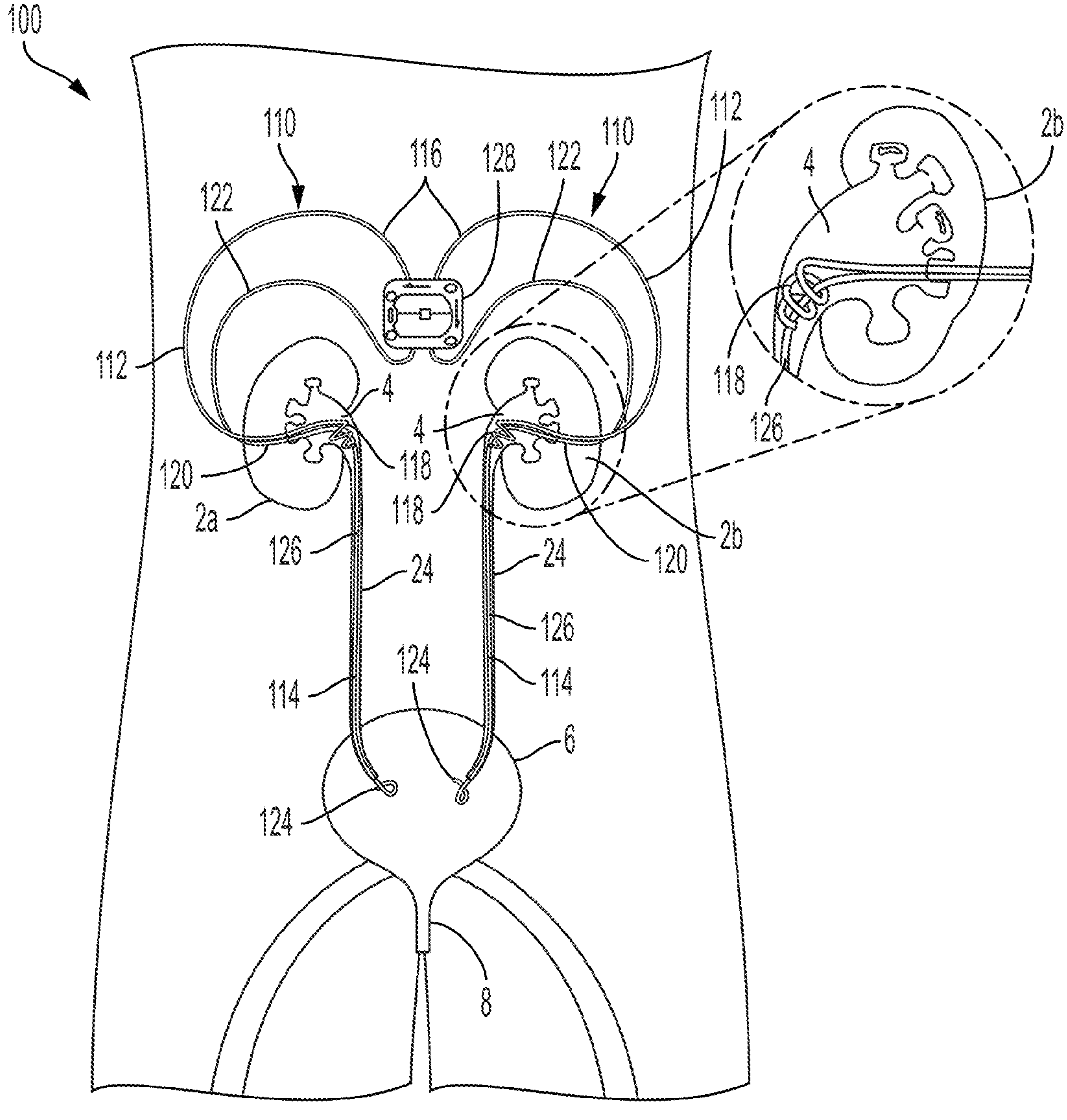
FIG. 1A is a schematic drawing showing a negative pressure therapy system comprising an implanted negative pressure source, according to an example of the present disclosure.

As used herein, the singular form of "a", "an", and "the" include plural referents unless the context clearly states otherwise.

As used herein, the terms "right", "left", "top", and derivatives thereof shall relate to the invention as it is oriented in the drawing figures. The term "proximal" refers to the portion of the catheter device that is manipulated or contacted by a user and/or to a portion of an indwelling catheter nearest to the urinary tract access site, for example the urethra or a percutaneous access opening in the patient's body. The term "distal" refers to the opposite end of the catheter device that is configured to be inserted into a patient and/or to the portion of the device that is inserted farthest into the patient's urinary tract. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

The systems and treatment methods of the present disclosure are configured to provide negative pressure to the urinary tract of a patient for removal of fluid from the urinary tract. As used herein, the "patient" can be any species of the human or animal kingdom having kidney(s), a renal system and/or a urinary system. Non-limiting examples of patients include mammal(s), such as human(s) and/or non-mammalian animal(s). Non-limiting examples of mammal(s) include primate(s) and/or non-primate(s). Primate(s) include human(s) and non-human primate(s), including but not limited to male(s), female(s), adult(s) and children. Non-limiting examples of non-human primate(s) include monkey(s) and/or ape(s), for example chimpanzee(s). Non-limiting examples of non-primate(s) include cattle (such as cow(s), bull(s) and/or calves), pig(s), camel(s), llama(s), alpaca(s), horse(s), donkey(s), goat(s), rabbit(s), sheep, hamster(s), guinea pig(s), cat(s), dog(s), rat(s), mice, lion(s), whale(s), and/or dolphin(s). Non-limiting examples of non-mammalian animal(s) include bird(s) (e.g., duck(s) or geese), reptile(s) (e.g., lizard(s), snake(s), or alligator(s)), amphibian(s) (e.g., frog(s)), and/or fish. In some examples, the animals can be zoological animals, human pets and/or wild animals.

For the purposes of this specification, unless otherwise indicated, all numbers expressing quantities of ingredients, reaction conditions, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention.

As used herein, the term "about" means "close to" and that variation from the exact value that follows the term is within amounts that a person of skill in the art would understand to be reasonable. For example, when the term "about" is used with respect to a numerical value, the value may vary within a reasonable range, such as within +/−10%, +/−5%, or +/−1% of the stated value.

Notwithstanding that the numerical ranges and parameters setting forth the broad scope of the invention are approximations, the numerical values set forth in the specific examples are reported as precisely as possible. Any measured numerical value, however, may inherently contain certain errors resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

As used herein, "negative pressure" means that the pressure applied to the proximal end of the bladder catheter or the proximal end of the urinary catheter, respectively, is below the existing pressure at the proximal end of the bladder catheter or the proximal end of the urinary catheter, respectively, prior to application of the negative pressure, e.g., there is a pressure differential between the proximal end of the bladder catheter or the proximal end of the urinary catheter, respectively, and the existing pressure at the proximal end of the bladder catheter or the proximal end of the urinary catheter, respectively, prior to application of the negative pressure. This pressure differential causes fluid from the kidney to be drawn into the urinary catheter or bladder catheter, respectively, or through both the urinary catheter and the bladder catheter, and then outside of the patient's body. For example, negative pressure applied to the proximal end of the bladder catheter or the proximal end of the urinary catheter can be less than atmospheric pressure (less than about 760 mm Hg or about 1 atm), or less than the pressure measured at the proximal end of the bladder catheter or the proximal end of the urinary catheter prior to the application of negative pressure, such that fluid is drawn from the kidney and/or bladder. In some examples, the negative pressure applied to the proximal end of the bladder catheter or the proximal end of the urinary catheter can range from about 0.1 mmHg to about 150 mm Hg, or about 0.1 mm Hg to about 50 mm Hg, or about 0.1 mm Hg to about 10 mm Hg, or about 5 mm Hg to about 20 mm Hg, or about 45 mm Hg (gauge pressure at the pump 710 or at a gauge at the negative pressure source). In some examples, the negative pressure source comprises a pump external to the patient's body for application of negative pressure through both the bladder catheter and the urinary catheter, which in turn causes fluid from the kidney to be drawn into the urinary catheter, through both the urinary catheter and the bladder catheter, and then outside of the patient's body. In some examples, the negative pressure source comprises a vacuum source external to the patient's body for application and regulation of negative pressure through both the bladder catheter and the urinary catheter, which in turn causes fluid from the kidney to be drawn into the urinary catheter, through both the urinary catheter and the bladder catheter, and then outside of the patient's body. In some examples, the vacuum source is selected from the group consisting of a wall suction source, vacuum bottle, and manual vacuum source, or the vacuum source is provided by a pressure differential. In some examples, the negative pressure received from the negative pressure source can be controlled manually, automatically, or combinations thereof. In some examples, a controller is used to regulate negative pressure from the negative pressure source. Non-limiting examples of negative and positive pressure sources are discussed in detail below. Also, systems for providing negative pressure therapy are also disclosed in International Patent Appl. Publication No. WO 2017/015351 entitled "Ureteral and Bladder Catheters and Methods for Inducing Negative Pressure to Increase Renal Perfusion" and International Patent Appl. Publication No. WO 2017/015345 entitled "Catheter Device and Method for Inducing Negative Pressure in a Patient's Bladder", each of which is incorporated by reference herein its entirety.

Fluid retention and venous congestion are central problems in the progression to advanced renal disease. Excess sodium ingestion coupled with relative decreases in excretion leads to isotonic volume expansion and secondary compartment involvement. In some examples, the present invention is generally directed to systems and methods for inducing a negative pressure in at least a portion of the bladder, ureter, and/or kidney(s), e.g., urinary system, of a patient. While not intending to be bound by any theory, it is believed that applying a negative pressure to at least a portion of the bladder, ureter, and/or kidney(s), e.g., urinary system, can offset the medullary nephron tubule re-absorption of sodium and water in some situations. Offsetting re-absorption of sodium and water can increase urine production, decrease total body sodium, and improve erythrocyte production. Since the intra-medullary pressures are driven by sodium and, therefore, volume overload, the targeted removal of excess sodium enables maintenance of volume loss. Removal of volume restores medullary hemostasis. Normal urine production is 1.48-1.96 L/day (or 1-1.4 ml/min).

Fluid retention and venous congestion are also central problems in the progression of prerenal Acute Kidney Injury (AKI). Specifically, AKI can be related to loss of perfusion or blood flow through the kidney(s). Accordingly, in some examples, the present invention facilitates improved renal hemodynamics and increases urine output for the purpose of relieving or reducing venous congestion. Further, it is anticipated that treatment and/or inhibition of AKI positively impacts and/or reduces the occurrence of other conditions, for example, reduction or inhibition of worsening renal function in patients with NYHA Class III and/or Class IV heart failure. Classification of different levels of heart failure are described in *The Criteria Committee of the New York Heart Association*, (1994), *Nomenclature and Criteria for Diagnosis of Diseases of the Heart and Great Vessels*, (9th ed.), Boston: Little, Brown & Co. pp. 253-256, the disclosure of which is incorporated by reference herein in its entirety. Reduction or inhibition of episodes of AKI and/or chronically decreased perfusion may also be a treatment for Stage 4 and/or Stage 5 chronic kidney disease. Chronic kidney disease progression is described in National Kidney Foundation, K/DOQI *Clinical Practice Guidelines for Chronic Kidney Disease: Evaluation, Classification and Stratification*. Am. J. Kidney Dis. 39:S1-S266, 2002 (Suppl. 1), the disclosure of which is incorporated by reference herein in its entirety.

Also, the urinary catheters, ureteral stents and/or bladder catheters disclosed herein can be useful for preventing, delaying the onset of, and/or treating end-stage renal disease ("ESRD"). The average dialysis patient consumes about $90,000 per year in healthcare utilization for a total cost to the US government of $33.9 Billion. Today, ESRD patients comprise only 2.9% of Medicare's total beneficiaries, yet they account over 13% of total spending. While the incidence and costs per patient have stabilized in recent years, the volume of active patients continues to rise.

The five stages of advanced chronic kidney disease ("CKD") are based upon glomerular filtration rate (GFR). Stage 1 (GFR >90) patients have normal filtration, while stage 5 (GFR <15) have kidney failure. Like many chronic diseases, the diagnosis capture improves with increasing symptom and disease severity.

The CKD 3b/4 subgroup is a smaller subgroup that reflects important changes in disease progression, healthcare system engagement and transition to ESRD. Presentation to the emergency department rises with severity of CKD. Among the US Veteran's Administration population, nearly 86% of the incident dialysis patients had a hospital admission within the five years preceding the admission. Of those, 63% were hospitalized at initiation of dialysis. This suggests a tremendous opportunity to intervene prior to dialysis.

Despite being further down the arterial tree than other organs, the kidneys receive a disproportionate amount of cardiac output at rest. The glomerular membrane represents a path of least resistance of filtrate into the tubules. In healthy states, the nephron has multiple, intricate, redundant means of auto-regulating within normal ranges of arterial pressure.

Venous congestion has been implicated in reduced renal function and is associated with the systemic hypervolemia found in later stages of CKD. Since the kidney is covered with a semi-rigid capsule, small changes in venous pressure translate into direct changes in the intratubule pressures. This shift in intratubule pressure has been shown to upregulate reabsorption of sodium and water, perpetuating the vicious cycle.

Regardless of the initial insult and early progression, more advanced CKD is associated with decreased filtration (by definition) and greater azotemia. Regardless of whether the remaining nephrons are hyperabsorbing water or they are just unable to filtrate sufficiently, this nephron loss is associated with fluid retention and a progressive decline in renal function.

The kidney is sensitive to subtle shifts in volume. As pressure in either the tubule or capillary bed rises, the pressure in the other follows. As the capillary bed pressure rises, the production of filtrate and elimination of urine can decline dramatically. While not intending to be bound by any theory, it is believe that mild and regulated negative pressure delivered to the renal pelvis decreases the pressure among each of the functioning nephrons. In healthy anatomy, the renal pelvis is connected via a network of calyces and collecting ducts to approximately one million individual nephrons. Each of these nephrons are essentially fluid columns connecting Bowman's space to the renal pelvis. Pressure transmitted to the renal pelvis translates throughout. It is believed that, as negative pressure is applied to the renal pelvis, the glomerular capillary pressure forces more filtrate across the glomerular membrane, leading to increased urine output.

It is important to note that the tissues of the urinary tract are lined with urothelium, a type of transitional epithelium. The tissues lining the inside of the urinary tract are also referred to as uroendothelial or urothelial tissues, such as mucosal tissue of the ureter and/or kidney and bladder tissue. Urothelium has a very high elasticity, enabling a remarkable range of collapsibility and distensibility. The urothelium lining the ureter lumen is surrounded first by the lamina propria, a thin layer of loose connective tissue, which together comprise the urothelial mucosa. This mucosa is then surrounded by a layer of longitudinal muscle fibers. These longitudinal muscle fibers surrounding the urothelial mucosa and the elasticity of the urothelial mucosa itself allow the ureter to relax into a collapsed stellate cross-section and then expand to full distention during diuresis. Histology of any normal ureteral cross-section reveals this star-shaped lumen in humans and other mammals generally used in translational medical research. Wolf et al., "Comparative Ureteral Microanatomy", JEU 10: 527-31 (1996).

The process of transporting urine from the kidney to the bladder is driven by contractions through the renal pelvis and peristalsis distally through the rest of the ureter. The renal pelvis is the widening of the proximal ureter into a funnel-shape where the ureter enters the kidney. The renal pelvis has actually been shown to be a continuation of the ureter, comprised of the same tissue but with one additional muscle layer that allows it to contract. Dixon and Gosling, "The Musculature of the Human Renal Calyces, Pelvis and Upper Ureter", J. Anat. 135: 129-37 (1982). These contractions push urine through the renal pelvis funnel to allow peristaltic waves to propagate the fluid through the ureter to the bladder.

Imaging studies have shown that the ureter of the dog can readily increase to up to 17× its resting cross-sectional area to accommodate large volumes of urine during diuresis. Woodburne and Lapides, "The Ureteral Lumen During Peristalsis", AJA 133: 255-8 (1972). Among swine, considered to be the closest animal model for the human upper urinary tract, the renal pelvis and most proximal ureter are actually shown to be the most compliant of all ureteral sections. Gregersen, et al., "Regional Differences Exist in Elastic Wall Properties in the Ureter", SJUN 30: 343-8 (1996). Wolf's comparative analysis of various research animals' ureteral microanatomy to that of humans revealed comparable thickness of lamina propria layer relative to whole ureter diameter in dogs (29.5% in humans and 34% in dogs) and comparable percentage of smooth muscle relative to total muscular cross-sectional area in pigs (54% in humans and 45% in pigs). While there are certainly limitations to the comparisons between species, dogs and pigs have historically been strong foci in studying and understanding human ureter anatomy and physiology, and these reference values support this high level of translatability.

There is much more data available on structure and mechanics of pig and dog ureters and renal pelves than on human ureters. This is due partly to the invasiveness required for such detailed analyses as well as the inherent limitations of various imaging modalities (MRI, CT, ultrasound, etc.) to attempt to accurately identify size and composition of such small, flexible, and dynamic structures clinically. Nevertheless, this ability for the renal pelvis to distend or completely collapse in humans is a hurdle for nephrologists and urologists seeking to improve urine flow.

While not intending to be bound by any theory, the present inventors theorized that the application of negative pressure might help to facilitate fluid flow from the kidney, and that a very particular tool, designed to deploy a protective surface area in order to open or maintain the opening of the interior of the renal pelvis while inhibiting the surrounding tissues from contracting or collapsing into the fluid column under negative pressure, is needed to facilitate the application of negative pressure within the renal pelvis. The flow tube, flow member, and/or catheter designs of the present invention disclosed herein provide a protective surface area to inhibit surrounding urothelial tissues from contracting or collapsing into the fluid column under negative pressure. It is believed that the catheter designs of the present invention disclosed herein can successfully maintain the stellate longitudinal folding of the ureteral wall away from the central axis and protected holes of the catheter drainage lumen, and can inhibit natural sliding of the catheter down the stellate cross-sectional area of the ureteral lumen and/or downward migration by peristaltic waves.

Also, flow tube, flow member, and/or catheter designs disclosed herein can avoid an unprotected open hole at the distal end of the drainage lumen which fails to protect surrounding tissues during suction. While it is convenient to think of the ureter as a straight tube, the true ureter and renal pelvis can enter the kidney at a variety of angles. Lippincott Williams & Wilkins, Annals of Surgery, 58, FIGS. 3 & 9 (1913). Therefore, it would be difficult to control the orientation of an unprotected open hole at the distal end of the drainage lumen when deploying such a catheter in the renal pelvis. This single hole may present a localized suction point that has no means of either reliable or consistent distancing from tissue walls, thereby permitting tissue to occlude the unprotected open hole and risking damage to the tissue. Also, catheter designs of the present invention disclosed herein can avoid placement of a balloon having an unprotected open hole at the distal end of the drainage lumen close to the kidney which may result in suction against and/or occlusion of the calyces. Placement of a balloon having an unprotected open hole at the distal end of the drainage lumen at the very base of the uretero-renal pelvis junction may result in suction against and occlusion by renal pelvis tissue. Also, a rounded balloon may present a risk of ureteral avulsion or other damage from incidental pulling forces on the balloon.

Delivering negative pressure into the kidney area of a patient has a number of anatomical challenges for at least three reasons. First, the urinary system is composed of highly pliable tissues that are easily deformed. Medical textbooks often depict the bladder as a thick muscular structure that can remain in a fixed shape regardless of the volume of urine contained within the bladder. However, in reality, the bladder is a soft deformable structure. The bladder shrinks to conform to the volume of urine contained in the bladder. An empty bladder more closely resembles a deflated latex balloon than a ball. In addition, the mucosal lining on the interior of the bladder is soft and susceptible to irritation and damage. It is desirable to avoid drawing the urinary system tissue into the orifices of the catheter to maintain adequate fluid flow therethrough and avoid injury to the surrounding tissue.

Second, the ureters are small tube-like structures that can expand and contract to transport urine from the renal pelvis to the bladder. This transport occurs in two ways: peristaltic activity and by a pressure gradient in an open system. In the peristaltic activity, a urine portion is pushed ahead of a contractile wave, which almost completely obliterates the lumen. The wave pattern initiates in the renal pelvis area, propagates along the ureter, and terminates in the bladder. Such a complete occlusion interrupts the fluid flow and can prevent negative pressure delivered in the bladder from reaching the renal pelvis without assistance. The second type of transport, by pressure gradient through a wide-open ureter, may be present during large urine flow. During such periods of high urine production, the pressure head in the renal pelvis would not need to be caused by contraction of the smooth muscles of the upper urinary tract, but rather is generated by the forward flow of urine, and therefore reflects arterial blood pressure. Kiil F., "Urinary Flow and Ureteral Peristalsis" in: Lutzeyer W., Melchior H. (Eds.) Urodynamics. Springer, Berlin, Heidelberg (pp. 57-70) (1973).

Third, the renal pelvis is at least as pliable as the bladder. The thin wall of the renal pelvis can expand to accommodate multiple times the normal volume, for example as occurs in patients having hydronephrosis.

More recently, the use of negative pressure in the renal pelvis to remove blood clots from the renal pelvis by the use of suction has been cautioned against because of the inevitable collapse of the renal pelvis, and as such discourages the use of negative pressure in the renal pelvis region. Webb, *Percutaneous Renal Surgery: A Practical Clinical Handbook*. p 92. Springer (2016).

While not intending to be bound by any theory, the tissues of the renal pelvis and bladder are flexible enough to be drawn inwardly during delivery of negative pressure to conform to the shape and volume of the tool being used to deliver negative pressure. Analogous to the vacuum sealing of a husked ear of corn, the urothelial tissue will collapse around and conform to the source of negative pressure. To prevent the tissue from occluding the lumen and impeding the flow of urine, the present inventors theorized that a protective surface area sufficient to maintain the fluid column when mild negative pressure is applied would prevent or inhibit occlusion.

The present inventors determined that there are specific features that enable a negative pressure and/or catheter tool to be deployed successfully in and deliver negative pressure through the urological region that have not been previously described. These require a deep understanding of the anatomy and physiology of the treatment zone and adjacent tissues. The catheter must comprise a protective surface area within the renal pelvis by supporting the urothelium and inhibiting the urothelial tissue from occluding openings in the catheter during application of negative pressure through the catheter lumen. For example, establishing a three dimensional shape or void volume, that is free or essentially free from urothelial tissue, ensures the patency of the fluid column or flow from each of the million nephrons into the drainage lumen of the catheter.

Since the renal pelvis is comprised of longitudinally oriented smooth muscle cells, the protective surface area would ideally incorporate a multi-planar approach to establishing the protected surface area. Anatomy is often described in three planes, sagittal (vertical front to back that divides the body into right and left parts), coronal (vertical side to side dividing the body into dorsal and ventral parts) and transverse (horizontal or axial that divides the body into superior and inferior parts, and is perpendicular to the sagittal and coronal planes). The smooth muscle cells in the renal pelvis are oriented vertically. It is desirable for the catheter to also maintain a radial surface area across the many transverse planes between the kidney and the ureter. This enables a catheter to account for both longitudinal and horizontal portions of the renal pelvis in the establishment of a protective surface area. In addition, given the flexibility of the tissues, the protection of these tissues from the openings or orifices that lead to the lumen of the catheter tool is desirable. The catheters discussed herein can be useful for delivering negative pressure, positive pressure, or can be used at ambient pressure, or any combination thereof.

In some examples, a deployable/retractable expansion mechanism or retention portion is utilized that, when deployed, creates and/or maintains a patent fluid column or flow between the kidney and the catheter drainage lumen. This deployable/retractable mechanism, when deployed, creates the protective surface area within the renal pelvis by supporting the urothelium and inhibiting the urothelial tissue from occluding openings in the catheter during application of negative pressure through the catheter lumen. In some examples, the retention portion is configured to be extended into a deployed position in which a diameter of the retention portion is greater than a diameter of the drainage lumen portion.

In some examples, systems of the present disclosure use a negative pressure therapy device comprising a urinary catheter in fluid communication with a negative pressure source for delivering negative pressure to or inducing negative pressure in portion(s) of the urinary tract of a patient, such as in the renal pelvis or kidney. The applied negative pressure draws fluid, such as urine, into an inflow lumen of the urinary catheter. The urinary catheter can also be configured to expel urine drawn into the inflow lumen by the negative pressure to other areas or portions or the urinary tract through an outflow lumen.

More specifically, as described in further detail herein, the urinary catheter can comprise an inflow member that comprises or defines the inflow lumen and an outflow member that comprises or defines the outflow lumen. The inflow member and the outflow member are generally fluidly connected together, such that fluid, such as urine, passes directly or indirectly from the inflow lumen of the inflow member to the outflow lumen of the outflow member. In some examples, the inflow member is integral with the outflow member forming a continuous tube, such that the inflow lumen is contiguous with the outflow lumen. In other examples, both the inflow member and the outflow member can be connected to the negative pressure source.

In some examples, the inflow member and/or the outflow member of the urinary catheter can comprise control structures, flow controllers, and/or can be connected to flow manipulating devices for controlling negative pressure or positive pressure applied through lumens of the inflow member and/or the outflow member. For example, the inflow member and/or the outflow member can comprise combinations of individually controllable lumens comprising lumen or flow control portions or devices. The lumen or flow control portions or devices can comprise passive control mechanisms (e.g., flow or pressure activated mechanical valves, as well as pumps and other flow manipulating components) and/or active control mechanisms (e.g., user or sensor-activated pumps or valves). As an example, these lumens may be configured to regulate various specific negative pressures through one or more of the lumens while concurrently regulating various specific positive pressures through one or more different lumens. In a similar manner, the inflow and/or outflow members can also comprise valves and other flow control components configured to provide one or more ambient pressure lumens through the inflow or outflow members(s). These lumen or flow control mechanisms can also be used to regulate interactions between one or more lumens. Example interactions between one or more lumens can comprise regulated segmentation of fluid flow in one or more lumens and transfer of a fluid connection to one or more different lumens. In some examples, lumens may comprise multiple pressure and/or flow control mechanisms and multiple inter- or intra-luminal connections.

The negative pressure source can be configured to draw fluid, such as urine, through the inflow lumen and to an inlet or suction side of the negative pressure source, and to expel the fluid through a discharge side or outlet of the negative pressure source and through the outflow lumen to other areas of the urinary tract of the patient. Once expelled back to the urinary tract, the fluid, such as urine, can be expelled from the body by natural processes. For example, fluid, such as urine, can be expelled from a distal end of the outflow member to the ureter or bladder and discharged from the body through the urethra.

Negative Pressure Therapy Systems with Urinary Catheters

Negative pressure therapy systems 100, 200, 400 are shown in FIGS. 1A, 1B, 2A, 4A, and 4C. The systems 100, 200, 400 comprise negative pressure therapy devices comprising one or more urinary catheters 110. For example, as shown in FIG. 1A, a system 100 can comprise two urinary catheters 110, one of which is deployed in the right kidney and ureter and another which is deployed in the left kidney and ureter. In other examples, systems 100, 200, 400 can comprise only one urinary catheter 110 deployed in one kidney of a patient. Regardless of the number of urinary catheters 110 in the system 100, 200, 400, the urinary catheter 110 generally comprises an inflow member 112 and an outflow member 114, each of which are at least partially deployed within a urinary tract of the patient for drawing fluid, such as urine, from the urinary tract through the inflow member 112 and discharging the fluid back into a same or a different portion of the urinary tract through the outflow member 114.

Figure 1B:
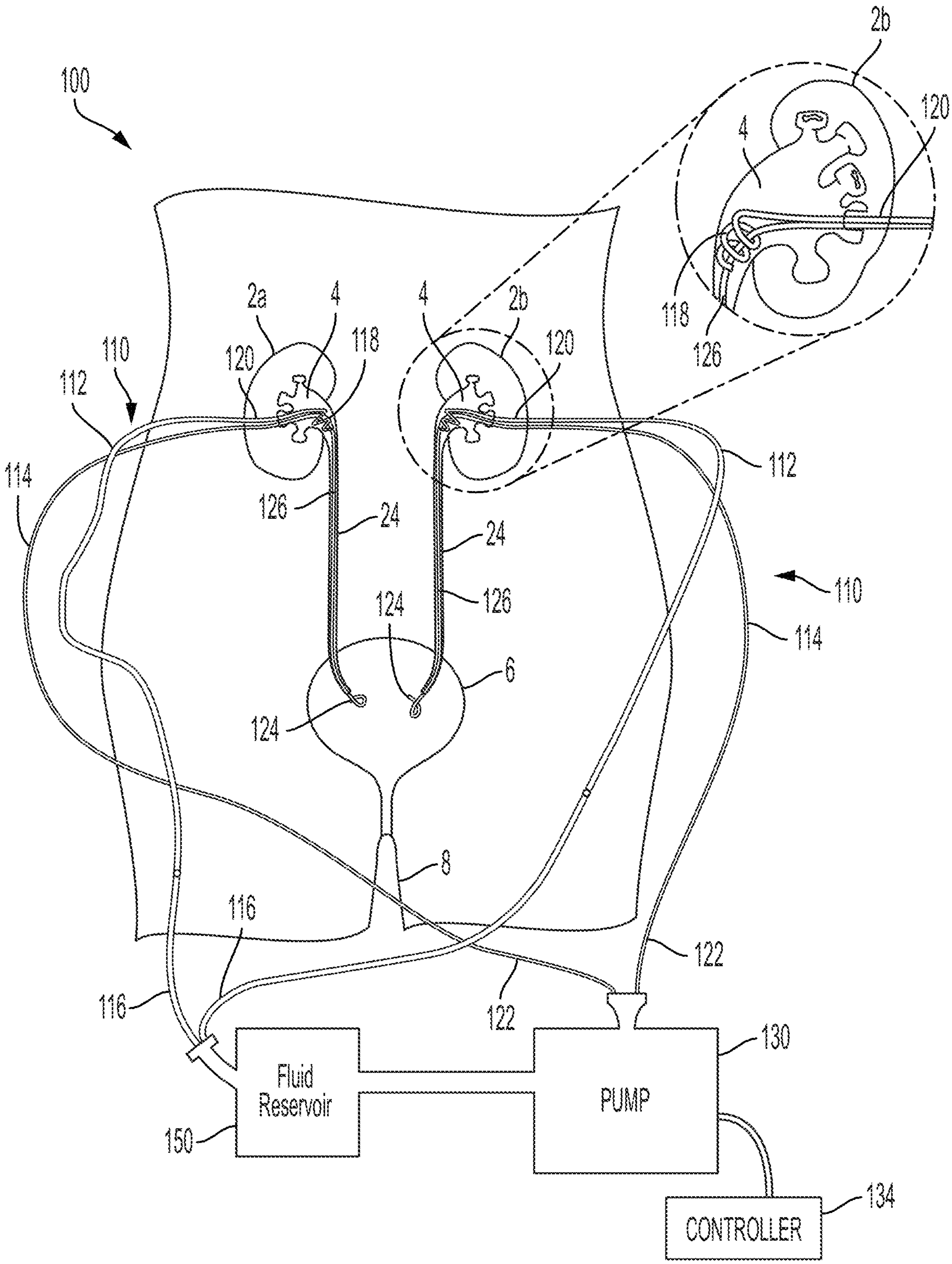
FIG. 1B is a schematic drawing showing another exemplary negative pressure therapy system comprising an external negative pressure source, according to an example of the present disclosure.

The inflow member 112 and outflow member 114 can be configured for insertion into the patient's body through one or more percutaneous openings or incisions. Further, the inflow member 112 and the outflow member 114 can enter the urinary tract through an incision or puncture in one of the kidneys 2*a*, 2*b*. For example, as shown in FIGS. 1A and 1B, the inflow member 112 and the outflow member 114 can pass into the urinary tract through a puncture at a posterior portion of the kidney 2*a*, 2*b*. The inflow member 112 can terminate in the kidney or renal pelvis. As shown in FIGS. 1A and 1B, the outflow member 114 extends past the inflow member 112, through the ureter, to the bladder. In some examples, proximal portions of the urinary catheters may extend through the percutaneous openings or incisions (as shown in FIG. 1B). In other examples, once deployed, the entire urinary catheter 110 is positioned in the body, such as within the abdominal cavity and urinary tract of the patient.

As described in further detail herein, the inflow member 112 and the outflow member 114 are configured to be positioned within the urinary tract in proximity to each other without interfering with fluid flow through lumens of the inflow member 112 and the outflow member 114. For example, the inflow member 112 and the outflow member 114 can be deployed in a configuration or arrangement which prevents the members 112, 114 from crimping, tangling, or otherwise contacting each other in any way that would block or restrict fluid flow through lumens of the members 112, 114. In some examples, as described in further detail herein, the inflow member 112 can adopt a coiled or expanded configuration, in which the outer periphery of the coiled or expanded member 112 defines a three-dimensional shape or space. In such cases, the outflow member 114 can be configured to pass through the three-dimensional shape or space defined by the inflow member 112.

As shown in FIGS. 1A, 1B, 2A, 4A, and 4C, a urinary tract of a patient comprises a patient's right kidney 2*a* and left kidney 2*b*. The kidneys 2*a*, 2*b* are responsible for blood filtration and clearance of waste compounds from the body through urine. Urine produced by the right kidney 2*a* and the left kidney 2*b* is drained into a patient's bladder 6 through tubules, namely, a right ureter 24 and a left ureter 24. For example, urine may be conducted through the ureters 24 by peristalsis of the ureter walls, as well as by gravity. A distal portion of the ureter 24 and/or kidney 2*a*, 2*b* known as the renal pelvis 4 is a cornucopia-shaped structure extending between the ureters 24 and kidneys 2*a*, 2*b*. The ureters 24 enter the bladder 6 through a ureter opening or orifice. The bladder 6 is a flexible and substantially hollow structure adapted to collect urine until the urine is excreted from the body. The bladder 6 is transitionable from an empty position to a full position. Normally, when the bladder 6 reaches a substantially full state, urine is permitted to drain from the bladder 6 to a urethra 8 through a urethral opening or sphincter located at a lower portion of the bladder 6. Contraction of the bladder 6 can be responsive to stresses and pressure exerted on a trigone region of the bladder 6, which is the triangular region extending between ureteral orifices and the urethral opening or sphincter. The trigone region is sensitive to stress and pressure, such that as the bladder 6 begins to fill, pressure on the trigone region increases. When a threshold pressure on the trigone region is exceeded, the bladder 6 begins to contract to expel collected urine through the urethra 8.

In some examples, the inflow member 112 comprises an inflow lumen 142 configured to be in fluid communication with a negative pressure source, which can be positioned within or outside of the urinary tract. The inflow member 112 further comprises (i) a proximal portion 116, (ii) a retention portion 118 configured to be deployed within a renal pelvis of the urinary tract, and (iii) an intermediate portion 120 between the proximal portion 116 and the retention portion 118 configured to extend through at least a portion of the kidney 2*a*, 2*b* to the renal pelvis 4. As used herein, "portions" of the urinary catheter 110 can refer to different regions or areas of a single contiguous tube or catheter. In other examples, the portions of the urinary catheter can be separate tube segments that are permanently or temporarily connected together end-to-end, providing a continuous lumen through the proximal portion 116, the intermediate portion 120, and the distal or retention portion 118 of the inflow member 112. As used herein, the "proximal" portion of the inflow member 112 can refer to portions of the inflow member 112 extending from a negative pressure source through the abdominal cavity to the urinary tract. In some examples, as shown in FIG. 1A, the entire proximal portion of the inflow member 112 is within the abdominal cavity. In other examples, as shown in FIG. 1B, the proximal portion 116 of the inflow member 112 passes through the percutaneous opening or incision meaning that the proximal portion 116 comprises both portions in the abdominal cavity and external portions outside of the patient's body. As used herein, the "intermediate" portion 120 of the inflow member 112 can refer to portions of the inflow member extending through the urinary tract (e.g., through the kidney and renal pelvis) between the proximal portion 116 and the retention portion 118.

As described in further detail herein, the retention portion 118 of the inflow member can comprise one or more drainage holes (not shown in FIGS. 1A and 1B) leading to the inflow lumen 142. The drainage hole(s) can be an opening, perforations, fluid ports, or similar spaces extending through a sidewall of the retention portion 118. The drainage hole(s) is positioned so that fluid in the renal pelvis and/or kidney is drawn through the drainage hole to the inflow lumen 142 of the inflow member 112 due to negative pressure delivered or induced by the negative pressure source.

The outflow member 114 comprises an outflow lumen 144 configured to be in fluid communication with the negative pressure source. Similar to the inflow member 112, the outflow member 114 comprises (i) a proximal portion 122, (ii) a distal portion comprising a distal end 124 configured to be positioned in the ureter 24 or bladder 6, and (iii) an intermediate portion 126 extending from the proximal portion 122 to the distal end 124. As previously described, as used herein, "portions" can refer to different areas of a single continuous elongated member or tube or to separate tube segments that are permanently or temporarily connected together forming a continuous lumen. Further, as used herein, the "proximal portion" of the outflow member 114 can refer to the portion of the outflow member 114 extending from the negative pressure source through the abdominal cavity. The proximal portion 122 can be entirely within the abdominal cavity (as shown in FIG. 1A) or partially within the abdominal cavity and partially external to the patient (as shown in FIG. 1B). As used herein, the "intermediate portion" of the outflow member 114 can refer to portions of the outflow member 114 passing through the urinary tract from the proximal portion 122 to the distal portion or distal end 124 of the outflow member 114. For example, the intermediate portion 126 of the outflow member 114 can pass through the kidney 2*a*, 2*b*, renal pelvis 4, ureter 24, and, in some examples, through the ureteral orifice into the bladder 6. As described in further detail herein, the distal portion or distal end 124 of the outflow member 114 is configured to be deployed in the ureter 24 or bladder 6 of the urinary tract.

In some examples, the intermediate portion 126 of the outflow member 114 can extend through a space at least partially defined by the retention portion 118 of the inflow member 112. As previously described, the retention portion 118 of the inflow member 112 can be configured to be deployed in the kidney 2*a*, 2*b* and/or renal pelvis 4 of the urinary tract. The intermediate portion 126 of the outflow member 114 can extend through the kidney 2*a*, 2*b* and urinary tract, past the retention portion, to other portions of the ureter 24 or bladder 6 of the patient.

The urinary catheter 110 of the present disclosure is configured to transmit the negative pressure from the negative pressure source to the urinary tract of the patient. In some examples, the negative pressure source is an implanted or implantable pump 128, which can be positioned within or outside of the urinary tract, as shown in FIGS. 1A, 2A, 4A, and 4C. As used herein, an "implantable" or "implanted" pump is a pump that is capable of being inserted into a patient's body through an insertion site, such as through an incision through the patient's skin. An "implantable pump" may be fixed in position within, for example, a body cavity by sutures. As described in further detail herein, the pump 128 may be implanted in the abdominal cavity, peritoneum, or subcutaneous space of the patient, and outside of the urinary tract of the patient. In some examples, all portions of the pump 128 can be configured to be implanted or inserted within a body cavity or body of a patient. In other examples, as described in further detail herein, some portions of the pump 128, such as fluid contacting portions of the pump 128, can be implanted, while other components of the pump 128 (e.g., a controller, power supply, output components, and/or visual display) can be positioned outside of the patient's body and are in electronic communication with implanted components of the pump 128 by a wired or wireless electronic connection.

The implantable or implanted pump 128 disclosed herein can be configured to be used, for example, by ambulatory patients for providing continuous or periodic negative pressure therapy to the renal pelvis and/or kidneys over a prolonged treatment period, such as a treatment period of several days, several weeks, or more. As used herein, an "ambulatory patient" refers to a patient that, while undergoing negative pressure therapy, is capable of standing, moving from a first location to a second location by, for example, walking or being pushed in a wheel chair, and performing normal life activities without being inconvenienced or restricted by components of the pump 128. Accordingly, in order to be used for ambulatory patients, the components of the pump 128, such as components of the pump mechanism, electronic processing and control circuitry, and power supply, are either implanted or worn by the patient, so that the patient can move and perform normal daily activities without being restricted by the pump 128 or other components of the system 100, 200, 400. For a wheelchair bound patient, some components of the pump 128 and system 100, 200, 400 may also be attached to the wheelchair, rather than being worn by the patient. Also, any wires or tubing of the pump 128 external to the patient's body should be short in length to avoid restricting movement of the patient. Further, in some examples, the pump 128 for the ambulatory patient expels urine to the bladder through the outflow member 114, rather than to an external urine collection container. In some examples, urine expelled into the bladder is removed from the bladder by a conventional bladder catheter (not shown) inserted through the urethra, as are known in the art. In some examples, any of the negative pressure sources of the present disclosure (e.g., any of the internal pumps 128 or external pumps 130 disclosed herein) can be configured for use in treating non-ambulatory patients, such as a patient spending at least a portion of their time in hospital bed or in a seated position.

In other examples, with specific reference to FIG. 1B, the negative pressure source 102 is the external pump 130. In that case, the inflow member 112 and/or the outflow member 114 pass through a percutaneous incision or opening through the patient's skin, such as an incision or opening in the patient's abdomen, for transporting fluid from the urinary tract to the external pump 130. The external pump 130 can comprise a reservoir 132 for collecting fluid drawn from the patient's urinary tract. The external pumps 130 shown in FIG. 1B can be portable and/or wearable pumps 130, configured to be carried, for example, in a pocket, fanny pack, holster, or harness worn by the patient. In other examples, the external pumps 130 can be free-standing or stationary pumps configured to be positioned, for example, on a table, shelf, IV pole, bedside table, and/or attached to other pieces of furniture, such as to a bed frame. The external pump 130 can also comprise or be electrically connected to a controller 134 for controlling operation of the pump by, for example, turning the pump on or off and/or adjusting operating parameters of the pump 130 to provide negative pressure therapy according to a predetermined protocol or schedule. The system 100 can also comprise an external reservoir 150 for collecting fluid drawn through the urinary catheter 110 to the external pump 130.

In other examples, the negative pressure source can be a vacuum source or source of negative pressure. For example, negative pressure for treating a patient can be obtained from a regulated wall source, such as a wall source or wall vacuum port at a hospital or another medical facility.

In some examples, the inflow member 112 and the outflow member 114 define one or multiple tubular lumens (e.g., the inflow lumen(s) 142 and outflow lumen(s) 144) that permit fluid flow through the inflow and/or outflow members 112, 114 to the internal pump 128 or the external pump 130. In some examples, the tubular lumens 142, 144 can generally comprise a circular cross-section with the same cross-sectional area along an entire axial length of the lumens 142, 144. In other examples, the lumens 142, 144 can comprise portions with a non-circular cross-sectional shape and/or portions of varying cross-sectional area. In some examples, the lumens 142, 144 are free from obstructions and do not include flow restrictors, flow straighteners, valves, or other passive or active flow modifiers. In other examples, as previously described, the one or multiple lumens 142, 144 of the inflow member 112 and/or the outflow member 114 can comprise various passive or active flow control structures, including valves, pumps, impellers and other mechanisms which affect intensity of negative or positive pressure passing through the lumen(s) 142, 144.

Figure 1C:
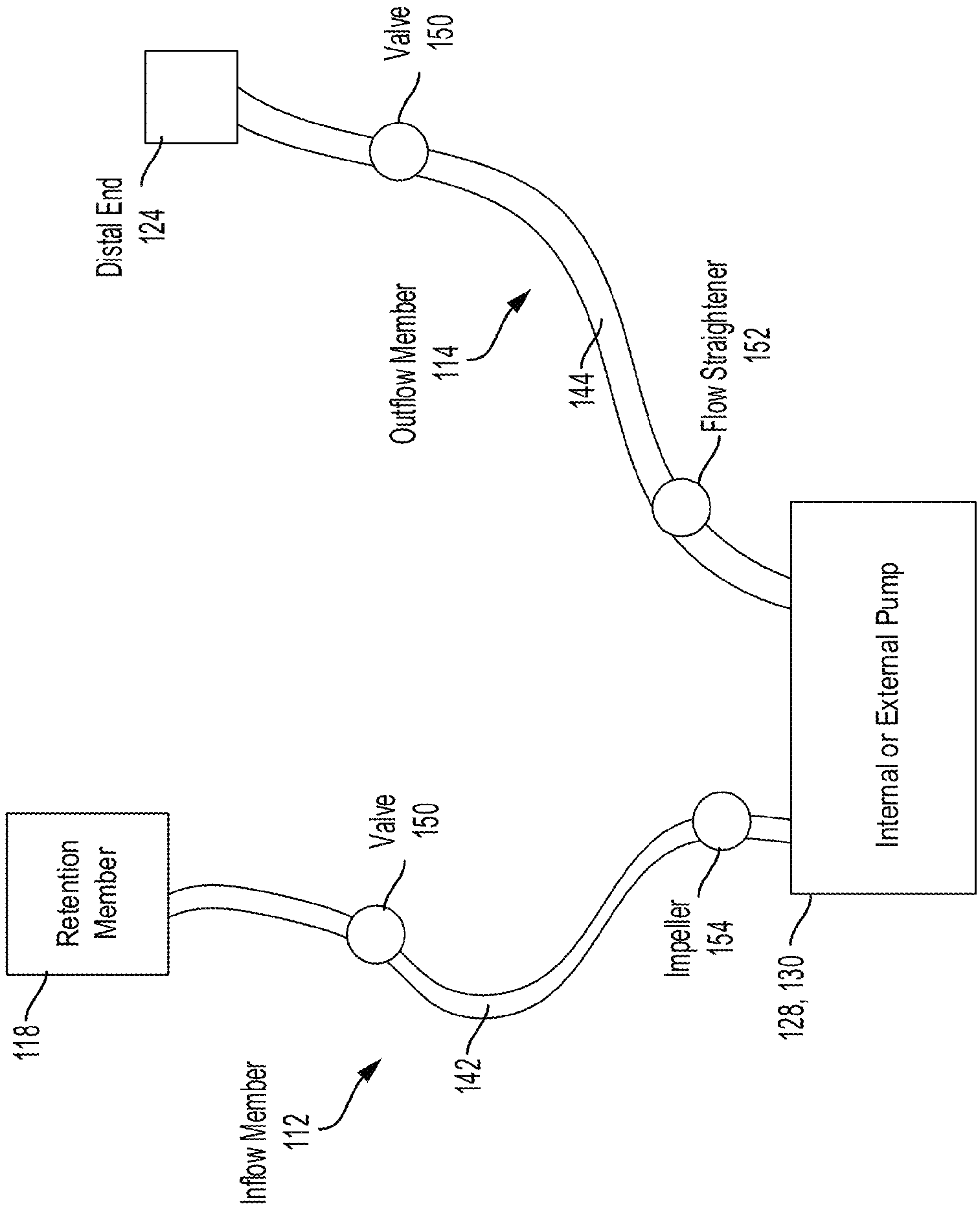
FIG. 1C is a schematic drawing showing an exemplary urinary catheter with flow control mechanisms for controlling fluid flow and/or applied positive or negative pressure through lumens of the urinary catheter.

FIG. 1C is a schematic drawing showing an inflow member 112 comprising an inflow lumen 142 and an outflow member 114 comprising an outflow lumen 144. The inflow member 112 extends from an internal or external pump 128, 130 to a retention member 118. The outflow member 114 extends from the external or internal pump 128, 130 to a distal end 124. The inflow member 112 and the outflow member 114 further comprise passive or active flow control mechanisms positioned in lumens 142, 144 of the inflow member 112 and the outflow member 114 for controlling the negative pressure or positive pressure applied through the lumens 142, 144. In some example, the flow control mechanisms include valves 150, such as mechanical one-way or check valves (e.g., duckbill valves, swing check valves, lift check valves, etc.), mechanical two-way valves, mechanical three-way valves, solenoid valves, or other passive or active valves known in the art. The flow control mechanisms can also include flow restrictors or flow straighteners 152, as well as pump components, such as an impeller 154. As previously described, the flow control mechanisms can be passive, such as valves 150 and other components that automatically open or close when the negative pressure or positive pressure applied through the lumen(s) 142, 144 is above or below a threshold value. Accordingly, the valves 150 and other components can be a safety feature preventing negative pressure or positive pressure above or below a threshold intensity from being applied to structures of the patient's urinary tract. The valves 150 and other components can also be active mechanisms, such as pumps components (e.g., the impeller 154) or valves 150, which are activated, engaged, opened or closed by a user or in response to pressure values detected by, for example, sensors positioned in lumens 142, 144 of the inflow and/or outflow members 112, 114.

Figure 1D:
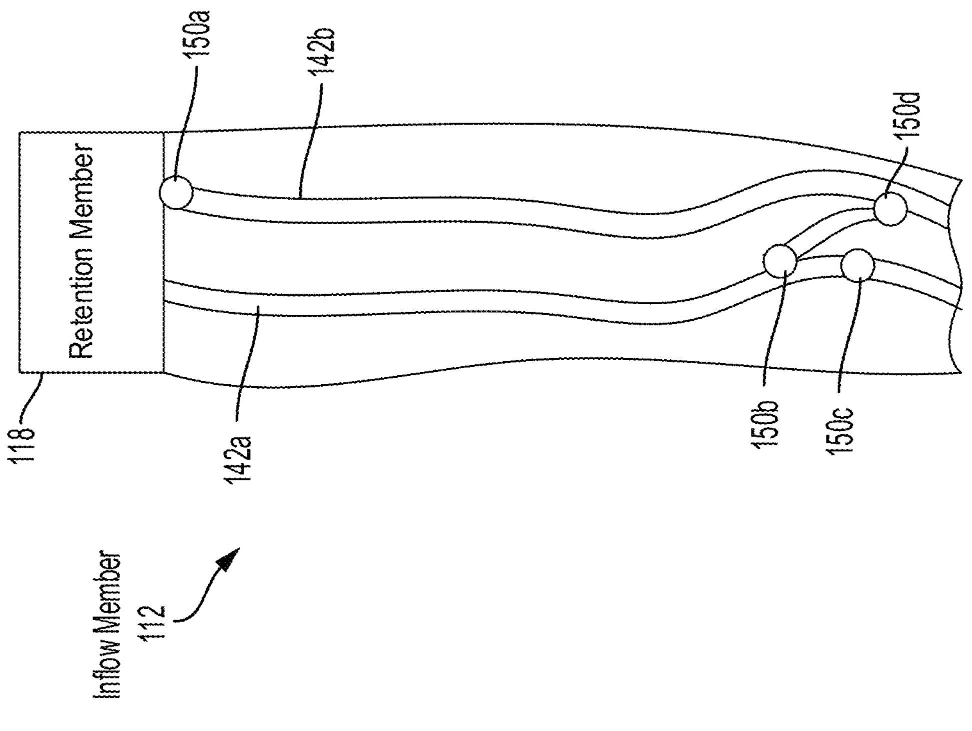
FIG. 1D is a schematic drawing of another example of a urinary catheter with fluid control mechanisms for controlling fluid flow and/or applied positive or negative pressure through lumens of the urinary catheter.

In some examples, valves 150 and other flow control mechanisms can also be positioned to control interactions between lumens 142, 144 of the inflow member 112 or the outflow member 114 for regulating fluid flow through different lumens 142, 144 and/or for transferring fluid between the different lumens 142, 144 of the member(s) 112, 114. FIG. 1D is a schematic drawing showing an exemplary inflow member 112 comprising multiple lumens 142*a*, 142*b*. As shown in FIG. 1D, the lumens 142*a*, 142*b* of the inflow member 112 are jointed together along some portions of the lumens 142. At other portions of the inflow member 112, the lumens 142*a*, 142*b* are separate. Valves 150*a*, 150*b*, 150*c*, 150*d* are positioned in the inflow member 112 for controlling fluid flow through the multiple lumens 142*a*, 142*b*. In some instances, one or more of the valves 150*a*, 150*b*, 150*c*, 150*d* can be closed defining a single fluid flow path through the inflow member 112 and preventing fluid from passing through other sections of the lumens 142*a*, 142*b*. In other examples, valves 150*a*, 150*b*, 150*c*, 150*d* can be opened creating multiple flow paths through the inflow member 112 thereby increasing an amount of fluid that can pass through the inflow member 112 and/or a maximum flow rate through the inflow member 112, which may allow for a higher intensity of positive or negative pressure to be applied through the lumens 142*a*, 142*b* than when only a single flow path is available.

Negative Pressure Systems with Hemodynamic Monitoring

In some examples, the urinary catheters 110, devices, systems 100, 200, 400, and treatment methods of the present disclosure can be used to treat any patient who may benefit from fluid removal. For example, the urinary catheters 110, devices, systems 100, 200, 400, and treatment methods described hereinabove can be used to remove fluids that cause venous congestion by increasing urine and/or sodium output. Increased fluid retention, fluid overload, venous congestion, increased blood pressure, and/or edema can be indications of worsening or decompensated heart failure, which can appear days or weeks before other symptoms that would lead to hospitalization of the patient. Other symptoms of decompensation can include dyspnea, fatigue, swelling of extremities, rapid or irregular heartbeat, or persistent cough or wheezing. It would be beneficial to begin treatment for venous decongestion and/or fluid removal with the urinary catheters 110, devices, systems 100, 200, 400, and treatment methods of the present disclosure as early as possible and prior to onset of symptoms that require hospitalization. In some instances, use of the urinary catheters 110, devices, systems 100, 200, 400, and methods of the present disclosure may slow down or stop a patient's progression towards acute decompensation, so that hospitalization can be avoided. In some examples, the urinary catheters 110, devices, systems 100, 200, 400, and methods of the present disclosure may improve patient condition by relieving or reducing stress on the patient's heart so that the patient is less likely to compensate in the future. The urinary catheters 110, devices, systems 100, 200, 400, and methods of the present disclosure may reduce occurrence of compensation, improve patient outcomes, patient quality of life, and/or life expectancy by providing earlier treatment for conditions known to contribute to worsening heart failure than provided by currently available treatment methods.

A number of hemodynamic indicators or parameters, particularly parameters that indicate increases in filling pressure for pulmonary arteries, can provide early indications of worsening congestion. In other examples, parameters representative of an amount of fluid retained within a patient's body, such as body impedance and/or thoracic impedance can be relied upon to indicate congestion. Hemodynamic parameters that may indicate increases in filling pressure may include, for example, blood pressure, pulmonary artery pressure, central venous pressure, or pulmonary capillary wedge pressure. A magnitude of these parameters may increase in the days or weeks prior to decompensation and may represent increasing congestion. Pulmonary artery pressure, as used herein, means a direct blood pressure measurement obtained from the right or left pulmonary artery of a patient. The systems 100, 200, 400 and treatment methods described hereinafter provide examples of how hemodynamic parameters, for example pulmonary artery pressure, can be used to control aspects of a renal negative pressure therapy system in order to control excretion of fluid from the patient's body. The systems 100, 200, 400 and treatment methods may provide one or more beneficial effects, such as reducing and/or alleviation of fluid overload and/or conditions leading to decompensation of the patient.

In some examples, patients with acute decompensation and/or increased cardiovascular stress due to physiological status of the patient may have a blood pump implanted to assist the heart in blood circulation. Non-limiting examples of such blood pumps can comprise, for example, a left ventricular assist device or a left ventricular support device. Such devices can be configured to provide blood flow (usually continuous fluid flow) through tubing extending between an opening in a wall of the patient's left ventricle and an opening on the aorta. When properly installed and in use, the blood pump can be configured to increase blood flow volume through vasculature of the patient and/or to assist the heart in circulation. The increased circulation support provided by the implanted blood pump can reduce stress on the heart, which if not addressed for a period of time, could weaken the heart and contribute to the progression to heart failure.

Pulmonary artery pressure measurements can also be used to control other aspects of patient treatment within the scope of the present disclosure. For example, pulmonary artery pressure may be used to determine when certain medications should be delivered to a patient and/or to control dosing for such medications. Pulmonary artery pressure measurements can also be used, for example, to control other treatment devices provided to the patient. For example, any or all of the negative pressure systems 100, 200, 400 of the present disclosure can be adapted to include and/or to provide negative pressure therapy treatment in combination with left ventricular support provided by a blood pump. Further, systems 100, 200, 400 can be adapted for use along with the pulmonary artery pressure sensors and blood pump, within the scope of the present disclosure.

Figure 2A:
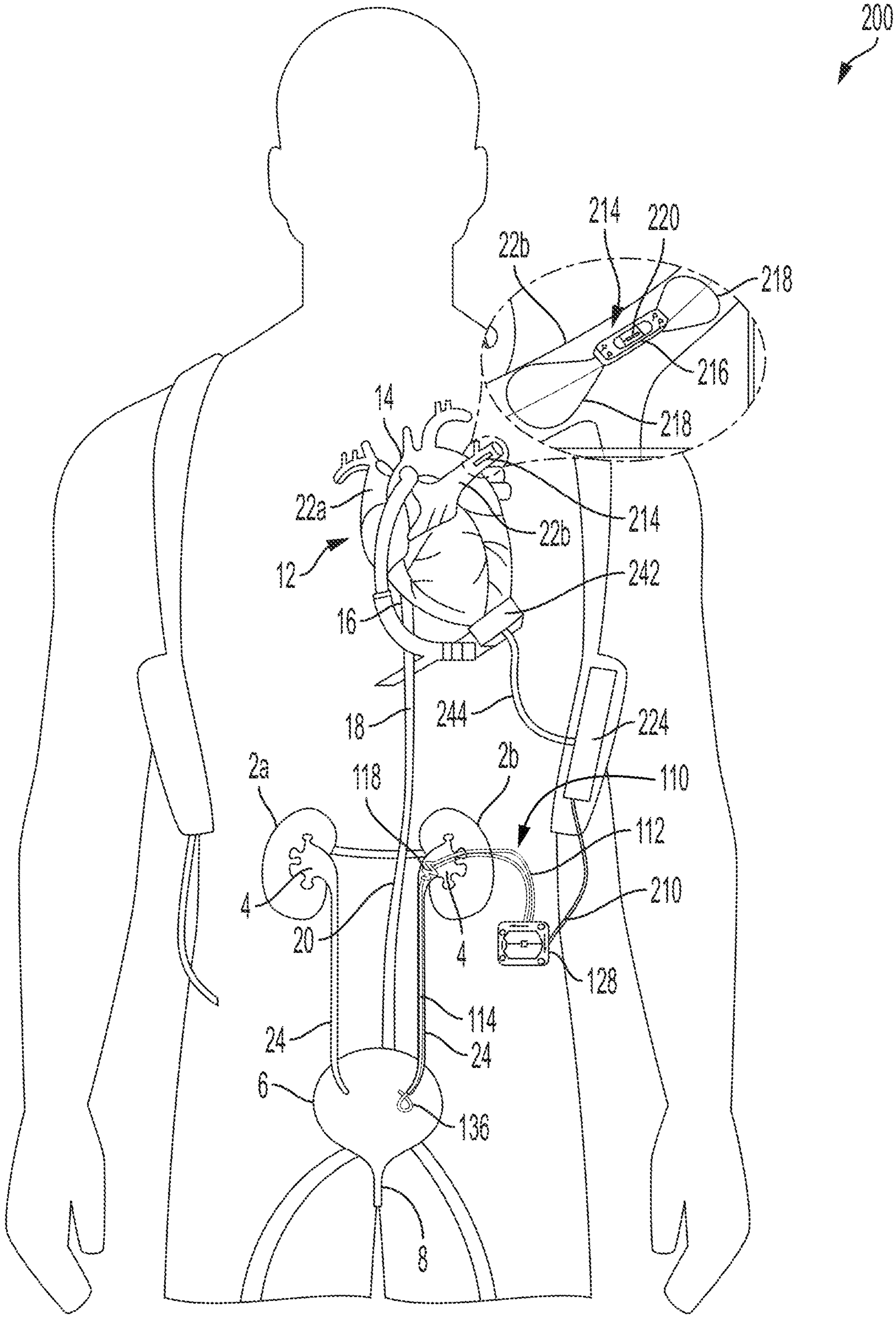
FIG. 2A is a schematic drawing showing a negative pressure therapy system comprising an implanted negative pressure source, implanted pulmonary artery pressure sensors, and circulation support devices, according to an example of the present disclosure.

An exemplary negative pressure therapy system 200 comprising an implanted negative pressure pump 128, pulmonary artery pressure sensor, and a blood pump is shown in FIG. 2A. As shown in FIG. 2A, the system 200 further comprises a urinary catheter 110 including many of the previously described features. In particular the urinary catheter 110 is partially positioned within the urinary tract and comprises an inflow member 112 comprising a retention portion 118 deployed within the renal pelvis 4, an intermediate portion 120, and a proximal portion 116 connected to the pump 128 for providing the negative pressure to the renal pelvis and/or kidney. The urinary catheter 110 also comprises the outflow member 114 extending from the pump 128 and having a distal end 124 deployed within the bladder 6. As previously described, fluid from the pump 128 is discharged into the bladder 6 from the outflow lumen 144 of the outflow member 114.

It is also understood that other types of negative pressure therapy and/or pump systems, as well as other urinary catheters 110, can also be configured to include the pulmonary artery pressure sensors and blood pump, within the scope of the present disclosure of the present disclosure. For example, the pulmonary artery pressure sensor and blood pump of the present disclosure can be configured for use with any type of indwelling pump, implantable pump, or external pump (for an ambulatory or non-ambulatory patient) and associated pump systems within the scope of the present disclosure.

A number of additional organs and other anatomical structures are also shown in FIG. 2A including cardiopulmonary organs and associated structures including the patient's heart 12, aorta (including the aortic arch 14, descending thoracic aorta 16, suprarenal abdominal aorta 18, and segments of the infra-renal aorta 20), and right and left pulmonary arteries 22*a*, 22*b*. Portions of the urinary tract including the right kidney 2*a* and left kidney 2*b*, the right and left ureters 24, the bladder 6, and the urethra 8 are also shown in FIG. 2A.

As shown in FIG. 2A, the negative pressure therapy systems 200 for removing fluid from the urinary tract of the patient comprises the previously described urinary catheter 110 deployed in the renal pelvis 4 and bladder 6, and a sensor 214 configured to detect signal(s) representative of pulmonary artery pressure of the patient and communicate the signal(s) representative of the pulmonary artery pressure to other electronic devices, such as to the implanted pumps 128. Pulmonary artery pressure refers to blood pressure of the right and/or left pulmonary artery 22*a*, 22*b* measured directly by the sensor 214 and/or pressure transducer implanted or deployed within the pulmonary arteries 22*a*, 22*b*. Pulmonary artery pressure can be an early indicator of worsening heart failure. In particular, increasing pulmonary pressure means that the heart must work harder to force blood through the pulmonary arteries 22*a*, 22*b*. Continued vigorous pumping to overcome increasing pulmonary artery pressure places added stress on the patient's heart 12 hastening the progression to heart failure.

In some examples, the sensor 214 is an implanted pressure transducer deployed in the right or left pulmonary artery 22*a*, 22*b* of the patient. Preferably, the sensor 214 is deployed in the left descending pulmonary artery 22*b*. The sensor 214 can also be positioned elsewhere in the right or left pulmonary arteries 22*a*, 22*b*, as determined based on preference of the treating physician. The sensor 214 can be configured to be deployed for an extended period of time, such as for days, weeks, months, or years, for periodic or continuous monitoring of a patient's pulmonary artery pressure over time. In some examples, the sensor 214 can be deployed using a delivery catheter over a guidewire by a non-invasive deployment method through, for example, a femoral or carotid artery of the patient. In order to allow for delivery using the delivery catheter, the sensor 214 can comprise and/or be mounted to a flexible and/or rollable substrate 216. The substrate 216, desirably, can be folded or rolled to a small size compatible with conventional delivery catheters. When deployed from the delivery catheter at a desired implantation or deployment location, the substrate 216 can unfold or unroll to a deployed or use position. In some examples, the sensor 214 can further comprise anchors 218 for maintaining the sensor 214 in the desired implanted location. Exemplary sensors 214 and pulmonary artery pressure sensing systems that can be used with the negative pressure therapy systems 200 of the present disclosure can comprise, for example, the CardioMEMS™ implanted sensor and heart failure system by Abbott Laboratories or the Cordella™ sensor and heart failure system by Endotronix, Inc. Exemplary sensors that can be used with the systems 200 of the present disclosure are also described, for example, in U.S. Pat. No. 6,111,520, entitled "System and method for the wireless sensing of physical properties", U.S. Pat. No. 7,550,978, entitled "Communication with an Implanted Wireless Sensor", and U.S. Pat. No. 8,021,307, entitled "Apparatus and method for sensor deployment and fixation", which are incorporated herein by reference in their entireties.

In some examples, the sensor 214 comprises a passive sensor comprising, for example, an inductor-capacitor circuit 220 configured to generate an electromagnetic field in response to an external radio frequency signal. Passive sensors are configured to generate radio frequency signals representative of the pressure when exposed to radio frequency signals from an external source. For example, the external source can be a radio frequency antenna 222 contained in an external control and/or reader device. When exposed to the radio frequency signal, the inductor-capacitor circuit 220 generates signals at a pressure-dependent resonant frequency that changes based on pressure surrounding and/or in proximity to the sensor 214. In other examples, the sensor 214 can be an active or powered sensor that receives power from a battery and/or from a dedicated power source. In that case, the sensor 214 can comprise, for example, a pressure transducer, such as a strain gauge, that measures pressure and a wireless transmitter or transceiver that periodically or continually communicates measured pressure values from the sensor 214 to a remote device, such as to the pump 128 or to the external controller (not shown in FIG. 2A).

The sensor 214 can further comprise structures, such as the anchors 218, for maintaining a position of the sensor 214 within the body lumen (i.e., within the right or left pulmonary artery 22*a*, 22*b*). For example, the anchors 218 can comprise loops, hooks, barbs, protrusions, and similar structures that, when deployed, are configured to contact a wall of the body lumen to prevent the sensor 214 from passing through the body lumen when exposed to pulsating blood flow.

Figure 2B:
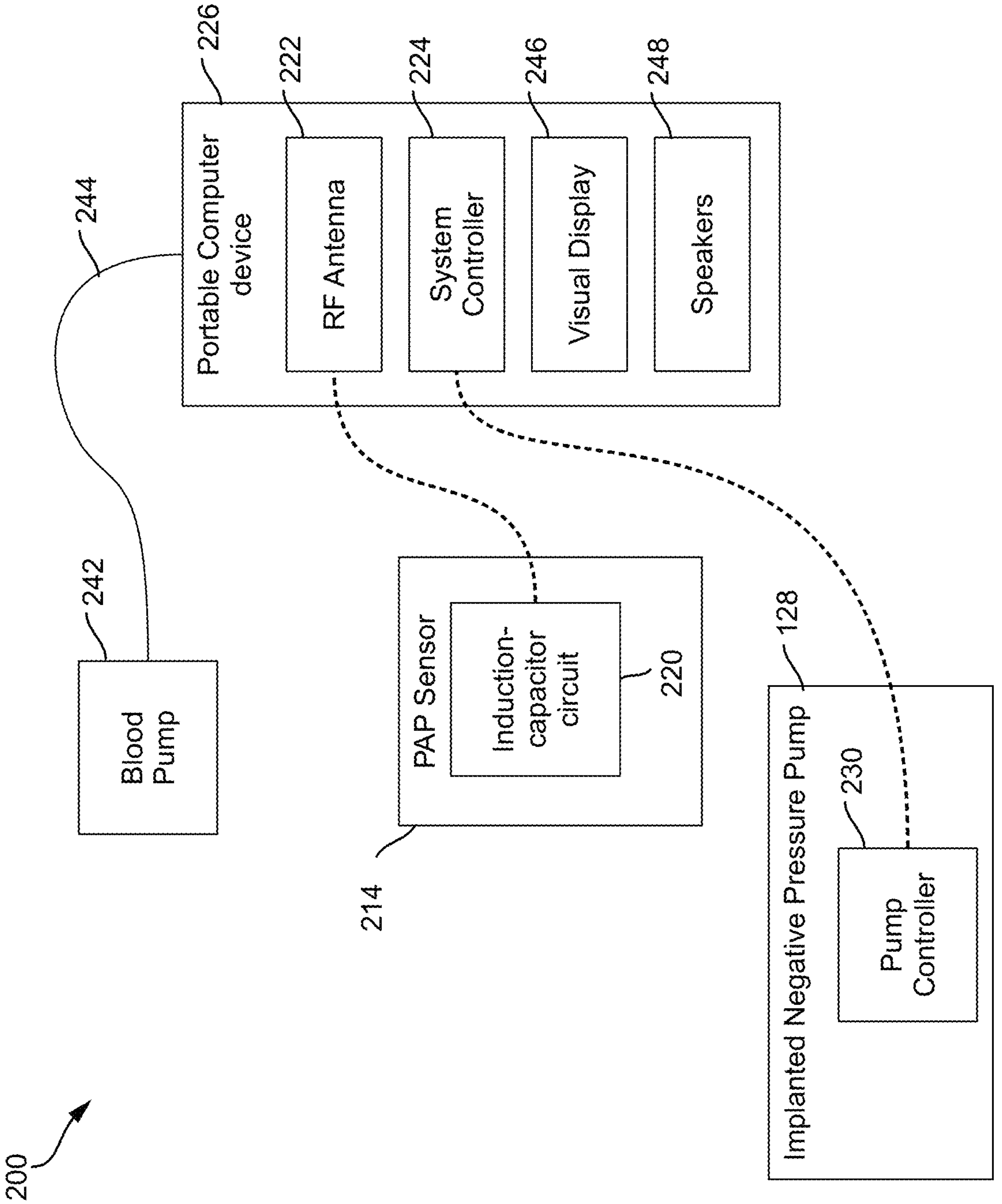
FIG. 2B is a schematic drawing showing electrical components of the system of FIG. 2A.

The systems 200 can further comprise an implanted or external system controller 224 that receives signals from the sensor 214 of the system 200 and generates control signals for controlling different treatment devices and other electronic components of the system 200. In some examples, the system controller 224 can be integrated with the implanted pump 128. In other examples, as shown in FIG. 2B, the system controller 224 can be integrated with an external portable computer device 226, such as a smart phone, computer tablet, personal digital assistant, remote controller, or similar portable electric device. As shown in FIG. 2B, the external computer device 226 can be electrically connected to the implanted pump 128 by, for example, a percutaneous wire 210 and, in particular, can be configured to provide instructions to a pump controller 230 for controlling operation of the pump 128. Alternatively, the external computer device 226 can be in communication with the implanted pump 128 and/or pump controller 230 by a wireless data connection, such as a short-range data connection using, for example, BLUETOOTH®. As described in further detail hereinafter, the portable computer device 226 can also comprise the radio frequency antenna 222 for interacting with and inducing generation of pressure-dependent signals for the sensor 214.

In some examples, the system controller 224 is configured to receive and process the signal(s) from the sensor 214 to determine if the patient's pulmonary artery pressure is above, below, or at a predetermined value. The system controller 224 can also receive sensor data from other patient physiological, pump, and/or environmental sensors of any of the previously described negative pressure therapy systems and/or from other sensing or monitoring devices receiving physiological information for the patient. For example, the system controller 224 can receive patient information from physiological sensors, such as capacitance and/or analyte sensors for measuring information representative of the chemical composition of generated urine, pH sensors for measuring acidity of urine, or temperature sensors for measuring urine temperature. The system controller 224 can also receive information from fluid sensors, such as fluid sensors positioned in the inflow member 112 or outflow member 114 of the urinary catheter 110 configured to measure fluid flow characteristics or parameters, such as fluid pressure or flow volume measured in the catheter 110. The system controller 224 can also receive information from a catheter probe positioned near the retention portion 116 that measures negative pressure in the renal pelvis 4 or kidney 2*a*, 2*b*. In some examples, the system controller 224 can also be configured to receive information about intra-abdominal pressure measured, for example, by a pressure sensor positioned on an external surface of an implanted pump 128.

The system controller 224 can also be configured to provide control signal(s), determined at least in part from the pulmonary artery pressure signal(s) received from the sensor 214, to the negative pressure source, such as to the pump 128, to: (a) apply negative pressure to a urinary catheter to remove fluid from the urinary tract of the patient when the patient's pulmonary artery pressure is above the predetermined value; or (b) to cease applying negative pressure when the patient's pulmonary artery pressure is at or below the predetermined value. The control signal(s) generated by the system controller 224 can also be based, at least in part, on sensed data from any of the other physiological, pump, and/or environmental sensors described herein.

The negative pressure source can be the implanted negative pressure therapy pump 128, as previously described. In other examples, the negative pressure source can also be a negative pressure system of a hospital or another medical facility that can be accessed by, for example, a wall-mounted negative pressure port. The pump 128 and/or other negative pressure source can be configured to provide negative pressure ranging from 0 mmHg to about 150 mmHg to the drainage lumen of the urinary catheter 110, as measured at the at least one fluid port of the pump 128 and/or at a proximal end of the urinary catheter.

As previously described, the system controller 224 is configured to provide operating instructions, in the form of control signals, to the negative pressure source, such as to the negative pressure therapy pump 128. The control signals are based, at least in part, on pulmonary artery pressure measurements received from the implanted pressure sensor(s) 214 and, in some examples, can provide a feedback loop in which continuously-obtained or periodic pulmonary artery pressure measurements are relied upon to incrementally adjust the applied negative pressure. For example, the system controller 224 can initially be configured to provide negative pressure therapy to the patient when a measured pulmonary artery pressure value is above a predetermined value. A target range for pulmonary artery pressure for a patient can be, for example, from 12 mmHg to 16 mmHg (diastolic) and from 18 mmHg to 25 mmHg (systolic). Accordingly, the predetermined value for pulmonary artery pressure can be, for example, when pulmonary artery pressure measured by the sensor 214 is above 16 mmHg (diastolic) and/or above 25 mmHg (systolic).

In a simple example, the negative pressure can be provided at a predetermined pressure level (i.e., a predetermined pressure of between 10 mmHg and 150 mmHg, as measured at a proximal end of the inflow member) for a predetermined duration of time (i.e., 30 minutes, 1 hour, 2 hours, 8 eight hours, 12 hours, or longer). After the predetermined duration, the pulmonary artery pressure can be measured again. If the measured pulmonary artery pressure remains above the predetermined value, negative pressure can continue to be applied to the patient for another instance of the predetermined duration. If measured pulmonary artery pressure is below the predetermined value, the system controller 224 can be configured to cease the application of the negative pressure.

In other examples, the system controller 224 can be configured to periodically incrementally increase or decrease the applied negative pressure. For example, the system controller 224 can be configured to periodically compare the pulmonary artery pressure of the patient to the predetermined value for pulmonary artery pressure. The system controller 224 can then be configured to provide additional control signals to the negative pressure source, such as to the implanted pump 128, to increase a magnitude of the negative pressure applied by the negative pressure source to the inflow member 112 of the urinary catheter 110, when the pulmonary artery pressure of the patient is greater than the predetermined value. For example, the control signals generated by the system controller 224 can cause an absolute value or magnitude of the applied negative pressure to increase by an incremental amount (i.e., 1 mmHg, 5 mmHg, or 10 mmHg) each time that a measured pulmonary artery pressure is greater than the predetermined value.

With reference again to FIG. 2A, the systems 200 can further comprise a blood pump 242, such as a left-ventricular assist device and/or a left ventricular support pump, implanted proximate to a left ventricle of the patient's heart. As described hereinabove, the negative pressure therapy system 200 of the present disclosure can be provided to assist in management of patient fluid status in an effort to relieve stress on the heart and other organ systems. In particular, elevated fluid levels can increase stress for the heart, weakening the heart muscle and hastening the progression towards heart failure. Accordingly, the systems 200 of the present disclosure can be used in conjunction with or can comprise the blood pump 242, for example, to relieve stress on the heart and/or help the heart to provide sufficient blood circulation.

The blood pump 242 can be in wired or wireless electronic communication with and can receive operating instructions, such as control signals, from the system controller 224. For example, as shown in FIG. 2A, the blood pump 242 can be in wired communication with the portable computer device 226 by a percutaneous wire 244. As shown in FIG. 2A, the blood pump 242 is positioned near the left ventricle of the patient's heart 12. The blood pump 242 is configured to draw blood from the left ventricle, through the pump 242 and associating tubing, and to expel the blood into the aorta proximate to the aortic arch 14. Generally, blood pumps 242 provide continuous blood flow through tubing extending from an incision or opening in the left ventricle to an incision in the aorta proximate to the aortic notch. The continuous blood flow can be provided at a constant cardiac output to assist the heart 12 in blood circulation. Implantable blood pumps 242 or left-ventricular assist devices are manufactured by a number of medical device manufacturers including Abbott Laboratories, HeartWare International, Medtronic, ReliantHeart Inc., and others. One exemplary blood pump 242 that can be used with the systems of the present disclosure is the HeartMate 3 LVAD manufactured by Abbott Laboratories. An exemplary blood pump 242 that can be used with the systems 200 of the present disclosure is described in U.S. Pat. No. 9,849,224, entitled "Ventricular assist devices", which is incorporated by reference herein in its entirety.

In some examples, the system controller 224 is configured to provide operating instructions, in the form of control signals, to the blood pump 242. For example, control signals can cause the blood pump 242 to begin providing circulation support for the patient, to cease providing circulation support for the patient, and/or to increase or decrease a flow rate for the pump 242 to increase or decrease a cardiac output volume and/or flow rate. In some examples, the operating instructions for the blood pump 242 are based, at least in part, on pulmonary artery pressure measurements for the patient received from the implanted sensor 214. Operating instructions and/or control signals for the blood pump 242 can be based, at least in part, on information from any of the one or more of sensors of the negative pressure therapy system discussed herein. For example, information detected by sensors about total urine output, rate of urine output, blood and/or urine characteristics and/or trends in patient physiological condition can be used to at least partially control the operation of the blood pump.

In some examples, the sensor 214 further comprises the inductor-capacitor circuit 220 or coil. The portable computer device 226 comprises the radio frequency antenna 222 that, as shown schematically in FIG. 2B, is configured to provide the radio frequency signal to the inductor-capacitor circuit 220 to induce the frequency response signal indicative of the measured pulmonary artery pressure. As previously described, the system controller 224 and/or another computer processor of the portable computer device 226 can be configured to determine the pulmonary artery pressure based on signals sensed by the sensor 214. Further, the system controller 224 can be configured to generate control signals for the implanted pump 128 and/or the blood pump 242 based on measured values for pulmonary artery pressure.

In some examples, the portable computer device 226 can comprise components for providing measured values and other feedback for a user, such as for a medical professional responsible for treatment of the patient. For example, the portable computer device 226 can comprise visual output components, such as a visual display screen 246 or touch screen display, and/or audio output components, such as speakers 248, that provide information and feedback to a user. For example, information about operational status of the implanted pump 128 (i.e., is the pump on or off), a magnitude of negative pressure being applied by the pump 128, and measured patient information or parameters, such as pulmonary artery pressure measured by the sensor 214, urine output, and any other measured parameters useful for determining a status of the patient and/or for monitoring negative pressure therapy.

Treatment Methods with Pulmonary Artery Pressure

The negative pressure therapy systems 200 of the present disclosure can be used in connection with treatment methods for removal of excess fluid from a patient. In some examples, the fluid removal methods can be used together with circulation support methods, such as providing circulation support using a blood pump (i.e., a left ventricular assist device). In some examples, the method for removing fluid from a patient comprises: (a) monitoring a pulmonary artery pressure of the patient; (b) determining if the patient's pulmonary artery pressure is above, below, or at a predetermined value; and (c) applying negative pressure to a urinary catheter to remove fluid from the urinary tract of the patient when the patient's pulmonary artery pressure is above the predetermined value or ceasing to apply the negative pressure when the patient's pulmonary artery pressure is at or below the predetermined value.

In some examples, use of the systems and treatment methods of the present disclosure for removal of fluid and/or increasing urine output are enhanced by administering medication to the patient along with, prior to, or after providing negative pressure therapy for the patient. The method can comprise, for example: (a) administering at least one medicament to a patient, wherein the medicament increases urine output and/or sodium output from the patient; (b) monitoring a pulmonary artery pressure of the patient; (c) determining if the patient's pulmonary artery pressure is above, below, or at a predetermined value; and (d) applying negative pressure to a urinary catheter to remove fluid from the urinary tract of the patient when the patient's pulmonary artery pressure is above the predetermined value or ceasing application of the negative pressure when the patient's pulmonary artery pressure is at or below the predetermined value, wherein administering the at least one medicament occurs before, during, and/or after applying negative pressure.

In some examples, a method is provided for treating venous congestion and/or renal dysfunction in a patient in need thereof. The method can comprise, for example: (a) administering at least one medicament to a patient, wherein the medicament modulates at least one of electrolyte reabsorption, electrolyte excretion or renal blood flow in the patient; (b) applying negative pressure to a drainage lumen of a urinary catheter such that flow of urine from a ureter and/or kidney of the patient is transported within the drainage lumen to extract urine from the patient, (b) monitoring a pulmonary artery pressure of the patient; (c) determining if the patient's pulmonary artery pressure is above, below, or at a predetermined value; and (d) applying negative pressure to a urinary catheter to remove fluid from the urinary tract of the patient when the patient's pulmonary artery pressure is above the predetermined value or ceasing application of the negative pressure when the patient's pulmonary artery pressure is at or below the predetermined value, wherein administering the at least one medicament occurs before, during and/or after applying negative pressure.

In some examples, a method is provided for reducing fluid overload in a patient in need thereof. For example, the method can comprise: (a) administering at least one medicament to a patient, wherein the medicament modulates at least one of electrolyte reabsorption, electrolyte excretion or renal blood flow in the patient; (b) monitoring a pulmonary artery pressure of the patient; (c) determining if the patient's pulmonary artery pressure is above, below, or at a predetermined value; and (d) applying negative pressure to a urinary catheter to remove fluid from the urinary tract of the patient when the patient's pulmonary artery pressure is above the predetermined value or ceasing application of the negative pressure when the patient's pulmonary artery pressure is at or below the predetermined value, wherein administering the at least one medicament occurs before, during and/or after applying negative pressure.

In some examples, a method is provided for increasing renal blood flow in a patient in need thereof. The method comprises: (a) administering at least one medicament to a patient, wherein the medicament modulates renal blood flow in the patient; (b) monitoring a pulmonary artery pressure of the patient; (c) determining if the patient's pulmonary artery pressure is above, below, or at a predetermined value; and (d) applying negative pressure to a urinary catheter to remove fluid from the urinary tract of the patient when the patient's pulmonary artery pressure is above the predetermined value or ceasing application of the negative pressure when the patient's pulmonary artery pressure is at or below the predetermined value, wherein administering the at least one medicament occurs before, during and/or after applying negative pressure.

As used herein, "renal blood flow" can refer to a volume of blood reaching the kidneys of a patient per unit time. Blood passing through the kidneys is then filtered in glomerulus which in turn gives rise to the glomerular filtrate rate (GFR) which measures the efficiency in which a patient's kidneys are functioning. Thus, an increased blood volume passing through the glomerulus increases the opportunity for the blood to be filtered and/or excess fluids to be removed from the blood stream. In some examples, the medicament is a vasodilator as discussed elsewhere herein which increases the amount of blood that flows through the kidneys of a patient. In some examples, the medicament is one which increases renal blood flow.

In some examples, a method is provided for modulating electrolyte reabsorption and/or electrolyte excretion in a patient in need thereof. For example, the method can comprise: (a) administering at least one medicament to a patient, wherein the medicament modulates electrolyte reabsorption and/or electrolyte excretion in the patient; (b) monitoring a pulmonary artery pressure of the patient; (c) determining if the patient's pulmonary artery pressure is above, below, or at a predetermined value; and (d) applying negative pressure to a urinary catheter to remove fluid from the urinary tract of the patient when the patient's pulmonary artery pressure is above the predetermined value or ceasing application of the negative pressure when the patient's pulmonary artery pressure is at or below the predetermined value, wherein administering the at least one medicament occurs before, during and/or after applying negative pressure.

Electrolyte reabsorption and/or electrolyte excretion refer to a two-step process where (1) water and dissolved substances are passively or actively moved inside the tubule of the kidney through the tubule wall and into the space outside the tubule, and (2) water and/or dissolved substances move through the capillary walls back into the bloodstream of the patient. The movement can be via active or passive transport in either direction. Sodium is the most important essential substance that is reabsorbed because other nutrients (e.g., glucose, phosphate, amino acids, lactate, citrate, etc.) piggyback on the sodium co-transport proteins. When the proper sodium gradient is maintained, this process continues properly. When it is disrupted, reabsorption of vital and essential nutrients is likewise disrupted. In some examples, medicaments that help maintain this balance are used with the methods disclosed herein. In some examples, diuretic medicaments as discussed elsewhere herein are used to modulate electrolyte reabsorption and/or electrolyte excretion. In some examples, vasodilators as discussed elsewhere herein are used to modulate electrolyte reabsorption and/or electrolyte excretion.

In some examples, vasodilators and/or diuretic medicaments are provided for use in a method of inducing negative pressure in at least one location within the urinary tract of a patient having venous congestion and/or fluid overload.

In some examples, furosemide, or a pharmaceutically salt or formulation thereof, is provided for use in a method of inducing negative pressure in at least one location within the urinary tract of a patient to increase urine output from the patient.

In some examples, the use of a medicament is provided in a method for inducing negative pressure in at least one location within the urinary tract of a patient having venous congestion and/or fluid overload.

In some examples, the use of a medicament is provided in a method for inducing negative pressure in at least one location within the urinary tract of a patient having edema. In some examples, the medicament comprises one or more diuretic(s) and/or one or more vasodilator(s).

As used herein, the term "treating" or "treatment" of a medical condition or ailment is defined as: (1) preventing or delaying the appearance or development of one or more clinical symptoms of the state, disease, disorder or condition associated with or caused by said medical condition or ailment in the patient that may be afflicted with or predisposed to the state, disease, disorder or condition but does not yet experience or display clinical or subclinical symptoms of the state, disease, disorder or condition, (2) inhibiting the state, disease, disorder or condition associated with or caused by the medical condition or ailment, e.g., arresting or reducing the development of the state, disease, disorder or condition associated with or caused by the medical condition or ailment or at least one clinical or subclinical symptom thereof, and/or (3) relieving or ameliorating the state, disease, disorder or condition associated with or caused by the medical condition or ailment, e.g., causing regression or amelioration of the state, the state, disease, disorder or condition associated with or caused by the medical condition or ailment or at least one of its clinical or subclinical symptoms. The benefit to a subject to be treated is either statistically significant or at least perceptible to the patient or to the physician (e.g., decreased edema). "Treating" or "treatment" does not imply that the medical condition is cured or eliminated although that is one of several possible patient outcomes. Additional patient outcomes from being treated include the alleviation and/or reduction in severity of one or more symptoms of the medical condition or ailment. Thus, the methods contemplated herein are suitable to treat any form of venous congestion, edema and/or heart failure, or any other disease state or medical condition discussed herein. The methods contemplated herein are also be suitable to treat any medical condition or ailment where diuresis is desirable and/or would provide a medical benefit to the patient.

As used herein, "improving" or "improvement" with respect to a medical condition or ailment means reducing the severity of at least one symptom associated with a specific medical condition or ailment. Such an improvement may completely alleviate at least one symptom or it may provide partial relief from at least one symptom. In some examples, the medical condition is one in which increased urine output and/or sodium output is desirable or would provide a medical benefit to the patient. In some examples, the medical condition is venous congestion, and/or heart failure. In some examples, the medical condition exhibits edema as one of the symptoms. In some examples, "improving" means reducing edema in a patient in need thereof.

Edema can be categorized as trace/mild (0 points), moderate (1 point), or severe (2 points). Orthopnea can be assessed by determining if the patient needs at least 2 pillows to breathe comfortably (2 points) or absent (0 points). An Orthodema Score can be generated by the sum of the individual orthopnea and edema scores (below). A total score of 1 represents the presence of moderate edema without orthopnea. A score of 2 indicates the presence of orthopnea or severe peripheral edema, but not both. Scores of 1 to 2 represent low-grade congestion. High-grade congestion includes orthopnea and edema, with a score of 3 for orthopnea plus moderate edema, and a score of 4 if orthopnea is accompanied by severe edema.

Orthodema Scores

| | | |
|---|---|---|
| Mild edema, no orthopnea | 0 | No congestion |
| Moderate edema, no orthopnea | 1 | Low-grade orthodema/congestion |
| Severe edema OR orthopnea | 2 | |
| Moderate edema and orthopnea | 3 | High-grade orthodema/congestion |
| Severe edema and orthopnea | 4 | |

As used herein, the term "therapeutically effective amount" or "therapeutically effective dose" means the amount of a medicament or drug, that, when administered to a patient in need thereof for treating a medical condition or ailment, is sufficient to treat such medical condition. The "therapeutically effective amount" will vary depending on the specific medicament and the particular state, disease, disorder or condition being treated and its severity. It will also depend on the age, weight, physical condition and responsiveness of the patient to be treated. Thus, one or more of these parameters can be used to select and adjust the therapeutically effective amount of the medicament. Also, the amount can be determined using pharmacologic methods known in the art such as dose response curves. In some examples, the therapeutically effective dose is selected by the medical professional overseeing or administering the treatment of the patient and is based on the professional medical judgement of the medical professional. In some examples, the therapeutically effective dose of the medicament administered in the methods used in conjunction with at least one medical device as described elsewhere herein will be lower than the therapeutically effective dose when said medicament is administered alone (i.e., not in combination with a medical device as described herein). In some examples, the therapeutically effective dose is based on the Prescribing Information for the medicament administered to the patient. In some examples, the dose is the minimum dose listed as being effective for the medicament as described in the Prescribing Information for that medicament. In some examples, the dose is within the suggested dosage range for the medicament as included in the Prescribing Information for that medicament.

Venous congestion, heart impairment or heart failure are complex medical ailments where treatment may require administering one or more different medicaments to a patient. Patients are often administered multiple medicaments based on the nature and/or severity of their symptoms and medical condition.

In some examples of the present methods, a patient is administered at least one (one, two, or more) medicament(s). In some examples, when a patient is administered two or more medicaments, the medicaments may be in the same class or from different classes, and may be administered at the same time, or at different times as determined by the medical practitioner.

The administration of the at least one medicament can occur before, during and/or after applying negative pressure, at any time as determined by the medical practitioner. For example, the medicament(s) can be administered in a range of about two months before application of negative pressure to about 2 months after application of negative pressure, or at any time therebetween. In some examples, the medicament(s) can be administered in a range of about one week, or about 3 days, or about 1 day, or about 12 hours, or about 8 hours, or about 6 hours, or about 4 hours, or about 2 hours, or about 1 hour before application of negative pressure, or 0 to 60 minutes before application of negative pressure, or at any time during application of negative pressure, or 0 to 60 minutes after application of negative pressure, or about 1 hour, or about 2 hours, or about 4 hours, or about 6 hours, or about 8 hours, or about 12 hours, or about 1 day, or about 3 days, or about one week after application of negative pressure, or at any time therebetween. In some examples, the medicament is administered from about 1 to about 300 minutes before the application of negative pressure. In some examples, the medicament is administered about 15 minutes, or about 30 minutes, or about 45 minutes, or about 60 minutes, or about 90 minutes, or about 120 minutes, or about 150 minutes, or about 180 minutes, or about 2 hours, or about 2.5 hours, or about 3.5 hours, or about 4 hours, or about 5 hours, or about 6 hours, or about 9 hours, or about 12 hours before the application of negative pressure.

Different medicaments each have a different time period to reach its peak effectiveness. This time period is known to persons skilled in the art and the medical professional overseeing the treatment of the patient. It is often included in the Prescribing Information for the medicament. In some examples, the medicament is administered at such a time that the peak effectiveness of said medicament occurs while negative pressure is being induced in the urinary tract of the patient.

The medicament(s) can be administered orally, subcutaneously, intravenously, transdermally, by inhalation, etc. In some examples, the medicament is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 500 mg, or from about 1 mg to about 120 mg, or about 40 mg to about 120 mg, or from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 1000 mg/day, preferably 1 mg/day to 200 mg/day, given in a single dose or 2-4 divided doses. The exact dose, however, is determined by the attending clinician and is dependent on the potency of the compound administered, the age, weight, condition and response of the patient.

For administration of pharmaceutically acceptable salts of the above compounds, the weights indicated above refer to the weight of the acid equivalent or the base equivalent of the therapeutic compound derived from the salt.

A useful dosage can be about 0.001 to 500 mg/kg of body weight/day of the medicament(s), or about 0.01 to 25 mg/kg of body weight/day. In some examples, when the patient is administered a medicament(s), the dose is administered as a single dosage unit or it is divided into multiple doses. In some examples, the total daily dosage is administered in two, three, four or more divided doses. The exact timing and amount of each dose is determined by the attending medical professional based on the needs of the patient. For example, a first dose can be administered before the induction of negative pressure in the urinary tract of the patient and a second dose can be administered while negative pressure is being induced in the urinary tract of the patient. In some examples, the timing of the dose or doses is determined based on the Prescribing Information for the specific medicament administered to the patient.

Non-limiting examples of suitable medicaments for use in the present methods include, but are not limited to, one or more of angiotensin-converting enzyme inhibitor(s) (ACE inhibitor(s)), angiotensin II receptor blocker(s) (ARB(s)), beta blocker(s), diuretic(s), aldosterone antagonist(s), inotrope(s), angiotensin-receptor-neprilysin-inhibitor(s) (ARNI(s)), sodium glucose co-transporter(s) (SGLT-2), vasodilator(s), or combinations thereof. In some examples, the at least one medicament is selected from the group consisting of diuretic(s), SGLT-2 inhibitor(s), and combinations thereof. In some examples, the at least one medicament comprises at least one diuretic.

Diuretics, colloquially called water pills, are medicaments that increase the amount of water and salt expelled from the body as urine (i.e., by diuresis). Non-limiting examples of suitable diuretics for use in the present methods include, but are not limited to, one or more of loop diuretic(s), carbonic anhydrase inhibitor(s), potassium-sparing diuretic(s), calcium-sparing diuretic(s), osmotic diuretic(s), thiazide diuretic(s), miscellaneous diuretics or combinations thereof.

Loop diuretics are medicaments that act on the ascending limb of Henle in the kidney of a patient. They inhibit the reabsorption of sodium potassium chloride (NKCC2) co-transporter in the thick limb of the loop of Henle. By inhibiting reabsorption of sodium, the hypertonic filtrate inhibits the reabsorption of water via diffusion leading to volume removal. Non-limiting examples of suitable loop diuretics for use in the present methods include, but are not limited to, one or more of bumetanide, ethacrynic acid, torsemide, or furosemide. In some examples, the patient is administered bumetanide. In some examples, the patient is administered ethacrynic acid. In some examples, the patient is administered torsemide. In some examples, the patient is administered furosemide.

In some examples where the medicament is furosemide, a patient is administered from about 20 to about 600 mg/day, or about 20 to about 500 mg/day, or about 20 to about 400 mg/day, or about 20 to about 300 mg/day, or about 20 to about 200 mg/day, or about 20 to about 100 mg/day, or about 20 to 80 mg/day, or about 20 mg/day, or about 40 mg/day, or about 60 mg/day, or about 80 mg/day, or about 100 mg/day, or about 120 mg/day, or about 140 mg/day, or about 160 mg/day, or about 180 mg/day, or about 200 mg/day, or about 300 mg/day, or about 400 mg/day, or about 500 mg/day, or about 600 mg/day, in a single dose or divided into multiple doses.

In some examples where the medicament is bumetanide, a patient is administered from about 0.5 to 10 mg/day, or about 0.5 mg/day, or about 1 mg/day, or about 1.5 mg/day, or about 2 mg/day, or about 3 mg/day, or about 4 mg/day, or about 5 mg/day, or about 6 mg/day, or about 7 mg/day, or about 8 mg/day, or about 9 mg/day, or about 10 mg/day, in a single dose or divided into multiple doses.

In some examples where the medicament is torsemide, a patient is administered from about 1.25 to about 200 mg/day, or about 10 mg/day, or about 20 mg/day, or about 30 mg/day, or about 40 mg/day, or about 50 mg/day, or about 60 mg/day, or about 70 mg/day, or about 80 mg/day, or about 90 mg/day, or about 100 mg/day, or about 120 mg/day, or about 140 mg/day, or about 160 mg/day, or about 180 mg/day, or about 200 mg/day, in a single dose or divided into multiple doses.

In some examples where the medicament is ethacrynic acid, a patient is administered from about 25 to about 400 mg/day, or about 50 to about 200 mg/day, or about 50 mg/day, or about 75 mg/day, or about 100 mg/day, or about 125 mg/day, or about 150 mg/day, or about 175 mg/day, or about 200 mg/day, in a single dose or divided into multiple doses.

Thiazide diuretics act directly on the kidney and promote diuresis by inhibiting the sodium/chloride cotransporter in the distal tubule of the nephrons in the kidney of a patient. They decrease sodium reabsorption which decreases extracellular fluid and plasma volume. Non-limiting examples of suitable thiazide diuretics include, but are not limited to, one or more of indapamide, hydrochlorothiazide, chlorthalidone, metolazone, methyclothiazide, chlorothiazide, bendroflumethiazide, polythiazide, hydroflumethiazide, or combinations thereof. In some examples, the patient is administered indapamide. In some examples, the patient is administered hydrochlorothiazide. In some examples, the patient is administered chlorthalidone. In some examples, the patient is administered metolazone. In some examples, the patient is administered methyclothiazide. In some examples, the patient is administered chlorothiazide. In some examples, the patient is administered bendroflumethiazide. In some examples, the patient is administered polythiazide. In some examples, the patient is administered hydroflumethiazide. In some examples, the patient is administered from about 0.5 to about 1000 mg/day, or about 1 to 500 mg/day, or about 2 to 400 mg/, or about 3 to 300 mg/day, in a single dose or divided into multiple doses.

Carbonic anhydrase inhibitors reduce the activity of carbonic anhydrase, the enzyme that catalyzes the reaction between carbon dioxide and water to form carbonic acid and eventually bicarbonate. This reduces the reabsorption of bicarbonate in the proximal tubules of the kidneys of a patient which increases bicarbonate extraction. This causes an increase in both sodium and potassium extraction also. Non-limiting examples of suitable carbonic anhydrase inhibitors include, but are not limited to, one or more of acetazolamide, dichlorphenamide, methazolamide and combinations thereof. In some examples, the patient is administered acetazolamide. In some examples, the patient is administered dichlorphenamide. In some examples, the patient is administered methazolamide. In some examples, the patient is administered from about 0.5 to about 1000 mg/day, or about 1 to about 500 mg/day, or about 2 to about 400 mg/day, or about 3 to about 300 mg/day, in a single dose or divided into multiple doses Potassium-sparing diuretics increase diuresis without also causing an increase in potassium excretion. They function by inhibiting the sodium-potassium exchange in the distal convoluted tubules in the kidneys of a patient. Non-limiting examples of suitable potassium-sparing diuretics include, but are not limited to, one or more of eplerenone, triamterene, spironolactone, amiloride, or combinations thereof. In some examples, the patient is administered eplerenone. In some examples, the patient is administered triamterene. In some examples, the patient is administered spironolactone. In some examples, the patient is administered amiloride. In some examples, the patient is administered from about 0.5 to about 1000 mg/day, or about 1 to 500 mg/day, or about 2 to 400 mg/, or about 3 to 300 mg/day, in a single dose or divided into multiple doses.

Calcium-sparing diuretics reduce the rate of excretion of calcium by a patient. Certain thiazide and potassium-sparing diuretics are also calcium-sparing. The thiazide diuretics and potassium-sparing diuretics are also considered as calcium-sparing diuretics.

Osmotic diuretics inhibit the reabsorption of water and sodium. They are generally inert but function by increasing the osmolarity of the blood and renal filtrate in a patient. Non-limiting examples of suitable osmotic diuretics include, but are not limited to, one or more of mannitol and/or isosorbide. In some examples, the patient is administered mannitol. In some examples, the patient is administered isosorbide. In some examples, the patient is administered from about 0.5 to about 1000 mg/day, or about 1 to about 500 mg/day, or about 2 to about 400 mg/day, or about 3 to about 300 mg/day, in a single dose or divided into multiple doses.

Sodium-glucose cotransporter-2 (SGLT-2) inhibitors, also called gliflozins, inhibit the SGLT-2 proteins in the renal tubules in the kidneys that are responsible for reabsorbing glucose back into the bloodstream. As a result, more glucose is excreted in the urine. This helps lower the level of hemoglobin Alc which improves weight loss and lowers blood pressure. Non-limiting examples of suitable SGLT-2 inhibitors include, but are not limited to, one or more of ertugliflozin, canagliflozin, empagliflozin, dapagliflozin or combinations thereof. In some examples, the patient is administered ertugliflozin. In some examples, the patient is administered canagliflozin. In some examples, the patient is administered empagliflozin. In some examples, the patient is administered dapagliflozin. In some examples, the patient is administered from about 0.5 to about 1000 mg/day, or about 1 to about 500 mg/day, or about 2 to about 400 mg/day, or about 3 to about 300 mg/day, in a single dose or divided into multiple doses.

Non-limiting examples of suitable miscellaneous diuretics include, but are not limited to, one or more of pamabrom, glucose, mannitol, or combinations thereof. In some examples, the patient is administered pamabrom. In some examples, the patient is administered mannitol. In some examples, the patient is administered glucose. In most instances, the miscellaneous diuretics are over-the-counter medicaments where a doctor's prescription is not necessary. As such, a patient should carefully follow any instructions and warnings with respect thereto before taking any such medicament. In some examples, the dose taken by or administered to a patient should closely follow the recommended dosing regimen as provided with the medicament.

As used herein, the term "vasodilator" is defined as a drug that dilates (widens) blood vessels, allowing blood to flow more easily therethrough. Some vasodilators act directly on the smooth muscle cells lining the blood vessels. Other have a central effect, and regulate blood pressure most likely through the vasomotor center located within the medulla oblongata of the brain. Non-limiting examples of suitable vasodilators include, but are not limited to, one or more of nitrovasodilator(s) (such as nitroglycerin, isosorbide mononitrate, isosorbide dinitrate or sodium nitroprusside), ACE inhibitor(s), angiotensin receptor antagonist(s), phosphodiesterase inhibitor(s), direct vasodilator(s), adrenergic receptor antagonist(s), calcium channel blocking drug(s), alpha blocker(s), beta blocker(s), lymphthomimetic(s), vitamin(s), organic nitrate(s), serotonin receptor-blocking agent(s), angina blocking agent(s), other hypertensive agent(s), cardiac stimulating agent(s), agent(s) which improve renal, vascular function, sympathomimetic amine, and salts, derivatives, precursors, pharmaceutically active sequences or regions, natriuretic peptides (such as ularitide, cenderitide or serelaxin), peptidomimetic(s), mimetic(s), and mixtures thereof. In some examples, the patient is administered from about 0.5 to about 1000 mg/day, or about 1 to about 500 mg/day, or about 2 to about 400 mg/day, or about 3 to about 300 mg/day, in a single dose or divided into multiple doses.

As used herein, the term "RAAS inhibitor" refers to drugs that inhibit the renin-antiotensin-aldosterone system in a patient. In many instances RAAS inhibitors are also vasodilators as disclosed elsewhere herein. Non-limiting examples of suitable RAAS inhibitors diuretics include, but are not limited to, one or more of ACE inhibitor(s), angiotensin receptor antagonist(s), beta blocker(s), calcium channel blocker(s), and angiotensin receptor neprilysin inhibitors (ARNIs). In some examples, the patient is administered from about 0.5 to about 1000 mg/day, or about 1 to about 500 mg/day, or about 2 to about 400 mg/day, or about 3 to about 300 mg/day, in a single dose or divided into multiple doses.

Any of the medicaments disclosed can be used alone or in combination, and can be administered at the same time or at different times, for example as discussed herein.

In all aspects for the one or more medicaments administered in the methods disclosed herein, each medicament can be present in the form of a pharmaceutically acceptable formulation, and can include pharmaceutically acceptable excipients. In some examples, the medicament is in the form of one or more salt(s), ester(s), polymorph(s), or prodrug(s), as they exist. The pharmaceutically acceptable formulation may have received regulatory approval for commercial marketing or it may still be under development (e.g., clinical trials). In all aspects, the pharmaceutically acceptable formulation is deemed appropriate and suitable for administration to human patients."

While not intending to be bound by any theory, the present inventors theorized that the application of negative pressure might help to facilitate fluid flow from the kidney, and that a very particular tool, designed to deploy a protective surface area in order to open or maintain the opening of the interior of the renal pelvis while inhibiting the surrounding tissues from contracting or collapsing into the fluid column under negative pressure, is needed to facilitate the application of negative pressure within the renal pelvis. While not intending to be bound by any theory, the present inventors theorized that application of negative pressure before, during and/or after the use of medicaments as disclosed herein can unexpectedly and/or synergistically enhance the flow of fluid from the kidney. For example, Loop diuretics are medicaments that inhibit the reabsorption of sodium in the thick limb of the loop of Henle. By inhibiting the reabsorption of sodium, the hypertonic filtrate inhibits the reabsorption of water via solvent drag leading to increased urine volume. However, during congestion, renal blood flow is reduced and delivery of the medicament to the lumen of the tubule is reduced. As a consequence, the effectiveness of the loop diuretics is diminished. The application of negative pressure into the collection system of the kidney results in an increase in renal blood flow and filtrate delivered to the tubules, even during congestion. Combining these approaches leads to an augmentation of the urine produced via either method alone. Negative pressure will increase the production of filtrate, hence sodium delivery to the tubule. Negative pressure will also increase renal blood flow, hence delivery of more loop diuretic to the tubule. Therefore, more sodium can be blocked from reabsorption and more urine is produced.

Figure 3:
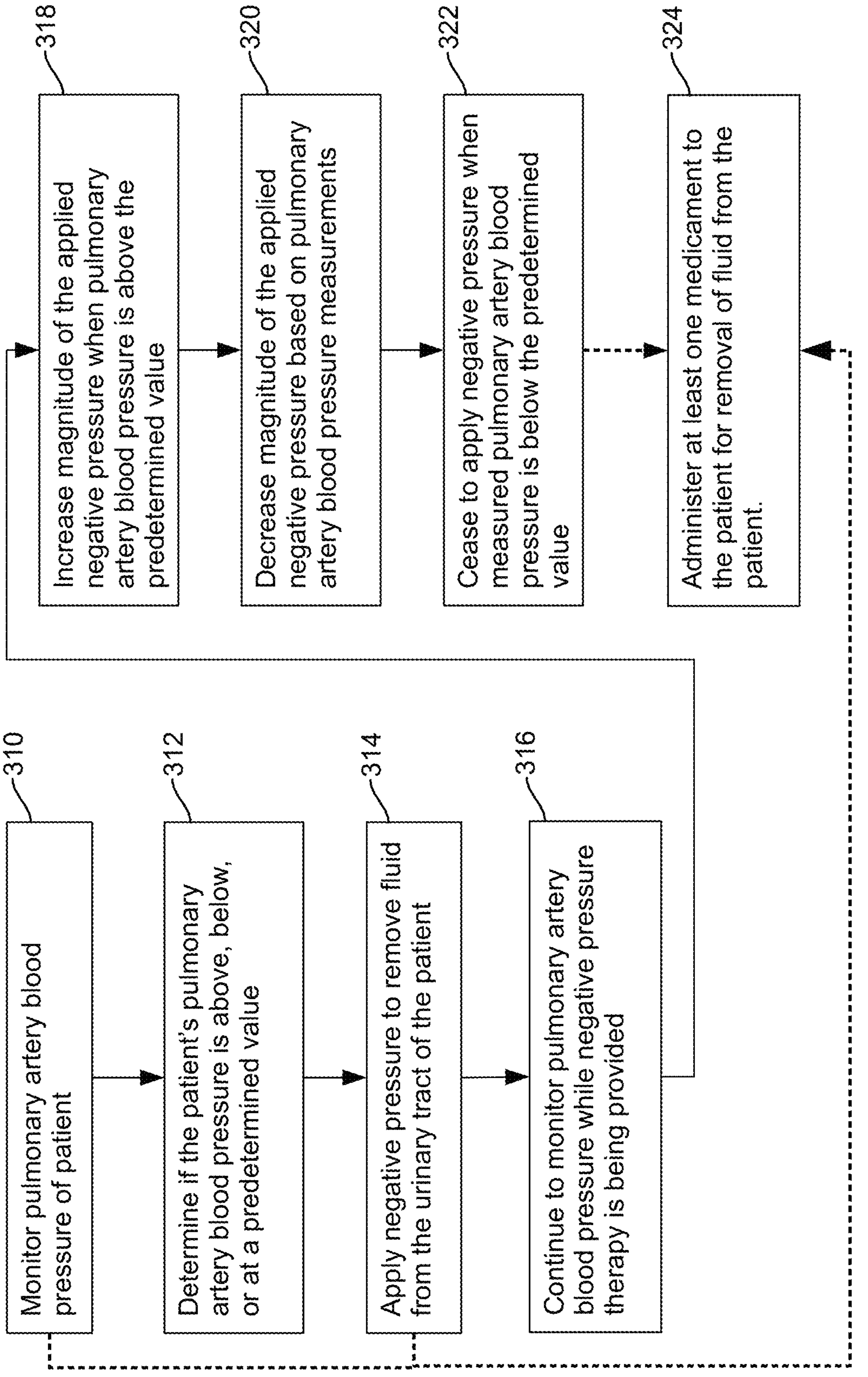
FIG. 3 is a flow chart showing steps for providing negative pressure therapy to a patient using pulmonary artery pressure measurements, according to an example of the present disclosure.

A method comprising the following steps for removing fluid from a patient using the devices and systems 200 described herein is shown in the flow chart of FIG. 3. In some examples, the methods disclosed herein can be used for treatment of an ambulatory patient who is asymptomatic for congestion, meaning that the patient is not showing physiological symptoms of decompensated heat failure (i.e., edema, dyspnea, shortness of breath, etc.). For patients with an implanted pulmonary artery pressure sensor, the patient's pulmonary artery pressure could be checked periodically (i.e., daily or every few days). If the patient's pulmonary artery pressure rises, a urinary catheter (i.e., a kidney percutaneous catheter or an indwelling catheter inserted in the urinary tract) could be provided in the patient's urinary tract for providing renal negative pressure therapy for the patient. Once the urinary catheter(s) are in place, renal negative pressure therapy treatment could be provided for any suitable period of time sufficient for relieving fluid overload and/or reducing the patient's pulmonary artery pressure. For example, renal negative pressure therapy could be provided to the patient for a period of time of about 12 hours to about 96 hours. After the regnal negative pressure therapy is completed, the urinary catheter(s) could be removed. After removal of the urinary catheter(s), the patient's pulmonary artery pressure measurements could continue to be monitored periodically (i.e., daily or every few days) to determine whether the patient would benefit from additional treatments of negative pressure therapy.

In some examples, as shown in the flowchart, a treatment method for a patient comprises, at step 310, monitoring the pulmonary artery pressure of the patient. As previously described, monitoring the pulmonary artery pressure can comprise, for example, exposing an implanted, passive pressure sensor 214 to a radio frequency signal generated by a radio frequency antenna of an external device, such as any of the previously described external portable computer devices 226 and/or the implantable pump 128, and monitoring a frequency response from the implanted sensor 214 with the radio frequency antenna. The implanted sensor 214 can be provided in the right pulmonary artery or the left pulmonary artery of the patient. The external portable computer device 226 can comprise electronic circuitry, such as the system controller 224, for receiving and processing the response signal to determine an instantaneous or real-time measurement for the pulmonary artery pressure of the patient. As previously discussed, monitoring the pulmonary artery pressure can comprise determining a pulmonary artery pressure for the patient continuously or at predetermined intervals, such as once an hour, once every two hours, once every four hours, or once a day.

At step 312, the method further comprises determining if the patient's pulmonary artery pressure is above, below, or at a predetermined value. The predetermined value or, in other examples, a predetermined range of acceptable values can be determined based on normal values for a healthy patient (i.e., for a patient without worsening heart failure). For example, the predetermined value can be within a range of about 12 mmHg to about 16 mmHg (diastolic) and from about 18 mmHg to about 25 mmHg (systolic). In other examples, the predetermined value can be a measured baseline value for a particular patient. For example, the predetermined value can be the patient's systolic and/or diastolic pulmonary artery pressure when the sensor 214 is first implanted in the patient's pulmonary artery 22*a*, 22*b*.

At step 314, the method can further comprise applying the negative pressure to the inflow member 112 of the urinary catheter 110 to remove fluid from the urinary tract of the patient when the patient's pulmonary artery pressure is above the predetermined value or ceasing to apply the negative pressure when the patient's pulmonary artery pressure is at or below the predetermined value. The negative pressure applied by the implanted pump 128 through the inflow member 112 can also be based, at least in part, on patient information from other sensors, such as any of the previously described physiological, pump parameter, and/or environmental sensors. For example, the system controller 224 may be configured to receive sensor data indicating a negative pressure at the renal pelvis and may modify operating parameters of the pump 128 based on the received pressure measurements from the renal pelvis. In other examples, operating parameters of the pump 128 could be modified based on, for example, patient urine output, a total amount of urine that has passed through the catheter and/or pump, analyte concentration of the collected urine, and/or trends in physiological parameters of the patient detected by the sensors.

In some examples, applying negative pressure therapy can comprise deploying the retention portion 118 of the inflow member 118 in the kidney and/or renal pelvis. Once the retention portion 118 is deployed, the negative pressure can be applied at a predetermined magnitude (i.e., a magnitude of from 10 mmHg to 150 mmHg) for a predetermined duration (i.e., one hour, two hours, or four hours). After the predetermined duration, the pulmonary artery pressure can be detected again. If the detected pulmonary artery pressure remains above the predetermined value, negative pressure can be applied again at the predetermined magnitude for the predetermined duration. If the detected pulmonary artery pressure is below the predetermined value, then the method can comprise ceasing to apply the negative pressure for a predetermined duration.

In some examples, the system controller 224 can be configured to automatically modify the applied negative pressure in response to measured pulmonary artery pressure values and/or in response to sensor measurements from other physiological, pump parameter, and/or environmental sensors of the system 200. In other examples, modification of negative pressure therapy can be performed manually by, for example, a medical professional or, in some instances, by the patient. For example, the user (either the trained medical professional or patient) may review pulmonary artery pressure measurements displayed on, for example, the visual display 246 of the external portable computer device 226. The user may determine when to turn-on or to turn-off the implanted pump 128 and/or to adjust a magnitude of the applied negative pressure based on the displayed measured values for pulmonary artery pressure.

In some examples, the method further comprises, at step 316, continuing to monitor the pulmonary artery pressure of the patient while negative pressure therapy is being provided. For example, continuing to monitor the pulmonary artery pressure can including periodically receiving measurements for the patient's pulmonary artery pressure at predetermined intervals. The method can further comprise, at step 318, increasing a magnitude of the negative pressure applied by the negative pressure source when the patient's pulmonary artery pressure is above the predetermined value. For example, increasing the magnitude of the negative pressure can comprise increasing the magnitude of the pressure incrementally (i.e., by a predetermined about, such as 1.0 mmHg, 0.5 mmHg, or 0.1 mmHg) each time that a new measurement for pulmonary artery pressure is received that is greater than the predetermined value.

At step 320, optionally, the method can further comprise a step of decreasing the magnitude of the negative pressure applied to the inflow member 112 of the urinary catheter 110 based on pulmonary artery pressure measurements received from the external portable computer device 226 and/or pump 128. For example, the magnitude of the negative pressure may be reduced by a set amount (i.e., 1.0 mmHg, 0.5 mmHg, or 0.1 mmHg) each time that a measurement for pulmonary artery pressure is received that is less than the previously received pulmonary artery pressure value, even if the measured value remains above the predetermined value (i.e., the predetermined target value for systolic or diastolic pressure). Reducing a magnitude of the applied negative pressure incrementally by small amounts may serve to reduce severity of a transition between applying negative pressure and when no pressure is applied.

At step 322, the method can further comprise a step of ceasing to apply negative pressure when a measured pulmonary artery pressure for the patient is less than the predetermined or baseline value. For example, the system controller 224 can be configured to automatically turn off the pump 128 when the measured pulmonary artery pressure for the patient is below the predetermined value. In other examples, a user may manually turn off the pump 128 to cease applying negative pressure to the urinary tract of the patient when a pulmonary artery pressure value display, for example, on the visual display 246 of the external portable computer device 126 is below the predetermined value.

With continued reference to FIG. 3, removal of excess fluid from the patient by the negative pressure therapy system 200 and associated methods of the present disclosure can be enhanced by medication provided to the patient before, during, or after negative pressure therapy is applied to the urinary tract of the patient. For example, as shown at step 324, the method, optionally, further comprises administering at least one medicament to a patient. The medicament can be any of the previously described medications, therapeutic agents, and/or active agents having the effect of increasing urine output and/or sodium output from the patient. For example, the medicament can comprise a medicament known or expected to modulate electrolyte reabsorption, electrolyte excretion, and/or renal blood flow in the patient. Alternatively or in addition, the medicament can be a medicament known or expected to modulate renal blood flow. In still other examples, the medicament can be a medicament that modulates electrolyte reabsorption and/or electrolyte excretion in the patient.

As shown in FIG. 3, the medicament can be provided before, during, and/or after providing negative pressure therapy to the urinary system of the patient. In some examples, a decision to administer the medicament to the patient can be based on and/or modified in view of the pulmonary artery pressure measurements from the implanted sensor. For example, medication may be provided when a patient's pulmonary artery pressure is greater than a predetermined value. Medication may not be administered to the patient or an amount of medication provided to the patient or frequency with which medication is provided to the patient may be reduced when the patient's pulmonary artery pressure is below the predetermined value.

Negative Pressure Systems with Bioelectrical Impedance Monitoring

In other examples, a system 400 comprising the urinary catheters 110 and implanted pump 128 of the present disclosure can be configured to monitor and control applying negative pressure therapy based on measured values for bioelectrical impedance. Bioelectrical impedance (i.e., total body impedance or impedance for selected body regions) can be monitored to detect changes in fluid status of a patient. As used herein, "bioelectrical impedance" refers to impedance or resistance to flow of electrical current of biologic tissue, such as tissues, organs, and other anatomical structures of a patient. Total body impedance refers to measured impedance through major portions of the patient's body, such as an impedance measured between a wrist and a foot. Impedance can also be measured for specific body regions. For example, thoracic impedance can be monitored to detect a presence of fluid in a patient's thoracic region indicating onset of pulmonary edema. Impedance can also be measured, for example, through the abdominal cavity or other convenient body locations. It is believed that bioelectrical impedance may decrease (i.e., reduce in magnitude) in the days and weeks prior to an acute decompensation event, indicating that additional fluid is present and collecting in, for example, the thoracic cavity or other body cavities increasing overall congestion. Thoracic impedance, as used herein, refers to an impedance or resistance to flow of electrical current through at least one portion or portions of the thoracic cavity. The systems 400 and treatment methods described hereinafter provide examples of how hemodynamic parameters, namely total body and/or thoracic impedance, can be used to control aspects of a renal negative pressure therapy system in order to control excretion of fluid from the patient's body. The systems and treatment methods may provide one or more beneficial effects, such as reducing and/or alleviation of fluid overload and/or conditions leading to decompensation of the patient.

Figure 4A:
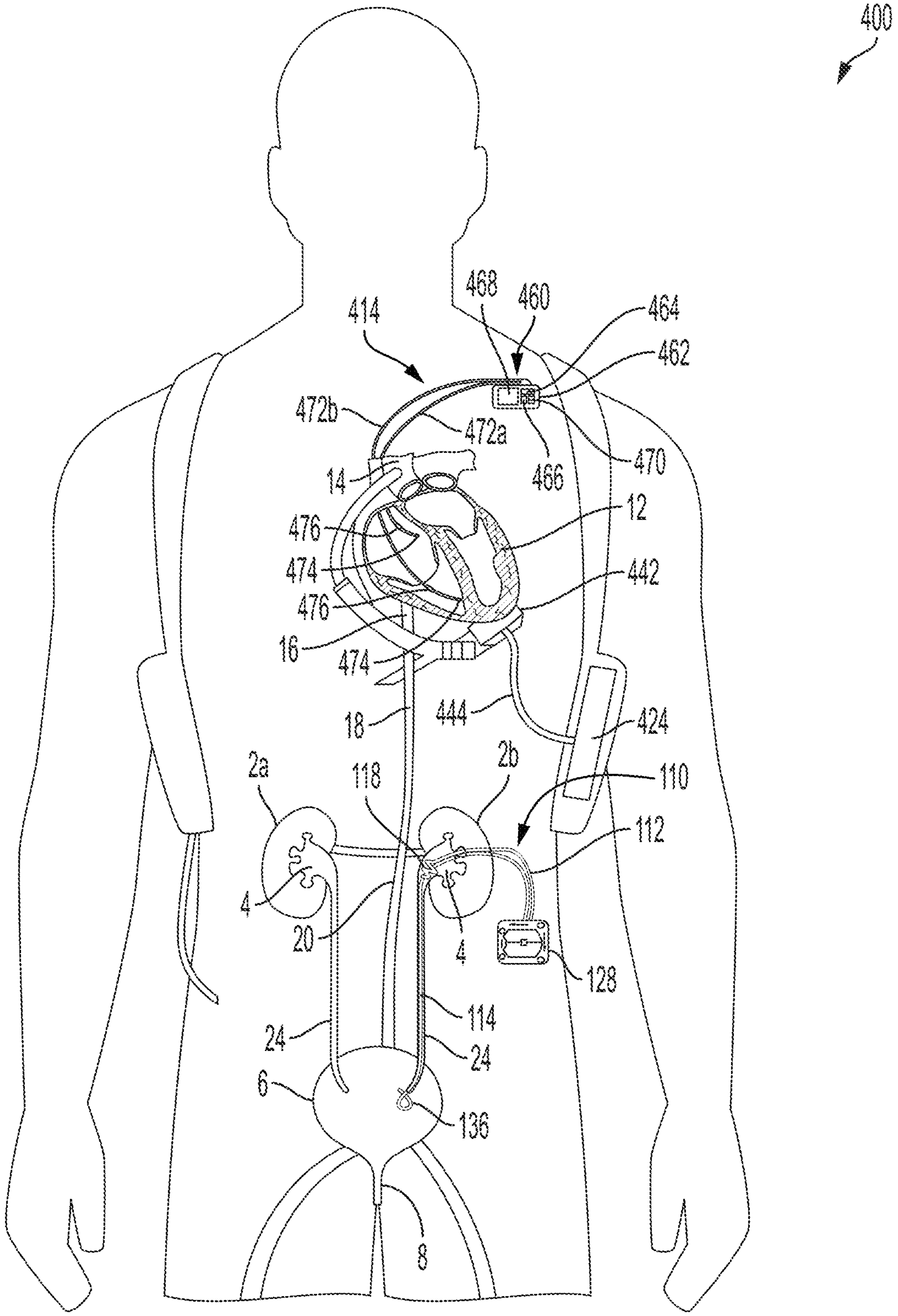
FIG. 4A is a schematic drawing showing a negative pressure therapy system comprising an implanted negative pressure source, implanted medical device for measuring thoracic impedance, and circulation support devices, according to examples of the present disclosure.

Optionally, in some examples, patients with acute decompensation and/or increased cardiovascular stress due to physiological status of the patient may have a blood pump, such as the blood pump shown in FIG. 4A, implanted to assist the heart in blood circulation.

Bioelectrical impedance can be measured by a number of different types of implanted or external impedance sensors 414 and/or by any other suitable method or device for measuring bioelectrical impedance as is known in the art. As described in further detail herein, thoracic impedance can be measured by an implanted or implantable medical device (IMD), such as an implantable cardiac pacemaker, an implantable cardioverter defibrillator, an implantable cardiac resynchronization device, an implantable cardiovascular monitor, or a therapeutic device that monitors and treats structural problems of the heart. Implantable medical devices are used to monitor, manage, and treat a variety of medical conditions including, for example, bradycardia, tachycardia, atrial fibrillation, ventricular fibrillation, heart failure, structural problems of the heart, rhythm problems, and other heart conditions. Non-limiting exemplary IMDs that can be configured to measure thoracic impedance for controlling the negative pressure therapy systems of the present disclosure are described, for example, in U.S. Pat. No. 7,329,226, entitled "System and method for assessing pulmonary performance through transthoracic impedance monitoring," which is incorporated by reference herein in its entirety. Additional non-limiting examples of implantable medical devices that measure thoracic impedance are described in U.S. Pat. No. 6,463,326, entitled "Rate adaptive cardiac rhythm management device using transthoracic impedance," U.S. Pat. No. 9,014,815, entitled "Electrode assembly in a medical electrical lead," and U.S. Pat. No. 7,603,170 entitled "Calibration of impedance monitoring of respiratory volumes using thoracic D.C. impedance," which are incorporated herein by reference in their entireties.

The systems 400 and devices of the present disclosure can also be adapted to use detected impedance measurements to control and/or to provide feedback about operation of the implanted pump 128 and/or an external pump 130 (shown in FIG. 1B). Impedance measurements can also be used to control other aspects of patient treatment within the scope of the present disclosure. For example, bioelectrical impedance may be used to determine when certain medications should be delivered to a patient and/or to control dosing for such medications. Impedance measurements can also be used, for example, to control other treatment devices provided to the patient.

FIG. 4A is intended to be an example of a type of pump system 400 that can be configured to comprise the device for measuring thoracic impedance and the blood pump. It is understood that other types of negative pressure therapy devices and/or pump systems can also be configured to comprise a thoracic impedance sensor, implantable medical device, and/or blood pump, within the scope of the present disclosure. For example, the implantable medical device and blood pump of the present disclosure can be configured for use with any type of indwelling pump, implantable pump, or external pump (for an ambulatory or non-ambulatory patient) and associated pump systems within the scope of the present disclosure.

FIG. 4A shows a system 400 comprising the urinary catheter 110 comprising the inflow member 112 and the outflow member 114. As in previous examples, the inflow member 112 comprises the retention portion 118 deployed in the kidney 2*a*, 2*b* and/or renal pelvis 4 of the urinary tract. The outflow member 114 can pass through a space defined by the retention portion 118 of the inflow member 112 and through the ureter 24 to the bladder 6. The system 400 further comprises a negative pressure source, such as the implanted pump 128, and an implanted blood pump 442. As in previous examples, the urinary catheter 110 is configured to transmit the negative pressure from the negative pressure source (i.e., the implanted pump 128 or external pump 130) to the urinary tract of the patient through the inflow member 112 and to discharge the fluid, such as urine, from the outflow member 114 back to the urinary tract of the patient.

As shown in FIG. 4A, the negative pressure therapy systems 400 further comprises the bioelectrical impedance sensor 414 configured to detect signal(s) representative of thoracic impedance of the patient and communicate the signal(s) representative of the thoracic impedance to other electronic devices, such as to the implanted pumps 128 and/or to any other implanted or external pump, electronic device, or external or remote controller, as described herein. As previously described, thoracic impedance, as measured by the bioelectrical impedance sensor 414, can be an early indicator of worsening decompensated heart failure. In particular, increasing congestion means that the heart must work harder to force blood through the pulmonary arteries 22*a*, 22*b*. Continued vigorous pumping to overcome increasing congestion places added stress on the patient's heart 12 hastening the progression to decongested heart failure.

The bioelectrical impedance sensor 414 can comprise and/or can be a component of an implantable medical device 460, as shown in FIG. 4A. The implantable medical device 460 can be provided at a variety of implantation sites within the patient's body. For example, the implantable medical device can be implanted subcutaneously to an implantation site in the thoracic region or abdomen of the patient. The implantable medical device 460 can also be implanted in other locations, such as adjacent to the patient's shoulder or in the upper arm. In other examples, the bioelectrical impedance sensor 414 can be any other implanted sensor or device capable of measuring thoracic impedance, such as an implantable patient monitoring device that does not provide therapeutic treatment for the patient. In other examples, the thoracic impedance sensor 414 can be partially or fully external to the patient's body. For example, the bioelectrical impedance sensor 414 can comprise an external electrode configured to be positioned on a surface of skin of the patient and to generate electrical pulses that are detected by an implanted electrode or sensor. In other examples, the bioelectrical impedance sensor 414 can comprise a first sensor or electrode configured to be positioned on a portion of the patient's skin that generates electrical pulses directed through the thoracic region of the patient and a second sensor or electrode positioned on another portion of the patient's skin that detects the pulses to determine thoracic impedance.

With continued reference to FIG. 4A, the implantable medical device 460 comprises an enclosure or housing 462 containing, for example, electrical components of the device, such as control circuitry 464, telemetry circuitry, such as a wireless data transmitter 466, and a rechargeable battery 468. The housing 462 can be formed from any suitable rigid biocompatible material, such as stainless steel or rigid plastic. The housing 462 can be sized to be implanted in the chest cavity or abdomen in a convenient manner, such as through a subcutaneous incision. The control circuitry 464 can be configured to control providing different types of shock therapy to the patient including, for example, providing pacing pulses, defibrillation pulses, transcutaneous electrical nerve stimulation (TENS) pulses, as well as any other type of therapeutic electric pulses, as are known in the art. The control circuitry 464 can also be configured to receive and control wireless transmission of signals representative of bioelectrical impedance detected by the implantable medical device 460 to external computing devices via the wireless transmitter 466.

The implantable medical device 460 further comprises a sensor or electrode, such as a pulse generator 470, positioned on the housing 462 of the implantable medical device 460 configured to provide energy pulses through a thoracic region of the patient for measuring thoracic impedance. In other examples, the pulse generator 470 for measuring thoracic impedance could be separate from the housing 462 of the implantable medical device 460 and could be connected to the control circuitry 464 of the implantable medical device 460 by, for example, wires or leads.

The implantable medical device 460 further comprises leads or lead wires 472*a*, 472*b* that extend from the housing 462 of the implantable medical device 460, through veins of the patient, to a chamber of the patient's heart 12. For example, as shown in FIG. 4A, the implantable medical device 460 comprises a first lead wire 472*a* with a distal end 474 in the patient's right atrium and a second lead wire 472*b* with a distal end 474 in the patient's right ventricle. The leads or lead wires 472*a*, 472*b* can comprise electrodes for generating and/or sensing electrical signals (referred to herein as sensing electrodes 476). In order to measure thoracic impedance, in some examples, an electrical signal, such as a test pulse, is generated by the electrode or pulse generator 470 on the housing 462. Electrical parameters of the test pulse can vary depending, for example, on the electrical components of the implantable medical device 460, implant location, or conductivity of the leads or lead wires 472*a*, 472*b*. In some examples, the test pulse is an electrical pulse having a pulse width of about 50 μs to about 500 μs and an amplitude of about 200 μA to 1000 μA. However, electrical parameters for the test pulse or for a constant electrical signal of predetermined duration can be adapted for particular implantable medical devices 460 and/or particular patients by those skilled in the art within the scope of the present disclosure.

The electrical signal or test pulse travels through the patient's thoracic region and is detected by the sensing electrodes 476 at the distal ends 474 of the lead wires 472*a*, 472*b*. A voltage of the detected signal can be divided by a magnitude of the current of the electrical pulse to determine impedance of the thoracic region. As previously described, changes in impedance of electrical signals detected by the sensing electrodes 476 indicate a change in fluid status of the patient. In other examples, electrical current generated by electrodes on the lead wires 472*a*, 472*b* can be detected by sensors or electrodes at other locations, such as by sensors or electrodes on the housing 462 of the implantable medical device 460. In many cases, voltage measurements from multiple electrodes at different positions on the lead wires 472*a*, 472*b* and/or housing 462 can be used to calculate thoracic impedance to reduce effects of errors caused by electrical interference from implanted devices and other conductive structures in the thoracic region. Also, as will be appreciated by those skilled in the art, the arrangement of the housing electrodes, pulse generators 470, and sensing electrodes 476 shown in FIG. 4A are examples of arrangements of electrodes and sensors that can be used to obtain accurate thoracic impedance measurements for a patient. Other arrangements of pulse generators 470, sensing electrodes 476, and lead wires 472*a*, 472*b* will be apparent to those skilled in the art within the scope of the present disclosure.

Figure 4B:
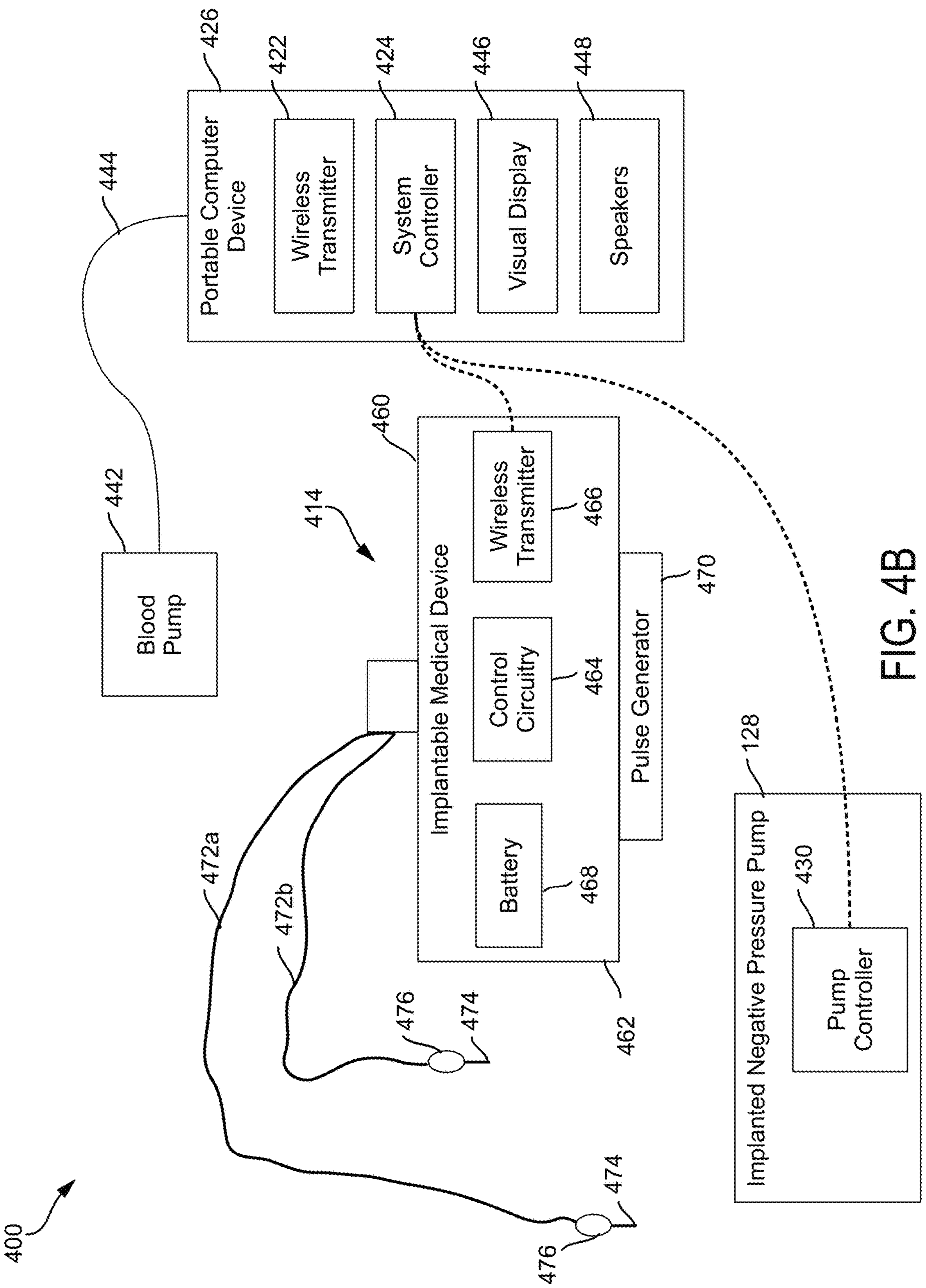
FIG. 4B is a schematic drawing showing electrical components of the negative pressure therapy system of FIG. 4A.

With reference to FIG. 4B, the system 400 can further comprise an indwelling, implanted, or external system controller 424 that receives signals from the bioelectrical impedance sensor 414 (i.e., from the wireless transceiver 466 of the implantable medical device 460) and generates control signals for controlling different treatment devices and other electronic components of the system 400. The system controller 424 can be a separate device or can be connected to or integral with various implanted or external electronic devices of the system 400. For example, the system controller 424 can be integral with the implanted pump 128 or with the external pump 130 (shown in FIG. 1B). In some examples, the system controller 424 can comprise a computer processor or microprocessor disposed on a printed circuit board within a housing of the implanted pump 128.

In some examples, the system controller 424 is configured to receive and process the signal(s) and/or data from the bioelectrical impedance sensor 414 to determine if the patient's bioelectrical impedance is above, below, or at a predetermined value. As used herein, the "predetermined value" for bioelectrical impedance can refer to a normal or target bioelectrical impedance value for a population of patients (i.e., a population comprising patients of a similar weight, height, body-mass index, age, gender, etc.). The "predetermined value" can also be a baseline value for a particular patient, such as a thoracic impedance value for the patient determined when the implantable medical device 460 is first implanted. While bioelectrical impedance is generally a patient and/or sensor specific value, in some examples, a normal thoracic impedance for a patient can be about 560 ohms to about 680 ohms. A bioelectrical impedance value of greater than about 680 ohms may indicate that the patient suffers from fluid overload and/or pulmonary edema. In some examples, a statistical approach could be applied for determining a baseline value for bioelectrical impedance for a patient. For example, a patient's bioelectrical impedance may be monitored for a period of time (i.e., from about 7 days to about 30 days) and a mean value for bioelectrical impedance and a standard deviations for the collected data could be calculated. In that case, any measured bioelectrical impedance value for the patient that differs from the calculated mean impedance value by more than, for example, two standard deviations could be determined to be abnormal. In the event that measured bioelectrical impedance for the patient is determined to be abnormal, therapeutic intervention, including applying negative pressure therapy, could be provided for the patient to address the changing fluid status of the patient.

The system controller 424 can be configured to wirelessly receive signals representative of measured impedance transmitted by the wireless transmitter 466 of the implantable medical device 460. The system controller 424 can also receive sensor data from other patient physiological, pump, and/or environmental sensors of any of the previously described negative pressure therapy systems and/or from other sensing or monitoring devices receiving physiological information for the patient. For example, the system controller 424 can receive patient information from physiological sensors, such as capacitance and/or analyte sensors for measuring information representative of the chemical composition of generated urine, pH sensors for measuring acidity of urine, or temperature sensors for measuring urine temperature. The system controller 424 can also receive information from fluid sensors positioned in the inflow member 112 or the outflow member 114 of the urinary catheter 110 configured to measure fluid flow characteristics or parameters, such as fluid pressure or flow volume measured in the inflow member 112 or the outflow member 114. The system controller 424 can also receive information from a catheter probe positioned near the retention portion 118 of the inflow member 112 that measures negative pressure in the renal pelvis 4 or kidney 2*a*, 2*b*. In some examples, the system controller 424 can also be configured to receive information about intra-abdominal pressure measured, for example, by a pressure sensor positioned on an external surface of an implanted pump 128.

The system controller 424 can also be configured to provide control signal(s), determined at least in part from the bioelectrical impedance data or signal(s) received from the thoracic sensor 414, to a negative pressure source to: (a) apply negative pressure to a urinary catheter to remove fluid from the urinary tract of the patient when the patient's bioelectrical impedance is below a predetermined value and/or a baseline value for the patient; or (b) to cease applying negative pressure when the patient's bioelectrical impedance is at or above the predetermined or baseline value. The control signal(s) generated by the system controller 424 can also be based, at least in part, on sensed data from any of the other physiological, pump, and/or environmental sensors described herein.

The negative pressure source can be the implanted negative pressure therapy pump 128 or the external negative pressure therapy pump 130 (shown in FIG. 1B). Alternatively, the negative pressure source can be any other negative pressure source known in the art and available in medical and/or patient treatment settings. For example, the negative pressure source can be a negative pressure system of a hospital or another medical facility that can be accessed by, for example, a wall-mounted negative pressure port. The pump 128 and/or other negative pressure source can be configured to provide negative pressure ranging from 5 mmHg to about 150 mmHg to the drainage lumen of the urinary catheter, as measured at the at least one fluid port of the pump 128 and/or at a proximal end of the urinary catheter.

As previously described, the system controller 424 is configured to provide operating instructions, in the form of control signals, to the negative pressure source, such as to the pump 128. The control signals are based, at least in part, on bioelectrical impedance (e.g., thoracic impedance and/or total body impedance) measurements received from the bioelectrical impedance sensor 414 and, in some examples, can provide a feedback loop in which continuously-obtained or periodic impedance measurements are relied upon to incrementally adjust the applied negative pressure. For example, the system controller 424 can initially be configured to provide negative pressure therapy to the patient when a measured impedance value is below a predetermined value and/or baseline value.

In a simple example, the negative pressure can be provided at a predetermined pressure level (i.e., a predetermined pressure of between 10 mmHg and 150 mmHg, as measured at a proximal end of the inflow member 112) for a predetermined duration of time (i.e., 30 minutes, 1 hour, 2 hours, 8 eight hours, 12 hours, or longer). After the predetermined duration, the bioelectrical impedance can be measured again. If the measured impedance remains below the predetermined and/or baseline value, negative pressure can continue to be applied to the patient for another instance of the predetermined duration. If measured bioelectrical impedance increases above the predetermined value and/or baseline value, the system controller 424 can be configured to cease the application of the negative pressure.

In other examples, the system controller 424 can be configured to periodically incrementally increase or decrease the applied negative pressure. For example, the system controller 424 can be configured to periodically compare the bioelectrical impedance of the patient to the predetermined value or the patient's baseline value for impedance. The system controller 424 can then be configured to provide additional control signals to the negative pressure source, such as to the implanted pump 128, to increase a magnitude of the negative pressure applied by the negative pressure source to the inflow member 112, when the bioelectrical impedance of the patient is less than the predetermined and/or baseline value. For example, the control signals generated by the system controller 424 can cause an absolute value or magnitude of the applied negative pressure to increase by an incremental amount (i.e., 1 mmHg, 5 mmHg, or 10 mmHg) each time that a measured impedance is less than the predetermined and/or baseline value.

With reference again to FIG. 4A, the system 400, optionally, can further comprise the blood pump 442, such as a left-ventricular assist device and/or a left ventricular support pump, implanted proximate to a left ventricle of the patient's heart. As described hereinabove, the negative pressure therapy system 400 of the present disclosure can be provided to assist in management of patient fluid status in an effort to relieve stress on the heart and other organ systems. In particular, elevated fluid levels can increase stress for the heart, weakening the heart muscle, and hastening the progression towards heart failure. Accordingly, the system 400 of the present disclosure can be used in conjunction with or can comprise the blood pump 442, for example, to relieve stress on the heart and/or help the heart to provide sufficient blood circulation.

The optional blood pump 442 can be in wired electronic connection via a percutaneous wire 444 (shown in FIG. 4A) or wireless electronic communication with and can receive operating instructions, such as control signals, from the system controller 424 and/or from a blood pump controller.

For example, as shown in FIG. 4A, the blood pump 442 can be in wired communication with the external portable computer device 426 comprising the system controller 424. In some examples, the optional blood pump 442 is positioned near the left ventricle of the patient's heart 12. The blood pump 442 is configured to draw blood from the left ventricle, through the pump 442 and associated tubing, and to expel the blood into the aorta proximate to the aortic arch 14. Generally, implanted blood pumps, such as the blood pump 442, provide continuous blood flow through tubing extending from an incision or opening in the left ventricle to an incision in the aorta proximate to the aortic notch. The continuous blood flow can be provided at a constant cardiac output to assist the heart 12 in blood circulation. Implantable blood pumps 442 or left-ventricular assist devices are manufactured by a number of medical device manufacturers including Abbott Laboratories, HeartWare International, Medtronic, ReliantHeart Inc., and others. One exemplary blood pump 242 that can be used with the systems of the present disclosure is the HeartMate 3 LVAD manufactured by Abbott Laboratories. An exemplary blood pump 442 that can be used with the systems 400 of the present disclosure is described in U.S. Pat. No. 9,849,224, entitled "Ventricular assist devices", which is incorporated by reference herein in its entirety.

In some examples, the system controller 424 is configured to provide operating instructions, in the form of control signals, to the blood pump 442. For example, control signals can cause the blood pump 442 to begin providing circulation support for the patient, to cease providing circulation support for the patient, and/or to increase or decrease a flow rate for the pump 442 to increase or decrease a cardiac output volume and/or flow rate. In some examples, the operating instructions for the blood pump 442 are based, at least in part, on bioelectrical impedance measurements for the patient received from the implanted sensor 414. Operating instructions and/or control signals for the blood pump 442 can be based, at least in part, on information from any of the one or more of sensors of the negative pressure therapy system discussed herein. For example, information detected by sensors about total urine output, rate of urine output, blood and/or urine characteristics, and/or trends in patient physiological condition can be used to at least partially control the operation of the blood pump.

As shown in FIG. 4B, the implantable medical device 460 comprises the control circuitry 464, wireless transmitter 466 for transmitting data to and/or receiving instructions from other implanted or external electronic devices, battery 468, and the pulse generator 470 mounted to the housing 462 of the device 460. The portable computer device 426 can comprise an antenna or wireless transmitter 422 that, as shown schematically in FIG. 4B, is configured to receive signals, such as the impedance measurements, from the wireless transmitter 466 of the implantable medical device 460. As previously described, the system controller 424 and/or another computer processor of the portable computer device 426 can be configured to receive and process the impedance measurements from the implantable medical device 460 to, for example, track changes in the patient's bioelectrical impedance. Further, the system controller 424 can be configured to generate control signals for the implanted pump 128 and/or blood pump 442 based on measured values for bioelectrical impedance.

In some examples, the portable computer device 426 can comprise components for providing measured values and other feedback for a user, such as for a medical professional responsible for treatment of the patient. The portable computer device 426 can comprise visual output components, such as a visual display screen 446 or touch screen display, and/or audio output components, such as speakers 448, that provide information and feedback to a user. For example, information about operational status of the pump 128 (i.e., is the pump on or off), a magnitude of negative pressure being applied by the pump 128, and measured patient information or parameters, such as measured bioelectrical impedance, urine output, and any other measured parameters useful for determining a status of the patient and/or for monitoring negative pressure therapy.

Figure 4C:
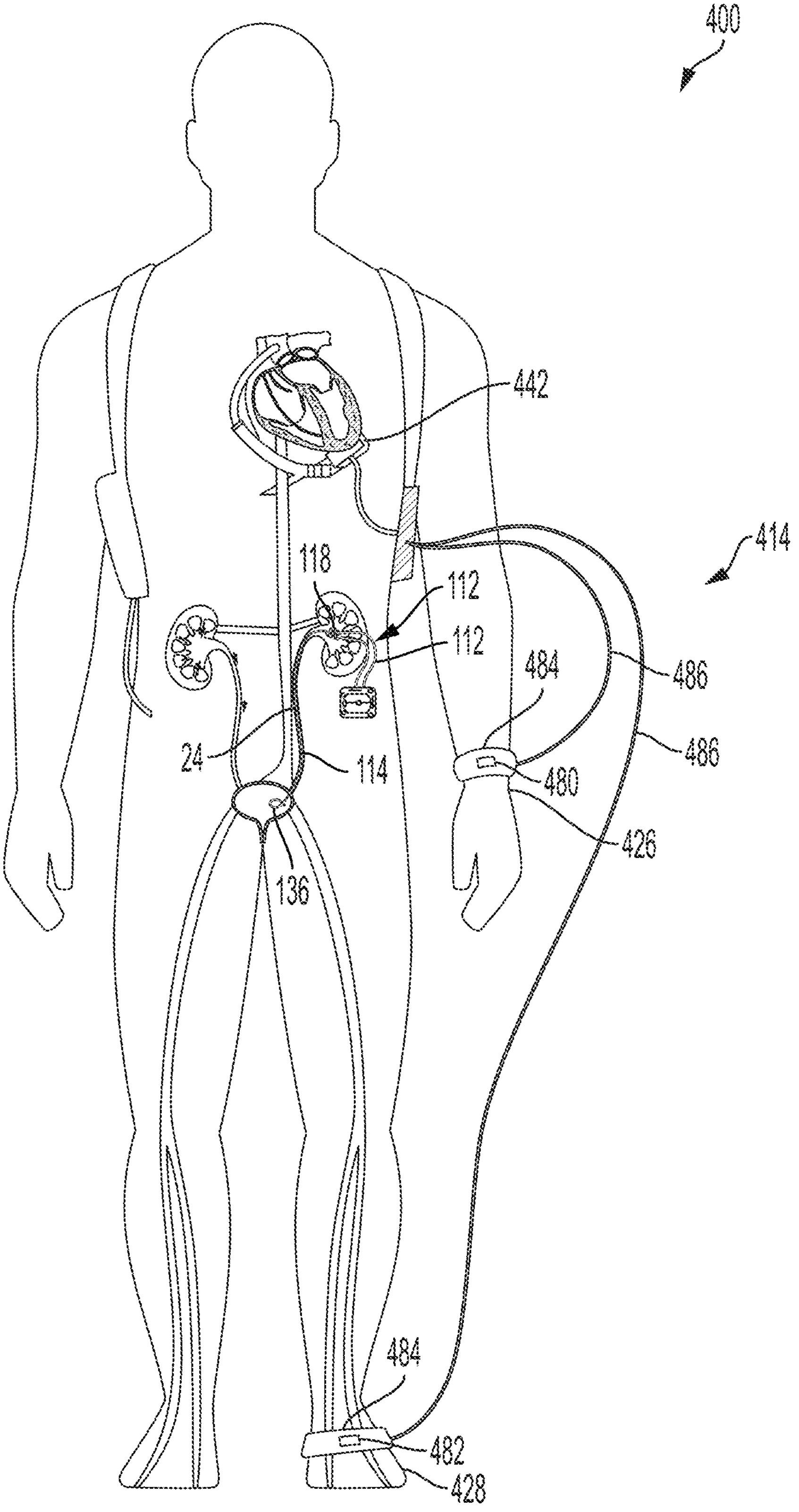
FIG. 4C is a schematic drawing showing another example of a negative pressure therapy system including external sensors for monitoring impedance, according to another example of the present disclosure.

FIG. 4C shows another exemplary negative pressure therapy system comprising the urinary catheter 110 comprising the inflow member 112 and outflow member 114, the implanted pump 128, and bioelectrical impedance sensor(s) 414. Optionally, the system further comprises the implanted blood pump 442. The bioelectrical impedance sensor(s) 414 can comprise two or more electrodes, such as a first electrode 480 and a second electrode 482, positioned to measure total body impedance for the patient. In some examples, the bioelectrical impedance sensor(s) 414 or electrodes 480, 482 can be positioned externally, for example, positioned on the patient's body or extremities, and are configured to measure electrical signals passing through the body between bioelectrical impedance sensors 414 or electrodes 480, 482, for example, signals generated by one or more of the bioelectrical impedance sensor(s) or electrodes and received by the other of one or more of the bioelectrical impedance sensor(s) or electrodes. The bioelectrical impedance sensor(s) or electrodes can be positioned anywhere on the body, for example, the wrist, fingers, palm, arm, shoulder, ankle, leg, knee, thigh, or any other convenient location. In some examples, a first bioelectrical impedance sensor(s) or electrode(s) is positioned spaced apart from a second bioelectrical impedance sensor(s) or electrode(s) for measurement of an impedance signal passing through the body therebetween. For example, as shown in FIG. 4C, the first electrode 480 can be positioned on a wrist 26 of the patient. Alternatively, the first electrode 480 can be positioned on the fingers, palm, arm, shoulder, or any other convenient location. As shown in FIG. 4C, the second electrode 482 can be positioned on the patient's foot 28. Alternatively, the second electrode 482 may be positioned, for example, on the patient's ankle, leg, knee, thigh, or at any other convenient location spaced apart from the first electrode 480. In some examples, one or more of the bioelectrical impedance sensor(s) 414 or electrodes 480, 482 can be implanted or inserted internally within the patient, for example, subcutaneously proximate to the patient's hand, wrist, arm, shoulder, leg, ankle, or foot. In some examples, the bioelectrical impedance (for example thoracic impedance) is measured between two sites or regions of the thoracic cavity of the patient, such as between an electrode positioned in the heart and an implanted electrode external to the heart. Thoracic impedance may also be measured between an electrode positioned, for example, proximate to the sternum and an electrode positioned proximate to the spine. Thoracic impedance may also be measured between electrodes positioned on the right and left sides of the patient's rib cage.

Figure 4D:
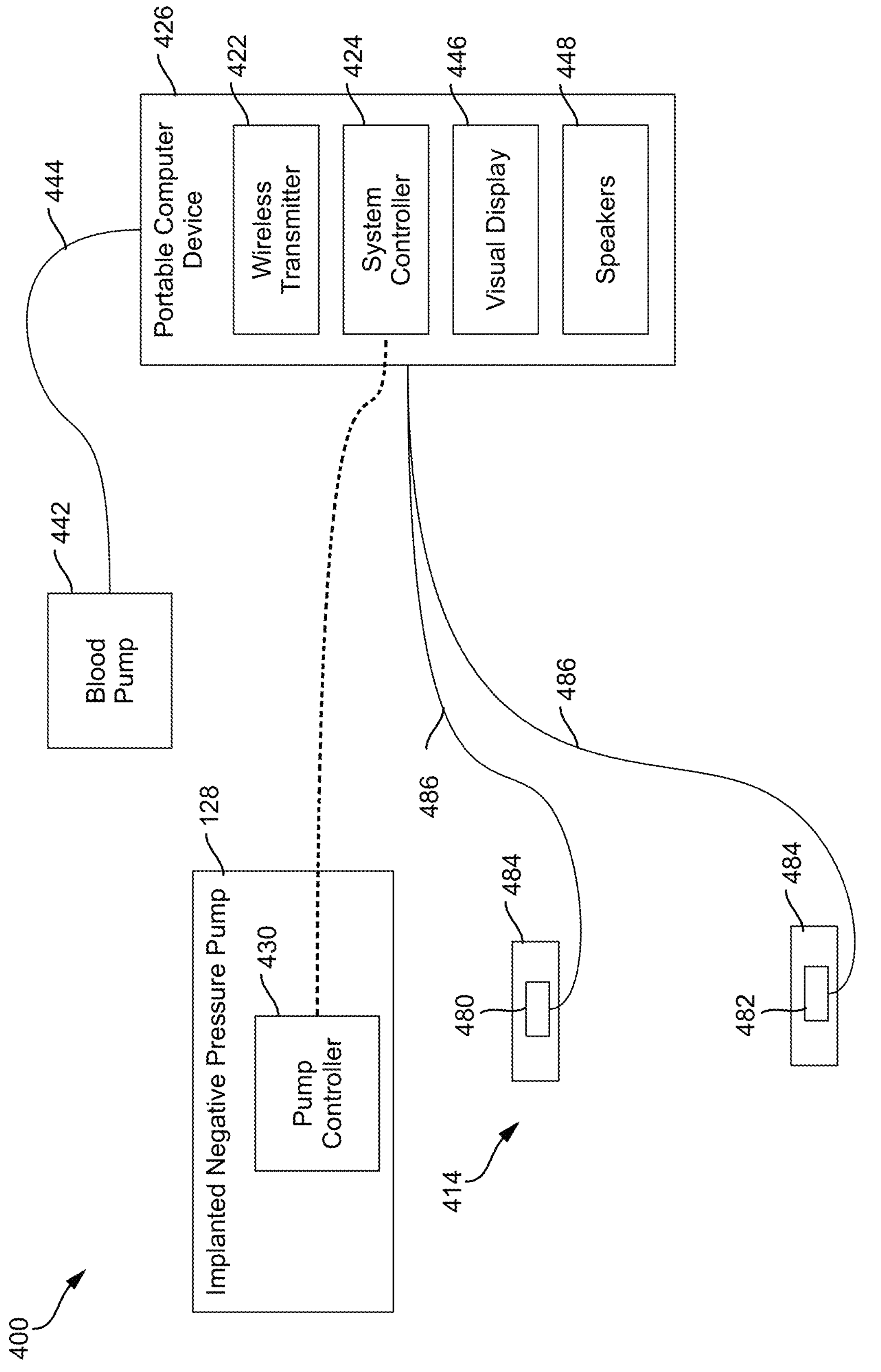
FIG. 4D is a schematic drawing showing electrical components of the negative pressure therapy system of FIG. 4C.

In some examples, the first electrode 480 and the second electrode 482 comprise or are mounted to a cuff 284 or bracelet for securing the electrode 480, 482 to the patient's body. In particular, at least a portion of the electrodes 480, 482 should be positioned in proximity to and/or in contact with the patient's skin so that high-quality electrical signals can be detected. The electrodes 480, 482 can be electrically connected by a wired or wireless electrical connection to a controller or monitoring device, such as to the portable computer device 426 comprising the system controller 424 (shown in FIG. 4D). For example, the electrodes 480, 482 can be electrically connected to the portable computer device 426 by wires 486, as shown in FIGS. 4C and 4D. As in previous examples, the electrodes 480, 482 can be configured to generate and detect electrical signals passing through the patient's body to determine a bioelectrical impedance for the patient. For example, the first electrode 480 can be a signal generating electrode that emits an electrical pulse through the patient's body. The second electrode 482 on the patient's foot 28 can be configured to detect the generated signal. As previously described, bioelectrical impedance can be calculated by dividing the electrical current for the electrical pulse by the detected response voltage. A reported bioelectrical impedance value can be an aggregate value (i.e., a mean average value) determined from periodic bioelectrical impedance measurements from the electrodes 480, 482.

A non-limiting example of a patient monitoring system for monitoring fluid status of a patient based on bioelectrical impedance measurements, which can be used with the negative pressure therapy systems of the present disclosure, is the Body Composition Monitor (BCM) by Fresenius Medical Care of Bad Homburg, Germany. The BCM system is a bioelectrical impedance monitor configured to determine electrical resistance measurements for total body water (TBW) and/or extracellular water (ECW) of a patient using external electrodes mounted to a patient's wrist and foot. The BCM system can be configured for use in a clinical setting with external electrodes connected to a stationary monitor device. Alternatively, the external electrodes of the BCM system can be connected to a portable monitor, such as the portable computer device 426 shown in FIG. 4D. Another non-limiting exemplary system for monitoring fluid status of a patient based on bioimpedance measurements is disclosed in U.S. Pat. No. 9,980,663, entitled "Method and arrangement for determining an overhydration parameter or a body composition parameter," which is incorporated herein by reference in its entirety.

Treatment Methods with Bioimpedance

The negative pressure therapy systems 400 comprising the urinary catheter 110 of the present disclosure can be used in connection with treatment methods for removal of excess fluid from a patient. Treatment can be controlled or modified based on biometric impedance measurements for the patient. In some examples, the fluid removal methods can be used together with circulation support methods, such as providing circulation support using a blood pump (i.e., a left ventricular assist device). In some examples, the method for removing fluid from a patient comprises: (a) monitoring a bioelectrical impedance of the patient; (b) determining if the patient's bioelectrical impedance is above, below, or at a predetermined value and/or a baseline value for the patient; and (c) applying negative pressure to a urinary catheter to remove fluid from the urinary tract of the patient when the patient's bioelectrical impedance is below the predetermined and/or baseline value or ceasing to apply the negative pressure when the patient's impedance is at or above the predetermined and/or baseline value.

Figure 5:
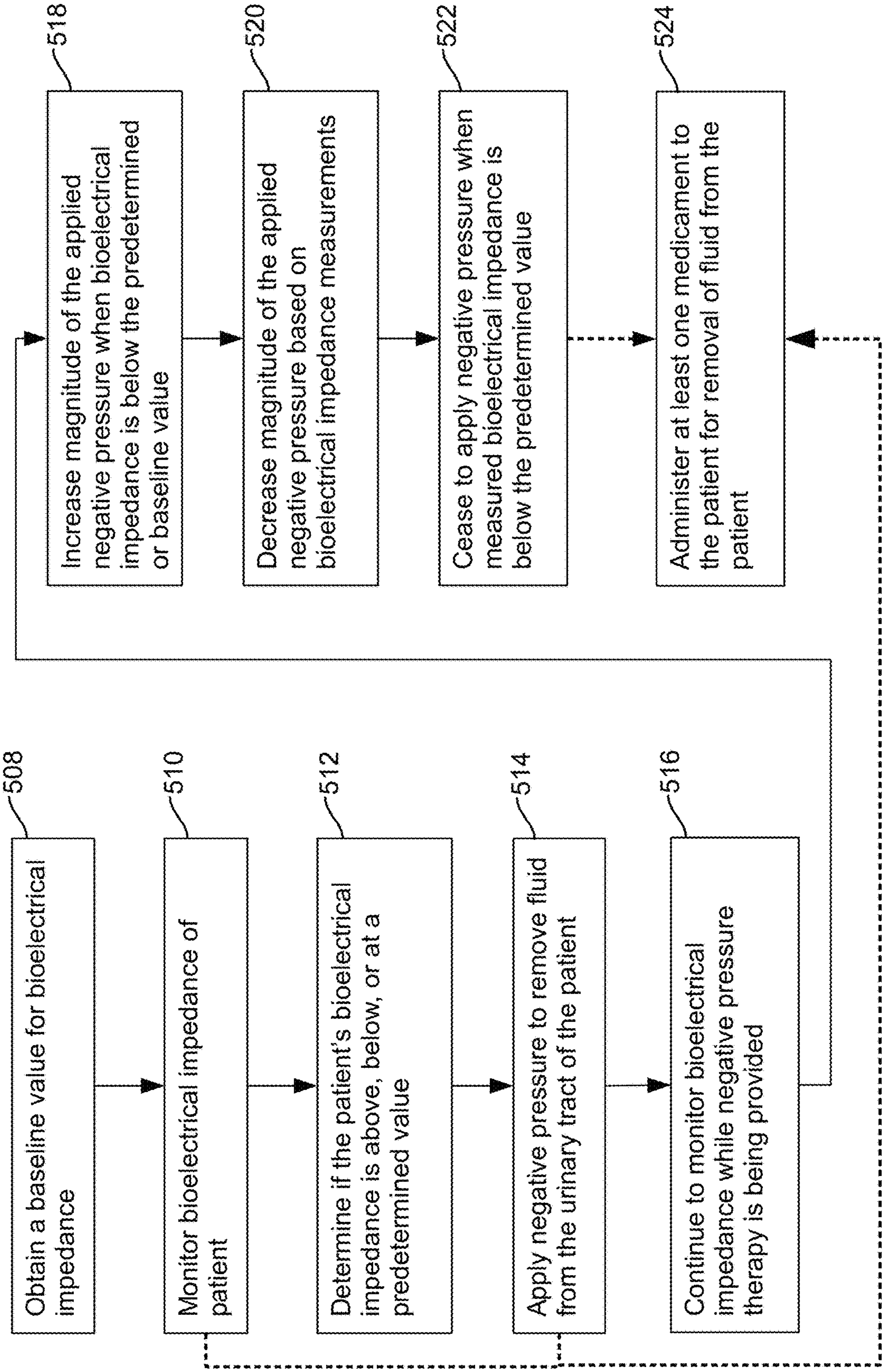
FIG. 5 is a flow chart showing steps for providing renal negative pressure therapy to a patient using bioelectrical impedance measurements, according to an example of the present disclosure.

A method comprising the following steps for removing fluid from a patient using the devices and systems 400 described herein is shown in the flow chart of FIG. 5. In some examples, the methods disclosed herein can be used for treatment of an ambulatory patient who is asymptomatic for congestion, meaning that the patient is not showing severe physiological symptoms of decompensated heat failure (i.e., edema, dyspnea, shortness of breath, etc.), which would require hospitalization. In order to assess physiological status of an ambulatory, asymptomatic patient, the bioelectrical impedance sensor 414 can be used to periodically (i.e., daily or every few days) check impedance measurements. For example, the implantable medical device 460 can be used to check the thoracic impedance measurements. In other examples, external electrodes 480, 482 can be used to detect a total body impedance for the patient. If the patient's bioelectrical impedance decreases from a predetermined or baseline value, the urinary catheter 110 can be provided in the patient's urinary tract for providing renal negative pressure therapy for the patient. Once the urinary catheter 110 is in place, renal negative pressure therapy treatment could be provided for any suitable period of time sufficient for relieving fluid overload and/or reducing the patient's thoracic impedance. For example, renal negative pressure therapy could be provided to the patient for a period of time of about 12 hours to about 96 hours. After the renal negative pressure therapy is completed, the urinary catheter(s) could be removed. After removal of the urinary catheter 110, the patient's bioelectrical impedance measurements could continue to be monitored periodically (i.e., daily or every few days) to determine whether the patient would benefit from additional treatments of negative pressure therapy.

In some examples, as shown in the flowchart, a treatment method for a patient comprises, at step 508, obtaining a baseline value for bioelectrical impedance (i.e., thoracic impedance, total body impedance, or impedance of any other body region) for the patient from a bioelectrical impedance sensor 414, such as from an implantable medical device 460 implanted, for example, in a thoracic region of the patient. The method further comprises, at step 510, monitoring the bioelectrical impedance of the patient. As previously described, monitoring bioelectrical impedance can comprise, for example, applying electrical current (i.e., an electrical pulse having a current of a predetermined magnitude) from either an external electrode or an electrode of the implantable medical device 460 and measuring a voltage response with other external or implanted electrodes or sensors, such as with electrodes or sensors of the implantable medical device 460. The measured voltage can be divided by a magnitude of the applied current to determine bioelectrical impedance. As previously described, a measured thoracic impedance value can be an aggregate (i.e., a mean average value) of measured values for electrical pulses transmitted between different electrodes on the housing 462 and lead wires 472*a*, 472*b* of the implantable medical device 460. Signal(s) and/or data for the measured thoracic impedance can be transmitted from the implantable medical device 460 to the external portable computer device 426 by the wireless transmitter 466 of the implantable medical device 460. As previously described, the portable computer device 426 can comprise electronic circuitry, such as the system controller 424, for receiving and processing the signal(s) and/or data from the implantable medical device 460 for controlling other components of the system 400. Monitoring the bioelectrical impedance can comprise determining a bioelectrical impedance for the patient continuously or at predetermined intervals, such as once an hour, once every two hours, once every four hours, or once a day.

At step 512, the method further comprises determining if the patient's bioelectrical impedance is above, below, or at a predetermined value and/or is above, below, or at the baseline value for the patient. The predetermined value or, in other examples, a predetermined range of acceptable values can be determined based on normal values for a healthy patient (i.e., for a patient without worsening heart failure). The baseline value can be a value for bioelectrical impedance for the patient obtained, at step 508, when an impedance sensor 414 comprising external electrodes and/or an implantable medical device 460 is first used for the patient.

At step 514, the method can further comprise applying the negative pressure to the inflow member 112 of the urinary catheter 110 to remove fluid from the urinary tract of the patient when the patient's bioelectrical impedance is below the predetermined value or ceasing to apply the negative pressure when the patient's bioelectrical impedance is at or above the predetermined value. The negative pressure applied by the pump 128 through the inflow member 112 can also be based, at least in part, on patient information from other sensors, such as any of the previously described physiological, pump parameter, and/or environmental sensors. For example, the system controller 424 may be configured to receive sensor data indicating a negative pressure at the uretero-renal pelvis junction or renal pelvis and may modify operating parameters of the pump 128 based on the received pressure measurements from the renal pelvis. In other examples, operating parameters of the pump 128 could be modified based on, for example, patient urine output, a total amount of urine that has passed through the catheter and/or pump, analyte concentration of the collected urine, and/or trends in physiological parameters of the patient detected by the sensors.

In some examples, applying negative pressure therapy can comprise deploying the retention portion 118 of the inflow member 112 in the renal pelvis and/or kidney 2*a*, 2*b* of the patient. In some examples, the negative pressure is applied at a predetermined magnitude (i.e., a magnitude of from 10 mmHg to 150 mmHg) for a predetermined duration (i.e., one hour, two hours, or four hours). After the predetermined duration, the bioelectrical impedance can be detected again. If the detected bioelectrical impedance remains below the predetermined and/or baseline value, negative pressure can be applied again at the predetermined magnitude for the predetermined duration. If the detected bioelectrical impedance is above the predetermined value, then the method can comprise ceasing to apply the negative pressure for a predetermined duration.

In some examples, the system controller 424 can be configured to automatically modify the applied negative pressure in response to measured bioelectrical impedance values and/or in response to sensor measurements from other physiological, pump parameter, and/or environmental sensors of the system 400. In other examples, modification of negative pressure therapy can be performed manually by, for example, a medical professional or, in some instances, by the patient. For example, the user (either the trained medical professional or the patient) can review bioelectrical impedance measurements displayed on, for example, the visual display 446 of the external portable computer device 426. The user may determine when to turn-on or to turn-off the implanted pump 128 and/or to adjust a magnitude of the applied negative pressure based on the displayed measured values for bioelectrical impedance.

In some examples, the method further comprises, at step 516, continuing to monitor the bioelectrical impedance of the patient while negative pressure therapy is being provided. For example, continuing to monitor the bioelectrical impedance can including periodically receiving measurements for the patient's bioelectrical impedance at predetermined intervals. The method can further comprise, at step 518, increasing a magnitude of the negative pressure applied by the negative pressure source when the patient's bioelectrical impedance is below the predetermined and/or baseline value. For example, increasing the magnitude of the negative pressure can comprise increasing the magnitude of the pressure incrementally (i.e., by a predetermined about, such as 1.0 mmHg, 0.5 mmHg, or 0.1 mmHg) each time that a new measurement for bioelectrical impedance is received that is greater than the predetermined value.

At step 520, optionally, the method can further comprise a step of decreasing the magnitude of the negative pressure applied to the inflow member 112 of the urinary catheter 110 based on bioelectrical impedance measurements received from the external portable computer device 426 and/or pump 128. For example, the magnitude of the negative pressure may be reduced by a set amount (i.e., 1.0 mmHg, 0.5 mmHg, or 0.1 mmHg) each time that a measurement for bioelectrical impedance is received that is greater than the previously received bioelectrical impedance value, even if the measured value remains above the predetermined value (i.e., the predetermined target value for systolic or diastolic pressure). Reducing a magnitude of the applied negative pressure incrementally by small amounts may serve to reduce severity of a transition between applying negative pressure and when no pressure is applied.

At step 522, the method can further comprise a step of ceasing to apply negative pressure when a measured bioelectrical impedance for the patient increases above the predetermined or baseline value for the patient. For example, the system controller 424 can be configured to automatically turn off the pump 128 when the measured bioelectrical impedance for the patient is above the predetermined or baseline value. In other examples, a user may manually turn off the pump 128 to cease applying negative pressure to the urinary tract of the patient when a bioelectrical impedance value displayed, for example, on the visual display 446 of the external portable computer device 426 is above the predetermined or baseline value.

With continued reference to FIG. 5, removal of excess fluid from the patient by the negative pressure therapy system 400 and associated methods of the present disclosure can be enhanced by medication provided to the patient before, during, or after negative pressure therapy is applied to the urinary tract of the patient. For example, as shown at step 524, the method, optionally, further comprises administering at least one medicament to a patient. The medicament can be any of the previously described medications, therapeutic agents, and/or active agents having the effect of increasing urine output and/or sodium output from the patient. For example, the medicament can comprise a medicament known or expected to modulate electrolyte reabsorption, electrolyte excretion, and/or renal blood flow in the patient. Alternatively or in addition, the medicament can be a medicament known or expected to modulate renal blood flow. In still other examples, the medicament can be a medicament that modulates electrolyte reabsorption and/or electrolyte excretion in the patient.

As shown in FIG. 5, the medicament can be provided before, during, and/or after providing negative pressure therapy to the urinary system of the patient. In some examples, a decision to administer the medicament to the patient can be based on and/or modified in view of the bioelectrical impedance measurements received from the impedance sensor 414, such as thoracic impedance measurements from the implantable medical device 460. For example, medication may be provided when a patient's bioelectrical impedance is greater than a predetermined value. Medication may not be administered to the patient or an amount of medication provided to the patient or frequency with which medication is provided to the patient may be reduced when the patient's bioelectrical impedance is below the predetermined value.

Negative Pressure Therapy Pumps

As previously described, the negative pressure source can be an implantable pump. Implantable pumps that can be used with any of the previously described negative pressure therapy systems 100, 200, 400 of the present disclosure for providing negative pressure therapy to a patient will now be described in further detail.

Figure 6A:
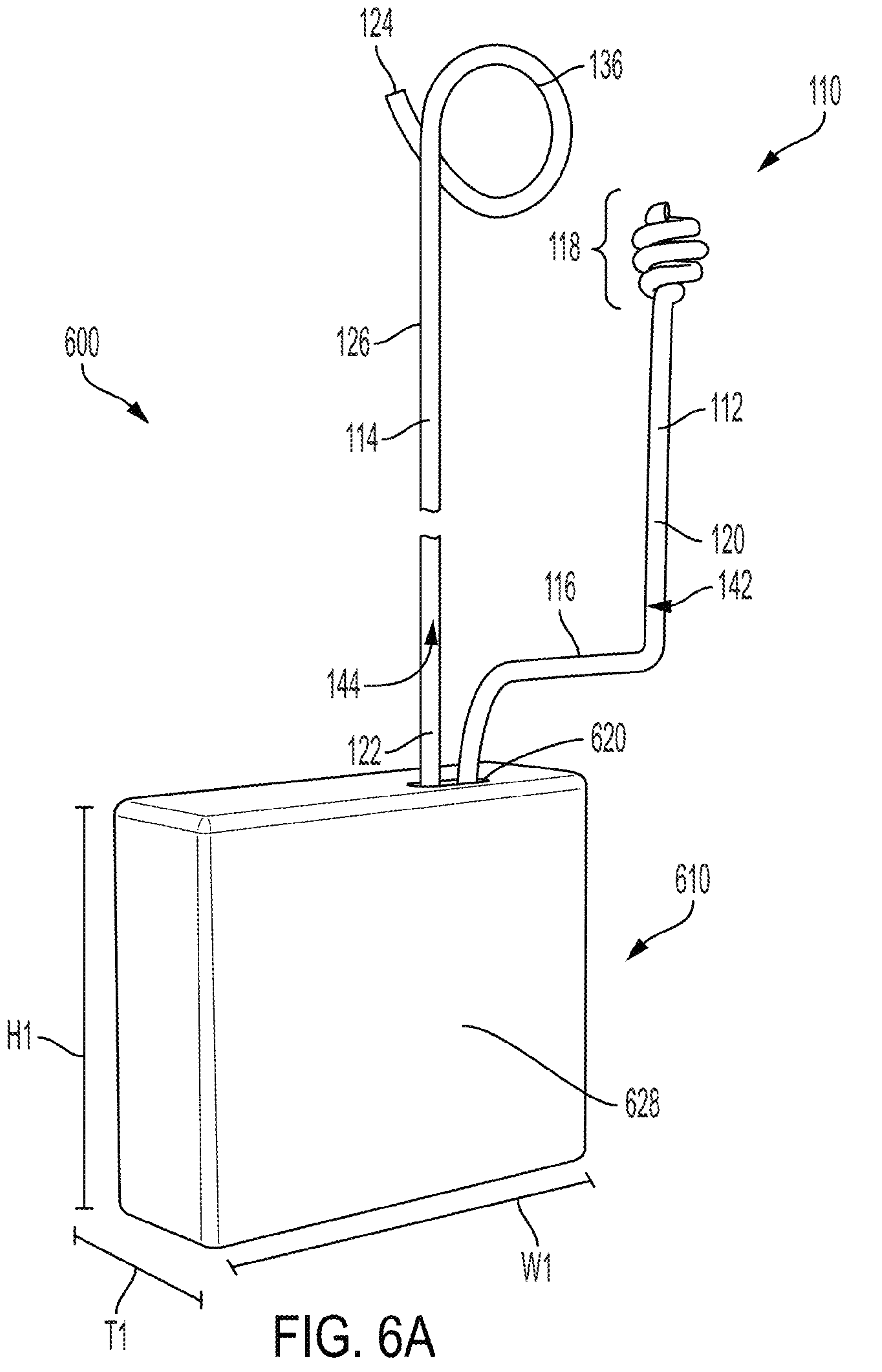
FIG. 6A is a perspective view of an implantable pump and a urinary catheter that can be used with the negative pressure therapy systems of the present disclosure.
Figure 6B:
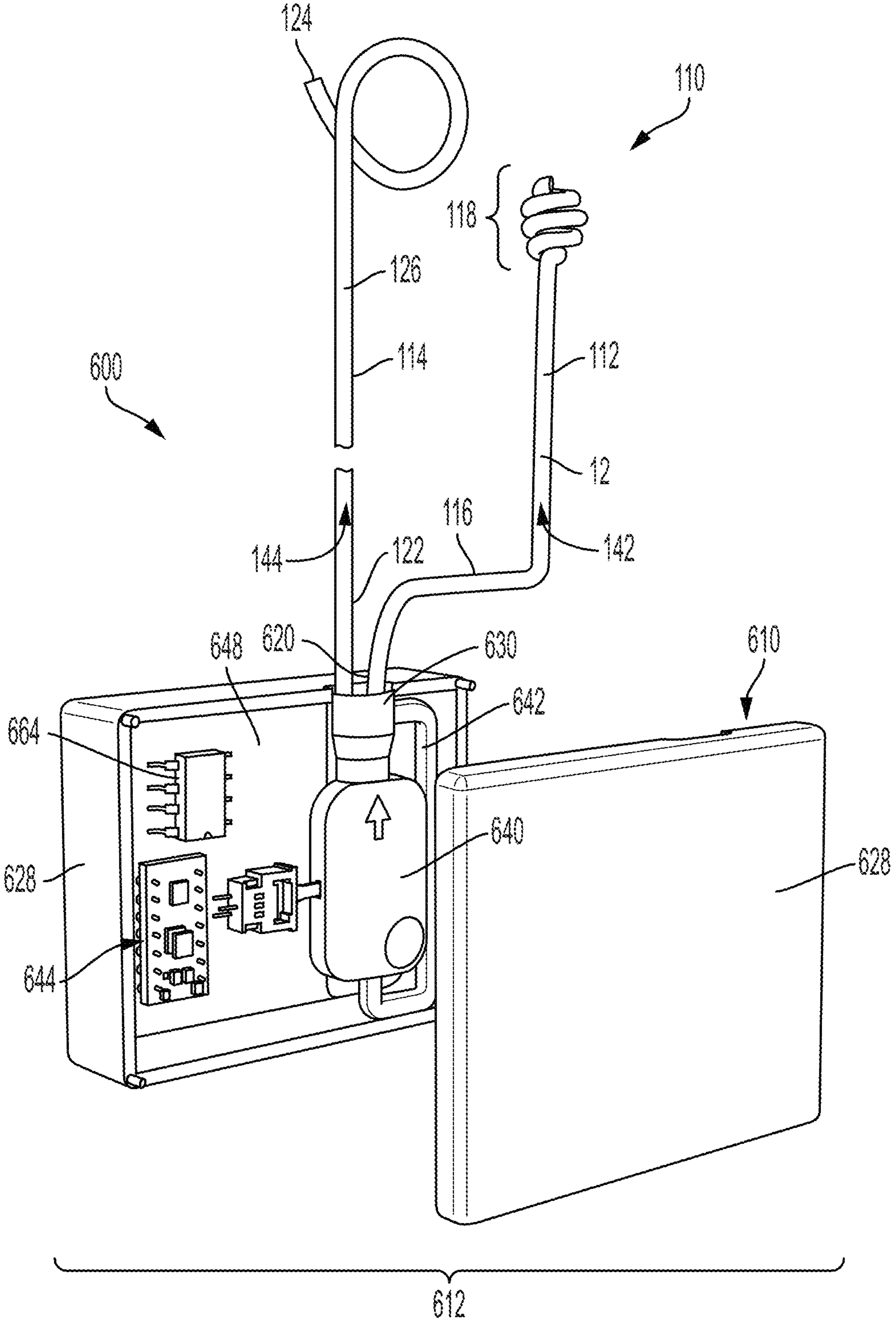
FIG. 6B is a perspective view of the implantable pump of FIG. 4A with a cover of the pump in an open position.
Figure 6C:
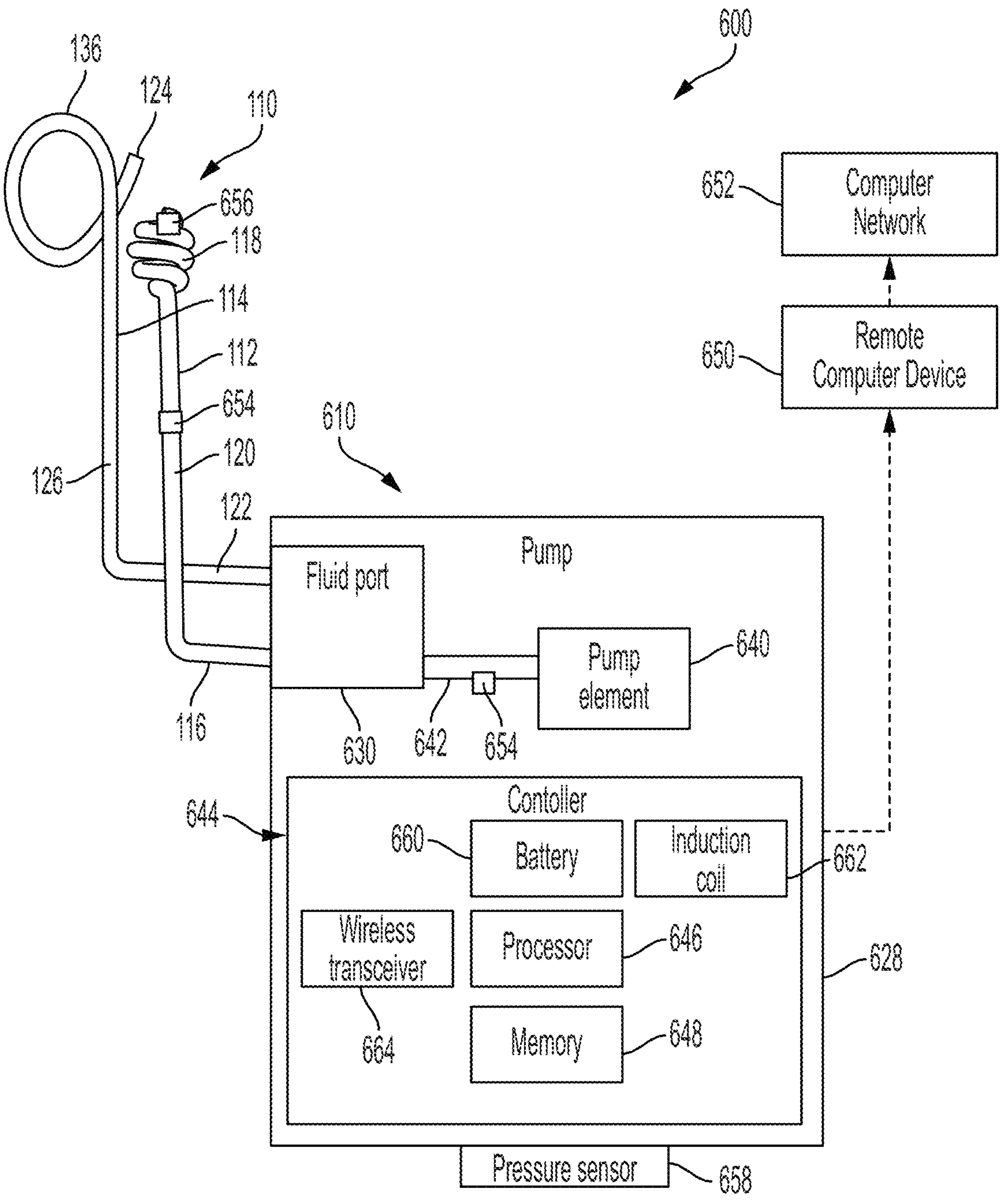
FIG. 6C is a schematic drawing of electrical components of the pump of FIGS. 6A and 6B, according to an example of the present disclosure.
Figure 7A:
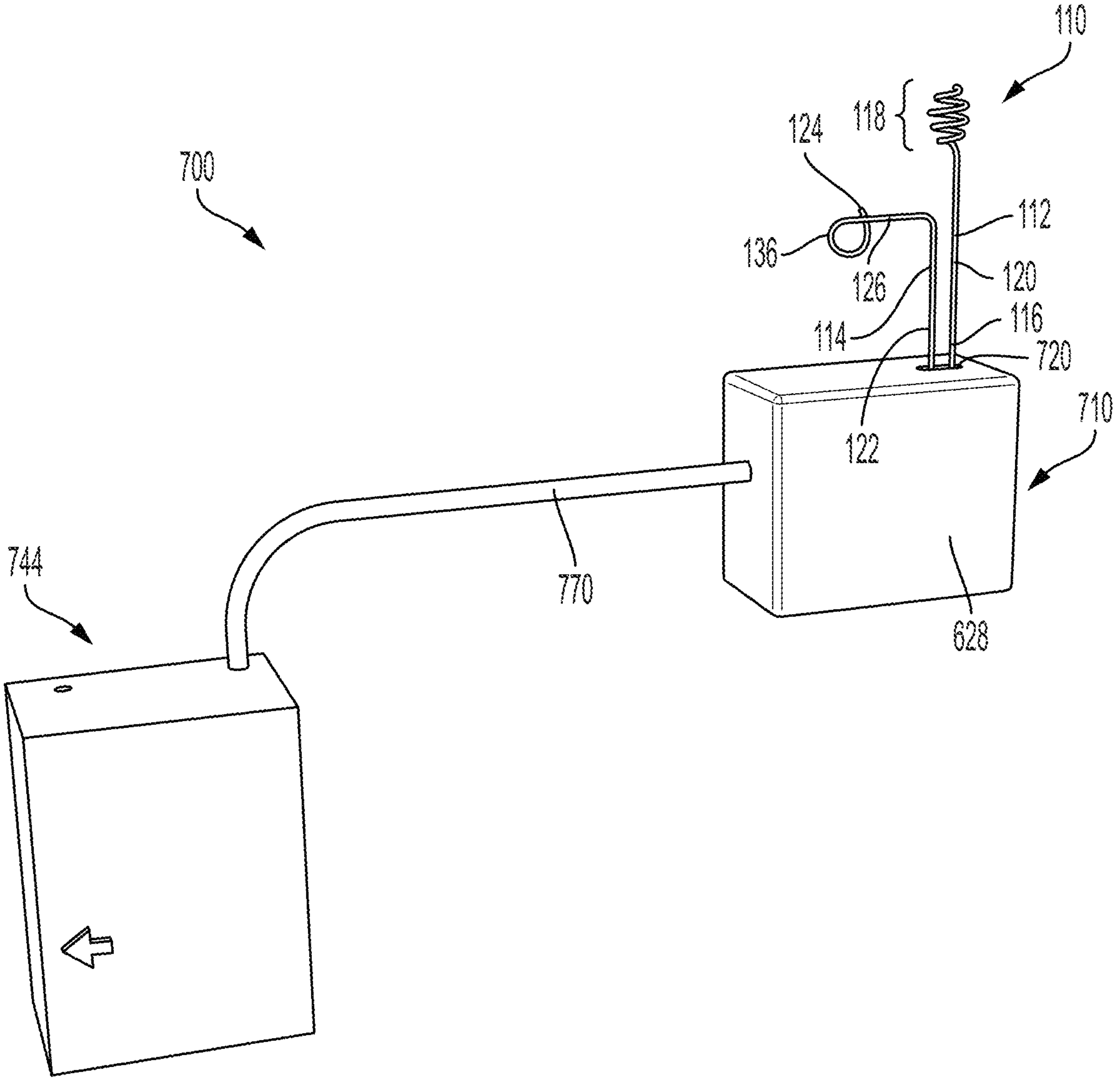
FIG. 7A is a perspective view of another example of an implantable pump and urinary catheter that can be used with the negative pressure therapy system of the present disclosure.
Figure 7B:
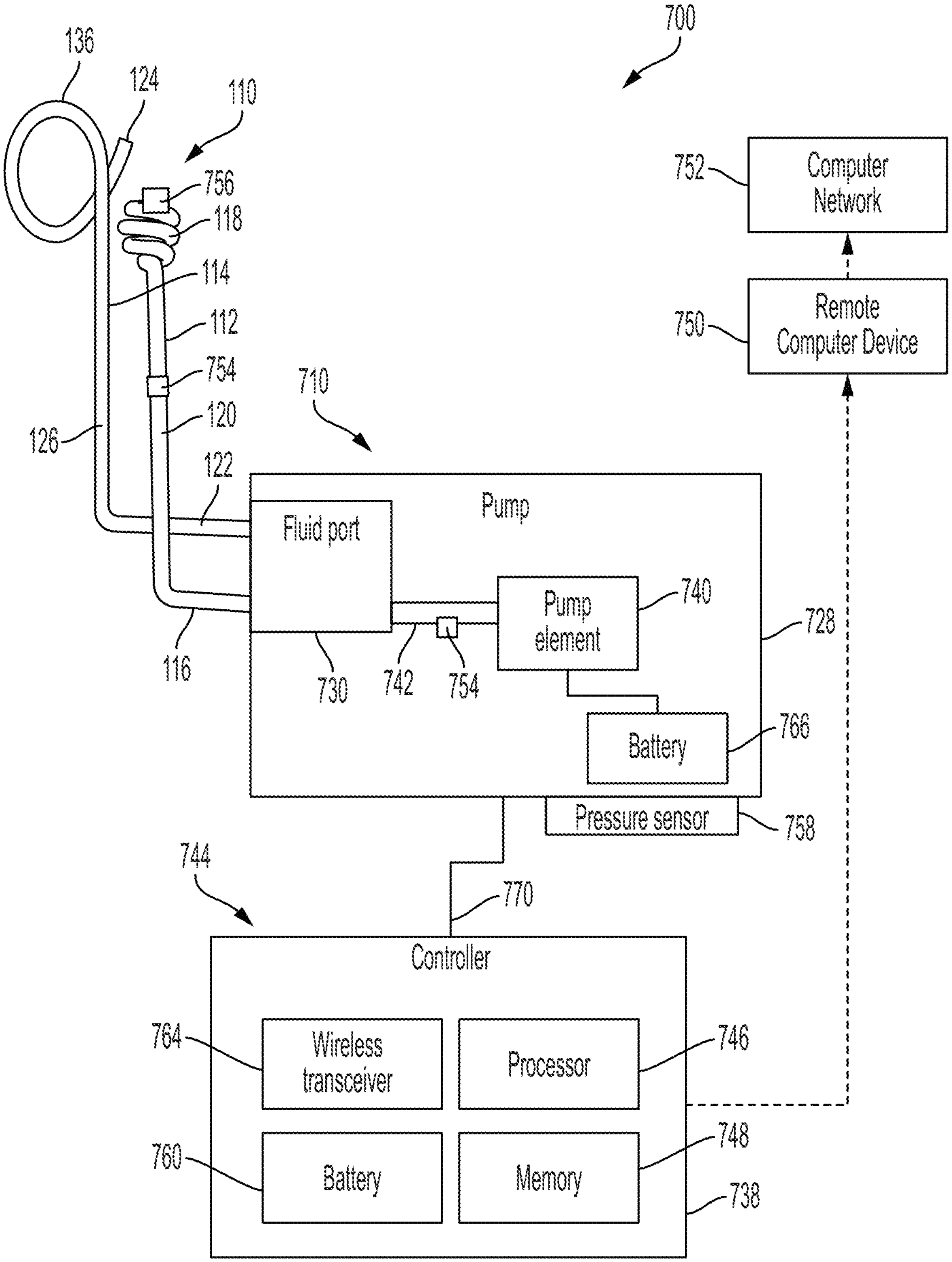
FIG. 7B is a schematic drawing of electrical components of the pump of FIG. 7A, according to an example of the present disclosure.

As previously described, the pumps of the present disclosure can be implantable pumps configured to be implanted outside of the urinary tract and within, for example, an abdominal cavity of the patient. More specifically, implantable pumps can be positioned, within the portions of the abdominal cavity, such as posterolateral to the kidney (shown in FIG. 11B), within the anterior abdomen (shown in FIGS. 1A, 2A, and 4A), posterolateral to the bladder wall (shown in FIG. 12), or at another convenient location within the abdominal cavity. In other examples, the implantable pump 128 can be a suitable size and shape to be inserted into the subcutaneous space or body cavity through an incision. In that case, the pump 128 can be sized to be secured within the subcutaneous space or body cavity by suturing portions of the pump 128 to body tissues using conventional suturing techniques, as are known in the art. As will be appreciated by those skilled in the art, conventional techniques for insertion and deployment of electronic implantable devices, such as implantable defibrillators and pacemakers, can be used for implanting the pump within the scope of the present disclosure. In some examples, the entire pump is implanted within the abdominal cavity (as shown in FIGS. 6A-6C). In other examples, fluid contacting portions of the pump can be implanted, while electrical and control portions of the pump can be external to the patient (as shown in FIGS. 7A and 7B). In some examples, a single implantable pump 128 can be connected to multiple urinary catheters 110, such as a first urinary catheter 110 implanted in a right kidney 2*a* of a patient and a left urinary catheter 110 in the left kidney 2*b* of the patient, as shown in FIG. 1A. In other examples, an implantable pump 128 can be only be connected to one urinary catheter 110, as shown in FIG. 12.

Implantable Pump and Urinary Catheter

FIGS. 6A-6C show a pump assembly 600 comprising a pump 610 and a urinary catheter 110 configured to provide negative pressure therapy to the kidney or renal pelvis of a patient. As in previous examples, the urinary catheter 110 comprises an inflow member 112 comprising the proximal portion 116, retention portion 118, and intermediate portion 120. The urinary catheter 110 also comprises an outflow member 114, which comprises a proximal portion 122, a distal end 124, and intermediate portion 126. As described in further detail herein, the distal end 124 of the outflow member 114 can comprise a retention portion 136, such as a pigtail coil, for retaining the distal end 124 of the outflow member 114 within the ureter or bladder.

The pump 610 comprises a housing 628 and fluid connectors, such as inlets, outlets, or port(s) 630 (shown in FIGS. 6B and 6C) accessible through one or more openings 620 in the housing 628. For example, both the inflow member 112 and the outflow member 114 can pass through a single oval shaped opening 620, as shown in FIG. 6A, to connect to the fluid port(s) 630 of the pump 610. In other examples, the housing 628 can comprise separate openings 620 for the inflow member 112 and the outflow member 114. The housing 628 can be formed from any suitable biocompatible material, which does not degrade when positioned in the body. Materials used for implantable cardiac devices, such implantable defibrillators and/or pacemakers, can be used for the housing 628. For example, the housing 628 can comprise stamped metals, such as stainless steel or titanium alloys. Alternatively or in addition, the housing 628 may comprise certain biocompatible rigid plastics, as are known in the art. The housing 628 can comprise rounded edges and/or curved surfaces, since hard edges and corners could irritate body tissues. In some examples, as shown in FIG. 6A, the housing 628 comprises a narrow box shaped structure having a height H1, a width W1, and narrower depth or thickness T1. In some examples, the height H1 and width W1 can each be about 45 mm to about 75 mm. The thickness T1 can be from about 5 mm to about 10 mm. In other examples, the housing 628 may be a substantially disc-shaped structure having opposing flat or substantially flat front and back sides connected by curved or rounded edges. The diameter of the disc-shaped housing can be about 25 mm to about 75 mm, and a thickness of the disc-shaped housing could be about 5 mm to 10 mm.

In some examples, the fluid port(s) 630 of the pump 610 are configured to connect to the proximal ends of the inflow member 112 and the outflow member 114 of the urinary catheter 110, thereby establishing fluid communication between a lumen 142 of the inflow member 112, a lumen 144 of the outflow member 114, and pumping components of the pump 610. The fluid port(s) 630 of the pump 610 can be sized to engage the ends of the inflow member 112 and the outflow member 114 and, accordingly, can have a diameter slightly larger than the external diameter of the inflow member 112 and the outflow member 114. In some examples, the pump 610 comprises a suction side inlet or port 630 for connecting to the proximal end of the inflow member 112 and a discharge side outlet or port 630 for connecting to the proximal end of the outflow member 114. In other examples, the pump 610 comprises a single fluid port 630 sized to receive the proximal ends of both the inflow member 112 and the outflow member 114 in, for example, a multi-lumen arrangements.

As shown in FIGS. 6B and 6C, the pump 610 comprises a pump chamber or pump element 640 fluidly connected to the fluid port(s) 630 via a conduit 642. The pump chamber or pump element 640 can comprise a rotodynamic pump and/or a positive displacement pump. As used herein, a "rotodynamic pump" refers to a pump mechanism configured to continuously impart kinetic energy to pumped fluid via a rotating pump element. The rotating pump element can comprise an impeller, turbine, propeller, screw, gear vane, rotor, or combinations thereof. A "positive displacement pump" refers to a pump element that moves fluid by trapping a fixed amount of fluid in a space and then forcing the trapped fluid through a discharge conduit or pipe. The pump chamber or element 640 for a positive displacement pump can comprise, for example, a reciprocating diaphragm. In some examples, the pump element 640 comprises a piezoelectric diaphragm pump. In other examples, the pump element 640 of the positive displacement pump comprises a peristaltic pump element.

The pump 610 further comprises the controller 644, which can be integral with the pump 610 and enclosed within the housing 628 of the pump 610. In other examples, the controller 644 can be an external controller connected to the pump 610 by a percutaneous wire (shown in FIGS. 7A and 7B) or wireless data connection.

As shown in FIG. 6C, the controller 644 can comprise the processor 646 and memory 648 configured to control operation of the pump 610. The controller 644 may further comprise a power source, such as a rechargeable battery 660 and/or induction coil 662 for providing power to the pump 610. The pump assembly 600 can further comprise sensors 654, 656, 658 electrically connected to the processor 646 and memory 648 of the controller 644. Specifically, the pump assembly 600 can comprise, for example, fluid sensors 654 positioned in the urinary catheter 110 and/or conduit 642, a retention portion probe 456, and an external pressure sensor 658. The controller 644 can be configured to receive and process information from the sensors 654, 656, 658 for controlling operation of the pump 610 and, in particular, for adjusting power output of the pump 610 to control a magnitude of negative pressure provided to the kidney and/or renal pelvis through the drainage lumen 142 of the inflow member 112 of the urinary catheter 110.

In some examples, the sensor 526 comprises a catheter probe or sensor 656 positioned near the retention portion 118 of the inflow member 112 configured to measure fluid pressure in the renal pelvis to determine a magnitude of negative pressure applied to the renal pelvis. The probe or sensor 656 can be electrically connected to the controller 644 and processor 646 by a wired connection extending through the inflow member 112 to the integrated controller 644 to provide feedback about operation of the pump 610.

In some examples, the sensor 658 comprises pressure sensors 658 positioned on external surfaces of components of the assembly for measuring pressure at various portions of the patient's body. For example, a pressure sensor 658 may be positioned on an exterior surface of the housing 628 of the pump 412, for a pump positioned in the abdominal cavity or peritoneum tissue. The pressure sensor 658 may be configured to detect intra-abdominal pressure of the patient as negative pressure therapy is provided to the patient.

The controller 644 can further comprise the wireless transceiver 664 (shown in FIGS. 6B and 6C). The wireless transceiver 664 can be configured to transmit information about the pump 610, the patient, and the negative pressure therapy provided to the patient determined by the sensors 654, 656, 658 to remote computer devices 650, computer networks 652, or the Internet. The wireless transceiver 664 can comprise a short-range transceiver, such as BLUETOOTH®, or a long range wireless transceiver. The wireless transceiver 664 can be configured to periodically or continuously transmit information from the controller 644 to the remote computer device 650 and/or computer network 652.

In some examples, the processor 646 and memory 648 of the controller 644 are configured to actuate the pump 610 by setting and/or adjusting operating parameters of the pump 610 in response to instructions stored on the memory 648 or received from an external source, such as the remote computer device 650 accessible over the computer network 652. The processor 646 and memory 648 can also be configured to control the pump chamber or element 640 based on feedback received from the sensors 654, 656, 658 of the pump assembly 600.

In some examples, the processor 646 and memory 648 are configured to receive and process information from the sensors 654, 656, 658 to determine parameters related to fluid flow and/or a condition of the patient. For example, information from fluid sensors 654 in the catheters 614, 616 and/or conduit 642 could be processed to determine flow rate or fluid pressure of fluid through the inflow member 112 of the urinary catheter 110 and/or fluid volume for urine drawn into the lumen 142 of the inflow member 112. Information from the retention portion probe 656 located on the retention portion 624 of the inflow member 112 could be used to determine negative pressure provided to the kidney or renal pelvis. Information from the pressure sensor 658 on the housing 628 could be used for determining the intra-abdominal pressure.

In some examples, the processor 646 and memory 648 of the controller 644 can be configured to control operating parameters of the pump 610 based on the determined fluid flow and patient parameters. For example, the processor 646 and memory 648 may be configured to adjust the pump 610 by reducing power supplied to the pump chamber or pump element 640 when a flow rate of fluid through the urinary catheter 110 or a magnitude of the negative pressure measured by the retention portion probe 656 is higher than an expected or threshold value, which can reduce the flow rate or flow volume for fluid drawn into the lumen 142 of the inflow member 112. Similarly, the processor 646 and memory 648 can be configured to adjust the pump 610 by increasing power for the pump chamber or pump element 640 when fluid flow through the inflow member 112 or magnitude of the negative pressure measured at the renal pelvis by the retention portion probe 656 is lower than expected or lower than a minimum threshold value to increase the flow rate and/or flow volume.

In some examples, operating parameters of the pump 610 can be determined based on measured physiological information about the patient, such as measured intra-abdominal pressure for the patient. It is believed that elevated intra-abdominal pressure can signify reduced renal function. In order to address elevated intra-abdominal pressure, the processor 646 and memory 648 can be configured to adjust the pump 610 by increasing power to the pump chamber or pump element 640 in order to increase a magnitude of negative pressure applied to the renal pelvis and kidneys. As discussed previously, increasing a magnitude of negative pressure applied to the renal pelvis and/or kidneys is expected to increase urine output, which is expected to reduce venous congestion and pressure. The processor 646 and memory 648 can be configured to cause the pump chamber or pump element 640 to continue to operate at an increased power until intra-abdominal pressure decreases below, for example, a target or threshold value.

Pump with Separate External Controller

FIGS. 7A and 7B show another example of an implantable pump assembly 700 comprising a pump 710 configured to be positioned in the patient's body, but outside of the urinary tract. As in previous examples, the pump assembly 700 comprises the urinary catheter 110 comprising the inflow member 112 and the outflow member 114 connected to the pump 710 through a fluid port 730. For example, the proximal portion 116 of the inflow member 112 can extend through an opening 720 in a housing 728 of the pump 710 and can be connected to a suction side inlet or port 730 of the pump 710. In a similar manner, a proximal portion 122 of the outflow member 114 can extend through a same or a different opening 720 in the housing 728 and can be connected to on the discharge side outlet or port 730 of the pump 710.

As shown in FIGS. 7A and 7B, the pump assembly 700 further comprises a separate controller 744 comprising a housing 738, which can contain control circuitry and/or a power supply for the pump 710. The separate controller 744 can be positioned at another location within the abdominal cavity from the pump 710, within the subcutaneous space, or outside of the patient's body. The external or remote controller 744 can be in wired or wireless communication with implanted portions of the pump assembly 700. For example, the pump 710 may receive power from an external power supply, such as a battery 760 in the controller 744, via a shielded percutaneous wire 770 extending between the pump 710 and the controller 744. By using a separate power supply, dimensions of the pump 710 can be minimized, because batteries or other power supply circuitry are not included in the housing 728 of the pump 710.

The urinary catheter 110 can be similar in shape and size to any of the previously described exemplary urinary catheters 110. As in previous examples, the urinary catheter 110 comprises the inflow member 112 and the outflow member 114. The inflow member 112 comprises the lumen 142 for conducting urine from the kidney and/or renal pelvis to the pump 710. As in previous examples, the outflow member 114 extends from the pump 710 to a drainage location for expelling collected fluid (e.g., urine) from the body. For example, the outflow member 114 can extend from the pump 710 to the ureter or bladder of the patient for discharging collected urine to the ureter or bladder. In that case, fluid (e.g., urine) expelled from the outflow member 114 can pass into the bladder and can naturally pass from the body through the urethra.

The pump assembly 700 further comprises the pump 710, which is configured to be implanted in the body. As in previous examples, the pump 710 is configured to provide or exert negative pressure to portions of the urinary tract through the lumen 142 of the inflow member 112. For example, when actuated, the pump 710 can exert negative pressure to the renal pelvis and kidney(s) to draw urine produced by the kidney(s) into the lumen 142 of the inflow member 112.

As shown in FIG. 7B, the controller 744 is enclosed within its own separate housing 738. In some examples, the controller 744 can be a hand-held computer device, such as a dedicated electronic device, smart phone, or computer tablet. In some examples, the controller 744 is worn by the patient in a holster, fanny pack, or pocket, so that it is held in place in close proximity to the pump 710, which is implanted in the body. As in the previous examples, the external controller 744 comprises the processor 746 and memory 748 configured to control operation of the pump 710. The controller 744 can be electrically connected to the pump 710 by the percutaneous shielded wire 770. The wire 770 extends from the controller 744, through a percutaneous access site, and to the pump 712. Beneficially, since the processing electronics and other components of the controller 744 are positioning in the housing 738 external to the patient, the pump 710 is smaller than in previous examples. Using a smaller pump 710 may make the device easier to implant and remove from the patient.

The processor 746 and memory 748 can transmit operating instructions from the controller 744 to the pump 710 via the wire 770. Also, the processor 746 and memory 748 can receive information about operation of the pump 710 via the wired connection 770. The controller 744 can also be electrically connected to sensors 754, 756 connected to the urinary catheter 110 or pump 710, such as the fluid sensors 754 positioned in the inflow member 112 of the urinary catheter 110 and/or in the conduit 742 between the fluid port 730 and the pump element 740, the retention portion probe 756, and the external pressure sensor 758 connected to the housing 728 of the pump 710. The external controller 744 further comprises the power source, such as the battery 760, for providing power to the pump 710 via the percutaneous wire 770. In some examples, the pump 710 can further comprise an auxiliary battery 766 configured to store power received via the wire 770 for operating the pump 710 and/or to allow the pump 710 to continue operating even when flow of electrical current from the controller 744 via the wire 770 is temporarily suspended.

The controller 744 may further comprise the wireless transceiver 764. As in previous examples, the wireless transceiver 764 can be configured to transmit information about the pump 710, patient, and negative pressure therapy received from the pump 710 and sensors 754, 756, 758 to remote computer devices 750, computer networks 752, or the Internet, as previously described. For example, the wireless transceiver 764 can transmit information from the controller 744 to a laptop computer or computer server, where it can be reviewed by users The wireless transceiver 764 generally comprises a long range wireless transceiver that periodically or continuously transmits information from the controller 744 to the remote computer devices or networks. In some examples, the wireless transceiver 764 is a WiFi transceiver that that transmits data to a computer network through a wireless gateway or router. In other examples, the wireless transceiver can be a cellular transceiver (e.g., a transceiver configured to transmit data via a 3G or 4G mobile network).

Urinary Catheters with Ureteral Retention Portions

Figure 9A:
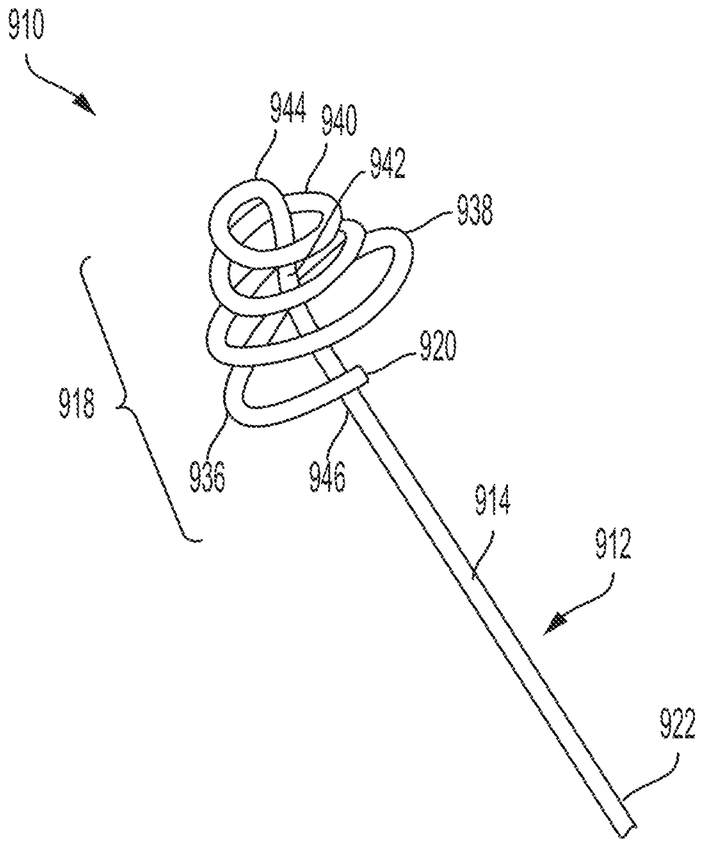
FIG. 9A is a perspective view of another exemplary inflow member of a urinary catheter, according to an example of the present disclosure.
Figure 9B:
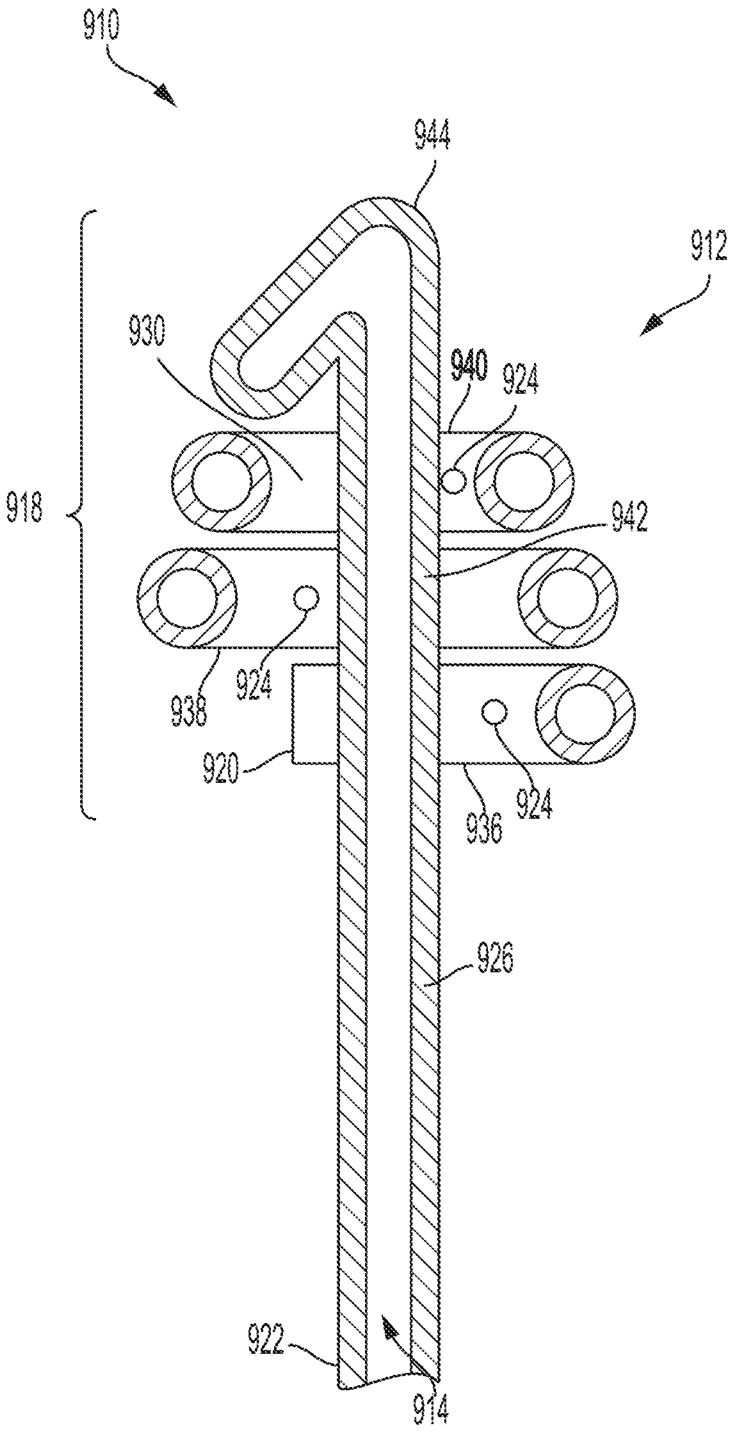
FIG. 9B is a cross-sectional view of the inflow member of the urinary catheter of FIG. 9A.
Figure 10A:
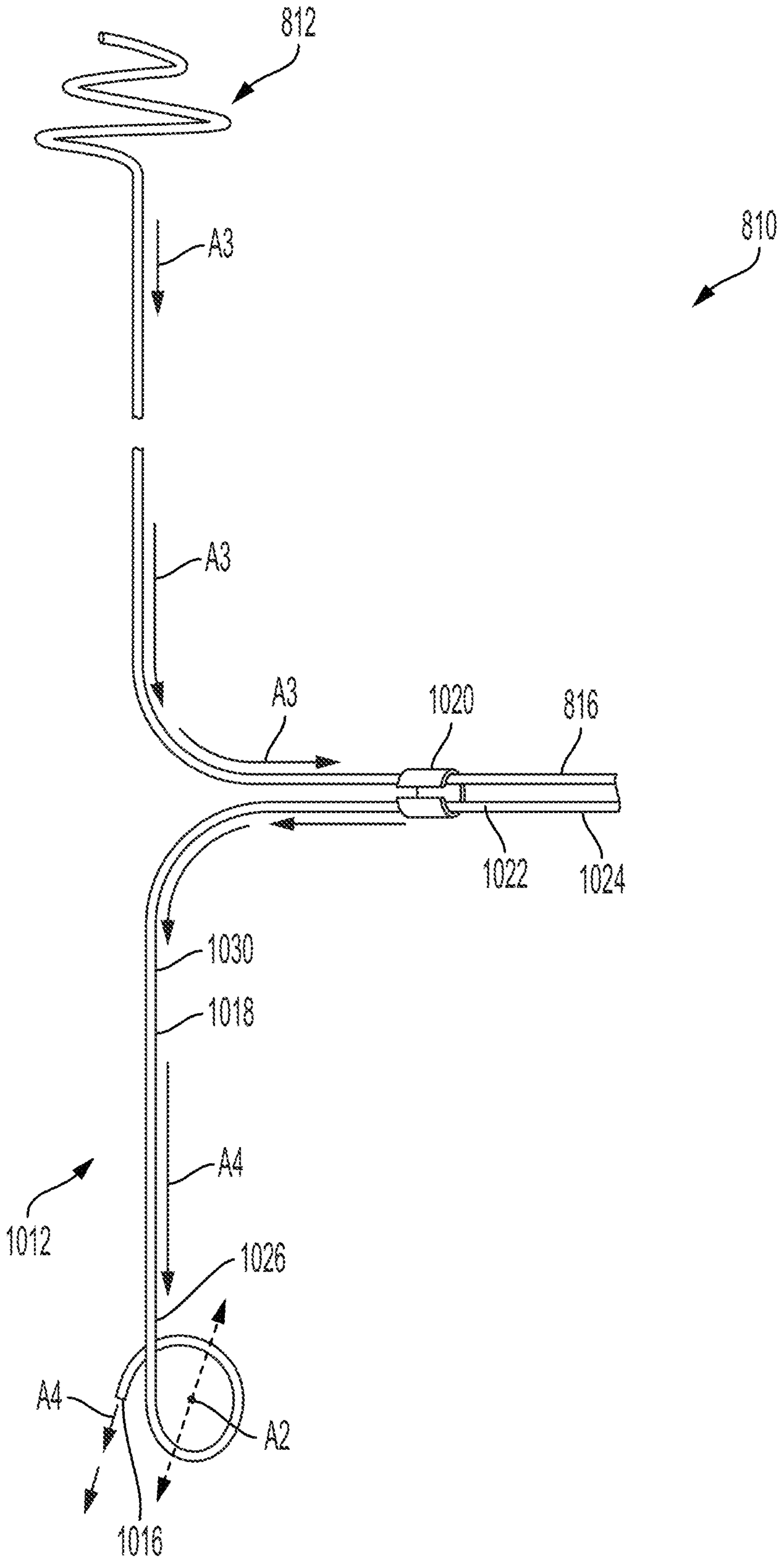
FIG. 10A is a schematic drawing showing a urinary catheter comprising an inflow member and an outflow member, according to an example of the present disclosure.
Figure 10B:
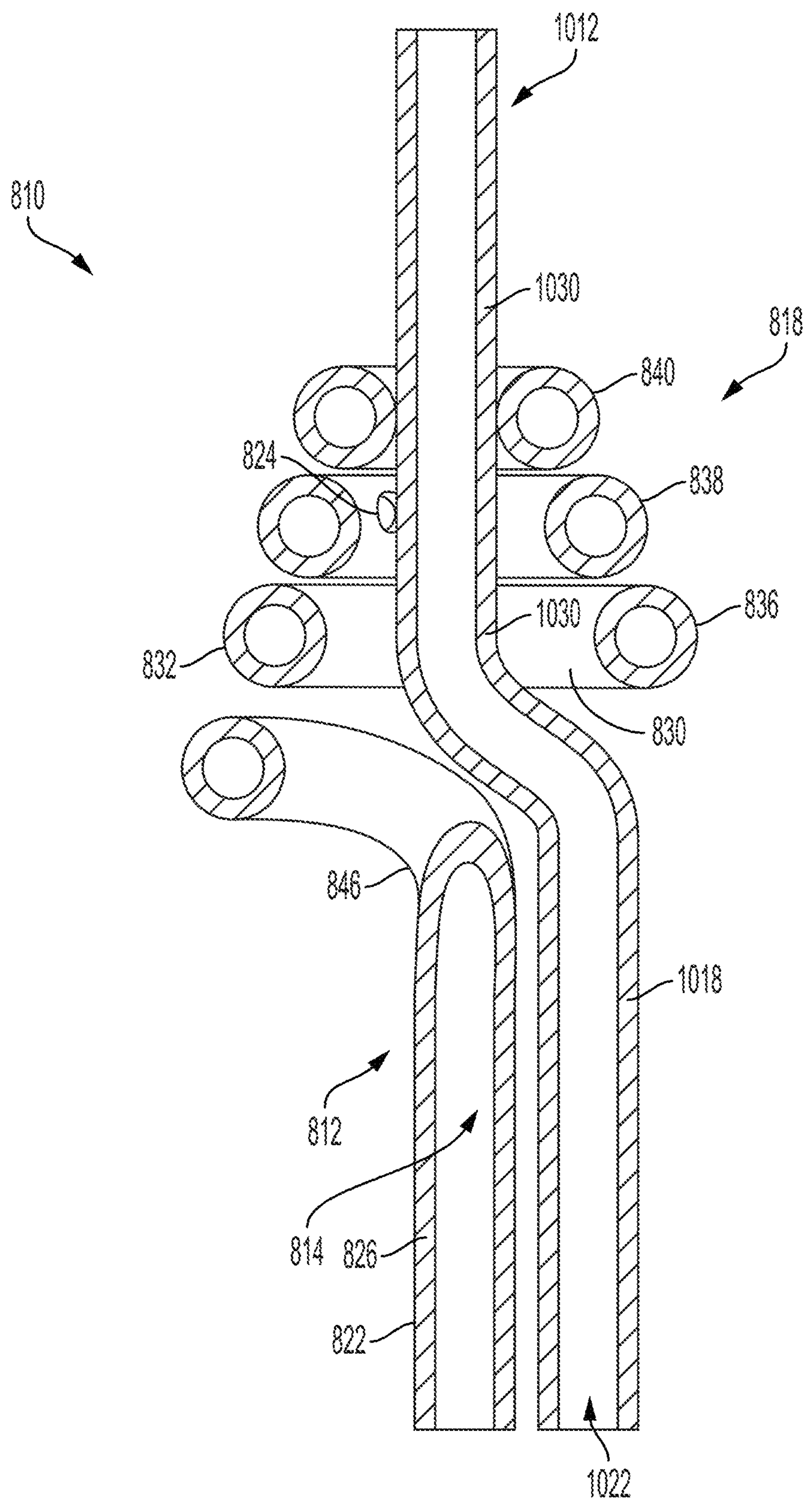
FIG. 10B is a schematic drawing of a cross-sectional view of the urinary catheter of FIG. 10A in a deployed configuration, with the outflow member extending through the inflow member, according to an example of the present disclosure.
Figure 10C:
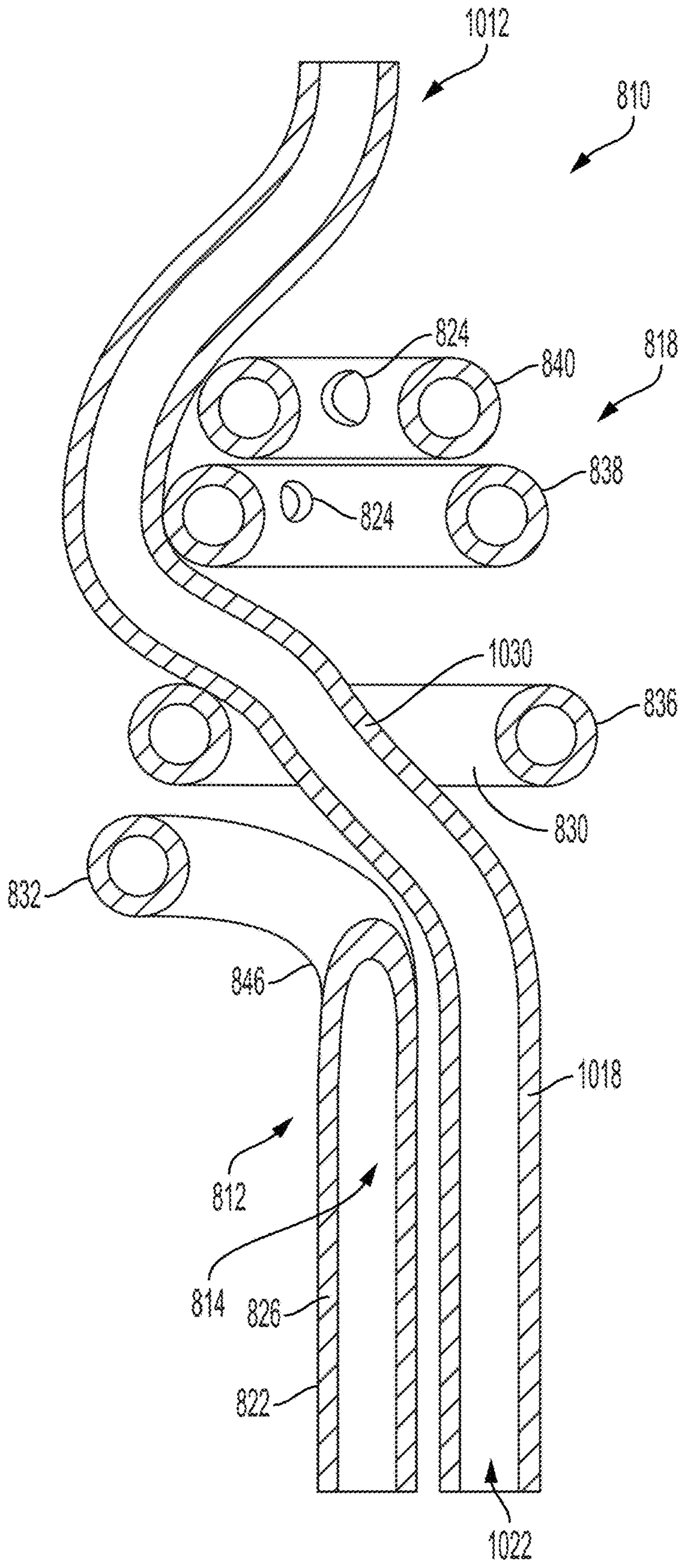
FIG. 10C is schematic drawing of a cross-sectional view of the urinary catheter of FIG. 10A in another exemplary deployed configuration, according to an example of the present disclosure.
Figure 10D:
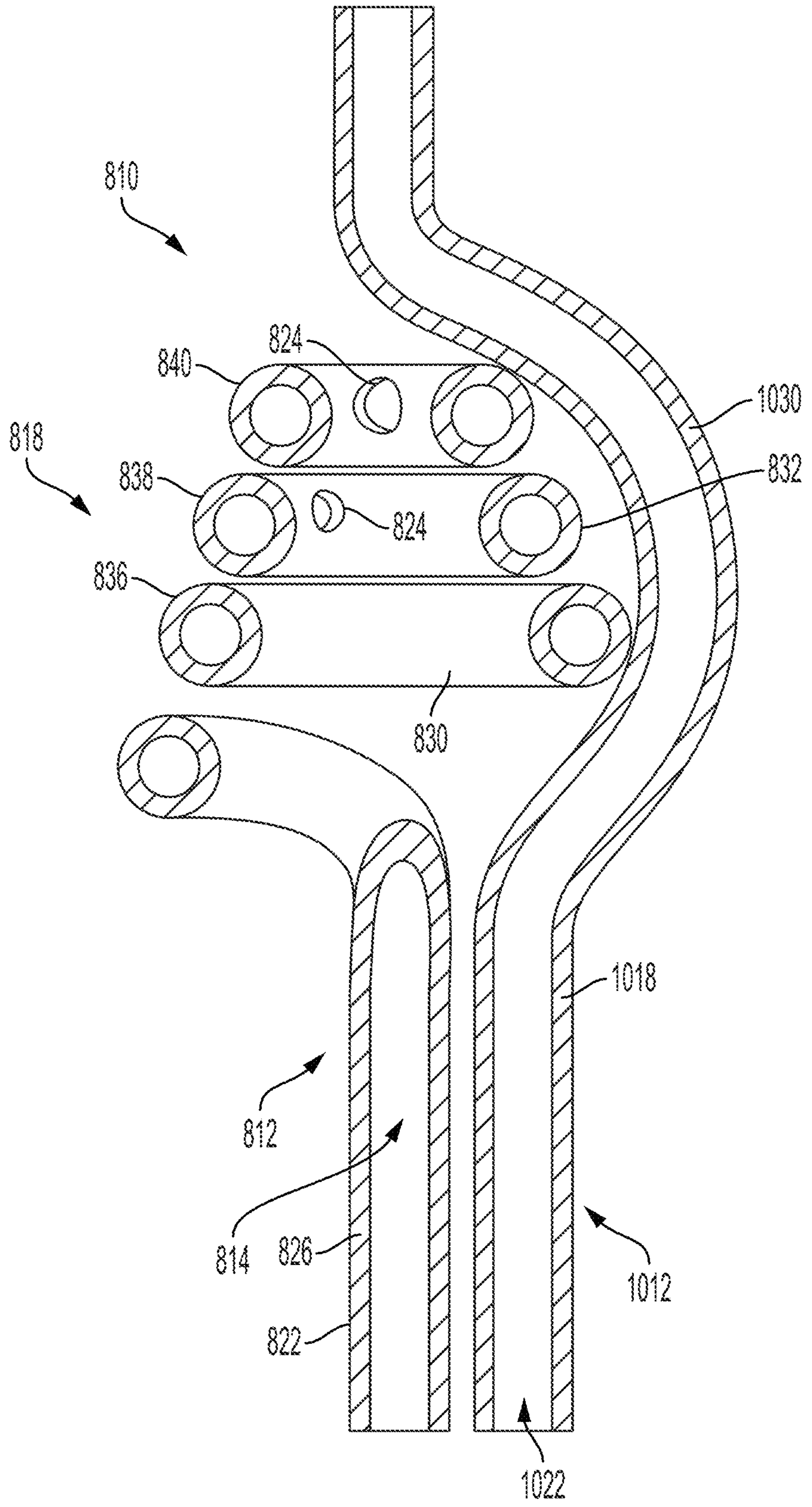
FIG. 10D is schematic drawing of a cross-sectional view of the urinary catheter of FIG. 10A in another exemplary deployed configuration, according to an example of the present disclosure.
Figure 10E:
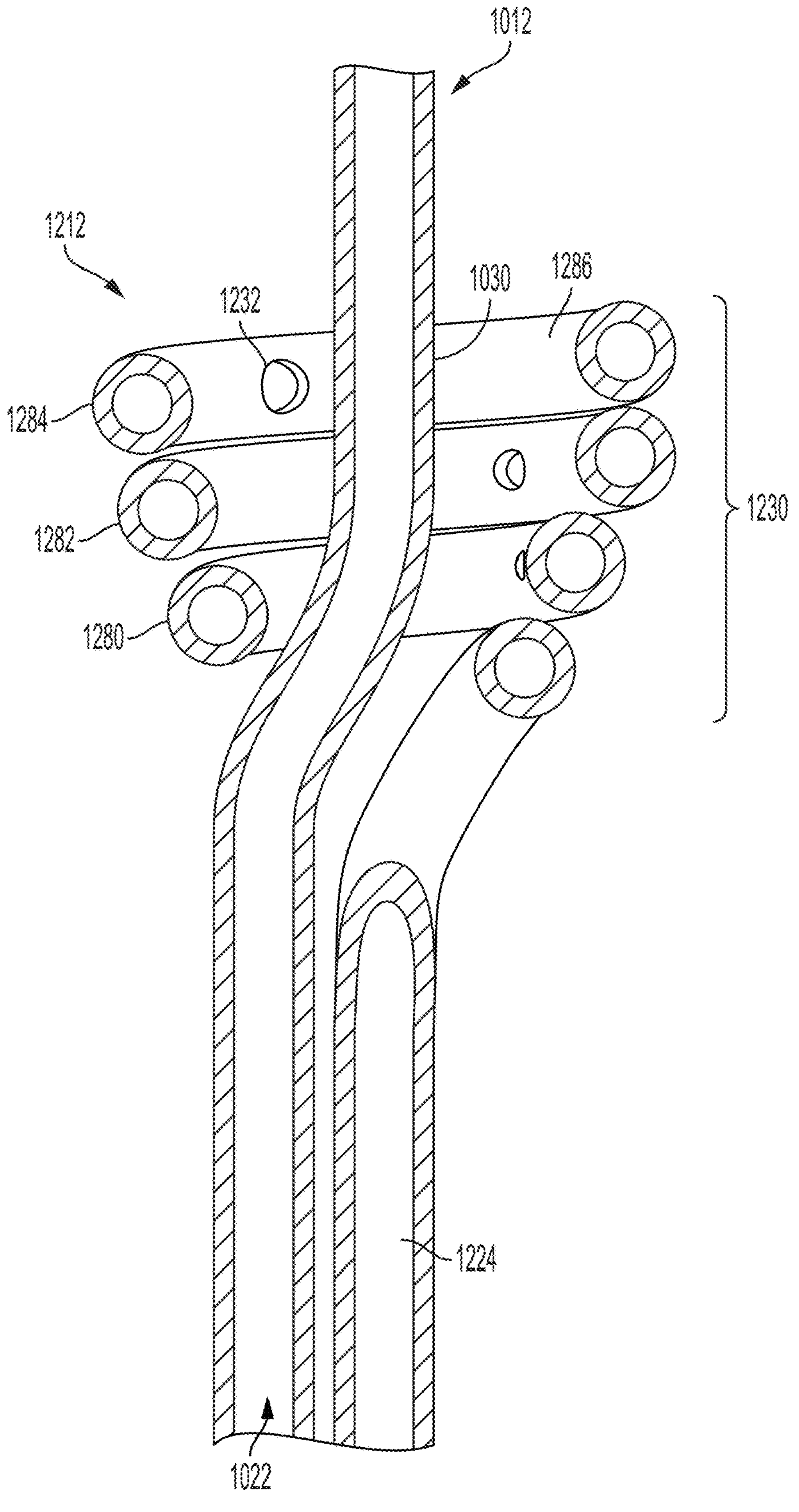
FIG. 10E is a schematic drawing of a cross-sectional view of another urinary catheter in a deployed configuration, with the outflow member extending through an inflow member, according to an example of the present disclosure.
Figure 10F:
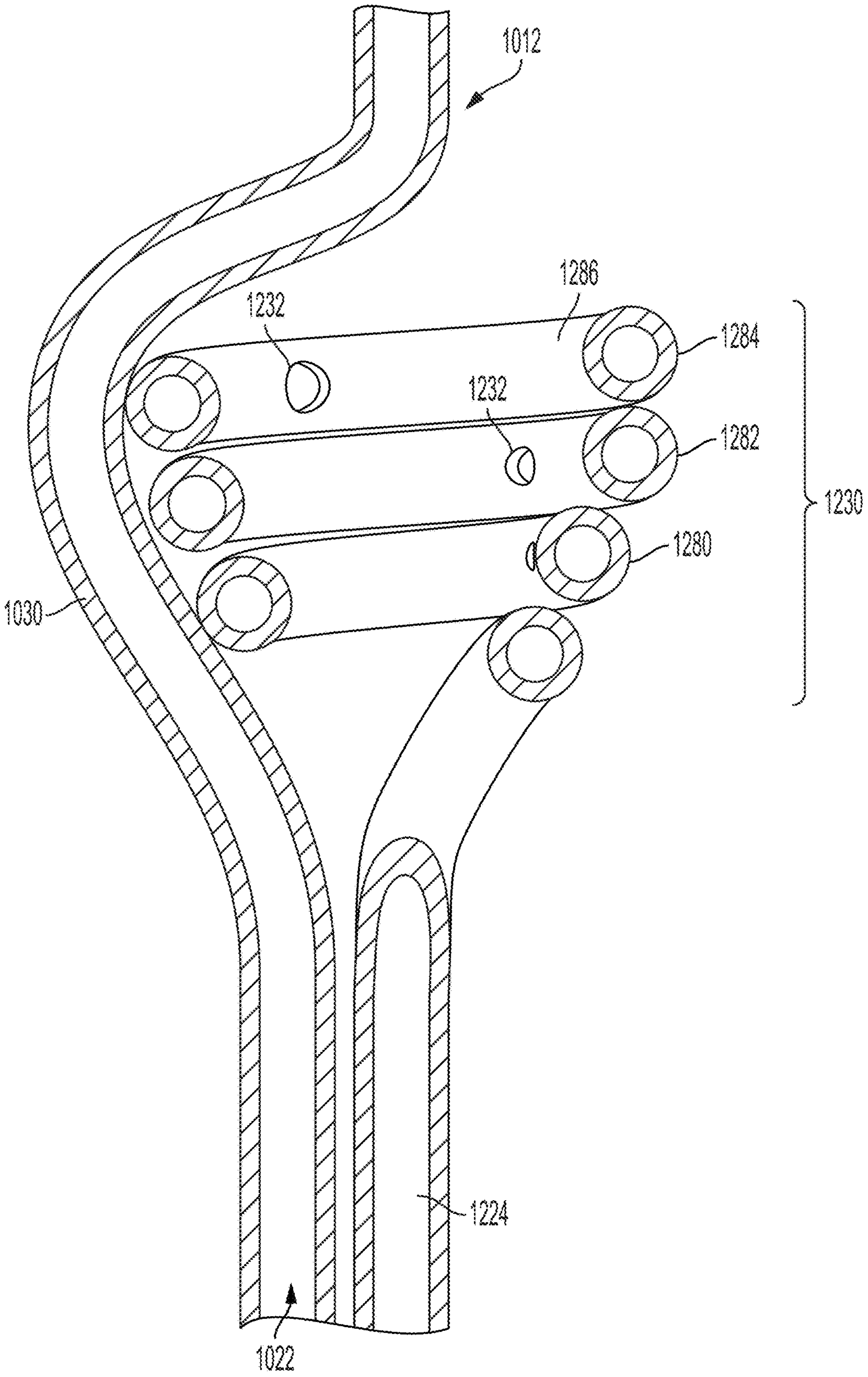
FIG. 10F is schematic drawing of a cross-sectional view of the urinary catheter of FIG. 10E in another exemplary deployed configuration, according to an example of the present disclosure.
Figure 11A:
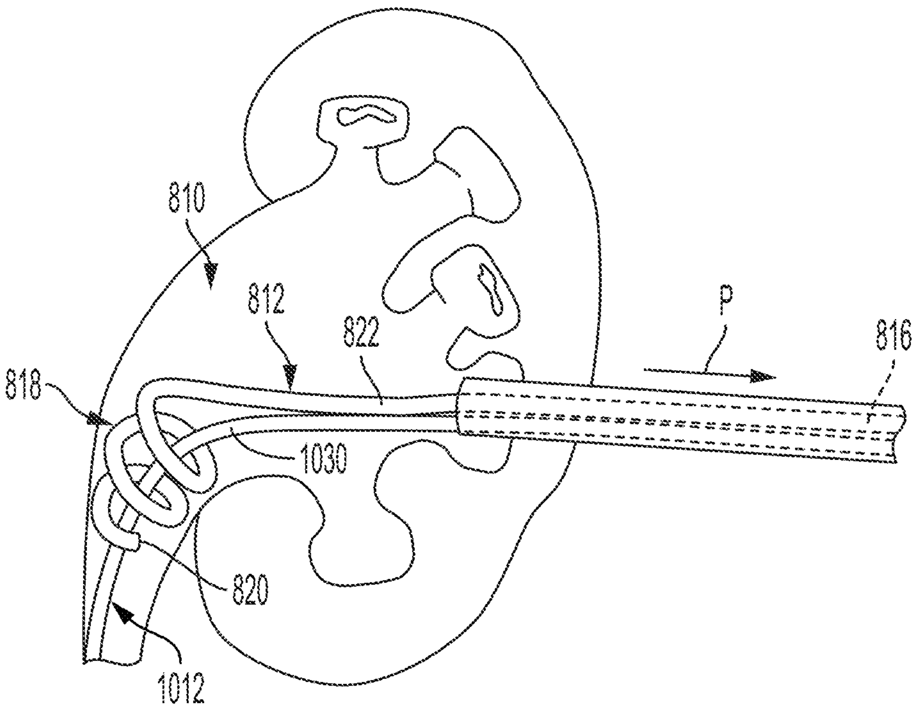
FIG. 11A is a schematic drawing showing an inflow member and an outflow member of a urinary catheter of FIG. 10A deployed within the urinary tract, according to an example of the present disclosure.

Examples of components of urinary catheters that can be used with the devices, systems, and methods of the present disclosure are shown in FIGS. 8A-12. Specifically, exemplary inflow members of the urinary catheter are shown in FIGS. 8A-9B. FIG. 10A shows an inflow member and an outflow member of the urinary catheter. FIGS. 10B and 10C show exemplary urinary catheters with the outflow member of the urinary catheter extending through a retention portion of the inflow member of the urinary catheter. FIGS. 11A-12 are schematic drawings showing portions of the inflow member and the outflow member of the urinary catheter deployed within the urinary tract of a patient. In particular, as shown in FIGS. 11A-12, the retention portion of the inflow member can be deployed within the renal pelvis and/or kidney of the urinary tract. A distal end or retention portion of the outflow member can be deployed in the ureter and/or bladder of the urinary tract.

As in previous examples, a urinary catheter 810 can comprise one or multiple separate or connected segments of an elongated tube defining inflow and/or outflow lumens. As previously described, the inflow and/or outflow lumens can comprise one or multiple passive or active flow control mechanisms, such as valves, flow restrictors, flow straighteners, pumps, and similar components, disposed in the lumens for controlling positive and/or negative pressure applied through the lumens of the urinary catheter 810. In particular, the urinary catheter 810 can comprise an inflow member 812 and an outflow member 1012 (shown in FIGS. 10A-10C). The members 812, 1012 can be formed from and/or can comprise one or more biocompatible polymer(s), such as polyurethane, polyvinyl chloride, polytetrafluoroethylene (PTFE), latex, silicone coated latex, silicone, polyglycolide or poly(glycolic acid) (PGA), Polylactide (PLA), Poly(lactide-co-glycolide), Polyhydroxyalkanoates, Polycaprolactone and/or Poly(propylene fumarate). Portions of the members 812, 1012 can also comprise and/or be impregnated with metal materials, such as copper, silver, gold, nickel-titanium alloy, stainless steel, and/or titanium.

Inflow Members of Urinary Catheters

Figure 8A:
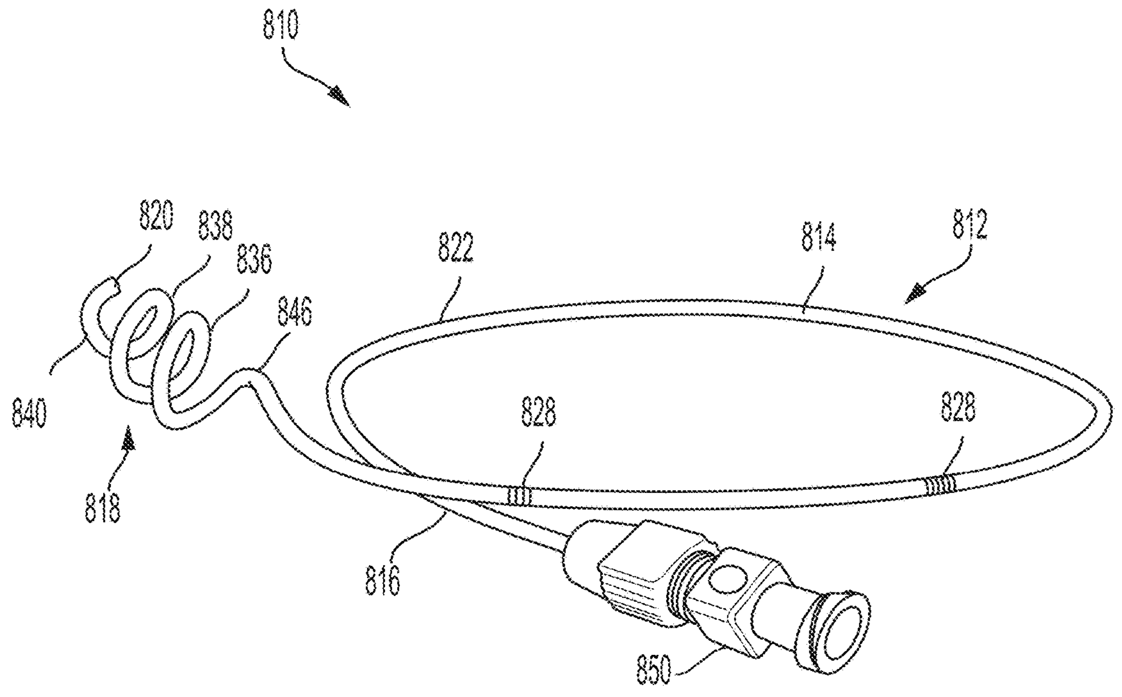
FIG. 8A is a perspective view of an inflow member of a urinary catheter, according to an example of the present disclosure.
Figure 8B:
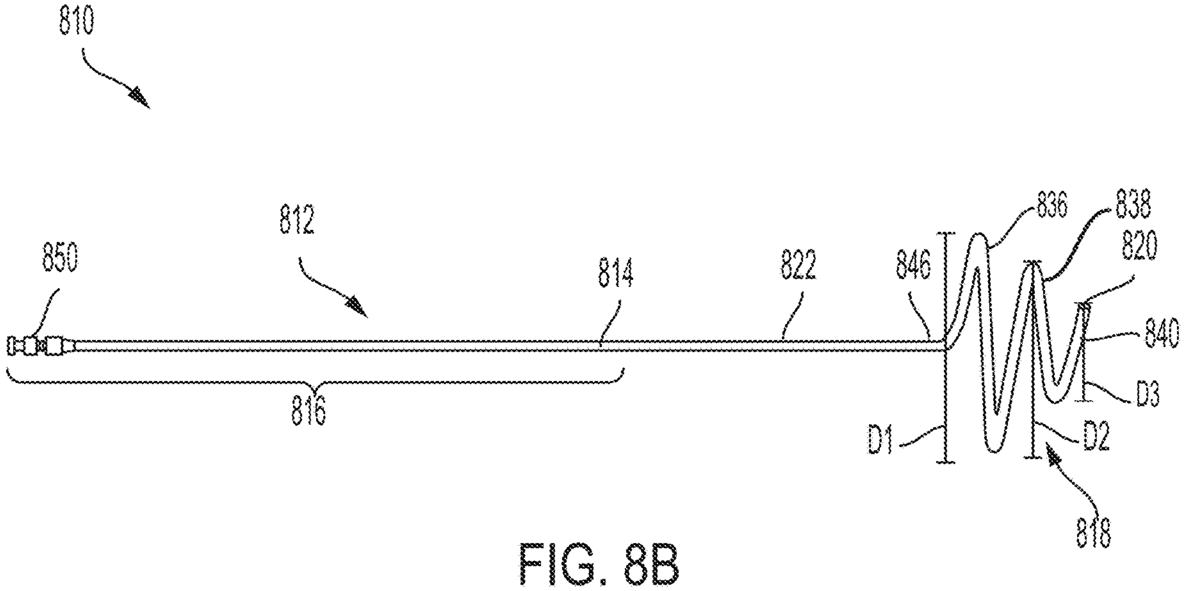
FIG. 8B is a front view of the inflow member of FIG. 8A, according to an example of the present disclosure.
Figure 8C:
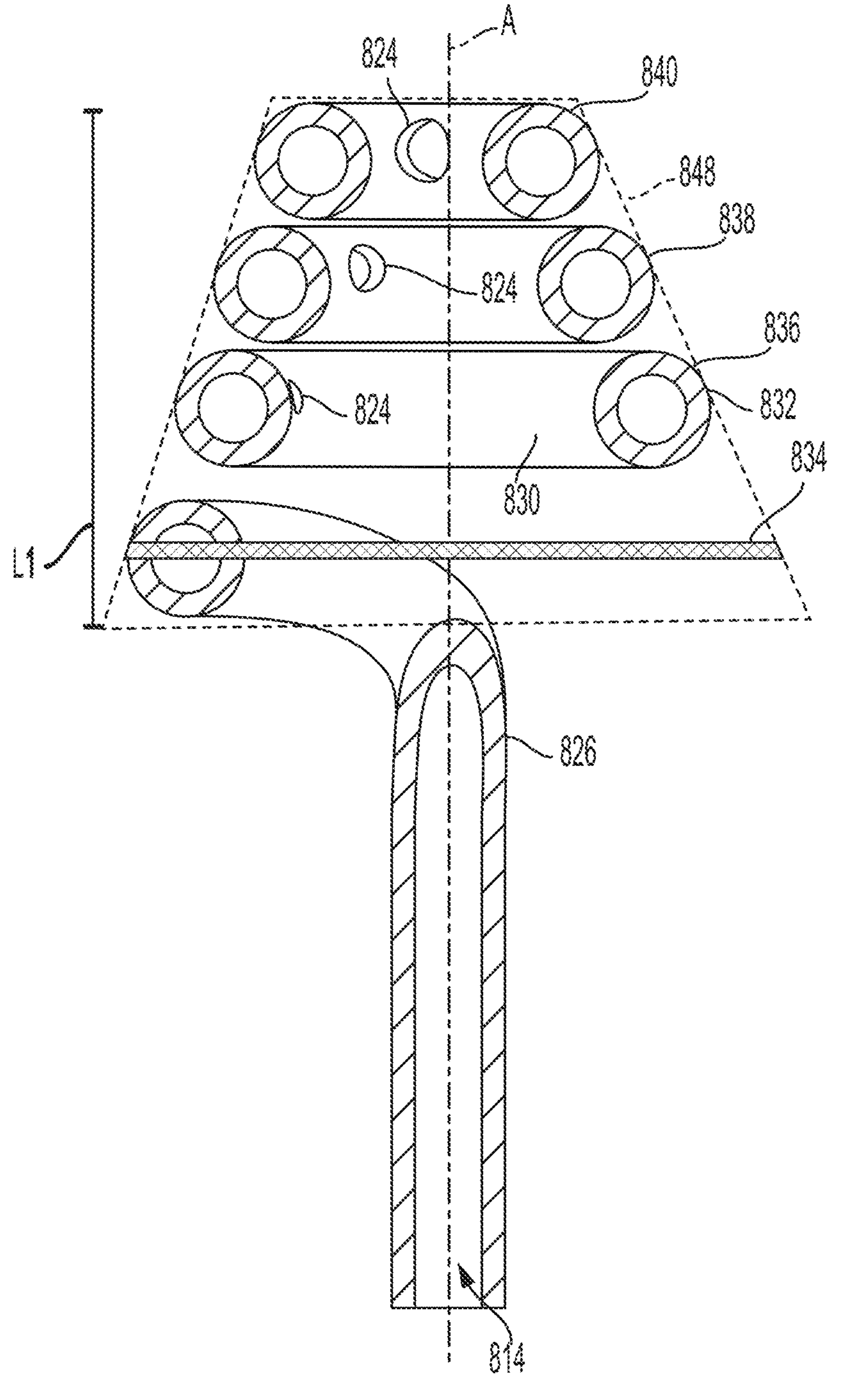
FIG. 8C is a cross-sectional view of the inflow member of FIG. 8A.

FIGS. 8A-8C show an exemplary inflow member 812 of a urinary catheter 810 configured for use with the negative pressure therapy devices, systems, and methods of the present disclosure. The inflow member 812 comprises, defines, or encloses an inflow lumen 814 configured to be in fluid communication with a negative pressure source, such as any of the previously described implanted or external pumps, such as implanted pumps configured to be positioned outside of the urinary tract. The inflow member 812 further comprises (i) a proximal portion 816, (ii) a retention portion 818 configured to be deployed within the kidney or renal pelvis of the urinary tract for retaining a distal end 820 or portion of the inflow member 812 within the kidney and/or renal pelvis, and (iii) an intermediate portion 822 between the proximal portion 816 and the retention portion 818. As previously described, the proximal portion 816 of the inflow member 812 can refer to the portion of the inflow member 812 extending from the negative pressure source through the abdominal cavity to, for example, a posterior or outer wall of the kidney. The retention portion 818 of the inflow member 812 can refer to the portion of the inflow member in the renal pelvis having a shape or structure that retains a distal end of the inflow member 812 in the renal pelvis. The intermediate portion 822 of the inflow member 812 can refer to portions of the inflow member 812 extending through the kidney and/or renal pelvis between the proximal portion 816 and the retention portion 818 of the inflow member 812.

The inflow member 812 should be of sufficient length to extend from the renal pelvis, through the kidney and, as shown in FIGS. 1A and 1B, to an implanted or external pump. For example, the inflow member 812 for an implanted pump can have a total length of about 10 cm to about 50 cm. The inflow member 812 for an external pump can have a total length of about 40 cm to about 60 cm. The retention portion 818 of the inflow member 812 can have a length L1 (shown in FIG. 8C) of about 15 mm to about 20 mm.

The diameter or size of the inflow member 812 can range from about 1 Fr to about 9 Fr (French catheter scale), or about 2 Fr to 8 Fr, or can be about 4 Fr. In some examples, the inflow member 812 can have an external diameter ranging from about 0.33 mm to about 3.0 mm, or about 0.66 mm to 2.33 mm, or about 1.0 mm to 2.0 mm, and an internal diameter ranging from about 0.165 mm to about 2.40 mm, or about 0.33 mm to 2.0 mm, or about 0.66 mm to about 1.66 mm.

In some examples, the proximal portion 816 of the inflow member 812 comprises a connector 850 at a proximal end of the inflow member 812 that is configured to be connected to the negative pressure source, such as the implanted or external pump. The connector 850 can comprise, for example, a luer connector, threaded connector, or a snap-fit connector for creating a fluid-tight seal between the connector 850 and the negative pressure source. When the connector 850 is connected to the negative pressure source, fluid flow from the lumen 814 of the inflow member 812 to the negative pressure source through the connector 850 can occur.

In some examples, the retention portion 818 of the inflow member 812 is configured to adopt an expanded configuration to retain portions of the inflow lumen 814 within the renal pelvis and/or kidney. For example, when deployed, a maximum outer diameter of the retention portion 818 of the inflow member 812 can be greater than a diameter of the inflow lumen 814. The retention portion 818 of the inflow member 812 further comprises one or more drainage holes 824 (shown in FIG. 8C), which can be an opening, port, perforation, or another space extending through a sidewall 826 of the retention portion 818, leading to the inflow lumen 814 of the inflow member 812. The drainage holes 824 can be configured such that, as negative pressure is applied through the inflow lumen 814 by the negative pressure source, fluid, such as urine, is drawn into the inflow lumen 814 through the drainage holes 824. The fluid passes through the inflow lumen 814 towards the negative pressure source.

In some examples, the retention portion 818 of the inflow member 812, when deployed, defines a three-dimensional shape 848 (shown in FIG. 8C) extending from the distal end 820 of the inflow member 812 to a proximal end 846 of the retention portion 818. The shape 848 of the retention portion 818 is sized and positioned to maintain patency of fluid flow between the kidney and/or renal pelvis and the proximal portion 816 of the inflow member 812. In particular, the retention portion 818 can be arranged or configured to inhibit mucosal tissue from appreciably occluding the drainage hole(s) 824 when the negative pressure is applied through the inflow member 812. In some examples, the three-dimensional shape 848 is a reverse conical shape or reverse frustoconical that resembles or matches a shape of the renal pelvis. In particular, a proximal end of the retention member 818 can be wider having a diameter matching a diameter of a portion of the renal pelvis proximate to the kidney. For example, a diameter of the proximal end of the retention portion 818 can be from about 10 mm to about 30 mm, or about 15 mm to 25 mm, or be about 20 mm. A distal end of the retention portion 818 can be narrower, having a diameter matching a portion of the renal pelvis that connects to the ureter. For example, a diameter of a distal end of the retention portion 818 can be from about 1 mm to 20 mm, or about 5 mm to 15 mm, or can be about 10 mm.

In some examples, the drainage hole(s) 824 or opening(s) of the inflow member 812 can be positioned anywhere along the sidewall 826 of the retention portion 818. For example, the drainage hole(s) 824 or openings can be uniformly positioned throughout the sidewall 826, or positioned in specified regions of the sidewall 826, such as closer to the distal end 820 of the inflow member 812 or closer to a proximal end of the retention portion 818. In other examples, drainage hole(s) 824 can be positioned as vertical, horizontal, or random groupings along a length or circumference of the sidewall 826 of the retention portion 818. The number of drainage hole(s) 824 or openings can vary from 1 to about 1000 or more, as desired. For example, in FIG. 8C, three openings or drainage holes 824 are shown. In some examples, each of the drainage holes 824 or opening can have an area which can be the same or different and can range from about 0.002 $mm^2$ to about 50 $mm^2$, or about 0.002 $mm^2$ to about 10 $mm^2$.

In some examples, the inflow member 812 further comprises one or more radiopaque bands 828 on the sidewall 826 of the inflow member 812. The radiopaque bands 828 can be positioned proximate to the retention portion 818 for identifying a location of the retention portion 818 using fluoroscopic imaging.

The retention portion 818 of the inflow member 812 can be integral with other portions of the inflow member 812 or can be a separate structure connected to the sidewall 826 of the inflow member 812 by an adhesive, fasteners, or other connectors, as are known in the art. The retention portions 818 disclosed herein can be formed from the same material as other portions of the inflow member 812. In other examples, retention portions 818 can be formed from a different material, such as a material having a different flexibility or stiffness than other portions of the inflow member 812, in order to impart desired mechanical properties for the retention portion 818. For example, the retention portion 818 can be formed from any of the aforementioned materials, for example a polymer such as polyurethane, flexible polyvinyl chloride, polytetrafluoroethylene (PTFE), latex, silicone, silicon, polyglycolide or poly(glycolic acid) (PGA), Polylactide (PLA), Poly(lactide-co-glycolide), Polyhydroxyalkanoates. Polycaprolactone and/or Poly(propylene fumarate).

In some examples, the retention portion 818 can be configured to be flexible and bendable to permit positioning of the retention portion 818 in the ureter and/or renal pelvis of the patient. The retention portion 818 is desirably sufficiently bendable to absorb forces exerted on the urinary catheter and to prevent such forces from being translated to the ureters. For example, if the retention portion 818 is pulled in the proximal direction P (shown in FIG. 11A) toward the kidney, the retention portion 818 can be sufficiently flexible to begin to unwind or be straightened so that it can be drawn through the ureter. Similarly, when reinserted into the renal pelvis or other suitable region within the kidney, the retention portion 818 can be biased to return to its deployed configuration.

In some examples, the retention portion 818 creates an outer periphery or protected surface area to prevent urinary tract tissues from constricting or occluding a fluid column extending between nephrons of the kidney and a lumen 814 of the inflow member 812. In some examples, the retention portion 818 may comprise an inwardly facing side or protected surface area 830 (shown in FIG. 8C) comprising the drainage hole(s) 824 for receiving fluid, such as urine, produced by the kidneys and an outwardly facing side or protective surface area 832, which can be free from or substantially free from the drainage holes 824. Desirably, the inwardly facing side or protected surface area 830 and the outwardly facing side or protective surface area 832 are configured such that, when negative pressure is applied through the inflow lumen 814, the urine is drawn into the lumen 814 through the one or more drainage holes 824, while mucosal tissues, such as tissue of the ureters and/or renal pelvis, are prevented from appreciably occluding the one or more drainage holes 824.

The retention portion 818 can have a variety of configurations and structures that retain portions of the inflow member 812 within the renal pelvis and/or kidney and protect the protected surface area 830 from mucosal tissues, such as pig tail coils, helical coils, funnels, umbrellas, baskets, axially and/or radially extending tines, expandable balloons, sponges, and other structures, as are known in the art. In some examples, the retention portion 818 comprises an expandable structure that transitions from a retracted state, when inserting or removing the catheter 810 from the patient, to an expanded or deployed state configured to anchor and retain the retention portion 818 in the renal pelvis and/or kidney. In order to sufficiently retain the inflow member 812 in the desired location within the urinary tract, in some examples, the retention portion 818, when deployed, defines the three-dimensional shape 848 sized and positioned to maintain patency of the fluid column flowing between the kidney and the proximal portion 816 of the inflow member 812. Further, desirably, at least a portion of the fluid produced by the kidneys flows through the retention portion 818 and lumen 814, rather than through the ureters. An area of two-dimensional slices 834 (shown in FIG. 8C) of the three-dimensional shape 848 defined by the deployed expandable retention portion 818 in a plane transverse to a central axis of the expandable retention portion 818 can decrease towards the distal end 820 of the expandable retention portion 818, giving the retention portion 818 the pyramid, trapezoidal, reverse conical or frustoconical shape. In some examples, a maximum cross-sectional area of the three-dimensional shape 848 defined by the deployed expandable retention portion 818 in a plane transverse to the central axis A (shown in FIG. 8C) of the expandable retention portion 818 is less than or equal to about 500 $mm^2$, or less than or equal to about 350 $mm^2$, or from 100 $mm^2$ to 500 $mm^2$, or from 200 $mm^2$ to 350 $mm^2$.

In some examples, the retention portion 818 comprises a coiled retention portion comprising an inverted helical coil. The coiled retention portion 818 can comprise a plurality of similarly sized coils or, for example, can comprise a plurality of proximal similarly sized coils and a distal-most coil having a smaller diameter than other coils of the plurality of coils. For example, the coiled retention portion 818 can comprise a plurality of helical coils 836, 838, 840 arranged such that an outer periphery or outer region of the helical coils 836, 838, 840 contacts and supports tissues of the kidney and/or renal pelvis to inhibit occlusion or blockage of protected drainage holes 824, ports, or perforations positioned in inwardly facing sides or protected surface areas 830 of the helical coils 836, 838, 840.

More specifically, in some examples, the retention portion 818 of the inflow member 812 comprises a proximal-most or first coil 836 having a first diameter D1 (shown in FIG. 8B) and a second coil 838 having a second diameter D2 (shown in FIG. 8B), which is smaller than the first diameter D1. In some examples, the retention portion 818 comprises more than two coils, such as three coils, four coils, five coils, or more coils. For example, as shown in FIGS. 8A-8C, the retention portion 818 further comprises a third or distal-most coil 840 with a smaller diameter D3 (shown in FIG. 8B) than other coils 836, 838 of the plurality of coils 836, 838, 840. A diameter of the coils 836, 838, 840, and/or a step distance or height between adjacent coils 836, 838, 840 can vary in a regular or irregular manner.

In some examples, the diameter of the coils 836, 838, 840 and step distance or height between adjacent coils is selected so that the retention portion 818 remains in the renal pelvis and/or kidney for a desired period of time. In particular, the coiled retention portion 818 is desirably large enough so that it remains in the renal pelvis and does not pass from the renal pelvis through the kidney until the inflow member 812 is ready to be removed. For example, the outer diameter D1 of the proximal most or first coil 836 can range from about 10 mm to about 30 mm, or about 15 mm to 25 mm, or be about 20 mm. The diameter D2 of the second can about 5 mm to 25 mm, or about 10 mm to 20 mm, or can be about 15 mm. The diameter D3 of the distal-most or third coil 8040 can range from about 1 mm to 20 mm, or about 5 mm to 15 mm, or can be about 10 mm.

In some examples, the retention portion 818 of the inflow member 812 can further comprise one or more mechanical stimulation devices (not shown) for providing stimulation to nerves and muscle fibers in adjacent tissues of the ureter(s) and renal pelvis. For example, the mechanical stimulation devices can comprise linear or annular actuators embedded in or mounted adjacent to portions of the sidewall 826 of the inflow member 812 and configured to emit low levels of vibration. In some examples, mechanical stimulation can be provided to portions of the ureters and/or renal pelvis to supplement or modify therapeutic effects obtained by application of negative pressure. While not intending to be bound by theory, it is believed that such stimulation affects adjacent tissues by, for example, stimulating nerves and/or actuating peristaltic muscles associated with the ureter(s) and/or renal pelvis. Stimulation of nerves and activation of muscles may produce changes in pressure gradients or pressure levels in surrounding tissues and organs which may contribute to or, in some cases, enhance therapeutic benefits of negative pressure therapy.

Other Examples of Inflow Members for Urinary Catheters

Figure 8D:
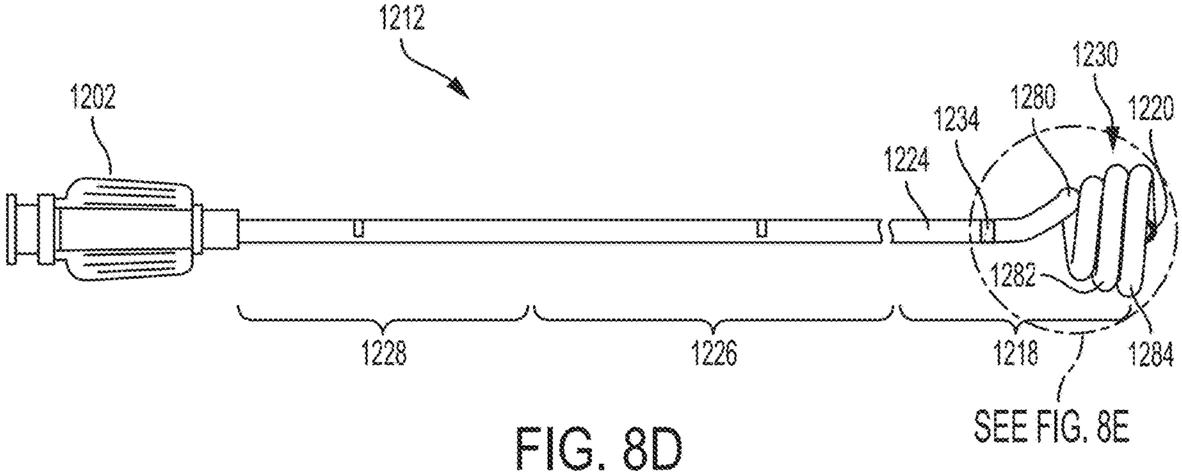
FIG. 8D is a perspective view of an inflow member of a urinary catheter, according to an example of the present disclosure.
Figure 8E:
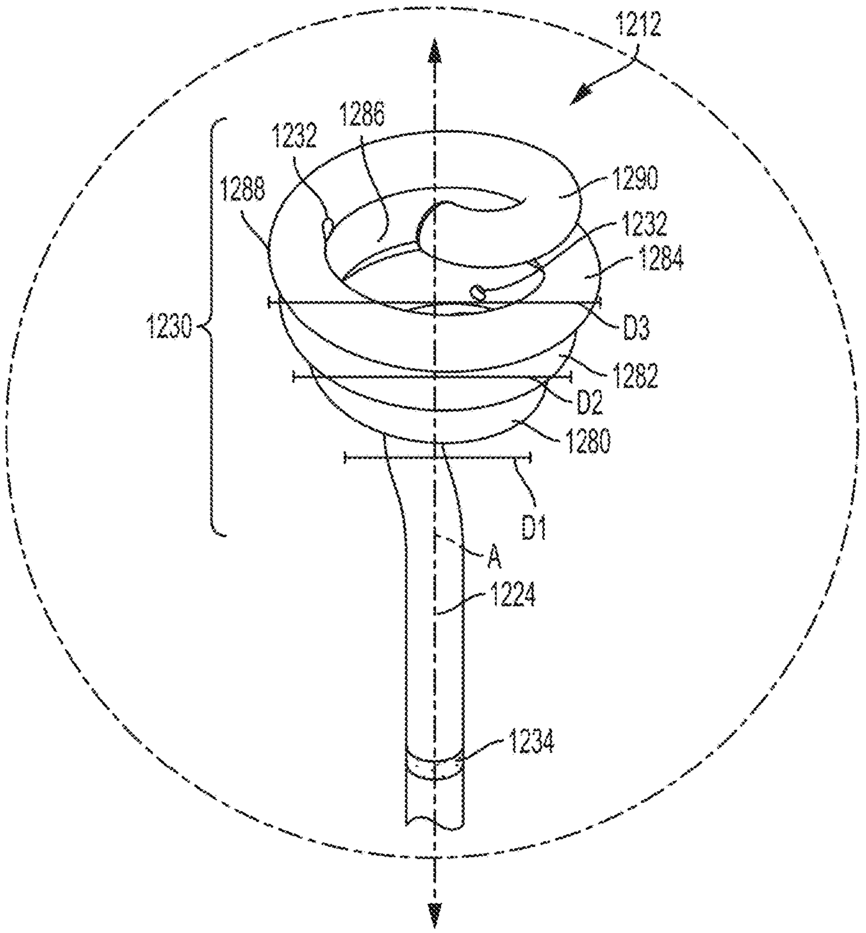
FIG. 8E is a perspective view of a retention portion of the inflow member of FIG. 8D.
Figure 8F:
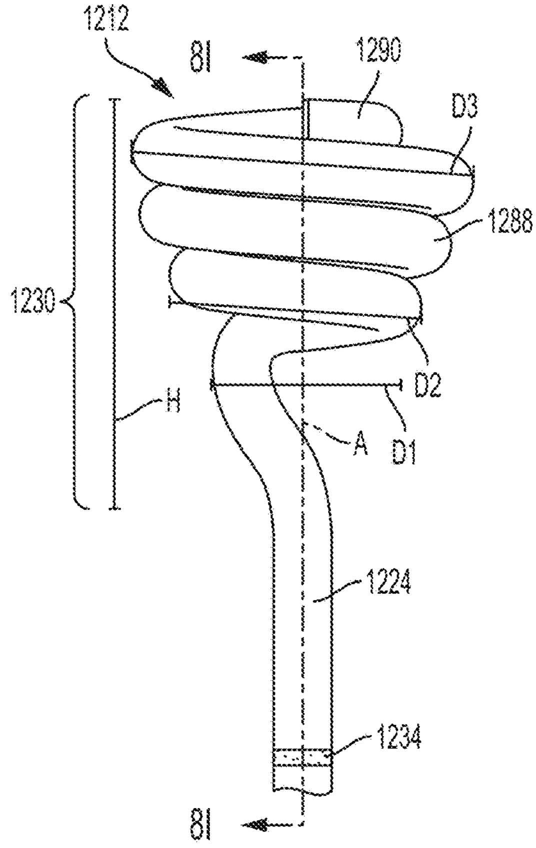
FIG. 8F is a front view of the retention portion of the inflow member of FIG. 8D.
Figure 8G:
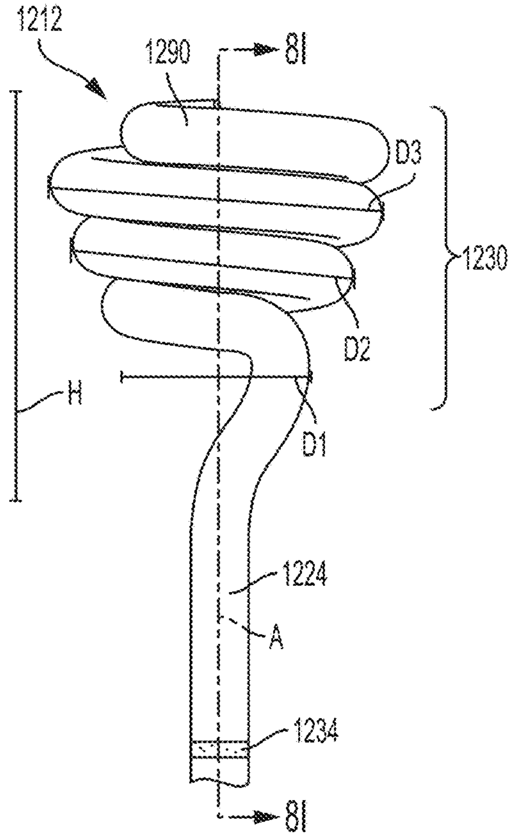
FIG. 8G is a rear view of the retention portion of the inflow member of FIG. 8D.
Figure 8H:
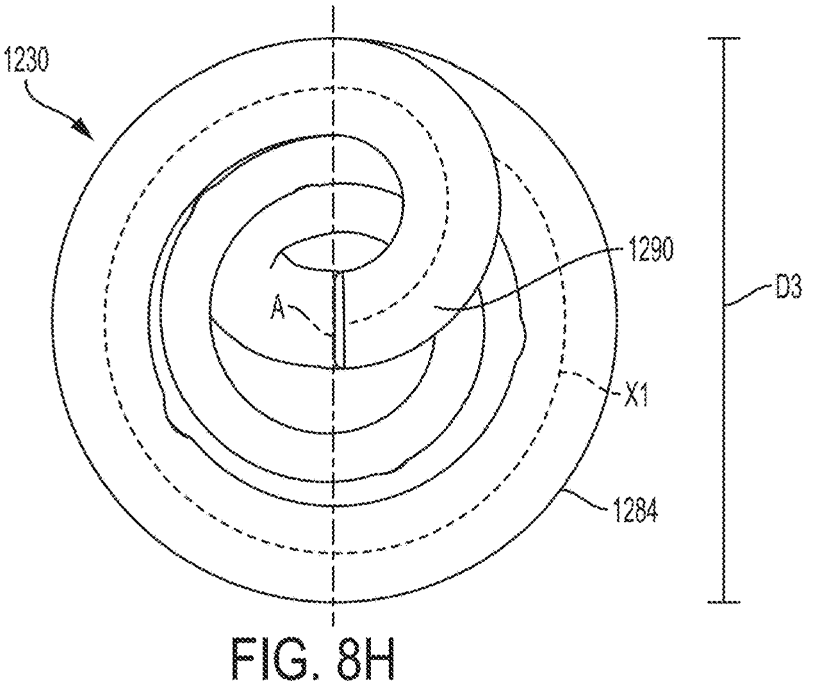
FIG. 8H is a top view of the retention portion of the inflow member of FIG. 8D.
Figure 8I:
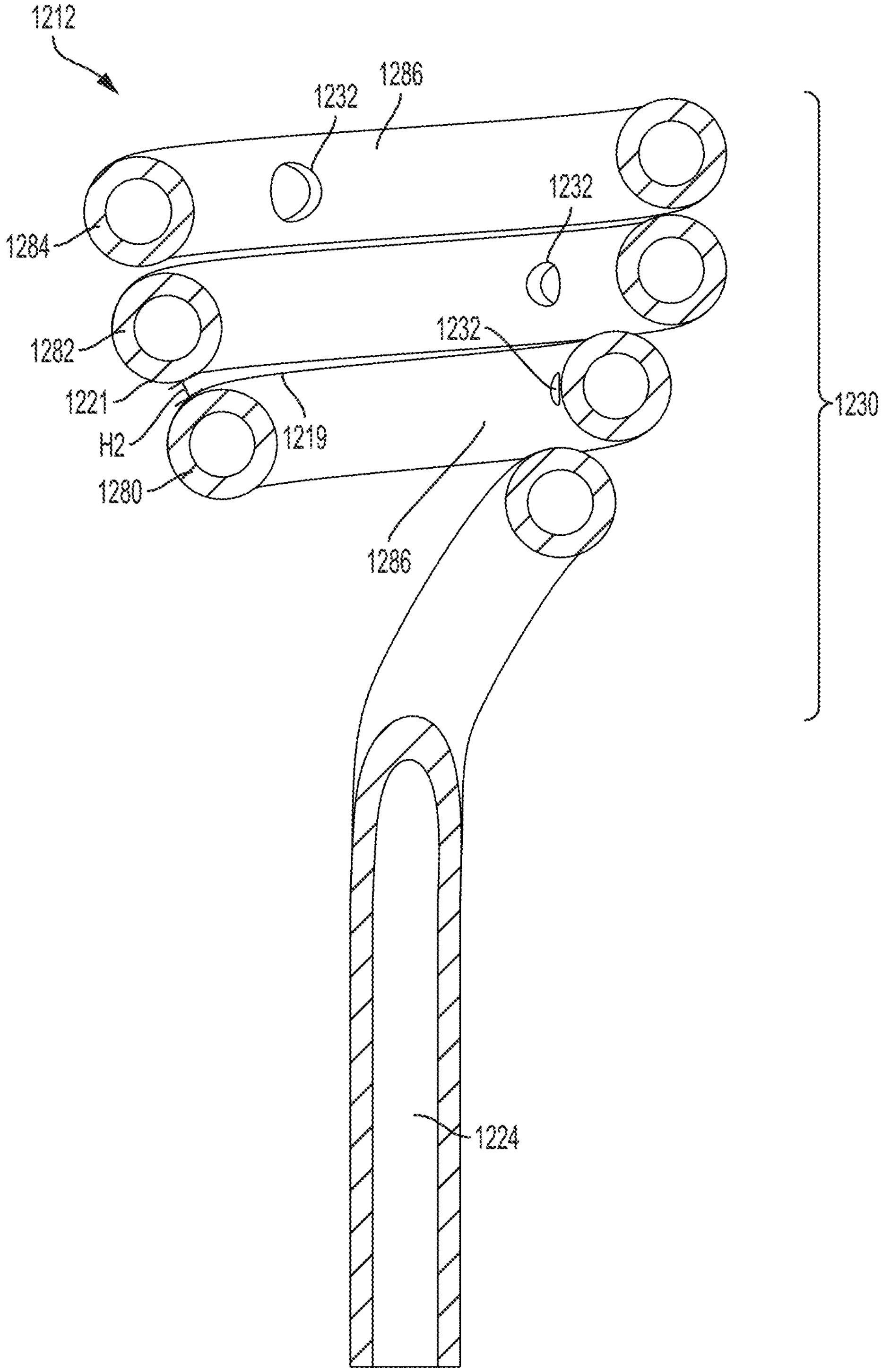
FIG. 8I is a cross-sectional view of the retention portion of the inflow member of FIG. 8D taken along line 8I-8I (shown in FIGS. 8G and 8H)
Figure 8J:
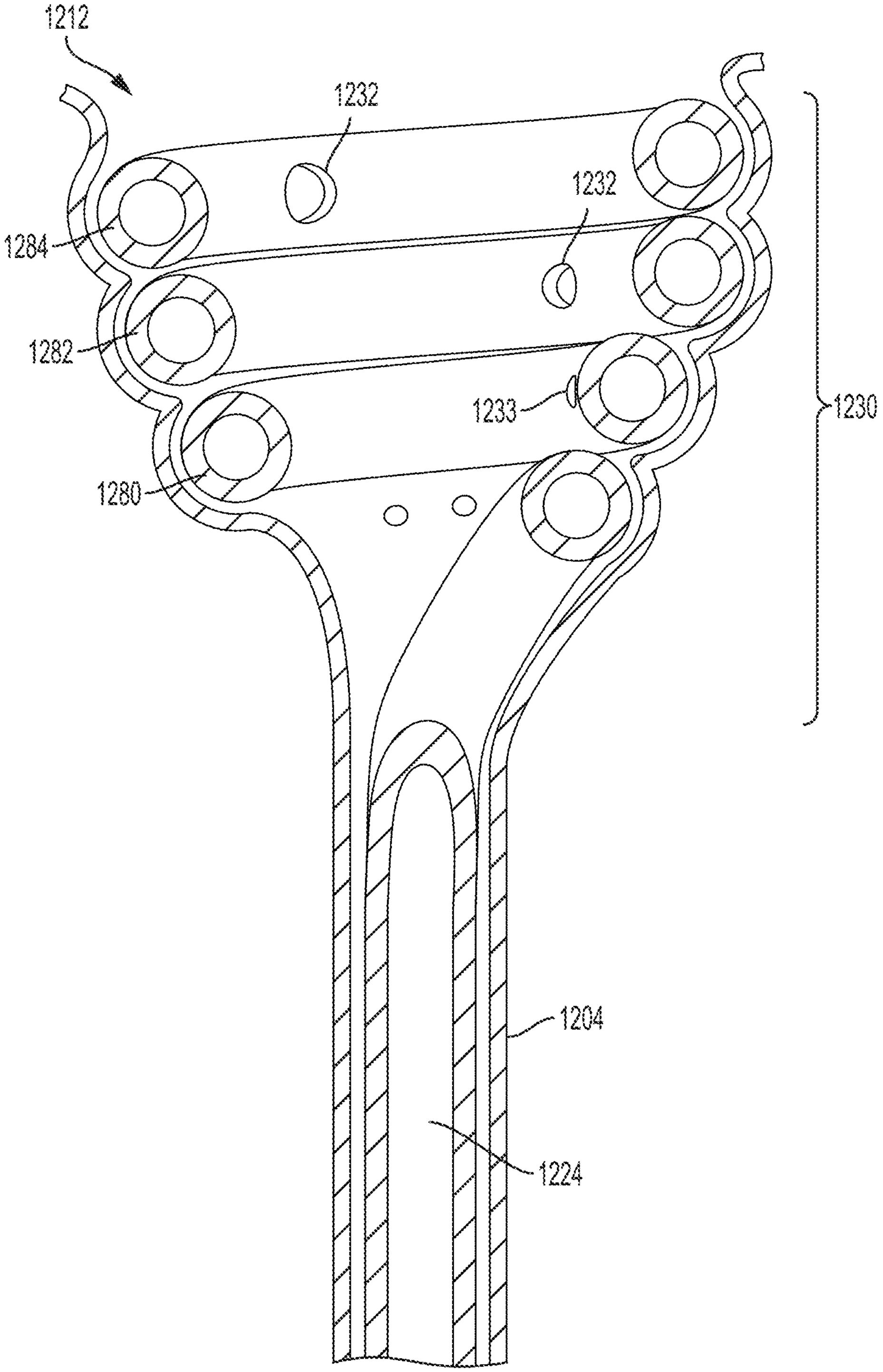
FIG. 8J is a cross-sectional view of the retention portion of the inflow member of FIG. 8D taken along line 8I-8I (shown in FIGS. 8G and 8H) positioned in the renal pelvis region of the kidney showing, in general, changes believed to occur in the renal pelvis tissue in response to application of negative pressure through the inflow member.
Figure 8K:
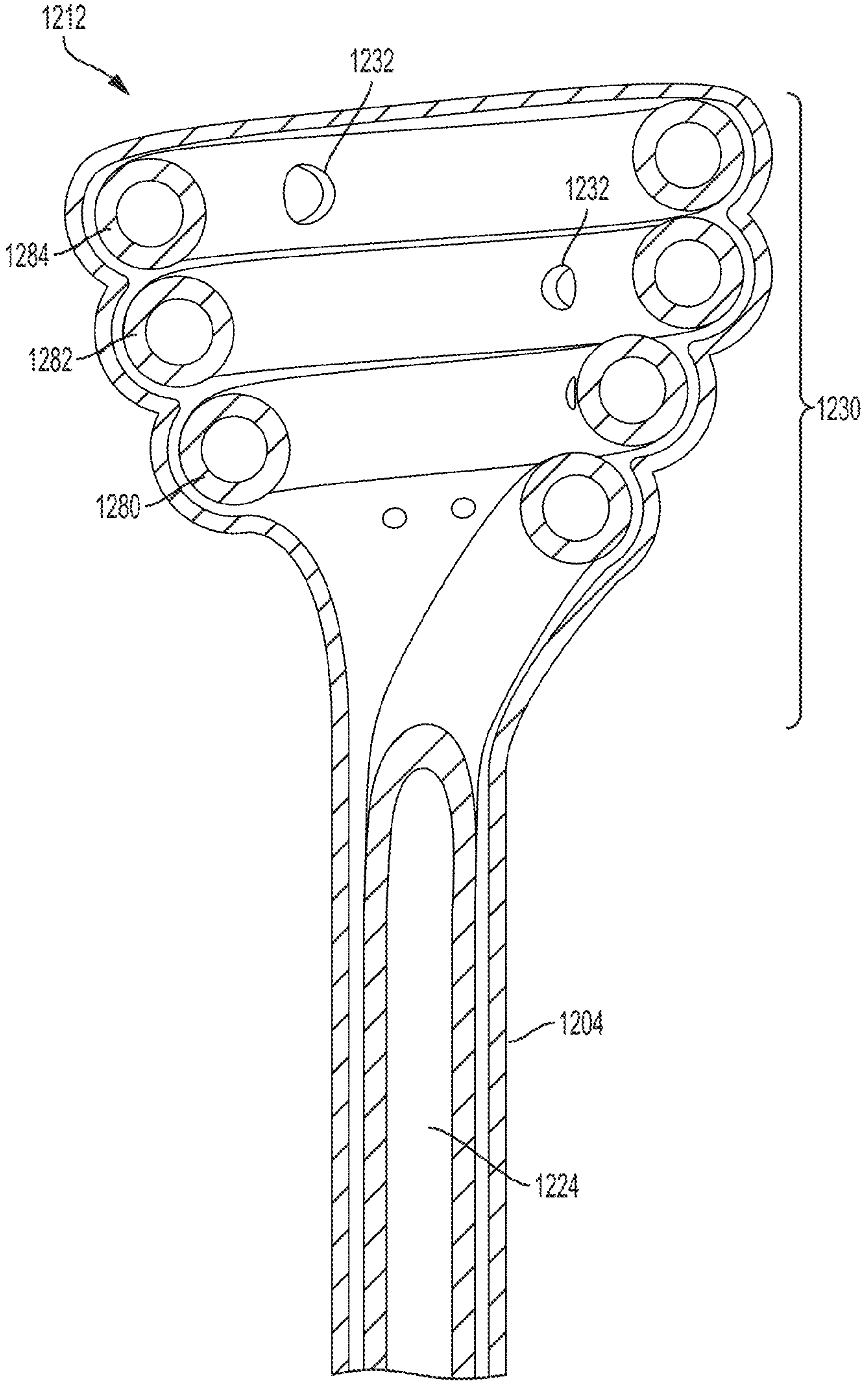
FIG. 8K is another cross-sectional view of the retention portion of the inflow member of FIG. 8D taken along line 8I-8I (shown in FIGS. 8G and 8H) positioned in the renal pelvis region of the kidney showing changes believed to occur in the renal pelvis tissue in response to application of negative pressure through the inflow member.

FIGS. 8D-8K show another exemplary inflow member 1212 that can be used with the negative pressure therapy devices and systems of the present disclosure. As shown in FIG. 8D, the inflow member comprises a proximal connector 1202 which, as in previous examples, can be used for connecting the inflow member 1212 to the negative pressure source. The inflow member 1212 further comprises a proximal portion 1228, an intermediate portion 1226, and a distal portion 1218. The distal portion 1218 comprises an open distal end 1220 for drawing fluid into an inflow lumen 1224 of the inflow member 1212 and a retention portion 1230 having a different arrangement of coils than previous examples.

As in previous examples, the retention portion 1230 can be flexible and bendable to permit positioning of the retention portion 1230 in the renal pelvis and/or kidney. For example, the retention portion 1230 is desirably sufficiently bendable to absorb forces exerted on the inflow member 1212 and to prevent such forces from being translated to the renal pelvis and/or kidney. Further, if the retention portion 1230 is pulled in the proximal direction, the retention portion 1230 can be sufficiently flexible to begin to unwind or be straightened so that it can be drawn through the renal pelvis and/or kidney. In some examples, the retention portion 1230 is integral with other portions of the inflow member 1212. In other examples, the retention portion 1230 can comprise a separate tubular member connected to and extending from the tube or inflow lumen 1224 of the inflow member 1212. In some examples, the inflow member 1212 also comprises radiopaque bands 1234 positioned proximate to the retention portion 1230 for identifying a location of the retention portion 1230 using fluoroscopic imaging.

With reference to FIGS. 8E-8K, as in previous examples, the retention portion 1230 can comprise perforations, drainage ports, drainage holes, or openings 1232 in a sidewall of the inflow member 1212. A position and size of the drainage holes or openings 1232 can vary depending upon a desired volumetric flow rate for each opening and size constraints of the retention portion 1230. In some examples, a diameter of each of the drainage holes or openings 1232 can range independently from about 0.05 mm to about 2.5 mm and have an area of about 0.002 $mm^2$ to about 5 $mm^2$. Drainage holes or openings 1232 can be positioned extending along on a sidewall of the inflow member 1212 in any direction desired, such as longitudinal and/or axial. In some examples, spacing between the closest adjacent edge of each of the drainage holes or openings 1232 can range from about 1.5 mm to about 15 mm. Fluid, such as urine, passes through one or more of the perforations, drainage ports, drainage holes, or openings 1232 and into the inflow lumen 1224. Desirably, the drainage holes or openings 1232 are positioned so that they are not occluded by tissues of the ureters or kidney when negative pressure is applied to the inflow lumen 1224. For example, the drainage holes or openings 1232 can be positioned on interior portions or protected surfaces area(s) of coils or other structures of the retention portion 1230 to avoid occlusion of the openings 1232. In some examples, an intermediate portion 1226 and/or proximal portion 1228 of the inflow member 1212 can be essentially free of or free from perforations, ports, drainage holes, or openings to avoid occlusion of openings along those portions of the inflow member 1212. In some examples, a portion 1226, 1228 (shown in FIG. 8D) which is essentially free from perforations, drainage holes, or openings comprises substantially fewer openings 1232 than other portions of the inflow member 1212. For example, a total area of openings 1232 of the distal portion 1218 of the inflow member 1212 may be greater than or substantially greater than a total area of openings of the intermediate portion 1226 and/or the proximal portion 1228 of the inflow member 1212. For example a total area of openings 1232 of the portions 1226, 1228, which are essentially free from drainage holes or openings 1232, can be less than 20%, less than 10%, less than 5%, less than 2%, or less than 1% of the total area of the drainage holes or openings of the distal portion 1218.

In some examples, the retention portion 1230 comprises helical coils 1280, 1282, 1284. For example, the retention portion 1230 can comprise a first or half coil 1280 and two full coils, such as a second coil 1282 and a third coil 1284. The first coil 1280 can comprise a half coil extending from 0 degrees to 180 degrees around a curvilinear central axis A of the retention portion 1230. In some examples, as shown the curvilinear central axis A is substantially straight and co-extensive with a curvilinear central axis of the inflow member 1212. In other examples, the curvilinear central axis A of the retention portion 1230 can be curved giving the retention portion 1230, for example, a cornucopia shape. The first coil 1280 can have a diameter D1 of about 1 mm to 20 mm and preferably about 8 mm to 10 mm. The second coil 1282 can be a full coil extending from 180 degrees to 540 degrees along the retention portion 1230 having a diameter D2 of about 5 mm to 50 mm, preferably about 10 mm to 20 mm, and more preferably about 14 mm±2 mm. The third coil 1284 can be a full coil extending between 540 degrees and 900 degrees and having a diameter D3 of between 5 mm and 60 mm, preferably about 10 mm to 30 mm, and more preferably about 18 mm±2 mm. In other examples, multiple coils 1282, 1284 can have the same inner and/or outer diameter. For example, an outer diameter of the full coils 1282, 1284, can each be about 18±2 mm.

In some examples, an overall height H of the retention portion 1230 ranges from about 10 mm to about 30 mm and, preferably about 18±2 mm. A height H2 (shown in FIG. 8I) of a gap between adjacent coils 1284, namely between a sidewall 1219 of the first coil 1280 and an adjacent sidewall 1221 (shown in FIG. 8I) of the second coil 1282 is less than 3.0 mm, preferably between about 0.25 mm and 2.5 mm, and more preferably between about 0.5 mm and 2.0 mm.

The retention portion 1230 can further comprise a distal-most curved portion 1290. For example, the distal most portion 1290 of the retention portion 1230, which comprises the open distal end 1220 of the inflow member 1212, can be bent inwardly relative to a curvature of the third coil 1284. For example, a curvilinear central axis X1 (shown in FIG. 8H) of the distal-most portion 1290 can extend from the distal end 1220 of the inflow member 1212 towards the curvilinear central axis A of the retention portion 1230.

The retention portion 1230 is capable of moving between a contracted position, in which the retention portion 1230 is straight for insertion into the patient's urinary tract, and the deployed position, in which the retention portion 1230 comprises the helical coils 1280, 1282, 1284. Generally, the retention portion 1230 of the inflow member 1212 is naturally biased toward the coiled configuration. For example, an uncoiled or substantially straight guidewire can be inserted through the retention portion 1230 to maintain the retention portion 1230 in a straight contracted position. When the guidewire is removed, the retention portion 1230 naturally transitions to its coiled position.

In some examples, the openings 1232 are disposed essentially only or only on a radially inwardly facing side 1286 or protected surface area or inner surface area 1000 of the coils 1280, 1282, 1284 to prevent occlusion or blockage of the openings 1232, 1233. A radially outwardly facing side 1288 of the coils 1280, 1282, 1284 can be essentially free of the openings 1232 meaning that a total area of openings 1232 on the inwardly facing side 1286 of the retention portion 1230 can be substantially greater than a total area of openings 1232 on the radially outwardly facing side 1288 of the retention portion 1230. For example, a total area of drainage holes or openings 1232 on the outwardly facing side 1288 can be less than 20%, less than 10%, less than 5%, less than 2%, or less than 1% of the total area of the drainage holes or openings 1232 on the inwardly facing side 1286.

Due to the arrangement of drainage holes or openings 1232 on the inwardly facing side 1286, when negative pressure is induced in the kidney and/or renal pelvis, mucosal tissue 1204 (shown in FIGS. 8J and 8K) of the ureter and/or kidney may be drawn against the retention portion 1230 and may occlude some openings 1232 on an outer periphery or protective surface area of the retention portion 1230. However, openings 1232 located on the radially inward side 1286 or protected surface area or inner surface area of the retention portion 1230 are not appreciably occluded when such tissues contacts the outer periphery or protective surface area of the retention portion 1230. Therefore, a risk of injury to the tissues from pinching or contact with the drainage holes or openings 1232 can be reduced or eliminated.

Another example of an inflow member 912 of a urinary catheter 910 configured for percutaneous insertion into the renal pelvis of a patient is shown in FIGS. 9A and 9B. As in previous examples, the inflow member 912 is formed from an elongated tube comprising a proximal end (not shown) and a distal end 920. The inflow member 912 further comprises a retention portion 918 positioned proximate to the distal end 920 of the inflow member 912, which is configured to retain the distal end 920 of the inflow member 912 within the kidney or renal pelvis of the patient. The retention portion 918 is a coiled retention portion comprising a plurality of coils 936, 938, 940. Unlike in previous examples, as shown in FIGS. 9A and 9B, the coils 936, 938, 940 are wrapped around a straight portion 942 of the elongated tube, with the distal end 920 of the inflow member 912 proximate to the proximal end 946 of the retention portion 918. Further, the distal-most portion of the retention portion 918 is formed by a bent portion 944, which forms a transition between the straight portion 942 and the plurality of coils 936, 938, 940.

As in previous examples, the size and orientation of the coils 936, 938, 940 is selected so that the retention portion 918 remains in the renal pelvis and does not pass into the ureter or retract back into the kidney. For example, the largest or proximal most coil 936 can be about 10 mm to 30 mm in diameter, or about 15 mm to 25 mm in diameter, or about 20 mm in diameter. Coils 938 and 940 can have a smaller diameter of, for example, 5 mm to 25 mm, or about 10 mm to 20 mm, or about 15 mm. As in previous examples, the coiled retention portion 918 can have a tapered appearance in which the coils 936, 938, 940 become progressively narrower, giving the retention portion 918 a reverse pyramid, trapezoidal, reverse conical, or frustoconical shape.

As in previous examples, the retention portion 918 further comprises the openings or drainage holes 924 (shown in FIG. 9B) positioned on a radially inward side or protected surface area 930 of the coiled retention portion 918. The drainage holes 924 are configured to allow fluid to pass from the renal pelvis or kidney to a lumen 914 of the inflow member 912 through the drainage holes 924 when negative pressure is applied to the lumen 914 by the negative pressure source, such as the implantable or external pump. In a similar manner, the distal end 920 of the inflow member 912 can be open to receive fluid from the patient's urinary tract or can be closed, such that fluid only passes to the lumen 914 through the drainage holes 924.

Since the coils 936, 938, 940 extend around the straight portion 942 and prevent tissue of the renal pelvis and/or kidneys from contacting the straight portion 942, drainage holes 924 can also be positioned on the straight portion 942 of the retention portion 918. As in previous examples, the retention portion 918 can be inserted through the kidney and renal pelvis in a linear orientation over a guidewire. When the guidewire is removed, the retention portion 918 adopts the coiled or deployed configuration.

Outflow Members of Urinary Catheters

FIG. 10A shows both the inflow member 812 and outflow member 1012 of the urinary catheter 810. Similar to the inflow member 812, the outflow member 1012 comprises an elongated tubular member comprising a proximal end (not shown), a distal end 1016, and a sidewall 1018 extending between the proximal end and the distal end 1016. The sidewall 1018 of the outflow member 1012 can be formed from a same material as the inflow member 812 or from a different material. For example, the outflow member 1014 can comprise biocompatible polymer(s), such as polyurethane, polyvinyl chloride, polytetrafluoroethylene (PTFE), latex, silicone coated latex, silicone, polyglycolide or poly (glycolic acid) (PGA), Polylactide (PLA), Poly(lactide-co-glycolide), Polyhydroxyalkanoates, Polycaprolactone and/or Poly(propylene fumarate). The outflow member 1012 can also comprise and/or be impregnated with metal materials, such as copper, silver, gold, nickel-titanium alloy, stainless steel, and/or titanium The diameter or size of the inflow member 1012 can be similar or identical to the inflow member 812. For example, the size of the outflow member 1012 can range from about 1 Fr to about 9 Fr (French catheter scale), or about 2 Fr to 8 Fr, or can be about 4 Fr. In some examples, the outflow member 1012 can have an external diameter ranging from about 0.33 mm to about 3.0 mm, or about 0.66 mm to 2.33 mm, or about 1.0 mm to 2.0 mm, and an internal diameter ranging from about 0.165 mm to about 2.40 mm, or about 0.33 mm to 2.0 mm, or about 0.66 mm to about 1.66 mm.

The total or axial length of the outflow member 1012 along a curvilinear axis of the outflow member 1012 generally is longer than an axial length of the inflow member 812. Accordingly, as shown, for example, in FIGS. 11A-11C, the distal end 1016 of the outflow member 1012 extends past the retention portion 818 of the inflow member 812 to the ureter or bladder of the urinary tract. For example, a total length of an outflow member 1012 that extends from an implanted pump to the bladder (as shown in FIG. 1A) can be from about 10 cm to about 50 cm. A total length of the outflow member 1012 that extends from an external pump, through a percutaneous opening or incision, and through the urinary tract to the bladder (as shown in FIG. 1B) can be from about 40 cm to about 60 cm. Further, as shown in FIGS. 10A-10C, in some examples, portions of the inflow member 812 and the outflow member 1012 can be substantially parallel. In particular, portions of the inflow member 812 and the outflow member 1012 passing from the negative pressure source or pump to the kidney can be parallel. Further, parallel sections or portions of the inflow member 812 and the outflow member 1012 can be connected together by, for example, a fastener, clip, or adhesive. An exemplary clip 1020 connecting portions of the inflow member 812 and the outflow member 1012 together is shown in FIG. 10A.

In some examples, the outflow member 1012 comprises, defines, or encloses an outflow lumen 1022 configured to be in fluid communication with the negative pressure source, such as an implantable or external pump. The lumen 1022 is configured to receive fluid, such as urine, discharged from the negative pressure source, and to conduct the fluid through the kidney and renal pelvis to the ureter or bladder of the urinary tract. As shown in FIGS. 10A-10C, the outflow member 1012 further comprises: (i) a proximal portion 1024 comprising the proximal end of the outflow member 1012, (ii) a distal portion 1026 comprising the distal end 1016 configured to be positioned in the ureter or bladder, and (iii) an intermediate portion 1030 extending from the proximal portion 1024 to the distal portion 1026 of the outflow member. As previously described, the proximal portion 1024 of the outflow member 1012 can refer to the portion of the outflow member 1012 extending from the negative pressure source through the abdominal cavity to, for example, a posterior or outer wall of the kidney. The distal portion 1026 can refer to the portion of the outflow member 1012 in the ureter or bladder proximate to the distal end 1024 of the outflow member 1012. The intermediate portion 1030 extends through the urinary tract from the proximal portion 1024 to the distal portion 1026.

In some examples, the distal end 1016 of the outflow member 1012 is open, such that, when deployed in the ureter or bladder, fluid passes from the outflow lumen 1022 of the outflow member 1012 through the open distal end 1022 to the ureter or bladder. In such examples, unlike the inflow member 812, the outflow member 1012 can be free from drainage holes. Alternatively, the distal portion 1026 of the outflow member 1012 can comprise holes, openings, fluid ports, or perforations extending through the sidewall 1018 of the outflow member 1012 for discharging fluid from the lumen 1022 of the outflow member 1012 to the ureter or bladder. Further, in some examples, the distal portion 1026 of the outflow member 1012 can comprise a retention portion 1028 for retaining the distal end 1016 of the outflow member within the ureter and/or bladder. As with the retention portion 818 of the inflow member 812, the retention portion 1028 of the outflow member 1012 can comprise or define a three-dimensional shape sized to restrict the distal end 1016 of the outflow member 1012 from being pulled from the bladder or ureter through the urinary tract. For example, the distal portion 1026 of the outflow member 1012 can pass through the ureteral orifice into the bladder and the retention portion 1028 can be deployed in the bladder. When deployed in the bladder, the retention portion 1028 can be wider and/or can have a diameter larger than the ureteral orifice to prevent the distal end 1016 of the outflow member 1012 from being pulled through the ureteral orifice and into the ureter.

The retention portion 1028 of the outflow member 1012 can be similar in configuration to the retention portion 818 of the inflow member 812, comprising, for example, one or more of pig tail coils, helical coils, funnels, baskets, umbrellas, axially and/or radially extending tines, expandable balloons, sponges, and/or other retaining structures. In some examples, as shown in FIG. 10A, the retention portion 1028 of the outflow member 1012 comprises a pigtail coil, which is a coil about an axis A2 that is not co-extensive with an axis of the outflow member 1012. For example, the axis A2 of the pig coil can be transverse or substantially transverse (e.g., within about 5% of transverse) to a curvilinear axis of the outflow member 1012. In other examples, the axis A2 of the pig-coil can be angled or oblique, but not transverse, relative to the curvilinear axis of the outflow member 1012. Dimensions of the retention portion 1028 or pigtail coil should be sufficient to retain the distal portion 1026 of the outflow member 1012 in the bladder. For example, the retention portion 1028 comprising the pigtail coil can have an outer diameter of from about 10 mm to about 20 mm. The retention portion 1028 comprising the pigtail coil can have an inner diameter from about 5 mm to about 15 mm.

In order to provide negative pressure therapy to the patient, as previously described, the negative pressure is induced in the inflow lumen 814 of the inflow member 812 by the negative pressure source to draw fluid from the renal pelvis into the inflow lumen 814. The fluid passes through the inflow lumen 814 towards the negative pressure source, in a direction of arrow A3 (as shown in FIG. 10A). The fluid then passes into the outflow lumen 1022 of the outflow member 1012, in a direction of arrow A4 (shown in FIG. 10A), and is discharged from the outflow lumen 1022 of the outflow member 1012 to the ureter or bladder through the open distal end 1016 of the outflow member 1012 and/or through holes, openings, or perforations in the sidewall 1018 of the distal portion 1026 of the outflow member 1012.

The inflow members 812 and the outflow members 1012 of the present disclosure can be made using various techniques for making catheters, shunts, stents, flexible tubes, and similar disposable or reusable medical devices, as are known in the art. For example, a method for making the inflow member 812 can initially comprise forming one or more drainage ports, openings, holes, or perforations on portions of an elongated tube. For example, drainage ports, openings, holes, or perforations can be formed by puncturing portions of the elongated tube using a needle, drill, or similar tool. The drainage ports can be equidistantly spaced along a length of the elongated tube. Alternatively, drainage ports may be spaced more closely together near the distal end of the elongated tube to improve distribution of negative pressure applied through the tube. The drainage ports can be the same size. Alternatively, drainage ports near the distal end of the tube may be larger to improve negative pressure distribution.

The method for making the inflow member 812 or the outflow member 1012 can further comprise forming a deployable retention portion on a distal portion of an elongated tube. The retention portion can be configured to transition between a contracted state and an expanded or deployed state. In the deployed state, the retention portion can comprise an inwardly facing side or protected surface and an outwardly facing side or protective surface. Desirably, the drainage ports, openings, holes, or perforations are positioned on the inwardly facing side or protected surface of the retention portion, when deployed. The outwardly facing side or protective surface, when deployed, can be substantially free from drainage ports, openings, holes, and perforations.

The retention portion can be formed using a variety of techniques. For coiled retention portions, the elongated tube may be wrapped around a template or mandrel for an extended period of time to impart a desired curvature for the coils.

Inflow Members and Outflow Members Deployed in the Urinary Tract

In some examples, the inflow member 812 and the outflow member 1012 are configured to be positioned or deployed in the kidney and/or renal pelvis such that, when deployed, the intermediate portion 1030 of the outflow member 1012 passes through the three-dimensional shape 848 (shown in FIG. 8C) defined by the retention portion 818 of the inflow member 812. For example, as shown in FIGS. 10B-10D, the intermediate portion 1030 of the outflow member 1012 passes through or about the conical or frustoconical three dimensional space or shape enclosed by portions of the coils 836, 838, 840 of the retention portion 818.

For example, as shown in FIG. 10B, when deployed, the outflow member 1012 extends through the conical space defined by the coils 836, 838, 840 of the retention portion 818 generally along an axis of the coils 836, 838, 840 of the retention portion 818. In this configuration, the outflow member 1012 passes through an opening defined by the distal-most coil 840. As previously described, the outflow member 1014 extends beyond the retention portion 818 of the inflow member 818 terminating in the ureter or bladder. In this configuration, the retention portion 818 of the inflow member 812 surrounds the intermediate portion 1030 of the outflow member 1012, which separates the intermediate portion 1030 of the outflow member 1012 from tissue of the renal pelvis preventing, for example, the renal pelvis from compressing, deforming, or otherwise limiting or restricting fluid flow through the outflow lumen 1022 of the outflow member 1012 as negative pressure is applied to the renal pelvis and/or kidney through the drainage holes 824 of the inflow member 812.

FIG. 10C shows another exemplary configuration for the inflow member 812 and outflow member 1012 of the urinary catheter 810. As shown in FIG. 10C, the outflow member 1012 passes partially through the space defined by the coils 836, 838, 840 of the inflow member 812. More specifically, as shown in FIG. 10C, the intermediate portion 1030 of the outflow member 1012 passes through the proximal-most or first coil 836 of the retention portion 818 of the inflow member 812. The outflow member 1012 then passes through a gap between the proximal-most or first coil 836 and the second coil 838. The outflow member 1012 then extends along the outer surface 832 of the retention portion 818 towards a distal end of the retention portion 818. As in previous examples, the outflow member 1012 then extends past the retention portion 818 through the ureter and/or bladder.

FIG. 10D shows another exemplary configuration for the inflow member 812 and the outflow member 1012, in which the outflow member 1012 extends about the outer surface 832 or periphery of the retention portion 818. Specifically, as shown in FIG. 10D, the intermediate portion 1030 of the outflow member 1012 is curved extending about the retention portion 818 of the inflow member 812, which an outer surface of the sidewall of the outflow member 1012 contacting the outer surface 832 of the retention portion 818. In this configuration, the tissue of the renal pelvis can be drawn against the outflow member 1012 when negative pressure is applied to the renal pelvis through the drainage holes 824 of the inflow member 812. Accordingly, in this configuration, the sidewall 1018 of the outflow member 1012 is desirably sufficiently rigid to resist deforming, kinking, or otherwise limiting or restricting fluid through the lumen 1022 of the outflow member 1012 due to forces exerted by the renal pelvis as the renal pelvis contracts about the retention portion 818 of the inflow member 812. In some examples, the configuration of FIG. 10D may be easier to deploy in the urinary tract because the outflow member 1012 does not need to be threaded through the coils 836, 838, 840 of the retention portion 818, as is required for configurations shown in FIGS. 10A and 10B.

FIGS. 10E and 10F show exemplary configurations for an inflow member 1212 (also shown in FIGS. 8D-8K) and the outflow member 1012. Specifically, as shown in FIG. 10E, the intermediate portion 1030 of the outflow member 1012 extends through an interior or protected space of the retention portion 1230 enclosed by the coils 1280, 1282, 1284. As shown in FIG. 10F, in another example, the intermediate portion 1030 of the outflow member 1012 extends about an outer surface or periphery of the coils 1280, 1282, 1284 of the retention portion 1230.

Regardless of the configuration of the inflow member 812, 1212 and the outflow member 1012 being used, in order to apply negative pressure to the renal pelvis, the inflow lumen 814 of the inflow member 812, 1212 is directly or indirectly fluidly connected to the lumen 1022 of the outflow member 1012 so that the fluid passes directly or indirectly from the inflow lumen 814 to the outflow lumen 1012. In some examples, as previously described, the inflow lumen 814 can be contiguous with the outflow lumen 1022. For example, the inflow member 812 can be integral with the outflow member 1012 forming a continuous tube extending from the retention portion 818 of the inflow member 812, 1212 to the distal end 1016 of the outflow member 1012. In that case, the negative pressure source can be a peristaltic pump configured to apply pressure to and deform portions of the continuous tube to produce negative pressure and/or to draw fluid through the continuous tube. In other examples, the inflow member 812, 1212 and the outflow member 1012 can be separate structures, such as separate elongated tube segments, which are connected to the negative pressure source, such as a pump. For example, the proximal portion 816, 1228 of the inflow member 812 can be connected to an inflow port of the pump and the proximal portion 1024 of the outflow member 1012 can be connected to the outflow port of the pump, such that fluid flows from the inflow lumen 814 to the outflow lumen 1022 through the pump.

As previously described, the urinary catheter 810 is configured to be deployed within the urinary tract of the patient. In particular, the retention portion 818 of the inflow member 812 is deployed within the renal pelvis and/or kidney. The distal end 1016 of the outflow member 1012 is configured to be positioned in the ureter or bladder. Examples of urinary catheters 810 deployed in the urinary tract are shown in FIGS. 11A-11D.

More specifically, FIG. 11A shows the retention portion 818 of the inflow member 812 deployed in the renal pelvis. Tissue of the renal pelvis surrounds and presses against the outer or protective surface 832 of the retention portion 818. The intermediate portion 1030 of the outflow member 1012 passes through the space defined by the coils 836, 838, 840 of the retention portion 818 of the inflow member 812. For example, as shown in FIG. 11A, the outflow member 1040 can pass through the third or distal-most coil 840 of the retention portion 818.

Figure 11B:
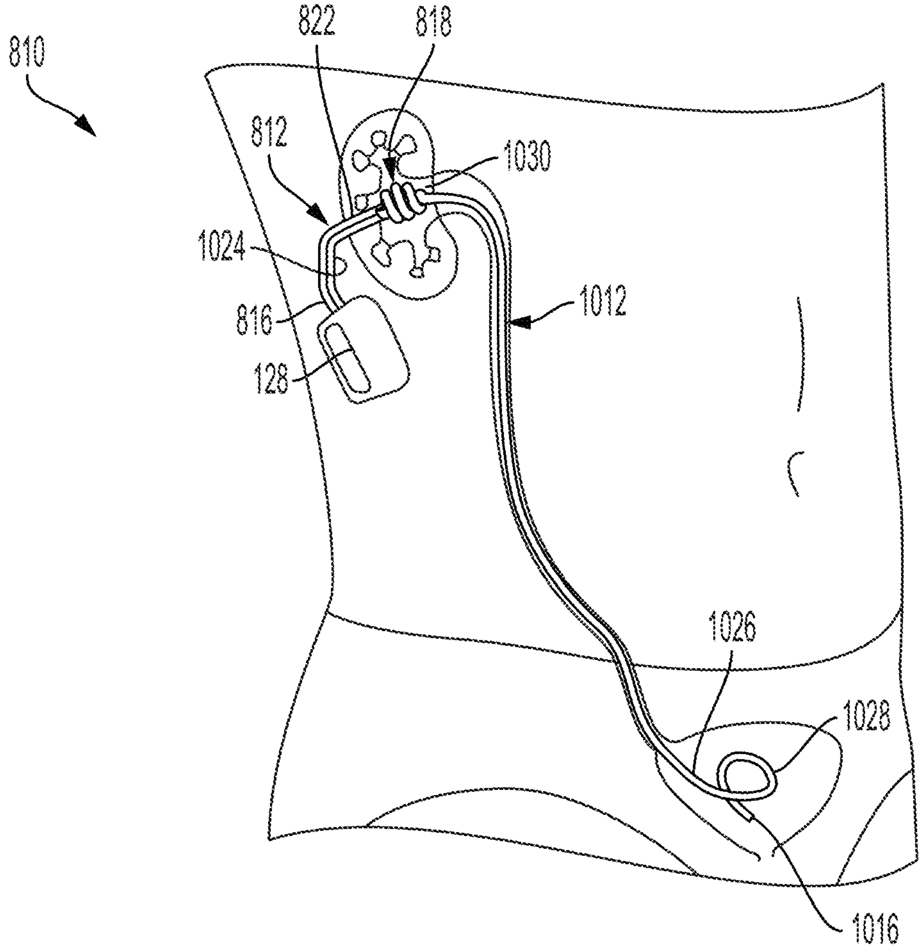
FIG. 11B is another schematic drawing of the inflow member and the outflow member of the urinary catheter of FIG. 10A deployed in the urinary tract of the patient.
Figure 12:
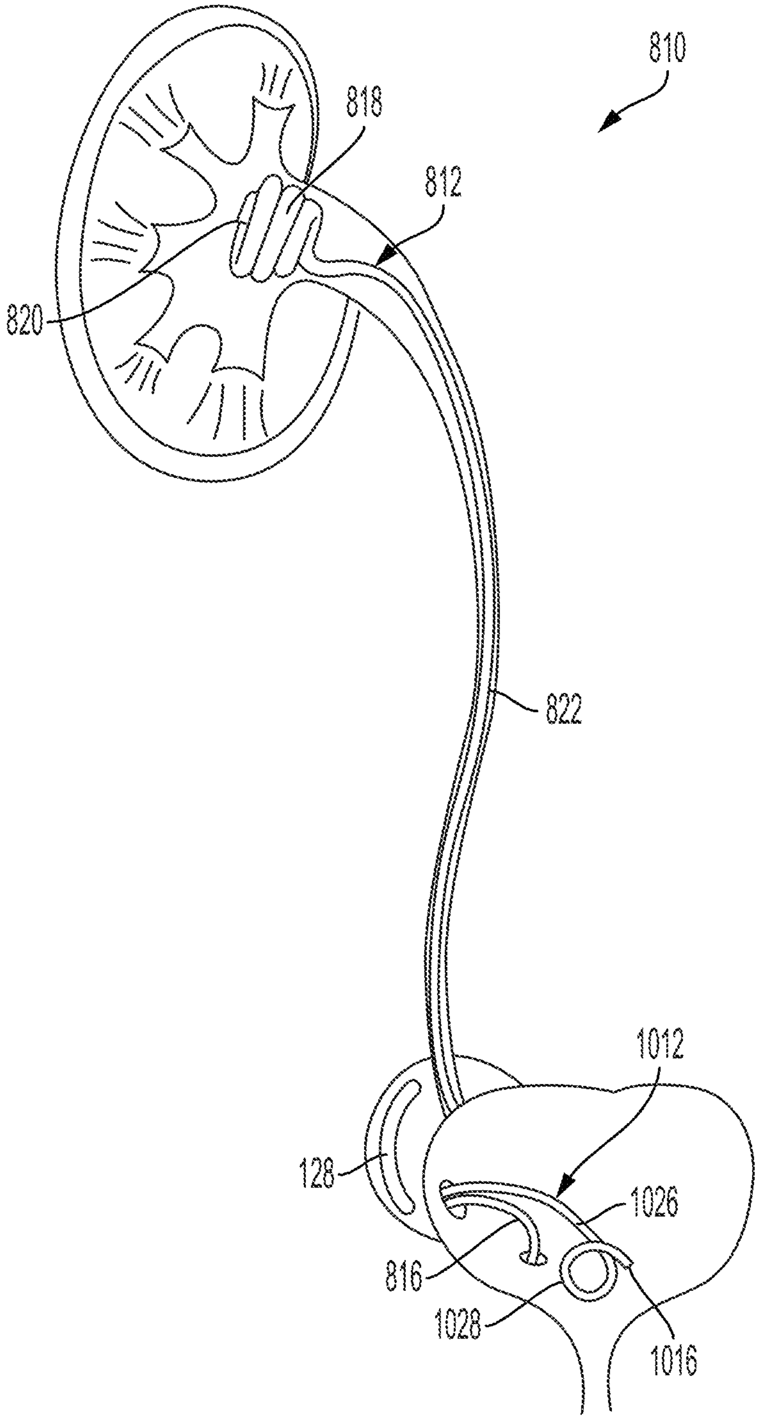
FIG. 12 is a schematic drawing showing another example of an inflow member and an outflow member of a urinary catheter deployed in the urinary tract of a patient, according to an example of the present disclosure.

As shown in FIG. 11B, the outflow member 1012 passes through the patient's ureter to the bladder. Specifically, the intermediate portion 1030 of the outflow member 1012 can extend through the kidney, renal pelvis, ureter, and ureteral orifice to the bladder. The distal end 1016 of the outflow member 1012 is positioned in the bladder. The distal portion 1026 of the outflow member 1012 can comprise the retention portion 1028, such as the pigtail coil, positioned in the bladder. The retention portion 1028 retains the distal end 1016 of the outflow member 1012 in the bladder. In particular, as previously described, the retention portion 1028 of the outflow member 1012 is large enough to prevent the distal end 1016 of the outflow member 1012 from being pulled through the ureteral orifice into the ureter. As shown in FIG. 11B, the pump 128 is positioned in the abdominal cavity proximate to the kidney. The inflow member 812 and the outflow member 1012 are connected to the pump 128.

Figure 11C:
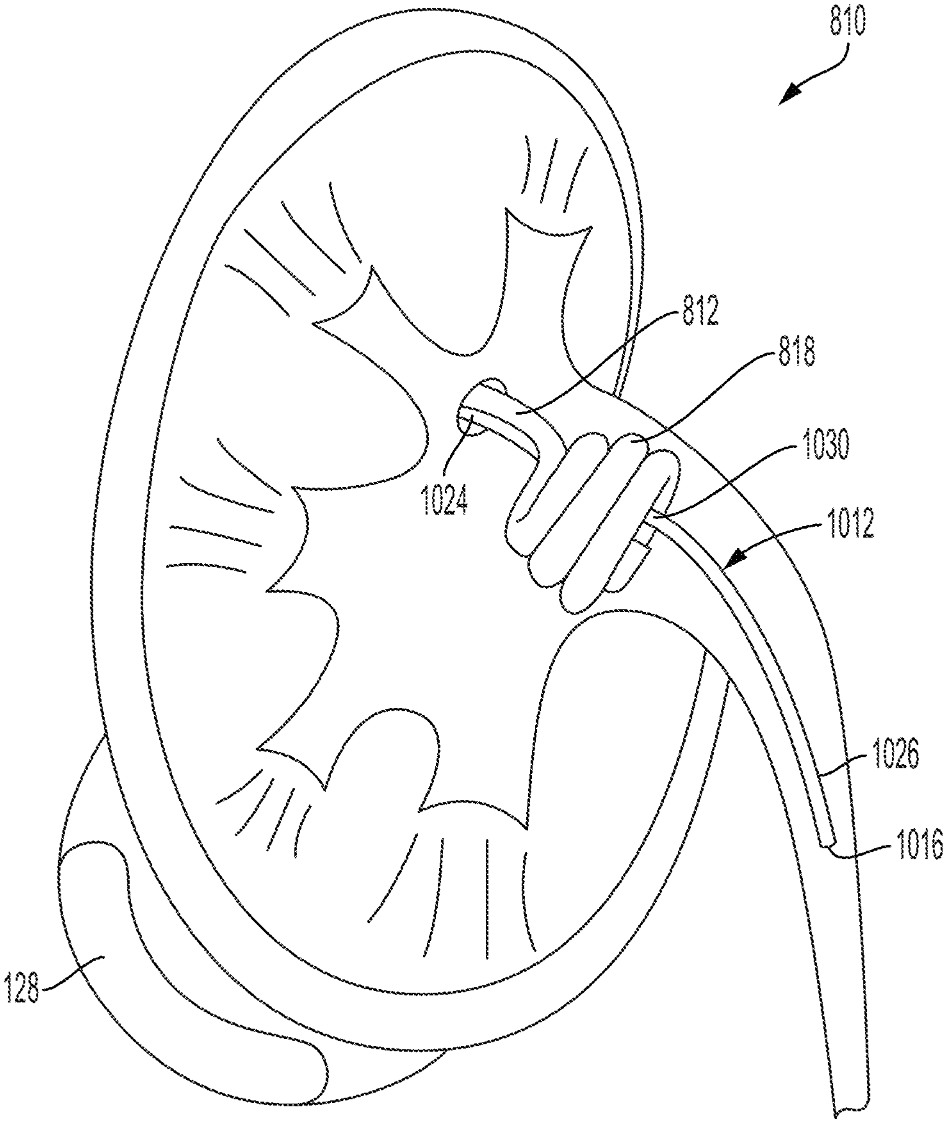
FIG. 11C is a schematic drawing of another example of an inflow member and an outflow member of a urinary catheter deployed in a urinary tract of a patient, according to an example of the present disclosure.

FIG. 11C shows another exemplary configuration of an inflow member 812 and an outflow member 1012 deployed in a urinary tract of a patient. As shown in FIG. 11C, the coiled retention portion 818 of the inflow member 812 is deployed in the renal pelvis. As in previous examples, the intermediate portion 1030 of the outflow member 1012 passes through the retention portion 818 of the inflow member and into the ureter. However, unlike in previous examples, the distal end 1016 of the outflow member 1012 is not positioned in the bladder. Instead, the distal end 1016 of the outflow member 1012 remains in the ureter. Fluid expelled from the distal end 1016 of the outflow member 1012 passes through the ureter to the bladder by natural processes. In some examples, the distal portion 1026 of the outflow member 1012 passes beyond the distal end of the retention portion 818 of the inflow member 812 by a distance of about 1.0 cm to about 5.0 cm. In particular, the distal end 1016 of the outflow member 1012 is desirably positioned within the ureter a sufficient distance from the retention portion 818 of the inflow member 812 so that negative pressure applied to the urinary tract through the inflow member 812 does not cause tissues of the ureter or renal pelvis to occlude the distal end 1016 of the outflow member 1012 or any openings, apertures, or drainage holes extending through the sidewall 1018 of the outflow member 1012. As shown in FIG. 11C, the urinary catheter 810 is connected to an implanted pump 128, which is positioned posterolateral to the kidney. As previously described, in other examples, the pump 128 can be positioned at other locations in the abdominal cavity, subcutaneous space, or at any other convenient location within the body.

FIG. 12 shows another example of a urinary catheter 810 comprising an inflow member 812 and an outflow member 1012 deployed in a urinary tract of the patient. As shown in FIG. 12, the inflow member 812 comprises an inflow lumen 814 configured to be in fluid communication with a negative pressure source, such as an implanted pump 128 positioned outside of the urinary tract and posterolateral to a wall of the bladder. The inflow member 812 further comprises (i) a proximal portion 816, which extends from the pump 128 to the bladder wall, (ii) a retention portion 818 configured to be deployed within a renal pelvis of the urinary tract to retain a distal end 820 of the inflow member 812 within the renal pelvis, and (iii) an intermediate portion 822 between the proximal portion 816 and the retention portion 818. The intermediate portion 822 can extend from the bladder, through the ureteral orifice and ureter, to the renal pelvis, where it connects to or is integral with the retention portion 818.

The outflow member 1012 of the urinary catheter 810 comprises an outflow lumen 1022 configured to be in fluid communication with the implanted pump 128 for conducting fluid from the pump 128 to the patient's bladder. The outflow member 1012 further comprises (i) a proximal portion 1024, which extends from the pump 128 towards the bladder, (ii) a distal portion 1026 comprising a retention portion 1028 configured to retain a distal end 1016 of the outflow member 1012 in the bladder, and (iii) an intermediate portion 1030 that extends from the proximal portion 1024 and through an opening in the bladder wall to the distal portion 1026 of the inflow member 1012 in the bladder.

As in previous examples, the retention portion 818 of the inflow member 812 can comprise a plurality of helical coils sized to fit within the renal pelvis. In some examples, the plurality of coils can be configured to adopt a conical or frustoconical shape when deployed, which matches a shape of the renal pelvis. In a similar manner, the retention portion 1028 of the outflow member 1012 can be a pigtail coil sized to prevent the distal end 1016 of the outflow member 1012 from being pulled out of the bladder through the opening in the bladder wall at inappropriate or unexpected times.

Deployment Methods for Urinary Catheters

Figure 13A:
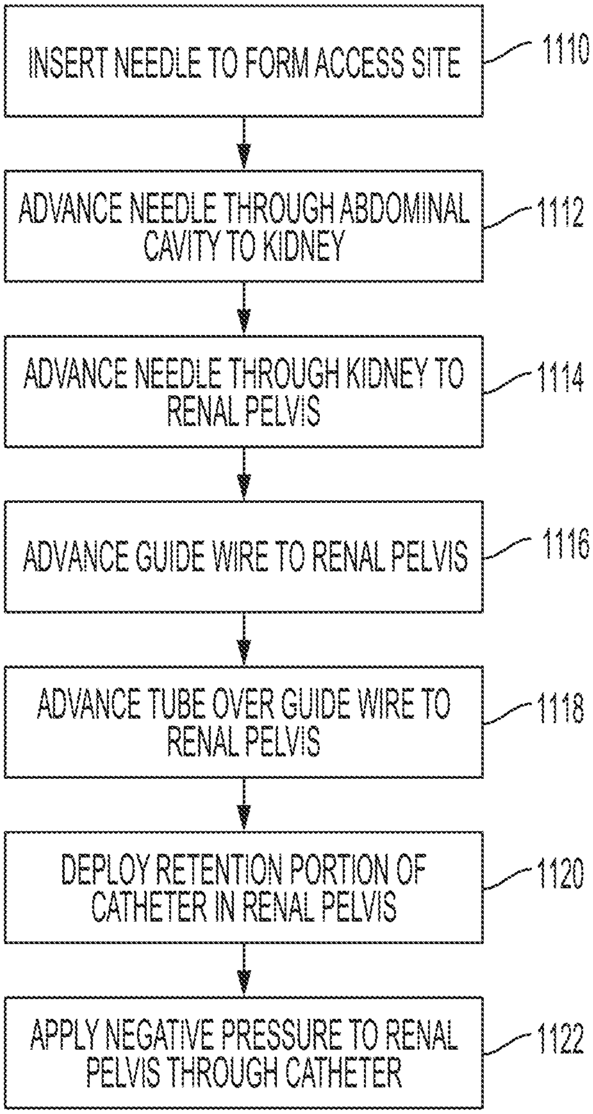
FIGS. 13A and 13B are flow charts showing methods for deploying and using the negative pressure therapy device and urinary catheter of the present disclosure.

Having described aspects of a urinary catheter 810 for applying negative pressure to a patient, a method for insertion and/or deployment of the urinary catheter 810 will now be described in connection with the flow charts of FIGS. 13A and 13B. Schematic drawings showing different aspects of the catheter deployment method are shown in FIGS. 14A-14H. Initially, as shown in FIG. 13A, at step 1110, a needle 1032 (shown in FIGS. 14A-14C) of a conical tip catheter is inserted into an abdominal region of the patient, thereby creating a percutaneous access site. The catheter and needle 1032 should be of sufficient size to permit the urinary catheter 810 to pass through the catheter and over the needle 1032. For example, the catheter can be about 3 Fr to about 10 Fr (French catheter scale), or from about 5 Fr to about 8 Fr, or about 6 Fr. In some examples, the catheter can have an external diameter ranging from about 0.5 mm to about 4 mm, and an internal diameter ranging from about 0.2 mm to about 3.5 mm. The needle 1032 can be from about 10 gauge to 30 gauge, or about 20 gauge to 25 gauge, and can have an outer diameter of from 0.3 mm to 3.5 mm, or about 0.5 mm to 1.0 mm. The needle 1032 can be any suitable length, such as from 10 mm to 50 mm, or about 30 mm.

Figure 14A:
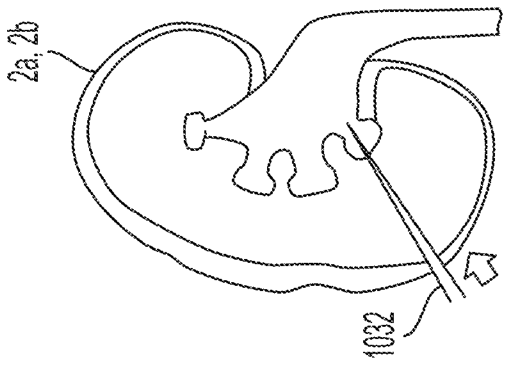
FIGS. 14A-14H are drawings showing steps for deploying the inflow member and the outflow member of a urinary catheter to a renal pelvis and ureter of a patient, according to examples of the present disclosure.
Figure 14B:
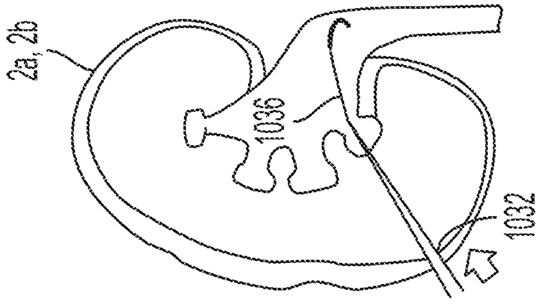
Figure 14C:
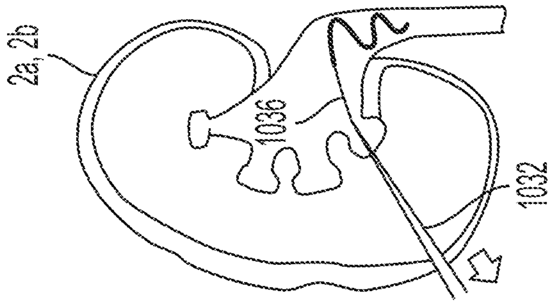
Figure 14D:
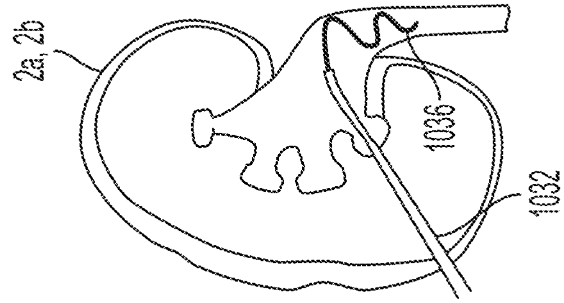
Figure 14E:
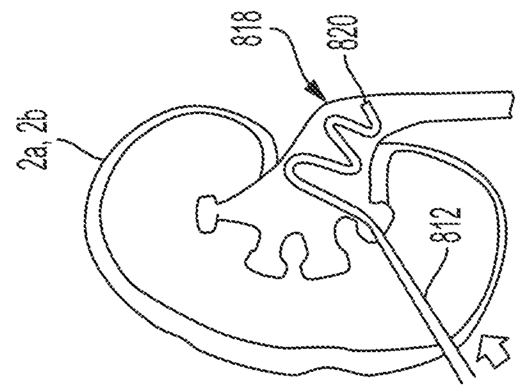
Figure 14H:
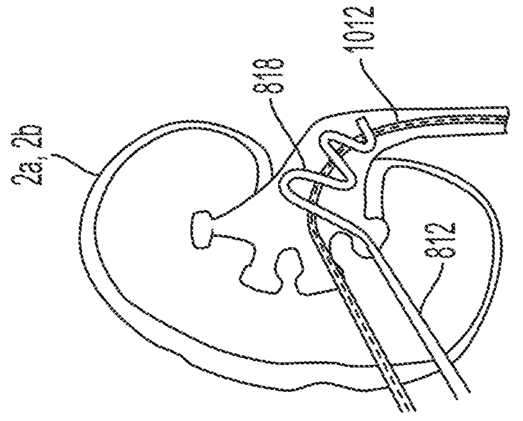

Once the needle 1032 is inserted through the patient's skin at an access site, at step 1112, the needle 1032 is advanced through the abdominal cavity and inserted into the kidney. At step 1114, the needle 1032 is advanced through the kidney and into the renal pelvis, as shown in FIG. 14B. Once the needle 1032 is advanced to the renal pelvis, at step 1116, a guidewire 1036 can be advanced to the renal pelvis through the needle 1032, as shown in FIG. 14C. Once the guidewire 1036 is in position, the needle 1032 can be retracted back through the catheter. Next, at step 1118, the inflow member 812 of the urinary catheter 810 can be inserted into the patient's abdominal cavity through the percutaneous access site and advanced to the renal pelvis over the guidewire 1036 and/or needle 1032, as shown in FIG. 14D. At step 1120, once a distal end 820 and retention portion 818 of the urinary catheter 810 reach the renal pelvis, the retention portion 818 can transition from its retracted state to the expanded or deployed state, as shown in FIG. 14E. As described herein, desirably, when deployed in the renal pelvis, the retention portion 818 maintains patency of fluid flow from the kidney into a lumen extending through at least a portion of the elongated tube.

In some examples, deploying the retention portion 818 can comprise retracting an outer tube or sheath in a proximal direction away from the retention portion 818. Once the outer tube or sheath is removed, the retention portion 818 automatically expands and returns to an unconstrained shape. In other examples, such as when the retention portion 818 comprises a coiled retention portion, retracting the guidewire 1036 causes the retention portion 818 to adopt the coiled or deployed configuration. Deploying the retention portion 818 can also comprise, for example, blowing up a balloon or releasing a cage-like structure to protect the distal end 820 and drainage holes 824 of the inflow member 812.

In some examples, as shown at step 1122, the proximal portion 816 of the inflow member 812 can be attached to the negative pressure source, such as an implanted or external pump, for applying negative pressure to the renal pelvis and/or kidney through the inflow member 812.

Figure 13B:
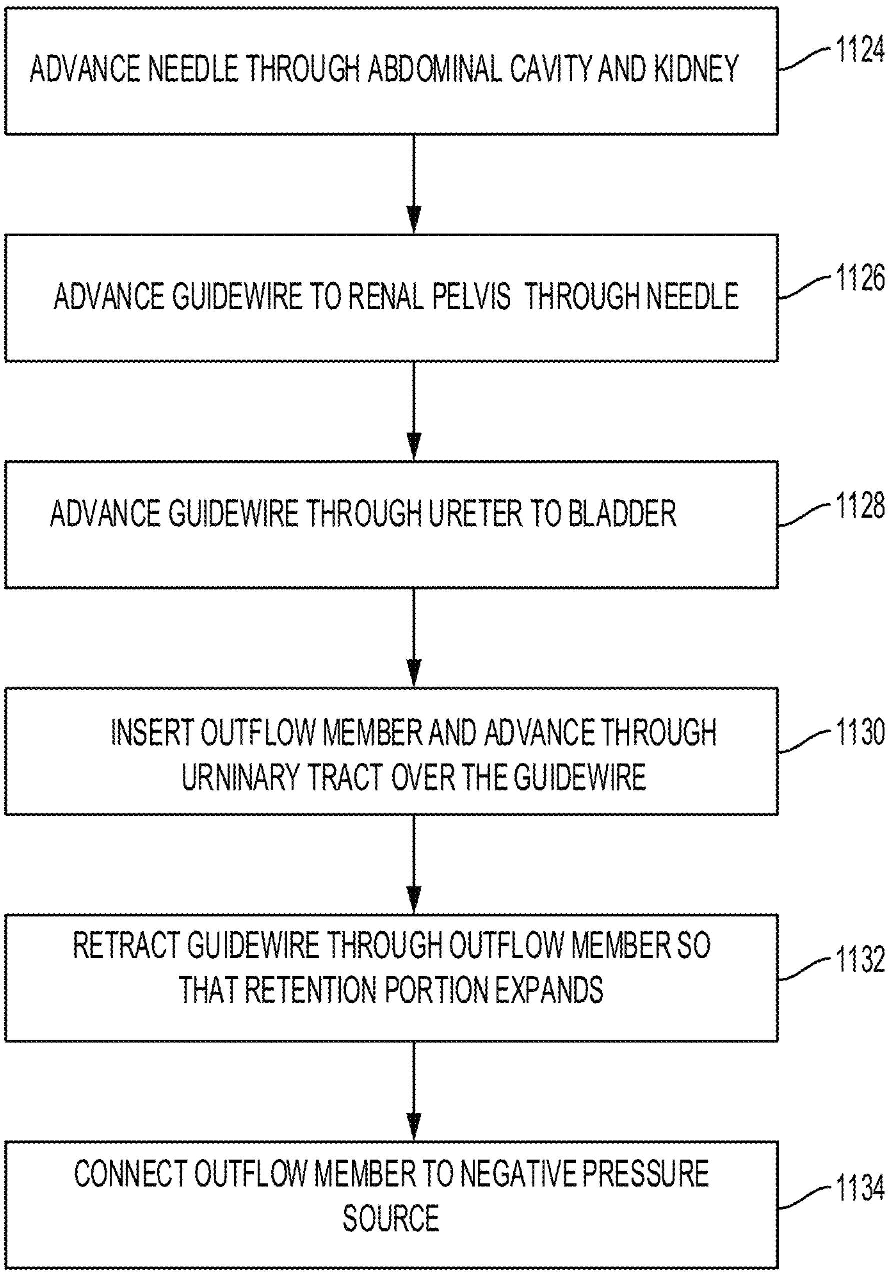
Figure 14G:
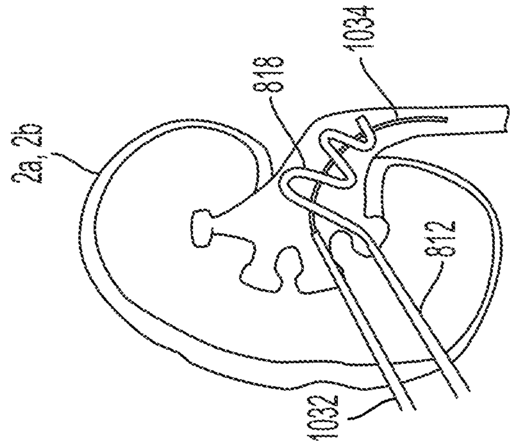
Figure 14F:
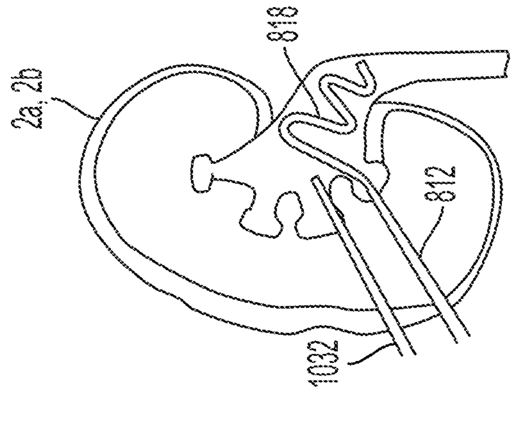

With reference to FIG. 13B, after the retention portion 818 of the inflow member 812 is deployed in the renal pelvis, the outflow member 1012 can be deployed. For example, at step 1124, another needle 1032 connected to a conical tip catheter can be advanced through the abdominal cavity and inserted into the kidney. Once the needle 1032 is advanced to the renal pelvis, at step 1126, another guidewire 1036 can be advanced to the renal pelvis through the needle 1032, as shown in FIG. 14F. At step 1128, the guidewire 1036 is then advanced through the ureter to the bladder. Once the guidewire 1036 is in position in the bladder, the needle 1032 can be retracted back through the catheter. Next, at step 1130, the outflow member 1012 of the urinary catheter 810 can be inserted into the patient's abdominal cavity through a percutaneous access site and advanced through the kidney, renal pelvis, and ureter to the bladder over the guidewire 1036 and/or needle 1032, as shown in FIG. 14G. At step 1132, once the distal end 1016 of the outflow member 1012 is advanced into the bladder, the guidewire 1036 can be retracted through the outflow member 1012 and into the catheter. As the guidewire 1036 is retracted from the distal portion 1026 of the outflow member 1012, the retention portion 1028 of the outflow member 1012 can transition to its expanded state. For example, removing the guidewire 1036 can cause the distal portion 1026 of the outflow member 1012 to form the pigtail coil or any other convenient coil or retention structure, as are known in the art. After the outflow member 1012 is fully deployed, with the distal portion 1026 in the ureter or bladder of the urinary tract, at step 1134, the outflow member 1012 can be connected to the negative pressure source. For example, the proximal portion 1024 of the outflow member 1012 can be connected to a discharge side outlet or port of the implanted or external pump so that fluid discharged from the pump enters the outflow lumen 1022 of the outflow member 1012 and passes through the lumen 1022 to the patient's bladder.

Once the inflow member 812 and the outflow member 1012 are connected to the negative pressure source, such as the pump, the negative pressure source can be activated to provide negative pressure therapy to the patent through the inflow lumen 814 of the inflow member 812. For example, negative pressure can be applied continuously for a predetermined period of time. In other examples, negative pressure can be applied as pressure pulses provided for short duration at predetermined intervals. In some examples, the negative pressure source, such as the pump, can alternate between providing negative pressure and positive pressure. It is believed that such alternating pressure therapy may further stimulate the kidneys resulting in increased urine production.

Drainage Hole Distribution for Urinary Catheters

With reference to FIGS. 15-18, in some examples, the distribution of the drainage holes or openings of the urinary catheters of the present disclosure can be optimized or selected to improve efficiency of the negative pressure therapy. For example, drainage holes 824 of the inflow member 812 can be sized and spaced to improve fluid flow through the retention portion 818. In particular, the present inventors have discovered that when a negative pressure is applied to the inflow lumen 814 of the inflow member 812 a majority of fluid is drawn into the inflow lumen 814 through proximal-most holes 824 or openings. In order to improve flow dynamics so that fluid is also received through more distal holes or openings and/or through an open distal end 820 of the inflow member 812, larger size or a greater number of holes 824 or openings can be provided towards the distal end 820 of the retention portion 818. For example, a total area of holes 824 or openings on a length of inflow member 812 near a proximal end 846 of the retention portion 818 may be less than a total area of holes 824 or openings of a similar sized length of the inflow member 812 located near the open distal end 820 of the inflow member 812. In particular, it may be desirable to produce a flow distribution through the inflow lumen 814 in which less than 1%, preferably less than 70%, and, more preferably, less than 55% of fluid flow is drawn into the inflow lumen 814 through a single hole 824 or opening or a small number of holes 824 or openings positioned near the proximal end 846 of the retention portion 818.

In many examples, the holes 824 or openings are generally a circular shape, although triangular, elliptical, square-shaped, diamond shaped, and any other opening shapes may also be used. Further, as will be appreciated by one of ordinary skill in the art, a shape of the holes 824 or openings may change as the inflow member 812 transitions between an uncoiled or elongated position and a coiled or deployed position. It is noted that while the shape of the holes 824 or openings may change (e.g., the orifices may be circular in one position and slightly elongated in the other position), the area of the holes or openings is substantially similar in the elongated or uncoiled position compared to the deployed or coiled position.

In some examples, the first coil 836 of the retention portion 818 can be free or essentially free from holes 824 or openings. For example, a total area of holes 824 or openings on the first coil 836 can be less than or substantially less than a total area of holes 824 or openings of coils 838, 840.

Additional examples of various arrangements of holes or openings that could be used for a coiled retention portion of the present disclosure are illustrated in FIGS. 15-18. As shown in FIGS. 15-18, a retention portion 1330 is depicted in its uncoiled or straight position, as occurs when a guidewire is inserted through the drainage lumen.

Figure 15:
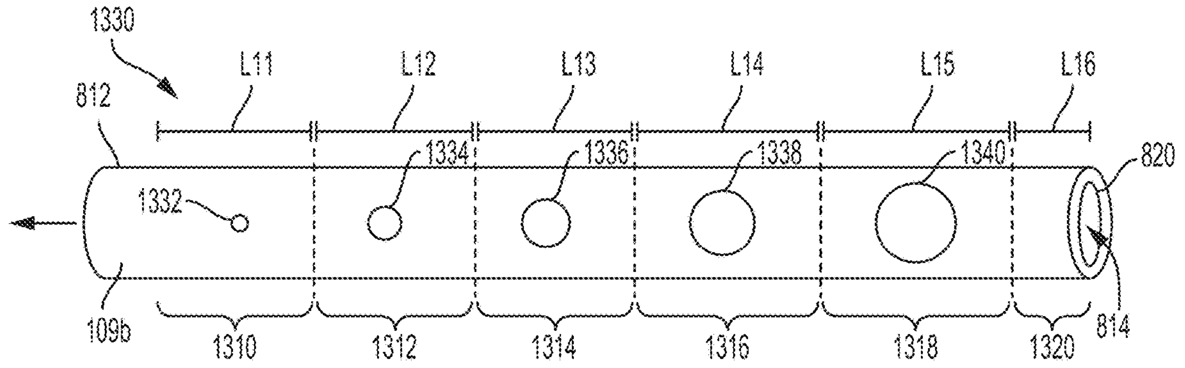
FIG. 15 is a schematic drawing of a retention portion of a urinary catheter in a constrained or linear position, according to an example of the present disclosure.

An exemplary retention portion 1330 is illustrated in FIG. 15. In order to more clearly describe positioning of openings of the retention portion 1330, the retention portion 1330 is referred to herein as being divided into a plurality of sections or perforated sections, such as a proximal-most or first section 1310, a second section 1312, a third section 1314, a fourth section 1316, a fifth section 1318, and a distal-most or sixth section 1320. One of ordinary skill in the art would understand that fewer or additional sections can be included, if desired. As used herein, "section" refers to a discrete length of the tube 1322 within the retention portion 1330. In some examples, sections are equal in length. In other examples, some sections can have the same length, and other sections can have a different length. In other examples, each section has a different length. For example, each of sections 1310, 1312, 1314, 1316, 1318 and 1320 can have a length L11-L16, respectively, ranging from about 5 mm to about 35 mm, and preferably from about 5 mm to 15 mm.

In some examples, each section 1310, 1312, 1314, 1316, 1318 and 1320 comprises one or more holes or openings 1332. In some examples, each section each comprises a single opening 1332. In other examples, the first section 1310 comprises a single opening 1332 and other sections comprise multiple openings 1332. In other examples, different sections comprise one or more openings 1332, each of the opening(s) having a different shape or different total area.

In some examples, the openings 1332 can be sized such that a total area of openings of the first section 1310 is less than a total area of openings of the adjacent second section 1312. In a similar manner, if the retention portion 1330 further comprises a third section 1314, then openings of a third section 1314 can have a total area that is greater than the total area of the openings of the first section 1310 or the second section 1312. Openings of the forth 1316, fifth 1318, and sixth 1320 sections may also have a gradually increasing total area and/or number of openings to improve fluid flow through the tube 1222.

As shown in FIG. 15, the retention portion 1330 of the tube comprises five sections 1310, 1312, 1314, 1316, 1318, each of which comprises a single opening 1332, 1334, 1336, 1338, 1340. The retention portion 1330 also comprises a sixth section 1320 which comprises the open distal end 1220 of the tube 1222. In this example, the opening 1332 of the first section 1310 has the smallest total area. For example, a total area of the opening 1332 of the first section can range from about 0.002 $mm^2$ and about 2.5 $mm^2$, or about 0.01 $mm^2$ and 1.0 $mm^2$, or about 0.1 $mm^2$ and 0.5 $mm^2$. In one example, the opening 1332 is about 55 mm from the distal end 1220 of the catheter, has a diameter of 0.48 mm, and an area of 0.18 $mm^2$. In this example, a total area of openings 1334 of the second section 1312 is greater than the total area of openings 1232 of the first section 1310 and can range in size from about 0.01 $mm^2$ to about 1.0 $mm^2$. The third 1336, fourth 1338, and fifth 1350 openings can also range in size from about 0.01 $mm^2$ to about 1.0 $mm^2$. In one example, the second opening 1334 is about 45 mm from the distal end of the catheter 1220, has a diameter of about 0.58 mm, and an area of about 0.27 $mm^2$. The third opening 1336 can be about 35 mm from the distal end of the catheter 1220 and have a diameter of about 0.66 mm. The fourth opening 1338 can be about 25 mm from the distal end 1220 and have a diameter of about 0.76 mm. The fifth opening 1340 can be about 15 mm from the distal end 1220 of the catheter and have a diameter of about 0.889 mm. In some examples, the open distal end 1220 of the tube 1222 has the largest opening having an area ranging from about 0.5 $mm^2$ to about 5.0 $mm^2$ or more. In one example, the open distal end 1220 has a diameter of about 0.97 mm and an area of about 0.74 $mm^2$.

As described herein, openings 1332, 1334, 1336, 1338, 1340 can be positioned and sized so that a volumetric flow rate of fluid passing through the first opening 1332 more closely corresponds to a volumetric flow rate of openings of more distal sections, when negative pressure is applied to the drainage lumen 814 of the inflow member 812, for example from the proximal portion 816 of the drainage lumen 814. As described above, if each opening were the same area, then, when negative pressure is applied to the drainage lumen 814, the volumetric flow rate of fluid passing through the proximal-most of first opening 1332 would be substantially greater than a volumetric flow rate of fluid passing through openings 1334 closer to the distal end 820 of the retention portion 1330. While not intending to be bound by any theory, it is believed that when negative pressure is applied, the pressure differential between the interior of the drainage lumen 814 and external to the drainage lumen 814 is greater in the region of the proximal-most opening and decreases at each opening moving towards the distal end of the tube. For example, sizes and positions of the openings 1332, 1334, 1336, 1338, 1340 can be selected so that a volumetric flow rate for fluid which flows into openings 1334 of the second section 1312 is at least about 30% of a volumetric flow rate of fluid which flows into the opening(s) 1332 of the first section 1310. In other examples, a volumetric flow rate for fluid flowing into the proximal-most or first section 1310 is less than about 60% of a total volumetric flow rate for fluid flowing through the proximal portion of the drainage lumen 1224. In other examples, a volumetric flow rate for fluid flowing into openings 1332, 1334 of the two proximal-most sections (e.g., the first section 1310 and the second section 1312) can be less than about 1% of a volumetric flow rate of fluid flowing through the proximal portion of the drainage lumen 1224 when a negative pressure, for example a negative pressure of about −45 mmHg, is applied to the proximal end of the drainage lumen.

As will be appreciated by one of ordinary skill in the art, volumetric flow rate and distribution for a catheter or tube comprising a plurality of openings or perforations can be directly measured or calculated in a variety of different ways. As used herein, "volumetric flow rate" means actual measurement of the volumetric flow rate downstream and adjacent to each opening or using a method for "Calculated Volumetric Flow Rate" described below.

For example, actual measurement of the dispersed fluid volume over time can be used to determine the volumetric flow rate through each opening 1332, 1334, 1336, 1338, 1340. In one exemplary experimental arrangement, a multi-chamber vessel comprising individual chambers sized to receive sections 1310, 1312, 1314, 1316, 1318, 1320 of the retention portion 1330 could be sealed around and enclose the retention portion 1330. Each opening 1332, 1334, 1336, 1338, 1340 could be sealed in one of the chambers. An amount of fluid volume drawn from the respective chamber into the tube 1522 through each opening 1332, 1334, 1336, 1338, 1340 could be measured to determine an amount of fluid volume drawn into each opening over time when a negative pressure is applied. The cumulative amount of fluid volume collected in the inflow member 812 by the implanted or external pump would be equivalent to the sum of fluid drawn into each opening 1332, 1334, 1336, 1338, 1340.

Alternatively, volumetric fluid flow rate through different openings 1332 1334, 1336, 1338, 1340 can be calculated mathematically using equations for modeling fluid flow through a tubular body. For example, volumetric flow rate of fluid passing through openings 1332 1334, 1336, 1338, 1340 and into the inflow lumen 814 can be calculated based on a mass transfer shell balance evaluation.

Figure 16:
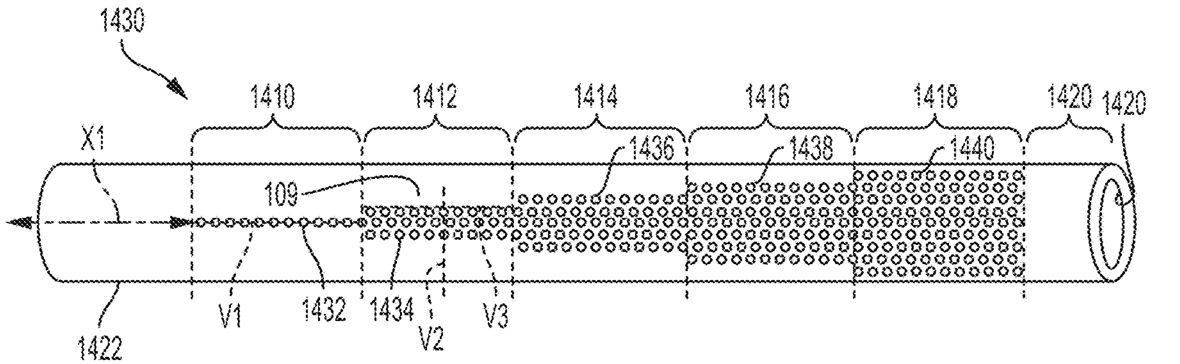
FIG. 16 is a schematic drawing of another example of a retention portion of a urinary catheter in a constrained or linear position, according to an example of the present disclosure.

Another exemplary retention portion 1430 with openings 1432, 1434, 1436, 1438, 1440 is illustrated in FIG. 16. As shown in FIG. 16, the retention portion 1430 comprises numerous smaller perforations or openings 1432, 1434, 1436, 1438, 1440. Each of the openings 1432, 1434, 1436, 1438, 1440 can have a substantially identical cross-sectional area or one or more openings 1432, 1434, 1436, 1438, 1440 can have different cross-sectional areas. As shown in FIG. 16, the retention portion 1430 comprises six sections 1410, 1412, 1414, 1416, 1418, 1420, such as are described above, wherein each section comprises a plurality of the openings 1432, 1434, 1436, 1438, 1440. In the example shown in FIG. 16, a number of openings 1432, 1434, 1436, 1438, 1440 per section increases towards the distal end 820 of the inflow member 812, such that a total area of openings 1432, 1434, 1436, 1438, 1440 in each section increases compared to a proximally adjacent section.

Figure 17:
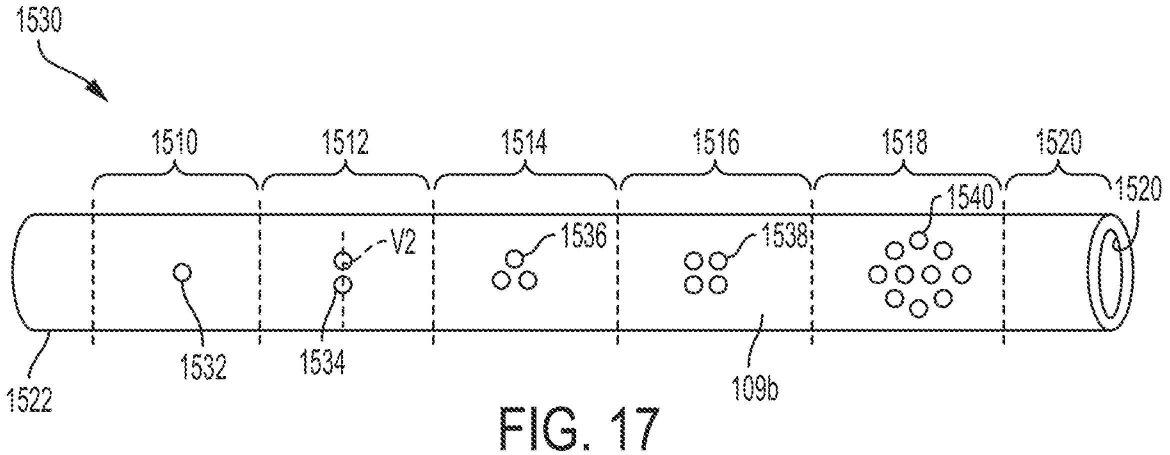
FIG. 17 is a schematic drawing of another example of a retention portion of a urinary catheter in a constrained or linear position, according to an example of the present disclosure.

As shown in FIG. 16, openings 1432 of the first section 1410 are arranged along a first virtual line V1, which is substantially parallel to a central axis X1 of the retention portion 1430. Openings 1434, 1436, 1438, 1440 of the second 1412, third 1414, fourth 1416, and fifth 1418 sections, respectively, are positioned on the sidewall of the tube 1422 in a gradually increasing number of rows, such that openings 1434, 1436, 1438, 1440 of these sections also line up around a circumference of the tube 1422. For example, some of the openings 1434 of the second section 1412 are positioned such that a second virtual line V2 extending around a circumference of the sidewall of the tube 1422 contacts at least a portion of multiple openings 1434. For example, the second section 1412 can comprise two or more rows of perforations or openings 1434, in which each opening 1434 has an equal or different cross-sectional area. Further, in some examples, at least one of the rows of the second section 1412 can be aligned along a third virtual line V3, which is parallel with the central axis X1 of the tube 1422, but is not co-extensive with the first virtual line V1. In a similar manner, the third section 1414 can comprise five rows of perforations or openings 1436, in which each opening 1436 has an equal or different cross-sectional area; the fourth section 1416 can comprise seven rows of perforations or openings 1438; and the fifth section 1418 can comprise nine rows of perforations or openings 1440. As in previous examples, the sixth section 1420 comprises a single opening, namely the open distal end 1420 of the tube 1422. In the example of FIG. 17, each of the openings has the same area, although the area of one or more openings can be different if desired.

Another exemplary retention portion 1530 with openings 1532, 1534, 1536, 1538, 1540 is illustrated in FIG. 17. The retention portion 1530 of FIG. 17 comprises a plurality of similarly sized perforations or openings 1532, 1534, 1536, 1538, 1540. As in previous examples, the retention portion 1530 can be divided into six sections 1510, 1512, 1514, 1516, 1518, 1520, each of which comprises at least one opening. The proximal-most or first section 1510 comprises one opening 1532. The second section 1512 comprises two openings 1534 aligned along the virtual line V2 extending around a circumference of the sidewall of the tube 1522. The third section 1514 comprises a grouping of three openings 1536, positioned at vertices of a virtual triangle. The fourth section 1516 comprises a grouping of four openings 1538 positioned at corners of a virtual square. The fifth section 1518 comprises ten openings 1540 positioned to form a diamond shape on the sidewall of the tube 1522. As in previous examples, the sixth section 1520 comprises a single opening, namely the open distal end 1520 of the tube 1522. The area of each opening can range from about 0.001 $mm^2$ and about 2.5 $mm^2$. In the example of FIG. 17, each of the openings has the same area, although the area of one or more openings can be different if desired.

Figure 18:
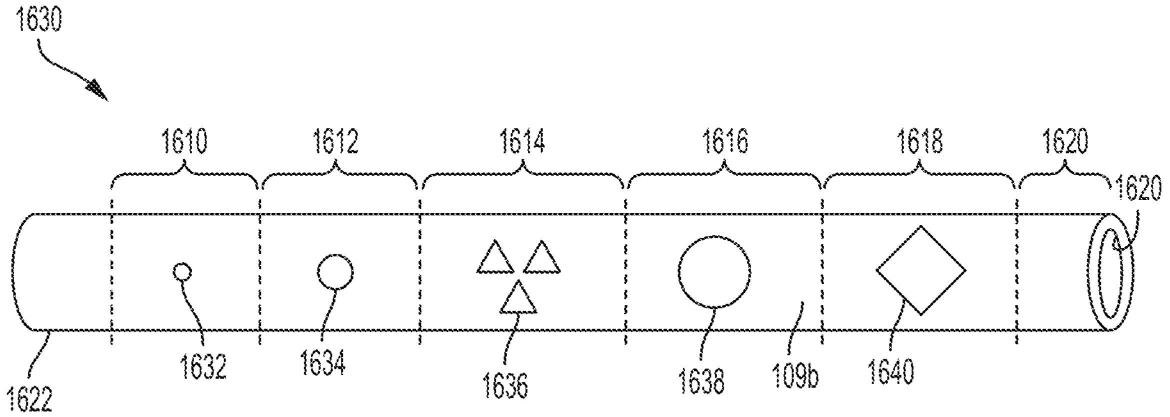
FIG. 18 is a schematic drawing of another example of a retention portion of a urinary catheter in a constrained or linear position, according to an example of the present disclosure.

Another exemplary retention portion 1630 with openings 1632, 1634, 1636, 1638, 1640 is illustrated in FIG. 18. The openings 1632 1634, 1636, 1638, 1640 of the retention portion 1630 have different shapes and sizes. For example, the first section 1610 comprises a single circular opening 1632. The second section 1612 has a circular opening 1634 with a larger cross-sectional area than the opening 1632 of the first section 1610. The third section 1614 comprises three triangular shaped openings 1636. The fourth section 1616 comprises a large circular opening 1638. The fifth section 1618 comprises a diamond shaped opening 1640. As in previous examples, the sixth section 1620 comprises the open distal end 1620 of the tube 1622. FIG. 18 illustrates one example of an arrangement of different shapes of openings in each section. It is understood that the shape of each opening in each section can be independently selected, for example the first section 1610 can have one or more diamond-shaped openings or other shapes. The area of each opening can be the same or different and can range from about 0.001 $mm^2$ and about 2.5 $mm^2$.

Coated and/or Impregnated Urinary Catheters

Referring to FIGS. 19A-19D, in some examples, at least a portion or all of the negative pressure therapy devices, such as any or all of the inflow members 812 and outflow member 1012 described herein, can be coated and/or impregnated with at least one of the coating/impregnant material(s) described herein. Portions or all of any of the devices described herein, generally designated collectively as coated devices 1910 shown in FIGS. 19A-19D, such as catheter(s), can be coated and/or impregnated with at least one of the coating/impregnant materials described herein.

In some examples, the coated device 1910 can be configured to facilitate insertion and/or removal of the coated device 1910 within a urinary tract of the patient and/or, once inserted, the at least one coating(s) and/or impregnation(s) 1922 can improve function of the device 1910. The coated devices 1910 can be configured for insertion in one or more of a ureter, renal pelvis, and/or kidney of a patient. The coated devices 1910 can be deployed to maintain an end 1944 or retention portion 1920 of the device 1910 at a desired position within the urinary tract. The device 1910 can be sized to fit securely at a desired position within the urinary tract, as described in detail herein. The device 1910 can be narrow enough in a retracted state so that the coated device 1910 can be easily inserted and removed. The device 1910 can have any of the configurations described herein, for example a catheter or stent. In some examples, the retention portion 1920 of a suitable catheter comprises a funnel, coil, balloon, cage, sponge, and/or combinations thereof.

In some examples, the at least one coating(s) and/or impregnation(s) 1922 can be present on and/or in at least the outer periphery or the protective surface area of the device 1910 that inhibits mucosal tissue from occluding the at least one protected drainage hole(s), port(s) or perforation(s) 1936 upon application of negative pressure through the catheter. In some examples, the at least one coating(s) and/or impregnation(s) 1922 can be present on and/or in any portion(s) of the device 1910, and/or on or in the entire device 1910. In some examples, the at least one coating(s) and/or impregnation(s) 1922 can be present on and/or in at least a portion(s) of the retention portion 1920, or on and/or in all of the retention portion 1920. In some examples, the at least one coating(s) and/or impregnation(s) 1922 can be present on and/or in at least a portion(s) of a surface of the device, or on and/or in the entire surface of the device. In some examples, the at least one coating(s) and/or impregnation(s) 1922 can be present on and/or in at least an outer surface 1928 of the device, or on and/or in the entire outer surface 1928 of the device. In some examples, the at least one coating(s) and/or impregnation(s) 1922 can be present on and/or in other portions of the device 1910, such as portions or all of the delivery catheters of any of the above described catheter assemblies. In some examples, the at least one coating(s) and/or impregnation(s) 1922 are formed from one or more flexible coating materials, which do not appreciably or substantially affect a flexibility of the coated and/or impregnated device 1910.

In some examples, the at least one coating(s) 1922 can comprise one or more coatings, for example one to ten coatings, or two to four coatings. In some examples, the material(s) from which the device 1910 is formed (device material(s) discussed herein) can be coated with at least one of the coating/impregnant material(s) discussed herein. The coating(s) 1922 may be applied or formed in layers, with the understanding that it is possible that components of one coating layer may migrate into one or more adjacent or proximate layers, and or into the surface or within the device 1910.

In some examples, the material(s) from which the device 1910 is formed (device material(s) discussed herein) can be impregnated with at least one of the coating/impregnant material(s) discussed herein. As used herein, "impregnated" means that at least a portion of the coating/impregnant material(s) discussed herein permeate beneath an outer surface of and/or within at least a portion of the device material(s) from which the device 1910 is formed. In some examples, different coating/impregnant material(s) and/or different amounts of respective coating/impregnant material(s) discussed herein can be used to impregnate different portions or regions of the device 1910. For example, the retention portion 1920 can be impregnated with at least one of the coating/impregnant material(s) described herein, such as at least one lubricant material(s) and/or at least one antimicrobial material(s), while the drainage tube is impregnated only with at least one antimicrobial material(s). Portions or all of the device 1910 can be both impregnated and/or coated, as desired. In some examples, there can be layers of different impregnants at different depths within the device 1910.

The at least one coating/impregnant material(s) (which can be used as a coating material(s) and/or impregnant material(s), referred to as "coating/impregnant material(s)" for brevity) comprises at least one (one or more) of lubricant(s), antimicrobial material(s), pH buffer(s) or anti-inflammatory material(s). In some examples, the at least one coating(s) and/or impregnation(s) 1922 can be used to improve short term or long term performance of the device 1910, reduce pain during insertion/removal of the device 1910 into the urinary tract, and/or mitigate risks associated with prolonged use of an indwelling device.

For example, at least a portion of the device 1910 can be coated and/or impregnated with at least one coating/impregnant material(s) comprising at least one lubricant(s). The at least one coating(s) and/or impregnation(s) 1922 comprising the at least one lubricant(s) can, for example, have a lower coefficient of friction than the uncoated/unimpregnated device, function as a lubricant, and/or become lubricated or slippery in the presence of fluid such as moisture or urine. The presence of a lubricant in the at least one coating(s) and/or impregnation(s) 1922 may make the device 1910 easier to deploy and remove. Generally, in some examples, the at least one coating(s) and/or impregnation(s) 1922 can comprise materials configured to address issues and sources of discomfort associated with indwelling catheters.

Alternatively or additionally, the device 1910 can be coated and/or impregnated with at least one of antimicrobial material(s), pH buffer(s) and/or anti-inflammatory material(s). The at least one of antimicrobial material(s), pH buffer(s) and/or anti-inflammatory material(s) may mitigate risks associated with prolonged use of indwelling catheters, such as tissue ingrowth through portions of the device, foreign body reactions caused when portions of the device contact surrounding fluid and/or tissues, infection to tissues surrounding the device, and/or formation of encrustations on portions of the device. Encrustations can be caused by, for example, protein adsorption and/or buildup of minerals or urine crystals.

In some examples, the at least one coating(s) and/or impregnation(s) 1922 comprises at least one lubricant. In some examples, outer surface(s) or layer(s) of the at least one coating(s) and/or impregnation(s) 1922 comprise at least one lubricant. Lubricious coating(s)/impregnant(s) can be described in terms of their degree of lubricity or kinetic coefficient of friction, or the amount of friction reduction provided compared to an uncoated device, or a device comprising one or more coating(s)/impregnant(s) having an outer layer(s) having a kinetic coefficient of friction which is greater than the kinetic coefficient of friction of a lubricant coated comparable device. The kinetic coefficient of friction can be determined using ASTM Method D1894-14 (March 2014). A rigid mandrel can be inserted through the inner lumen of the stent/catheter section being tested, which is sized to minimize the amount of open space inside the stent/catheter inner lumen and any potential resultant constriction of the inner lumen when the sled is dragged along the material. Alternatively, the catheter tube can be slit and opened into a flattened sheet for testing.

In some examples, the lubricant(s) can comprise at least one hydrophilic lubricant material. Exemplary hydrophilic lubricant materials comprise at least one (one or more) of polyethylene glycol, polyvinylpyrrolidone, polytetrafluoroethylene, polyvinyl alcohol, polyacrylamide, polymethacrylate, as well as other acrylic polymers or copolymers of the above-listed materials, or polyelectrolytes. An exemplary hydrophilic coating material/impregnant is ComfortCoat® polyelectrolyte-containing hydrophilic coating which is available from Koninklijke DSM N.V. Examples of suitable hydrophilic coating/impregnant material(s) comprising polyelectrolyte(s) are disclosed in U.S. Pat. No. 8,512,795, which is incorporated by reference herein.

In some examples, the at least one coating(s)/impregnation(s) 1922 can comprise at least one material(s) which is not hydrophilic. For example, one or more layers of the at least one coating(s) and/or impregnation(s) 1922 can be comprise or be formed from polytetrafluoroethylene (e.g., Teflon), siloxane(s), silicone or polysiloxane(s), or other slippery and/or low friction materials.

In some examples, the lubricant can comprise at least one polymer material(s), such as at least partially cross-linked polymer material(s) (e.g., a gel or hydrogel). In some examples, the at least one polymer material(s) readily takes up or entraps fluid or liquid. Gels or hydrogels are systems that comprise three-dimensional, physically or chemically bonded polymer networks that entrap fluid or liquid, such as water, in intermolecular space. As known in the art, a gel or hydrogel can refer to an at least partially cross-linked material comprising a substantial liquid portion, but which exhibits little or no flow when in a steady state. By weight, a gel is generally mostly liquid, but may behave like a solid due to the cross-linked structure. Due to their ability to accommodate high water content, porosity, and soft consistency, hydrogels closely simulate natural living tissue, Gels and hydrogels may be chemically stable or they may degrade and eventually disintegrate and dissolve. In some examples, the at least one lubricant is biocompatible.

For example, useful gels or hydrogels can comprise one or more of polyethylene glycol, polyvinylpyrrolidone, polytetrafluoroethylene, polyvinyl alcohol, polyacrylamide, polymethacrylate, and/or hydrogels comprising polyacrylic acid (PAA) and/or disulphide-crosslinked (poly(oligo(ethyleneoxide) monomethyl ether methacrylate)) (POEMA). As a result of taking up or entrapping fluid (such as moisture), some hydrophilic materials can become gel-like, slick, and/or smooth.

Accordingly, when in the presence of fluid (such as moisture and/or urine), the hydrophilic material of the lubricant can provide increased lubricity between the stent or catheter device 1910 and adjacent portions of the urinary tract of the patient.

Combinations or mixtures of hydrophilic lubricant material(s), non-hydrophilic lubricant material(s) and/or polymer lubricant material(s) can be used in the same coating/impregnant or different coating(s)/impregnant(s), or layers thereof, as desired. In some examples, the concentration of the at least one lubricant(s) in the at least one coating(s) and/or impregnation(s) 1922 prior to drying or curing can range from about 0.1 to about 99.9 weight percent or 100 weight percent based upon the total weight of the coating/impregnant material(s) composition, or about 20 to 100 weight percent, or about 50 to about 100 weight percent. In some examples, the concentration of the at least one lubricant(s) in the at least one coating(s) and/or impregnation(s) 1922 after drying or curing can range from about 0.1 to about 99.9 weight percent or 100 weight percent based upon the total weight of the dried or cured coating/impregnation, or about 20 to 100 weight percent, or about 50 to about 100 weight percent.

In some examples, the at least one coating(s) and/or impregnation(s) 1922 can comprise at least one antimicrobial material(s), for example to inhibit tissue growth and/or to prevent infection. For example, any of the at least one coating(s) and/or impregnation(s) 1922, such as the outermost layer 1924 and/or any of the sublayer(s) 1926, can comprise the at least one antimicrobial material itself, or one or more material(s) comprising the at least one antimicrobial material, for example a polymer matrix formed from a suitable biocompatible material impregnated with antimicrobial material(s). Alternatively or additionally, the sublayer(s) 1926 can comprise a liposome-coating or similar material, and can be configured to deliver bacteriophages or drug therapies. An antimicrobial material can refer to, for example, at least one of antiseptic material(s), antiviral material(s), antibacterial material(s), antifungal material(s), and/or an antibiotic material(s), such as antibiotic medication or therapeutic agent. Examples of suitable antibacterial, antifungal, and/or antiseptic agents and materials can comprise chlorhexidine, silver ions, nitric oxide, bacteriophages, sirolimus, and/or sulfonamides. Some antibacterial materials, such as sirolimus, may also act as an immunosuppressant to reduce a foreign body response induced by an indwelling catheter. Examples of suitable antibiotic materials that can be included in at least one coating(s) and/or impregnation(s) 1922 can comprise amdinocillin, levofloxacin, penicillin, tetracyclines, sparfloxacin, and/or vancomycin. Doses or concentrations of such antimicrobial medications can be selected to avoid or reduce occurrence of infection, such as are known to those skilled in the art, such as about 1 to about 100 mcg/cm$^3$. The antimicrobial and/or antibacterial materials of the coating(s) can also comprise materials such as heparin, phosphorylcholine, silicone dioxide, and/or diamond-like carbon, to inhibit any of protein adsorption, biofilm formation, mineral and/or crystal buildup, and similar risk factors. Other suitable antimicrobial materials, which provide useful functional properties for the coating(s), can comprise other antimicrobial peptides, caspofungin, chitosan, parylenes, as well as organosilanes and other materials that impart mechanical antimicrobial properties.

In some examples, the concentration of the at least one antimicrobial material(s) in the at least one coating(s) and/or impregnation(s) 1922 prior to drying or curing can range from about 0.1 to about 99.9 weight percent or 100 weight percent based upon the total weight of the coating/impregnant material(s) composition, or about 20 to 100 weight percent, or about 50 to about 100 weight percent. In some examples, the concentration of the at least one antimicrobial material(s) in the at least one coating(s) and/or impregnation(s) 1922 after drying or curing can range from about 0.1 to about 99.9 weight percent or 100 weight percent based upon the total weight of the dried or cured coating/impregnation, or about 20 to 100 weight percent, or about 50 to about 100 weight percent.

In some examples, the at least one coating(s) and/or impregnation(s) 1922 comprising the antimicrobial material(s) should provide suitable protection for the coated device 1910 for the entire usable life of the device 1910, although the time period in which antimicrobial properties are present may be shorter. Accordingly, the at least one coating(s) and/or impregnation(s) 1922 should be thick enough and contain enough antimicrobial material to continue to exhibit antimicrobial properties for the usable life of the coated device 1910, which can be from about 1 day to about one year, or from about 10 days to about 180 days, or from about 30 days to about 1 days.

In some examples, alternatively or additionally, the at least one coating(s) and/or impregnation(s) 1922 can comprise at least one pH buffering material(s) to buffer the pH of the fluid in the urinary tract, such as urine. Such a buffering material(s), for example, may reduce or eliminate encrustations, which may adhere to surfaces of the coated device 1910. A pH buffering material is believed to reduce encrustations by inhibiting or preventing formation of urine crystals, which often adhere to indwelling structures positioned within the urinary tract. For example, in the presence of organisms capable of producing the urease enzyme, local increases in ammonium concentration and pH can result in the formation of crystals of at least one of calcium phosphate, magnesium phosphate, or magnesium ammonium phosphate, while crystals of urates and oxalates are more commonly seen with decreased pH level. The pH of urine can range from about 4.5 to about 8.0, typically about 6.0.

When the pH of the fluid in the urinary tract rises above a predetermined value, such as 6.0 or 7.0, for example, the at least one coating(s) and/or impregnation(s) 1922 can release a portion or all of the at least one buffering material into the fluid. Alternatively or additionally, when the pH of the fluid in the urinary tract falls below a predetermined value, such as 5.5 or 6.0, for example, the at least one coating(s) and/or impregnation(s) 1922 can release a portion or all of the at least one buffering material into the fluid. Alternatively or additionally, the at least one coating(s) and/or impregnation(s) 1922 can release a portion or all of the at least one buffering material into the fluid when the concentration of at least one of calcium, magnesium, phosphorous, oxalates or uric acid reaches a predetermined value. For example in patients with elevated levels of at least one of calcium, magnesium, phosphorous, oxalates or uric acid in their fluid or urine, examples of suitable predetermined values of analytes at which the at least one coating(s) and/or impregnation(s) 1922 can release a portion or all of the at least one buffering material into the fluid are: for calcium at least about 15 mg/deciliter (dl), for magnesium at least about 9 mg/dl, for phosphorous at least about 60 mg/dl, for oxalates at least about 1.5 mg/dl, and for uric acid at least about 36 mg/dl. Calcium specifically is commonly referenced as a ratio to urinary creatinine, i.e., normal value would be urine calcium:urine creatinine <0.14. The levels of these analytes in fluid or urine can be determined using one or more of colorimetric analysis, spectrometry or microscopy methods of the fluid or urine samples. "Normal" values and reference ranges are often provided in units of 'mg/24 hrs' since the excretion is highly driven by dietary intake and so would be expected to be variable over time. Excretion of these analytes can also be significantly impacted by the use of certain medications, such as diuretics. A device could intrinsically "sense" and react to analyte levels by releasing one or more buffer agents as a result of the binding of analytes to at least a portion of or a component of a coating layer. Predetermined thresholds can be set for specific analytes in order to determine binding affinities of a coating layer so that different levels of binding would trigger release of varying amounts of the one or more buffer agents, as desired.

Examples of suitable pH buffering material(s) can comprise, for example, an acid salt impregnated in a dissolvable polymer material layer. As will be appreciated by those skilled in the art, as the acid salt dissolves in the presence of bodily fluid or moisture, an acid solution is produced. Desirably, the produced acidic solution inhibits formation of the encrustations, but is not so acidic as to damage body tissues. Examples of suitable acid salts that can be used as a suitable pH buffer layer can comprise weakly acidic salts, such as sodium citrate, sodium acetate, and/or sodium bicarbonate. In some examples, the pH buffering material(s) can be dispersed in a hydrogel, colloid and/or copolymer matrix, such as methacrylic acid and methyl methacrylate copolymer, and dispersed or layered with high affinity calcium- or phosphate-binding agent(s), such as ethylene glycol tetraacetic acid (EGTA).

In some examples, the concentration of the at least one pH buffering material(s) in the at least one coating(s) and/or impregnation(s) 1922 prior to drying or curing can range from about 0.1 to about 99.9 weight percent or 100 weight percent based upon the total weight of the coating/impregnant material(s) composition, or about 20 to 100 weight percent, or about 50 to about 100 weight percent. In some examples, the concentration of the at least one pH buffering material(s) in the at least one coating(s) and/or impregnation(s) 1922 after drying or curing can range from about 0.1 to about 99.9 weight percent or 100 weight percent based upon the total weight of the dried or cured coating/impregnation, or about 20 to 100 weight percent, or about 50 to about 100 weight percent.

In some examples, the at least one coating(s) and/or impregnation(s) 1922 can comprise outermost layer(s) 1924 and a single or multiple sublayer(s) 1926 (e.g., comprising either an antimicrobial sublayer or a pH buffering sublayer). In other examples, the sublayer(s) 1926 of the at least one coating(s) and/or impregnation(s) 1922 can comprise, for example, a first sublayer 1930 applied to the outer surface 1928 of the device 1910 comprising a pH buffering material, for example for reducing encrustation of urine crystals, and a second sublayer 1932 covering at least a portion of the first sublayer 1930. The second sublayer 1932 can comprise the antimicrobial material(s), for example. Alternatively, the first sublayer 1930 can comprise the antimicrobial material(s) and the second sublayer 1932 can comprise the pH buffering material(s).

In some examples, alternatively or additionally, the at least one coating(s) and/or impregnation(s) 1922 can comprise at least one anti-inflammatory material(s). Following insertion into the body, proteins and other biomolecules in the body, such as in the blood plasma and biological fluids, absorb onto the surface of the biomaterial of the device or implant. Nonspecific biomolecule and protein adsorption and subsequent leukocyte adhesion, known as "biofouling" may result. Subsequent inflammatory reactions can result, such as biomaterial-mediated inflammation, which is a complex reaction of protein adsorption, leukocyte recruitment/activation, secretion of inflammatory mediators, and fibrous encapsulation of part or all of the device or implant. Reducing the inflammatory response, for example by reducing the protein binding and ability of the immune response to propagate, can prevent or reduce possible injury to the urinary tract tissues by contact with the device in the absence or presence of negative pressure.

Non-limiting examples of suitable anti-inflammatory material(s) comprise anti-inflammatory agent(s) and non-fouling surface treatment material(s). Examples of suitable anti-inflammatory agent(s) comprise at least one of Dexamethasone (DEX), Heparin or Alpha-melanocyte-stimulating hormone α-MSH). Examples of suitable non-fouling surface treatment material(s) comprise at least one of polyethylene glycol-containing polymers, poly(2-hydroxyethyl methacrylate), poly(N-isopropyl acrylamide), poly(acrylamide), phosphoryl choline-based polymers, mannitol, oligomaltose, and taurine groups.

In some examples, the concentration of the at least one anti-inflammatory material(s) in the at least one coating(s) and/or impregnation(s) 1922 prior to drying or curing can range from about 0.1 to about 99.9 weight percent or 100 weight percent based upon the total weight of the coating/impregnant material(s) composition, or about 20 to 100 weight percent, or about 50 to about 100 weight percent. In some examples, the concentration of the at least one anti-inflammatory material(s) in the at least one coating(s) and/or impregnation(s) 1922 after drying or curing can range from about 0.1 to about 99.9 weight percent or 100 weight percent based upon the total weight of the dried or cured coating/impregnation, or about 20 to 100 weight percent, or about 50 to about 100 weight percent.

In some examples, the at least one coating(s) and/or impregnation(s) 1922 can comprise the outermost layer(s) 1924 and a single or multiple sublayer(s) 1926 comprising the at least one anti-inflammatory material(s). In some examples, the outermost layer(s) 1924 can comprise at least one pH buffer material, and one or more sublayer(s) 1926 can comprise the at least one anti-inflammatory material(s).

In some examples, an overall thickness of the at least one coating(s) and/or impregnation(s) 1922, or depth of impregnation into the device material(s), can range from about 0.001 micrometer (about 1 nanometer) to about 10.0 millimeters, or about 0.001 micrometer to about 5 mm, or about 0.001 mm to about 5.0 mm, or about 0.01 mm to about 1.0 mm, or about 0.001 micrometer to about 0.2 mm, after application and drying and/or curing of the coating(s)/impregnant(s). In some examples, each coating/impregnant layer within multiple coating(s)/impregnant(s) layers can have a thickness ranging from about 0.001 micrometer to about 10.0 millimeters, or about 0.001 micrometer to about 5.0 mm, or about 0.001 micrometer to about 500 micrometers, after application and drying or curing of the coating(s)/impregnant(s) layer.

In some examples, an overall thickness of the at least one hydrated or swelled coating(s) and/or impregation(s) 1922, or depth of impregnation into the device material(s), can range from about 0.1 micrometer to about 25.0 millimeters, or about 0.1 micrometer to about 500 micrometers, or about 20 micrometers±20%.

In some examples, the density of the coating/impregnant material(s) composition can range from about 0.1 to about 200 mg/microliter prior to drying or curing, or about 1 mg/microliter. The coating/impregnant material(s) to be applied to the device 1910, prior to drying or curing, can further comprise at least one carrier or adjuvant, such as water, alcohol(s), silica oils such as polydimethylsiloxane(s), and/or polymeric matrix materials such as hydrogels, for example comprising polyacrylic acid (PAA) and/or disulphide-crosslinked (poly(oligo(ethylene-oxide) monomethyl ether methacrylate)) (POEMA).

In some examples, the concentration of at least one of lubricant(s), antimicrobial material(s), pH buffer(s) or anti-inflammatory material(s) in the coating/impregnant material(s) composition prior to drying or curing can range from about 0.1 to about 99.9 weight percent or 100 weight percent based upon the total weight of the coating/impregnant composition used for the respective layer. In some examples, the coating/impregnant material(s) composition can be applied to the device 1910, prior to drying or curing, in an amount ranging from at about 0.001 mg/cm$^2$ to about 5 mg/cm$^2$, or about 2 mg/cm$^2$ g 50%, per layer. In some examples, for coating/impregnant material(s) composition comprising at least one antimicrobial(s), the coating(s)/impregnant(s) can be applied to the device 1910, prior to drying or curing, in an amount ranging from at about 0.001 mg/cm$^2$ to about 5 mg/cm$^2$, or about 2 mg/cm$^2$±50%, or about 0.005 mg/cm$^2$ to about 0.025 mg/cm$^2$ per layer.

In some examples, an outermost coating/impregnant layer(s) 1924 comprises the at least one lubricant. In some examples, the at least one lubricant (such as a hydrophilic material, gel or hydrogel) is configured to remain or to at least partially or fully dissipate when exposed to fluid (such as moisture and/or urine), such as occurs when the catheter device 1910 is deployed in the patient's urinary tract, to reveal or uncover other materials of the at least one coating(s) and/or impregnation(s) 1922 or the outer surface 1928 of the catheter device 1910 beneath the lubricant coating. For example, as the lubricant dissipates, one or more sublayer(s) or underlying layers positioned below the outermost layer(s) 1924 may be exposed. The lubricant of the outermost layer(s) 1924 can be configured to dissipate into surrounding fluid or tissue within a desired time period following implantation. Since the lubricant can be primarily intended to facilitate insertion and positioning of the coated device 1910, a portion or all of the outermost layer 1924 may dissipate within a rather short period of time following insertion in the urinary tract. For example, the outermost layer 1924 may be configured to entirely, substantially or partially dissipate within 6 hours to 10 days, or 12 hours to 5 days, or 1 day to 3 days, following insertion and/or placement within the urinary tract. As used herein, a material, such as a portion or all of the outermost layer 1924, substantially dissipates when at least about 1%, or at least about 95%, or about 95%, or about 98%, of the outermost layer 1924 has released from the surface of the catheter 1910, or coating beneath the outermost layer, and been absorbed into surrounding fluid and/or tissues, and/or expelled from the patient's body. In some examples, an outermost layer 1924 which dissipates within 1 day to 10 days can have a total thickness, prior to or when hydrated or activated, ranging from 0.01 micrometer to 5.0 millimeters, or 0.001 mm to 2.5 mm, or 0.01 mm to 1.0 mm. In some embodiments, a thickness of the outermost layer 1924 may be largely dependent on how long the outermost layer 1924 should remain in place when within the urinary tract before dissolving to expose sublayer(s) 1926 of the at least one coating(s) and/or impregnation(s) 1922 and/or the outer surface 1928 of the catheter device 1910.

Upon dissipation of the outermost layer 1924, material of one or more sublayer(s) 1926 positioned below the outermost layer(s) 1924 may remain in place to provide a particular property or function for an extended period of time or may be configured to release into surrounding fluid and/or tissue to, for example, provide a desired therapeutic or beneficial effect for the surrounding fluid and/or tissue. For example, the material of the one or more sublayer(s) 1926 can be configured for slow release into surrounding tissue over a period ranging from about 1 day to about one year, or about 30 days to about 180 days, or about 45 days to about 1 day. In some examples, a rate of dissipation for the sublayer(s) 1926 is dependent on a thickness of the outermost layer 1924. For example, the sublayer(s) 1926 can have a total thickness ranging from about 0.01 micrometer to 5.0 millimeter, or about 0.01 mm to 4.0 mm, or about 0.1 mm to 3.0 mm. In some examples, the thickness of the sublayer(s) 1926 can be selected so that it can remain, or dissolve and release materials, for improving function of the catheter device 1910 for the entire useful life or time that the device 1910 is within the urinary tract.

In other examples, the outermost layer 1924 can be configured to remain adhered to the coated device 1910, and in some examples to maintain its beneficial properties, throughout some or all of the time period in which the coated device 1910 is within the urinary tract. For example, the outermost layer(s) 1924 may remain in place for a period of up to 10 days, 45 days, 1 days, or up to, at least, one year, when within a patient's urinary tract. In order to maintain beneficial or hydrophilic properties for up to at least one year, the outermost layer 1924 may be as thin as or thinner than 0.01 mm, or may be thicker than 5.0 mm, possibly up to 10.0 mm thick. Alternatively or additionally, the outermost layer 1924 can be formed from a material that does not dissolve or degrade, or only degrades slowly when within the urinary tract. For example, certain slippery or low friction non-hydrophilic materials, such as polytetrafluoroethene (PTFE) (e.g., Teflon), may remain in place without dissolving for extended periods of time.

When configured to maintain properties, such as hydrophilic properties, for an extended duration, the outermost layer 1924 can be configured for time-dependent permeability or release, such that bulk material of the sublayer(s) 1926 can pass through the outermost layer(s) 1924 and to surrounding fluid and/or tissue. For example, the outermost layer 1924 can comprise structures and/or void spaces for permitting moisture or fluid to penetrate through the outermost layer 1924 and to the one or more sublayer(s) 1926. In order to obtain such permeability, the outermost layer(s) 1924 can comprise a composite material wherein bulk hydrophilicity is maintained, while the at least one contributing material of the outermost layer 1924 provides properties, such as selective diffusibility, solubility, and/or porosity (e.g., microporosity, mesoporosity, or macroporosity). According to International Union of Pure and Applied Chemistry (IUPAC) nomenclature, microporosity, mesoporosity, and macroporosity describe materials exhibiting pores with diameters of less than 2.0 nanometers, between 2.0 and 50 nanometers, and greater than 50 nanometers, respectively. Processes that may be used to form porous materials can comprise, for example, phase separation, gas foaming, and soft and hard templating techniques, as well as other selective and additive manufacturing methods.

Figure 19A:
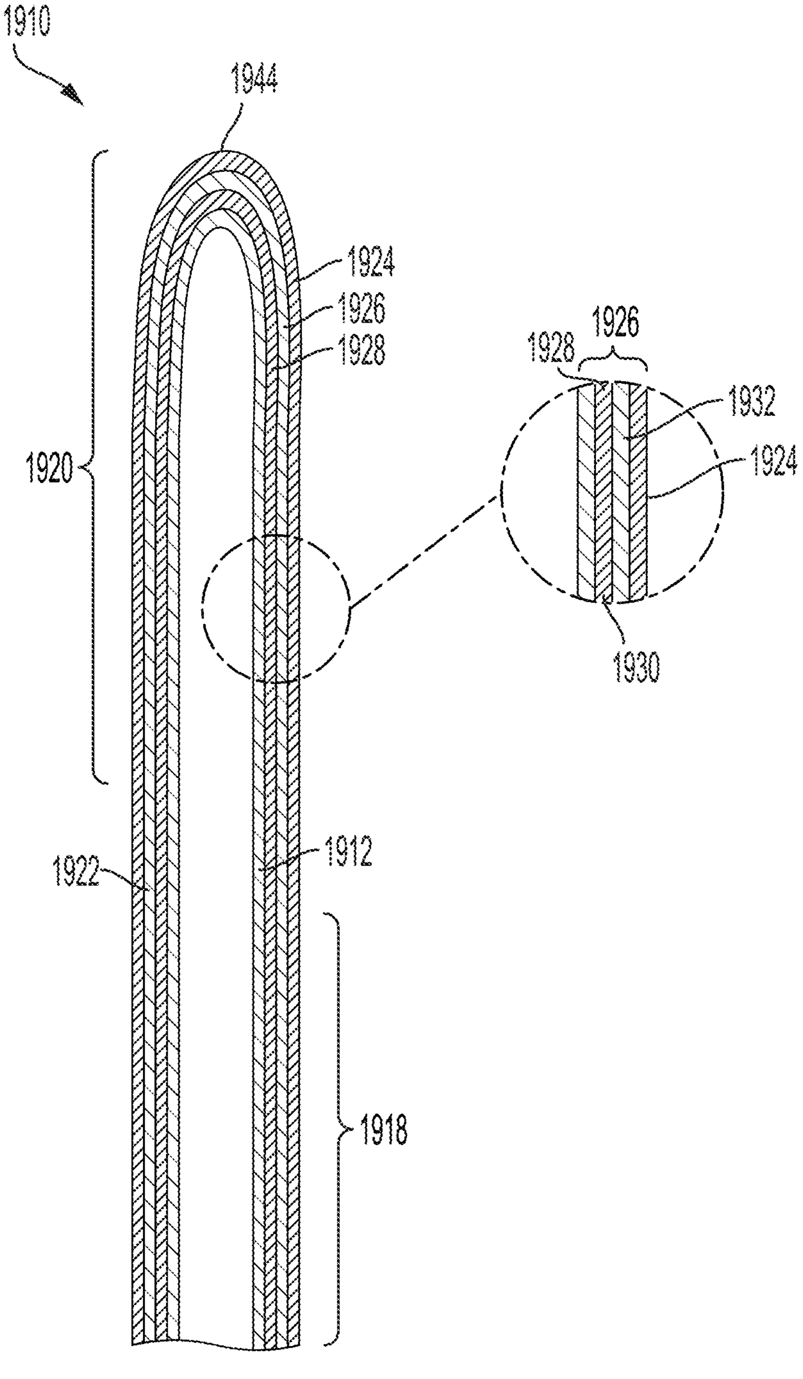
FIG. 19A is a cross-sectional view of a portion of another exemplary inflow member of a urinary catheter in a contracted or linear state, according to an example of the present disclosure.
Figure 19B:
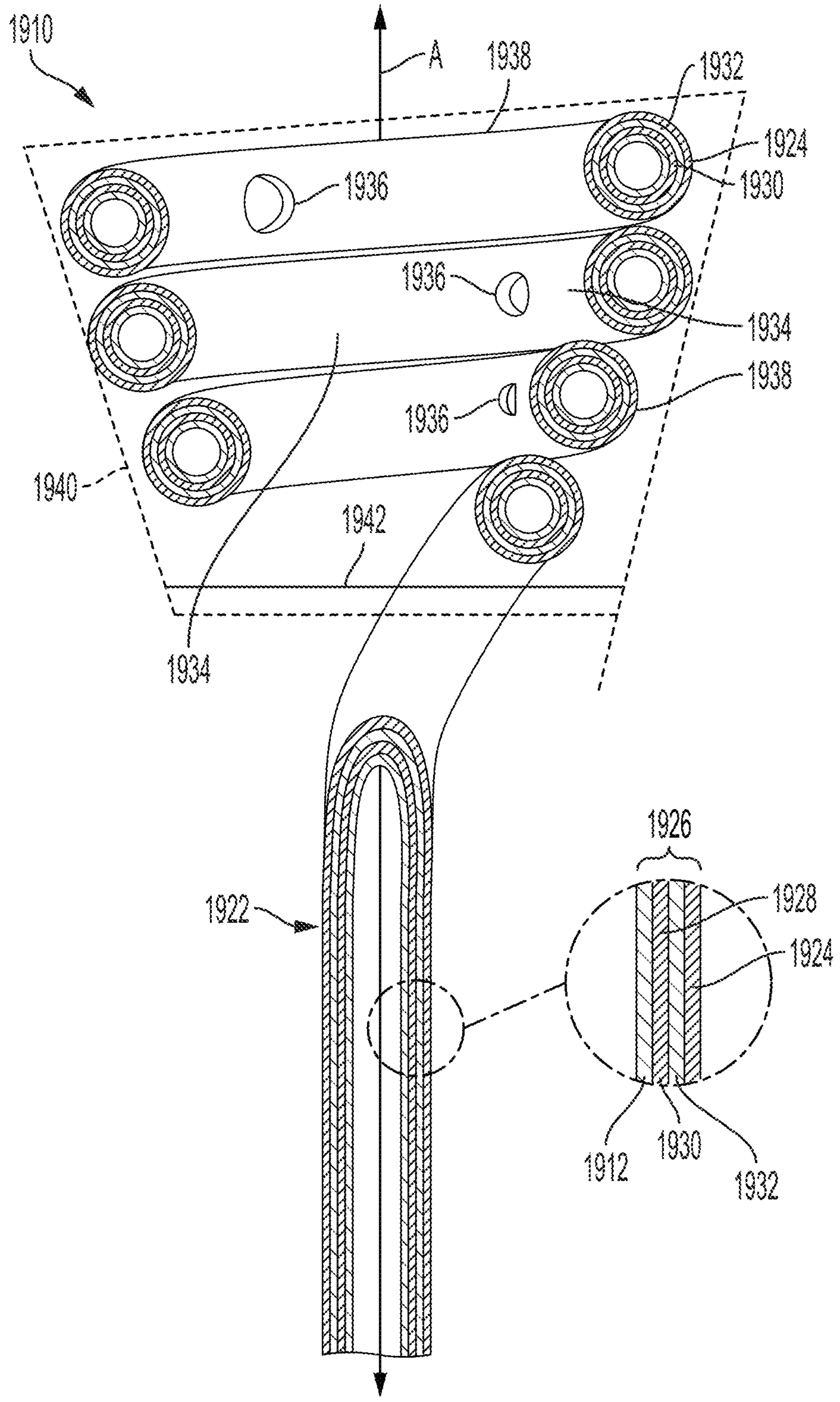
FIG. 19B is a cross-sectional view of a portion of the urinary catheter of FIG. 19A in a deployed or uncoiled state.
Figure 19C:
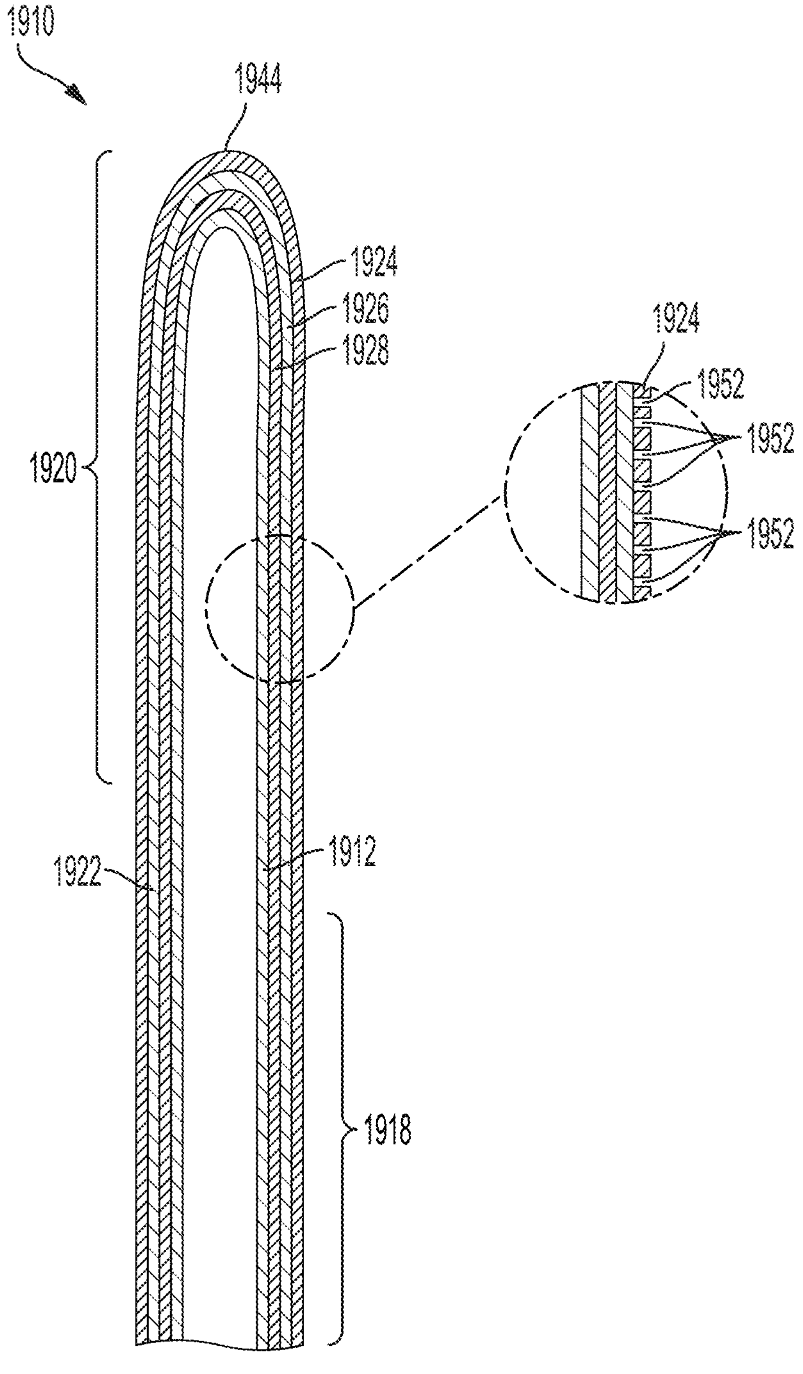
FIG. 19C is a cross-sectional view of a portion of another exemplary inflow member of a urinary catheter including another exemplary multi-functional coating, according to an example of the present disclosure.

Alternatively or additionally, as shown schematically in FIG. 19C, the outermost layer 1924 can comprise at least one opening(s), hole(s), space(s), and/or micro-channel(s) 1952 extending through the outermost layer 1924 to the one or more sublayer(s) 1926. The at least one opening(s), hole(s), space(s), and/or micro-channel(s) 1952 can be inherent, naturally occurring, or created (man-made) in the material of the outermost layer 1924. For example, the outermost layer 1924 may be naturally porous. In some examples, at least one opening(s), hole(s), space(s), and/or micro-channel(s) can be formed by any suitable process including, for example, pressing a pin or puncture needle through the cured outermost layer 1924. In other examples, the at least one opening(s), hole(s), space(s), and/or micro-channel(s) 1952 can be formed by etching or dissolving portions of the outermost layer 1924. The at least one opening(s), hole(s), space(s), and/or micro-channel(s) 1952 can be configured such that fluid, such as moisture, passes through the outermost layer 1924 to the sublayer(s) 1926, and dissolved material from the sublayer(s) 1926 passes through the at least one opening(s), hole(s), space(s), and/or micro-channel(s) 1952 of the outermost layer 1924 to the surrounding fluid and/or tissue. In some examples, the at least one opening(s), hole(s), space(s), and/or micro-channel(s) 1952 initially extend through the entire outermost layer 1924, such that fluid can penetrate to the one or more sublayer(s) 1926 as soon as the device 1910 is positioned in the urinary tract. In other examples, the at least one opening(s), hole(s), space(s), and/or micro-channel(s) 1952 may extend partially through the outermost layer 1924. In that case, fluid, such as moisture or urine, may collect in the at least one opening(s), hole(s), space(s), and/or micro-channel(s) 1952, causing portions of the at least one opening(s), hole(s), space(s), and/or micro-channel(s) 1952 to dissolve during an initial period following insertion into the urinary tract. Over time, the at least one opening(s), hole(s), space(s), and/or micro-channel(s) 1952 dissolve through the remaining portion of the outermost layer(s) 1924, eventually contacting and exposing portions of the one or more sublayer(s) 1926. In this way, release of the functional material(s) of the sublayer(s) 1926 is delayed until a period of time after the device 1910 is inserted into the urinary tract. The at least one opening(s), hole(s), space(s), and/or micro-channel(s) 1952 can be of any size and number sufficient for permitting fluid, such as moisture, to pass to contact the one or more sublayer(s) 1926 and for permitting dissolved material of the sublayer(s) 1926 to pass through the at least one opening(s), hole(s), space(s), and/or micro-channel(s) 1952 to surrounding body fluid and tissues. For example, the at least one opening(s), hole(s), space(s), and/or micro-channel(s) 1952 can have a cross-sectional area of about 0.01 micrometer$^2$ to about 1.0 millimeter$^2$, or about 0.1 mm$^2$ to about 0.5 mm$^2$, or about 0.2 mm$^2$ to about 0.4 mm$^2$. The at least one opening(s), hole(s), space(s), and/or micro-channel(s) 1952 can be formed in or on the outermost layer 1924 in a variety of configurations and arrangements. For example, the at least one opening(s), hole(s), space(s), and/or micro-channel(s) 1952 can be a plurality of openings having any configuration desired, for example, substantially circular, elliptical, or any shape in cross section. In other examples, the at least one opening(s), hole(s), space(s), and/or micro-channel(s) 1952 can be troughs or burrows extending in any direction (e.g., axially and/or or circumferentially) along a surface of or within the outermost layer(s) 1924.

As shown in FIGS. 19B and 19C, in some examples, the sublayer(s) 1926 are positioned between an outer surface 1928 of the device 1910 (such as elongated tube 1912) and the outermost layer(s) 1924. The sublayer(s) 1926 can be configured to improve long-term performance of the coated device 1910, for example, by addressing one or more of the above-described issues associated with prolonged use of the device 1910, such as an indwelling catheter. For example, the one or more sublayer(s) 1926 can improve long-term performance of the coated device 1910 by one or more of: inhibiting tissue ingrowth; mitigating a foreign body reaction for tissues surrounding the deployed coated device 1910; reducing infection of tissues surrounding the coated device 1910; and/or reducing encrustation of urine crystals onto the coated device 1910.

In some examples, the at least one coating(s) and/or impregnation(s) 1922 are intended to contact portions of fluid and/or tissue surrounding the coated device 1910, which can be brought into contact with the device 1910 by natural forces or applied negative pressure. Accordingly, the at least one coating(s) and/or impregnation(s) 1922 may need only to be applied to at least a portion or all of the outer periphery or the outwardly facing side, or the protective surface(s) 1938, of at least a portion of, such as the retention portion 1920, or all of the device 1910. In some instances, as previously described, the inner periphery, inwardly facing side, or protected surface area 1934 of the retention portion 1920, which comprises at least one protected drainage hole(s), port(s) or perforation(s) 1936, can be substantially free of or free from the at least one coating(s) and/or impregnation(s) 1922. Alternatively, as described in connection with FIG. 19D, both the protected surface 1934 and the protective surface 1938 of the device 1910 may be coated with the at least one coating(s) and/or impregnation(s) 1922, for example to provide one or more of the aforementioned benefits of the coating(s) and/or facilitate manufacturability (e.g., deposition of the coating onto the device 1910).

The at least one coating(s) and/or impregnation(s) 1922 described herein can be adapted for use with any or all of the devices 1910, such as the urinary catheters described herein. For example, the at least one coating(s) and/or impregnation(s) 1922 can be applied to a device 1910 comprising a distal portion 1918 comprising an expandable retention portion 1920 which, when deployed at a desired location within the kidney and/or renal pelvis, defines a three-dimensional shape 1940 sized and positioned to maintain patency of fluid flow between the kidney and a proximal portion 1914 and/or proximal end 1916 of the device 1910, such that at least a portion of the fluid flows through the expandable retention portion 1920. In that case, the at least one coating(s) and/or impregnation(s) 1922 may be applied to portions of the retention portion 1920 that contact a surface of the three dimensional shape 1940. Further, as in previously described examples, in order to match a size and shape of the renal pelvis, an area of two-dimensional slices 1942 of the three-dimensional shape 1940 defined by the deployed expandable retention portion 1920 in a plane transverse to a central axis A of the expandable retention portion 1920 can increase towards a distal end 1944 of the expandable retention portion 1920.

In some examples, the retention portion 1920 comprises a coiled retention portion extending radially from the renal pelvis to the kidney. The coiled retention portion 1920 can comprise at least a first coil 1946 having a first diameter and at least a second coil 1948 having a second diameter, which can be larger than the first diameter to correspond to a size and shape of the renal pelvis. In some examples, the at least one coating(s) and/or impregnation(s) 1922 need only be applied to the outer or protective surfaces 1938 of the coil(s) 1946, 1948 since only such outer or protective surfaces 1938 are contacted by body tissues. The protected surfaces 1934 of the coils 1946, 1948 may not be coated by the at least one coating(s) and/or impregnation(s) 1922.

In some examples, at least a portion or all of both of the protective surfaces 1938 and the protected surfaces 1934 of the device 1910, such as coil(s) 1946, 1948 can be coated by the at least one coating(s) and/or impregnation(s) 1922. For example, applying the at least one coating(s) and/or impregnation(s) 1922 to all surfaces of the device 1910 or elongated tube 1912 may be easier for manufacturing or production. In some examples, the device 1910, for example the entire elongated tube 1912, may be coated by a hydrophilic or outermost layer(s) 1924, since the elongated tube 1912 or device 1910 may be in a substantially linear (e.g., uncoiled) configuration during insertion through the patient's urinary tract. The sublayers 1930, 1932, which may help to improve long term performance of the device 1910, need only be applied to portions of the device 1910 or elongated tube 1912 likely to be contacted by bodily fluid or tissues (e.g., outwardly facing portions of the tube 1912).

Multi-Layer Coating(s)/Impregnant(s) for Sequential Functionality

Figure 19D:
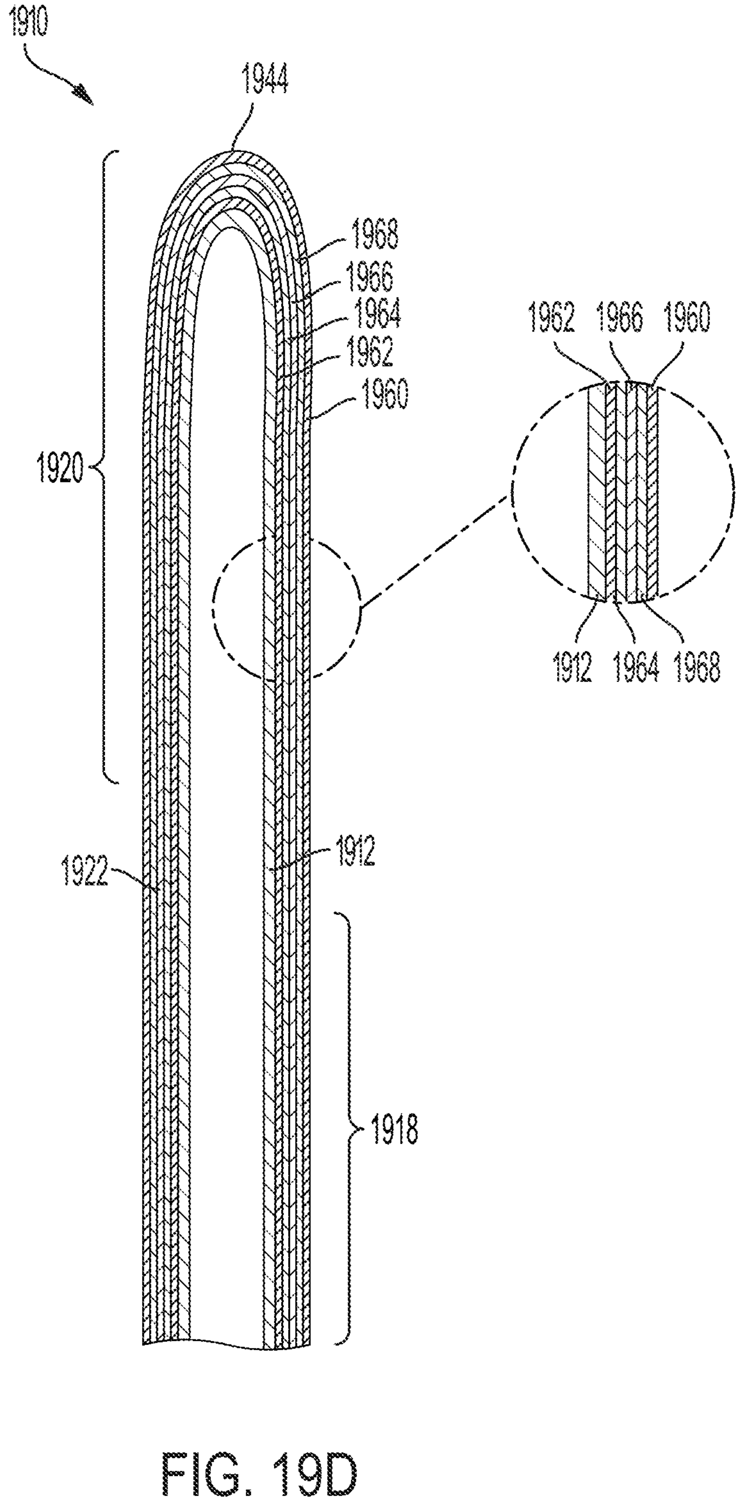
FIG. 19D is a cross-sectional view of another exemplary urinary catheter including another exemplary multi-functional coating, according to an example of the present disclosure.

In other examples, as shown in FIG. 19D, a coated device 1910 comprises one or more coating(s) and/or impregnation(s) 1922 having multiple or different functionalities. The coating(s) and/or impregnation(s) 1922 can be applied to at least a portion or all of the device 1910. As in prior examples, the coating(s) and/or impregnation(s) 1922 can comprise one or more outermost layer(s) 1960 and one or more innermost layer(s) 1962. The coating(s) and/or impregnation(s) 1922 can further comprise multiple sublayers 1964, 1966, 1968 positioned between the one or more outermost layer(s) 1960 and the one or more innermost layer(s) 1962. The multiple sublayers 1964, 1966, 1968 can be formed from different materials and can each address different issue(s) of indwelling catheters and/or provide different functional improvements for the device 1910. The one or more outermost layer(s) 1960 and multiple sublayers 1964, 1966, 1968 may be configured to dissipate sequentially, such that the coating(s) and/or impregnation(s) provides a first property or functionality for a predetermined period, a second property for a predetermined second period, and a third property for a predetermined third period. For example, the one or more coating(s) and/or impregnation(s) 1922 may be configured such that dissipation of outermost layer(s) 1960 and sublayers 1964, 1966, 1968 over time results in periodic and/or intermittent effects including, but not limited to, periods of antimicrobial and/or antibacterial effects cycled with intermittent periods of drug delivery. In some instances, drug delivery could be controlled to occur at pre-specified times, such as limiting drug delivery to a 12-hour release, or to a 24-hour release, or to a 48-hour release, following insertion of the coated device 1910 into the urinary tract. Similarly, another 12-hour release, 24-hour release, or 48 hour release of drug may be provided prior to removal of the coated device 1910.

The outermost layer(s) 1924 can be substantially similar in thickness and material properties to the outermost layers previously described. For example, the outermost layer(s) 1924 can provide a lubricious outer surface configured to make insertion and placement of the device 1910 in the urinary tract easier than when no lubricated coating is present. The outermost layer(s) 1960 can be configured to remain or can dissipate shortly after being implanted in the body, such as within from 1 day to 10 days of implantation.

The multiple sublayers 1964, 1966, 1968 can be selected such that the sublayers remain for a predetermined period and dissipate over the lifespan or intended duration of the catheter device 1910 in the urinary tract. For example, for a catheter designed to be present in the urinary tract for a period of ten to twenty days, each of five sublayers may be configured to dissipate or dissolve in about two to four days. As discussed above, in another example, a layer comprising a therapeutic agent may dissipate within 12 hours, 24 hours, or 48 hours of insertion. Sublayers containing other materials, such as antimicrobial materials and/or pH buffering materials, may dissipate over a longer period of time, such as over periods of 1 day to 10 days, or 2 days to 8 days, or 3 days to 5 days.

In some examples, the multiple sublayers 1964, 1966, 1968 comprise a first sublayer 1964, positioned below the outermost layer(s) 1960. The first sublayer 1964 can be configured to begin to dissipate into surrounding tissue when contacted by moisture, as occurs once portions of the outermost layer(s) 1960 dissipate. As in previous examples, material of the first sublayer 1964 can be configured to address issues with indwelling catheters and/or improve functional properties of the coating(s) 1922. For example, the first sublayer 1964 can comprise an antimicrobial layer that provides protection from ingress of microbes into or onto the coating(s) 1922 for a predetermined time period, such as a few days following implantation.

Over the course of the few hours and/or days following insertion, the first sublayer 1964 dissipates, exposing the second sublayer 1966 to fluid or moisture. The second sublayer 1966 can comprise one or more coating(s) and/or impregnation(s) material(s) for providing another property for improving a function of the device 1910. For example, the second sublayer 1966 can comprise a dose of the therapeutic agent, such as a dose of an antibiotic. The second sublayer 1966 can be configured to deliver the dose of the therapeutic agent over either a short period of time (e.g., a few hours or one day) or for slow release of the therapeutic agent over a slightly longer time period (e.g., from one day to ten days, or from 2 days to 8 days, or from 3 days to 5 days). Once the therapeutic agent is released and the second sublayer 1966 dissipates into surrounding fluid or tissues, a third sublayer 1968 can be exposed to moisture or fluid of the urinary tract. The third sublayer 1968 may comprise material(s) with additional or different functional properties. For example, the third sublayer 1968 can be a pH buffering layer for reducing or eliminating a presence of encrustations on the device 1910. In other examples, the third sublayer 1968 could be another antimicrobial and/or antibacterial layer. The third sublayer 1968 can be configured to remain in place for a number of hours or days, as was the case with previous sublayers or layers.

The device 1910 can further comprise one or more additional sublayer(s) 1926 including materials with different properties for addressing issues of indwelling catheters and/or for improving a function of the coating(s) 1922 and coated device 1910. For example, the coating(s) 1922 could comprise a number of therapeutic layers including a dose of an antibiotic agent positioned between sublayer(s) 1926 comprising antimicrobial materials. Accordingly, the coating(s) 1922 can provide intermittent antibiotic doses separated by time periods in which no antibiotic is being delivered, thereby reducing a risk that antibiotic concentration would increase above suitable levels.

In some examples, the coating(s) 1922 also comprise the innermost layer 1962 positioned between the outer surface 1960 of the device 1910 or elongated tube 1912 and an innermost sublayer 1964. The innermost layer 1962 can be similar in size and material composition to the outermost layers 1960 described herein. For example, the innermost layer 1962 may comprise any of the coating materials discussed above, such as a hydrophilic material that becomes lubricated when exposed to moisture. In some examples, the innermost layer 1962 can be exposed shortly before removal of the device 1910. Once exposed to fluid or moisture, the innermost layer 1962 can be configured to become slippery and lubricious, which assists in removal of the device 1910 through the urinary tract. For example, when the innermost layer 1962 becomes lubricated, the elongated tube 1912 of the device 1910 can slide more easily through body tissues, facilitating removal of the device 1910.

Treatment Methods for Removing Excess Fluid

Figure 20:
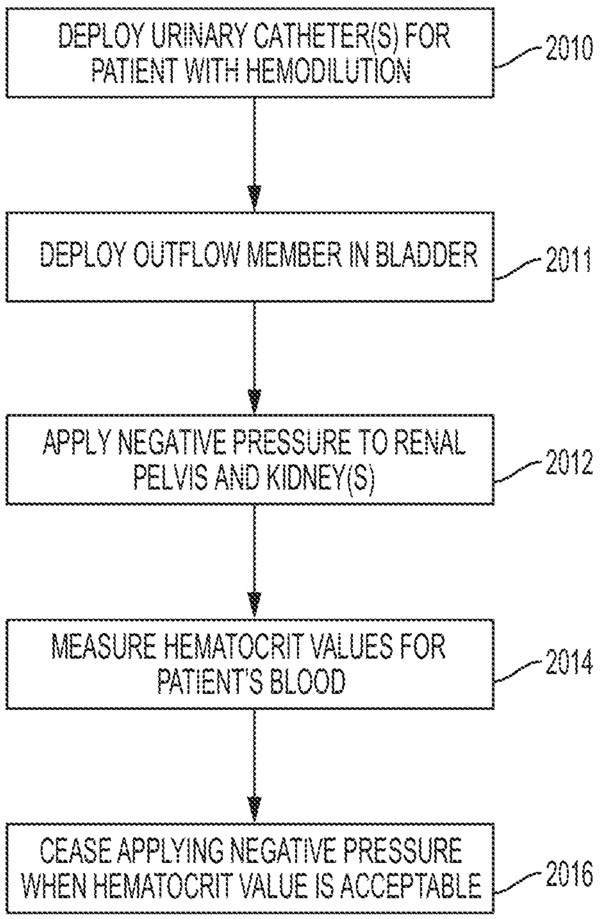
FIG. 20 is a flow chart illustrating a process for reducing creatinine and/or protein levels of a patient according to an example of the present disclosure.

Steps for removing excess fluid from a patient using the devices and systems described herein are illustrated in FIG. 20. As shown in FIG. 20, the treatment method comprises deploying an inflow member of a urinary catheter in the renal pelvis and/or kidney of a patient, as shown at box 2010. In some examples, the inflow member of the urinary catheter comprises one or more of any of the retention portions described herein. For example, a retention portion of the inflow member can comprise a tube defining a drainage lumen comprising a helical retention portion and a plurality of drainage holes, openings, or fluid ports. Alternatively, the retention portion can comprise a pigtail coil or another suitable expandable structure.

As shown at box 2012, the method further comprises applying negative pressure to the renal pelvis and/or kidney through the inflow member to induce or facilitate production of fluid or urine in the kidney(s) and to extract the fluid or urine from the patient. Desirably, negative pressure is applied for a period of time sufficient to reduce the patient's blood creatinine levels by a clinically significant amount.

Negative pressure may continue to be applied for a predetermined period of time. For example, a user may be instructed to operate the pump for the duration of a surgical procedure or for a time period selected based on physiological characteristics of the patient. In other examples, patient condition may be monitored to determine when sufficient treatment has been provided. For example, as shown at box 2014, the method may further comprise monitoring the patient to determine when to cease applying negative pressure to the patient's renal pelvis and/or kidneys. In some examples, a patient's hematocrit level is measured. For example, patient monitoring devices may be used to periodically obtain hematocrit values. In other examples, blood samples may be drawn periodically to directly measure hematocrit. In some examples, concentration and/or volume of urine expelled from the body through the bladder catheter may be monitored to determine a rate at which urine is being produced by the kidneys. In a similar manner, expelled urine output may be monitored to determine protein concentration and/or creatinine clearance rate for the patient. Reduced creatinine and protein concentration in urine may be indicative of over-dilution and/or depressed renal function. Measured values can be compared to the predetermined threshold values to assess whether negative pressure therapy is improving patient condition, and should be modified or discontinued. For example, as discussed herein, a desirable range for patient hematocrit may be between 25% and 40%. In other examples, as described herein, patient body weight may be measured and compared to a dry body weight. Changes in measured patient body weight demonstrate that fluid is being removed from the body. As such, a return to dry body weight represents that hemodilution has been appropriately managed and the patient is not over-diluted.

As shown at box 2016, a user may cause the negative pressure source or pump to cease providing negative pressure therapy when a positive result is identified. In a similar manner, patient blood parameters may be monitored to assess effectiveness of the negative pressure being applied to the patient's kidneys. For example, a capacitance or analyte sensor may be placed in fluid communication with tubing of an extracorporeal blood management system. The sensor may be used to measure information representative of blood protein, oxygen, creatinine, and/or hematocrit levels. Measured blood parameter values may be measured continuously or periodically and compared to various threshold or clinically acceptable values. Negative pressure may continue to be applied to the patient's bladder, kidney or ureter until a measured parameter value falls within a clinically acceptable range. Once a measured values fails within the threshold or clinically acceptable range, as shown at box 2016, application of negative pressure may cease.

In some examples, there is provided a method of removing excess fluid from a patient for systemic fluid volume management associated with chronic edematous, hypertension, chronic kidney disease and/or acute heart failure. According to another aspect of the disclosure, a method for removing excess fluid for a patient undergoing a fluid resuscitation procedure, such as coronary graft bypass surgery, by removing excess fluid from the patient is provided. During fluid resuscitation, solutions such as saline solutions and/or starch solutions, are introduced to the patient's bloodstream by a suitable fluid delivery process, such as an intravenous drip. For example, in some surgical procedures, a patient may be supplied with between 5 and 10 times a normal daily intake of fluid. Fluid replacement or fluid resuscitation can be provided to replace bodily fluids lost through sweating, bleeding, dehydration, and similar processes. In the case of a surgical procedure such as coronary graft bypass, fluid resuscitation is provided to help maintain a patient's fluid balance and blood pressure within an appropriate rate. Acute kidney injury (AKI) is a known complication of coronary artery graft bypass surgery. AKI is associated with a prolonged hospital stay and increased morbidity and mortality, even for patients who do not progress to renal failure. See Kim, et al., *Relationship between a perioperative intravenous fluid administration strategy and acute kidney injury following off-pump coronary artery bypass surgery: an observational study, Critical Care* 19:350 (2015). Introducing fluid to blood also reduces hematocrit levels which has been shown to further increase mortality and morbidity. Research has also demonstrated that introducing saline solution to a patient may depress renal functional and/or inhibit natural fluid management processes. As such, appropriate monitoring and control of renal function may produce improved outcomes and, in particular, may reduce post-operative instances of AKI.

Figure 21:
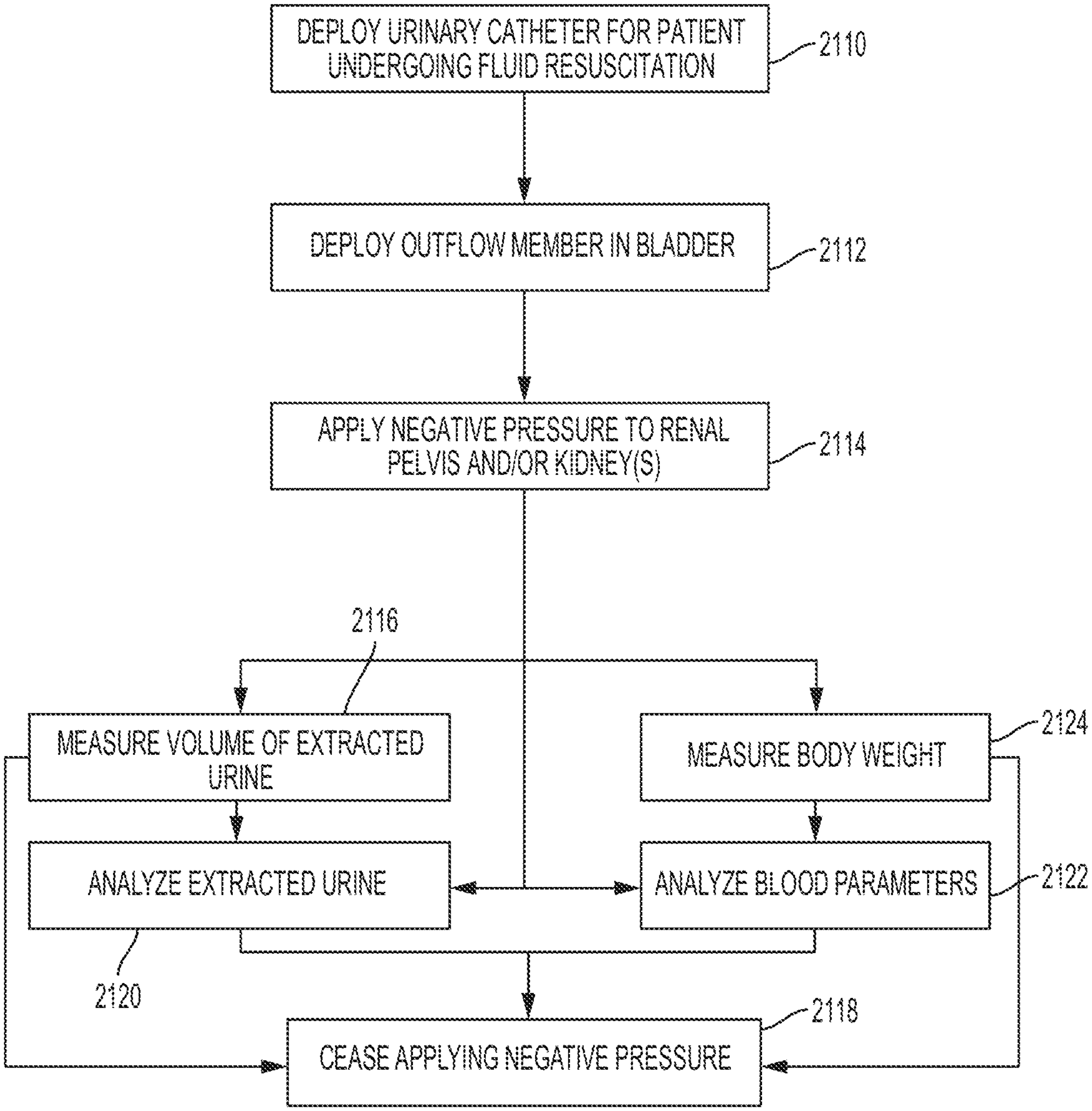
FIG. 21 is a flow chart illustrating a process for treating a patient undergoing fluid resuscitation according to an example of the present disclosure.

A method of treating a patient for removing excess fluid is illustrated in FIG. 21. As shown at box 2110, the method comprises deploying the retention portion of the inflow member of a urinary catheter in the renal pelvis and/or kidney of a patient, such that flow of urine from the ureter and/or kidney is not prevented by occlusion of the ureter and/or kidney. For example, a distal end of the inflow member of the urinary catheter may be positioned in the renal pelvis. In other examples, the catheter may be deployed in the kidney. The inflow member can comprise features of one or more of the urinary catheters described herein. For example, the catheter can comprise a tube defining a drainage lumen and comprising a helical retention portion and a plurality of drainage holes, openings, or ports. In other examples, the retention portion of the inflow member can comprise a pigtail coil.

As shown at box 2112, an outflow member of the urinary catheter can be deployed in the patient's bladder. As previously described, the outflow member is configured to conduct urine from the negative pressure source or pump to the bladder. Urine discharged from the outflow member can be excreted from the body through the urethra by natural processes.

As shown at box 2114, following deployment of the inflow member in the renal pelvis and/or kidney and the outflow member in the bladder, negative pressure is applied to the renal pelvis and/or kidney through the inflow member. For example, negative pressure can be applied for a period of time sufficient to extract urine comprising a portion of the fluid provided to the patient during the fluid resuscitation procedure. As described herein, negative pressure can be provided by an external pump connected to a proximal end or port of the bladder catheter. The pump can be operated continually or periodically dependent on therapeutic requirements of the patient. In some cases, the pump may alternate between applying negative pressure and positive pressure.

Negative pressure may continue to be applied for a predetermined period of time. For example, a user may be instructed to operate the pump for the duration of a surgical procedure or for a time period selected based on physiological characteristics of the patient. In other examples, patient condition may be monitored to determine when a sufficient amount of fluid has been drawn from the patient. For example, as shown at box 2116, fluid expelled from the body may be collected and a total volume of obtained fluid may be monitored. In that case, the pump can continue to operate until a predetermined fluid volume has been collected from the urinary and/or bladder catheters. The predetermined fluid volume may be based, for example, on a volume of fluid provided to the patient prior to and during the surgical procedure. As shown at box 2118, application of negative pressure to the renal pelvis and/or kidneys is stopped when the collected total volume of fluid exceeds the predetermined fluid volume.

In other examples, operation of the pump can be determined based on measured physiological parameters of the patient, such as measured creatinine clearance, blood creatinine level, or hematocrit ratio. For example, as shown at box 2120, urine collected form the patient may be analyzed by one or more sensors associated with the catheter and/or pump. The sensor can be a capacitance sensor, analyte sensor, optical sensor, or similar device configured to measure urine analyte concentration. In a similar manner, as shown at box 2122, a patient's blood creatinine or hematocrit level could be analyzed based on information obtain from the patient monitoring sensors discussed hereinabove. For example, a capacitance sensor may be placed in an existing extracorporeal blood system. Information obtained by the capacitance sensor may be analyzed to determine a patient's hematocrit ratio. The measured hematocrit ratio may be compared to certain expected or therapeutically acceptable values. The pump may continue to apply negative pressure to the patient's ureter and/or kidney until measured values within the therapeutically acceptable range are obtained. Once a therapeutically acceptable value is obtained, application of negative pressure may be stopped as shown at box 2118.

In other examples, as shown at box 2124, patient body weight may be measured to assess whether fluid is being removed from the patient by the applied negative pressure therapy. For example, a patient's measured bodyweight (including fluid introduced during a fluid resuscitation procedure) can be compared to a patient's dry body weight. As used herein, dry weights is defined as normal body weight measured when a patient is not over-diluted. For example, a patient who is not experiencing one or more of: elevated blood pressure, lightheadedness or cramping, swelling of legs, feet, arms, hands, or around the eyes, and who is breathing comfortably, likely does not have excess fluid. A weight measured when the patient is not experiencing such symptoms can be a dry body weight. Patient weight can be measured periodically until the measured weight approaches the dry body weight. When the measured weight approaches (e.g., is within between 5% and 10% of dry body weight), as shown at box 2118, application of negative pressure can be stopped.

The aforementioned details of treatment using the systems of the present invention can be used to treat a variety of conditions that can benefit from increased urine or fluid output or removal. For example, a method for preserving renal function by application of negative pressure to decrease interstitial pressure within tubules of the medullar region to facilitate urine output and to prevent venous congestion-induced nephron hypoxia in the medulla of the kidney is provided. The method comprises: deploying the inflow member of the urinary catheter to a renal pelvis and/or kidney of a patient; deploying an outflow member of the urinary catheter to a bladder of the patient; and applying negative pressure to a proximal end of the inflow member to induce negative pressure in a portion of the urinary tract of the patient for a predetermined period of time to remove fluid from the urinary tract of the patient.

In another example, a method for treatment of acute kidney injury due to venous congestion is provided. The method comprises: deploying an inflow member of a urinary catheter into a renal pelvis or kidney of a patient; deploying an outflow member of the urinary catheter to the bladder of the patient; and applying negative pressure to the proximal end of the inflow member to induce negative pressure in a portion of the urinary tract of the patient for a predetermined period of time to remove fluid from the urinary tract of the patient, thereby reducing venous congestion in the kidney to treat acute kidney injury.

In another example, a method for treatment of New York Heart Association (NYHA) Class III and/or Class IV heart failure through reduction of venous congestion in the kidney(s) is provided. The method comprises: deploying an inflow member of a urinary catheter to a renal pelvis and/or kidney of a patient; deploying an outflow member of the urinary catheter to the bladder of the patient; and applying negative pressure to the proximal end of the inflow member to induce negative pressure in a portion of the urinary tract of the patient for a predetermined period of time to remove fluid from the urinary tract of the patient to treat volume overload in NYHA Class III and/or Class IV heart failure.

In another example, a method for treatment of Stage 4 and/or Stage 5 chronic kidney disease through reduction of venous congestion in the kidney(s) is provided. The method comprises: deploying an inflow member of a urinary catheter to a renal pelvis or kidney of a patient; deploying an outflow member of the urinary catheter in the bladder of the patient; and applying negative pressure to the proximal end of the inflow member to induce negative pressure in a portion of the urinary tract of the patient to remove fluid from the urinary tract of the patient to reduce venous congestion in the kidney(s).

EXAMPLES

Inducement of negative pressure within the renal pelvis of farm swine was performed for the purpose of evaluating effects of negative pressure therapy on renal congestion in the kidney. An objective of these studies was to demonstrate whether a negative pressure delivered into the renal pelvis significantly increases urine output in a swine model of renal congestion. In Example 1, a pediatric Fogarty catheter, normally used in embolectomy or bronchoscopy applications, was used in the swine model solely for proof of principle for inducement of negative pressure in the renal pelvis. It is not suggested that a Fogarty catheter be used in humans in clinical settings to avoid injury of urinary tract tissues. In Example 2, a ureteral catheter 112 shown in FIGS. 2A and 2B of U.S. Pat. No. 9,744,331 ("the '331 patent"), and including a helical retention portion for mounting or maintaining a distal portion of the catheter in the renal pelvis or kidney, was used.

Example 1

Method

Figure 22:
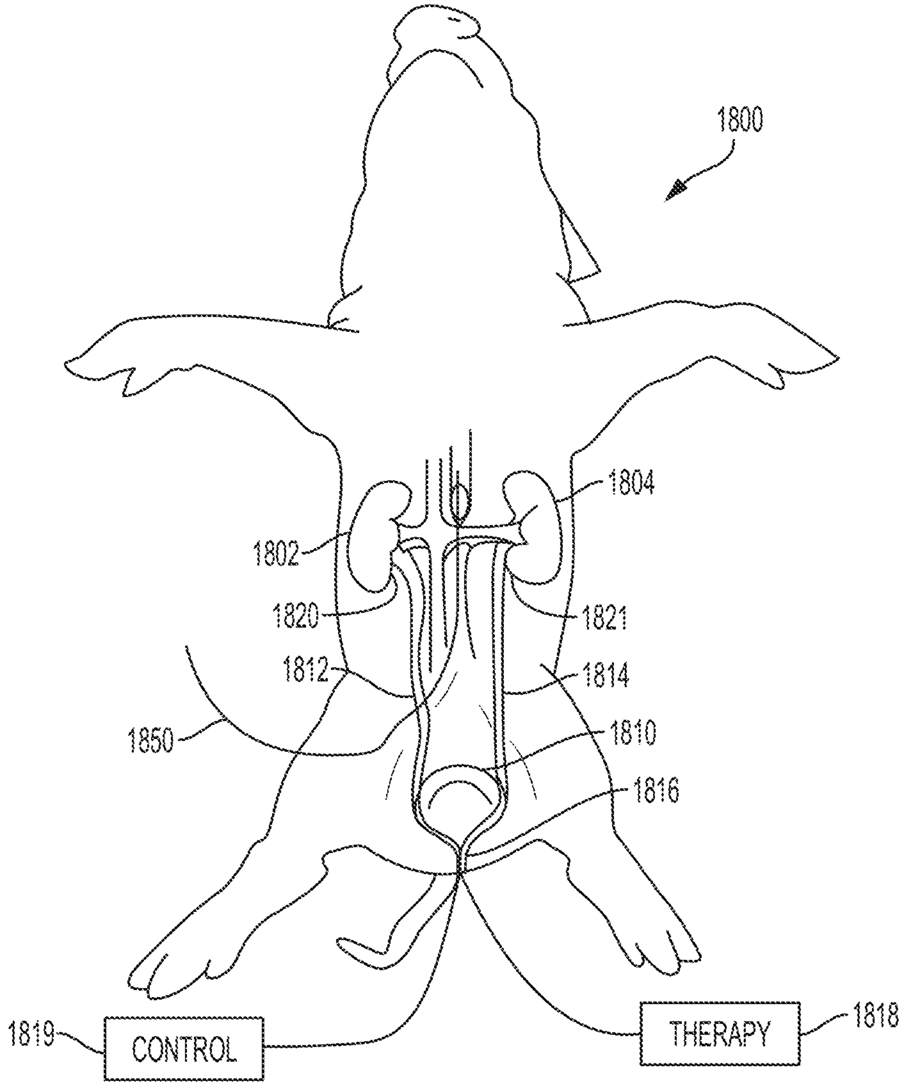
FIG. 22 is a schematic drawing of an experimental set-up for evaluating negative pressure therapy in a swine model according to the present disclosure.

Four farm swine 1800 were used for purposes of evaluating effects of negative pressure therapy on renal congestion in the kidney. As shown in FIG. 22, pediatric Fogarty catheters 1812, 1814 were inserted to the renal pelvis region 1820, 1821 of each kidney 1802, 1804 of the four swine 1800. The catheters 1812, 1814 were deployed within the renal pelvis region by inflating an expandable balloon to a size sufficient to seal the renal pelvis and to maintain the position of the balloon within the renal pelvis. The catheters 1812, 1814 extend from the renal pelvis 1802, 1804, through a bladder 1810 and urethra 1816, and to fluid collection containers external to the swine.

Urine output of two animals was collected for a 15 minute period to establish a baseline for urine output volume and rate. Urine output of the right kidney 1802 and the left kidney 1804 were measured individually and found to vary considerably. Creatinine clearance values were also determined.

Renal congestion (e.g., congestion or reduced blood flow in the veins of the kidney) was induced in the right kidney 1802 and the left kidney 1804 of the animal 1800 by partially occluding the inferior vena cava (IVC) with an inflatable balloon catheter 1850 just above to the renal vein outflow. Pressure sensors were used to measure IVC pressure. Normal IVC pressures were 1-4 mmHg. By inflating the balloon of the catheter 1850 to approximately three quarters of the IVC diameter, the IVC pressures were elevated to between 15-25 mm Hg. Inflation of the balloon to approximately three quarters of IVC diameter resulted in a 50-85% reduction in urine output. Full occlusion generated IVC pressures above 28 mm Hg and was associated with at least a 95% reduction in urine output.

One kidney of each animal 1800 was not treated and served as a control ("the control kidney 1802"). The ureteral catheter 1812 extending from the control kidney was connected to a fluid collection container 1819 for determining fluid levels. One kidney ("the treated kidney 1804") of each animal was treated with negative pressure from a negative pressure source (e.g., a therapy pump 1818 in combination with a regulator designed to more accurately control the low magnitude of negative pressures) connected to the ureteral catheter 1814. The pump 1818 was an Air Cadet Vacuum Pump from Cole-Parmer Instrument Company (Model No. EW-07530-85). The pump 1818 was connected in series to the regulator. The regulator was a V-800 Series Miniature Precision Vacuum Regulator—⅛ NPT Ports (Model No. V-800-10-W/K), manufactured by Airtrol Components Inc.

The pump 1818 was actuated to induce negative pressure within the renal pelvis 1820, 1821 of the treated kidney according to the following protocol. First, the effect of negative pressure was investigated in the normal state (e.g., without inflating the IVC balloon). Four different pressure levels (−2, −10, −15, and −20 mm Hg) were applied for 15 minutes each and the rate of urine produced and creatinine clearance were determined. Pressure levels were controlled and determined at the regulator. Following the −20 mm Hg therapy, the IVC balloon was inflated to increase the pressure by 15-20 mm Hg. The same four negative pressure levels were applied. Urine output rate and creatinine clearance rate for the congested control kidney 1802 and treated kidney 1804 were obtained. The animals 1800 were subject to congestion by partial occlusion of the IVC for 1 minutes. Treatment was provided for 60 minutes of the 1 minute congestion period.

Following collection of urine output and creatinine clearance data, kidneys from one animal were subjected to gross examination then fixed in a 10% neutral buffered formalin. Following gross examination, histological sections were obtained, examined, and magnified images of the sections were captured. The sections were examined using an upright Olympus BX41 light microscope and images were captured using an Olympus DP25 digital camera. Specifically, photomicrograph images of the sampled tissues were obtained at low magnification (20× original magnification) and high magnification (100× original magnification). The obtained images were subjected to histological evaluation. The purpose of the evaluation was to examine the tissue histologically and to qualitatively characterize congestion and tubular degeneration for the obtained samples.

Surface mapping analysis was also performed on obtained slides of the kidney tissue. Specifically, the samples were stained and analyzed to evaluate differences in size of tubules for treated and untreated kidneys. Image processing techniques calculated a number and/or relative percentage of pixels with different coloration in the stained images. Calculated measurement data was used to determine volumes of different anatomical structures.

Results

Urine Output and Creatinine Clearance

Urine output rates were highly variable. Three sources of variation in urine output rate were observed during the study. The inter-individual and hemodynamic variability were anticipated sources of variability known in the art. A third source of variation in urine output, upon information and belief believed to be previously unknown, was identified in the experiments discussed herein, namely, contralateral intra-individual variability in urine output.

Baseline urine output rates were 0.79 ml/min for one kidney and 1.07 ml/min for the other kidney (e.g., a 26% difference). The urine output rate is a mean rate calculated from urine output rates for each animal.

When congestion was provided by inflating the IVC balloon, the treated kidney urine output dropped from 0.79 ml/min to 0.12 ml/min (15.2% of baseline). In comparison, the control kidney urine output rate during congestion dropped from 1.07 ml/min to 0.09 ml/min (8.4% of baseline). Based on urine output rates, a relative increase in treated kidney urine output compared to control kidney urine output was calculated, according to the following equation:

$$\text{Relative Increase} = \frac{\text{Therapy Treated/Baseline Treated}}{\text{Therapy Control/Baseline Control}}$$

-continued $$\frac{0.12\ \text{mL/min}/0.79\ \text{mL/min}}{0.09\ \text{mL/min}/1.07\ \text{mL/min}} = 180.6\%\ \text{Relative Increase}$$

Thus, the relative increase in treated kidney urine output rate was 180.6% compared to control. This result shows a greater magnitude of decrease in urine production caused by congestion on the control side when compared to the treatment side. Presenting results as a relative percentage difference in urine output adjusts for differences in urine output between kidneys.

Figure 23:
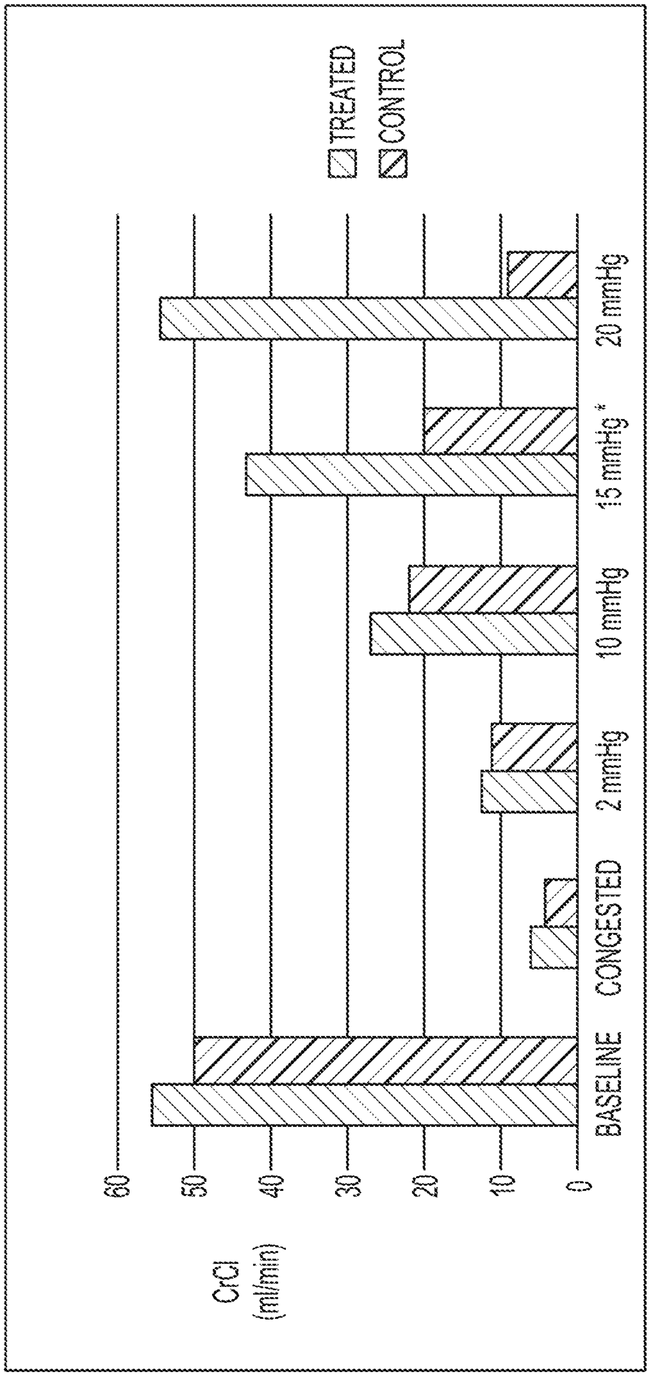
FIG. 23 is a graph of creatinine clearance rates for tests conducted using the experimental set-up shown in FIG. 22.

Creatinine clearance measurements for baseline, congested, and treated portions for one of the animals are shown in FIG. 23.

Gross Examination and Histological Evaluation

Based on gross examination of the control kidney (right kidney) and treated kidney (left kidney), it was determined that the control kidney had a uniformly dark red-brown color, which corresponds with more congestion in the control kidney compared to the treated kidney. Qualitative evaluation of the magnified section images also noted increased congestion in the control kidney compared to the treated kidney. Specifically, as shown in Table 1, the treated kidney exhibited lower levels of congestion and tubular degeneration compared to the control kidney. The following qualitative scale was used for evaluation of the obtained slides.

TABLE 1

| Lesion | Score |
|---|---|
| Congestion | |
| None: | 0 |
| Mild: | 1 |
| Moderate: | 2 |
| Marked: | 3 |
| Severe: | 4 |
| Tubular degeneration | |
| None: | 0 |
| Mild: | 1 |
| Moderate: | 2 |
| Marked: | 3 |
| Severe: | 4 |

Tabulated Results

| Animal ID/Organ/Gross lesion | Slide Number | Histologic lesions: Congestion | Tubular byaline casts | Granulomas |
|---|---|---|---|---|
| 6343/Left Kidney/Normal | R16-513-1 | 1 | 1 | 0 |
| 6343/Left Kidney/Normal with hemorrhagic streak | R16-513-2 | 1 | 1 | 0 |
| 6343/Right Kidney/Congestion | R16-513-3 | 2 | 2 | 1 |
| 6343/Right Kidney/Congestion | R16-513-4 | 2 | 1 | 1 |

As shown in Table 1, the treated kidney (left kidney) exhibited only mild congestion and tubular degeneration. In contrast, the control kidney (right kidney) exhibited moderate congestion and tubular degeneration. These results were obtained by analysis of the slides discussed below.

Figure 24A:
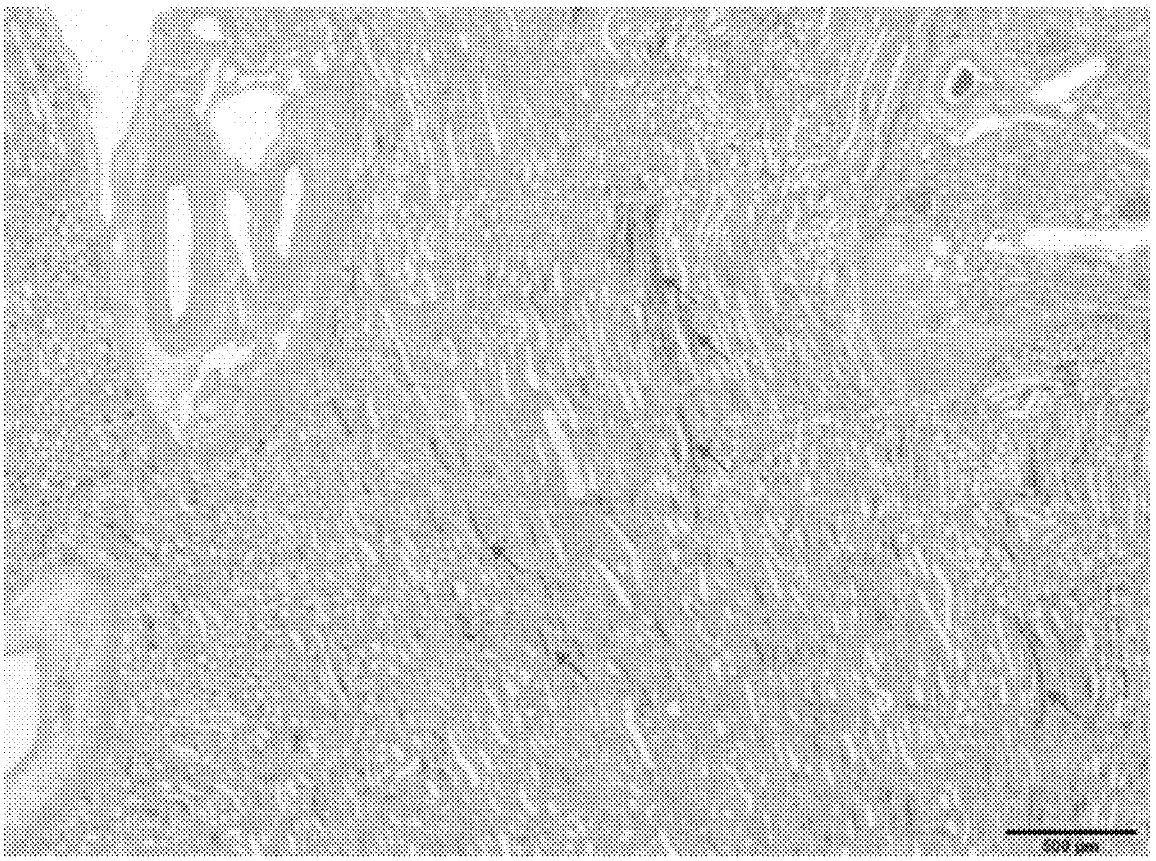
FIG. 24A is a low magnification photomicrograph of kidney tissue from a congested kidney treated with negative pressure therapy.
Figure 24B:
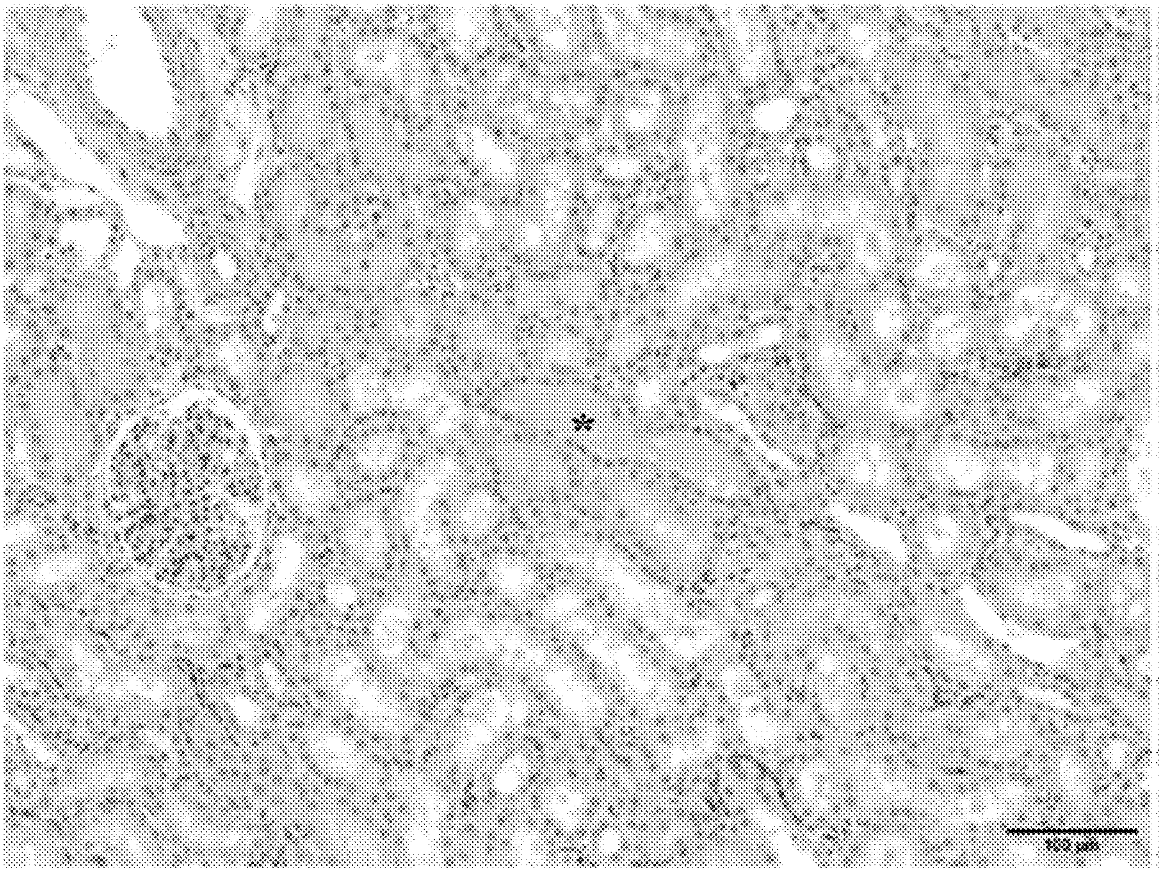
FIG. 24B is a high magnification photomicrograph of the kidney tissue shown in FIG. 24A.

FIGS. 24A and 24B are low and high magnification photomicrographs of the left kidney (treated with negative pressure) of the animal. Based on the histological review, mild congestion in the blood vessels at the corticomedullary junction was identified, as indicated by the arrows. As shown in FIG. 24B, a single tubule with a hyaline cast (as identified by the asterisk) was identified.

Figure 24C:
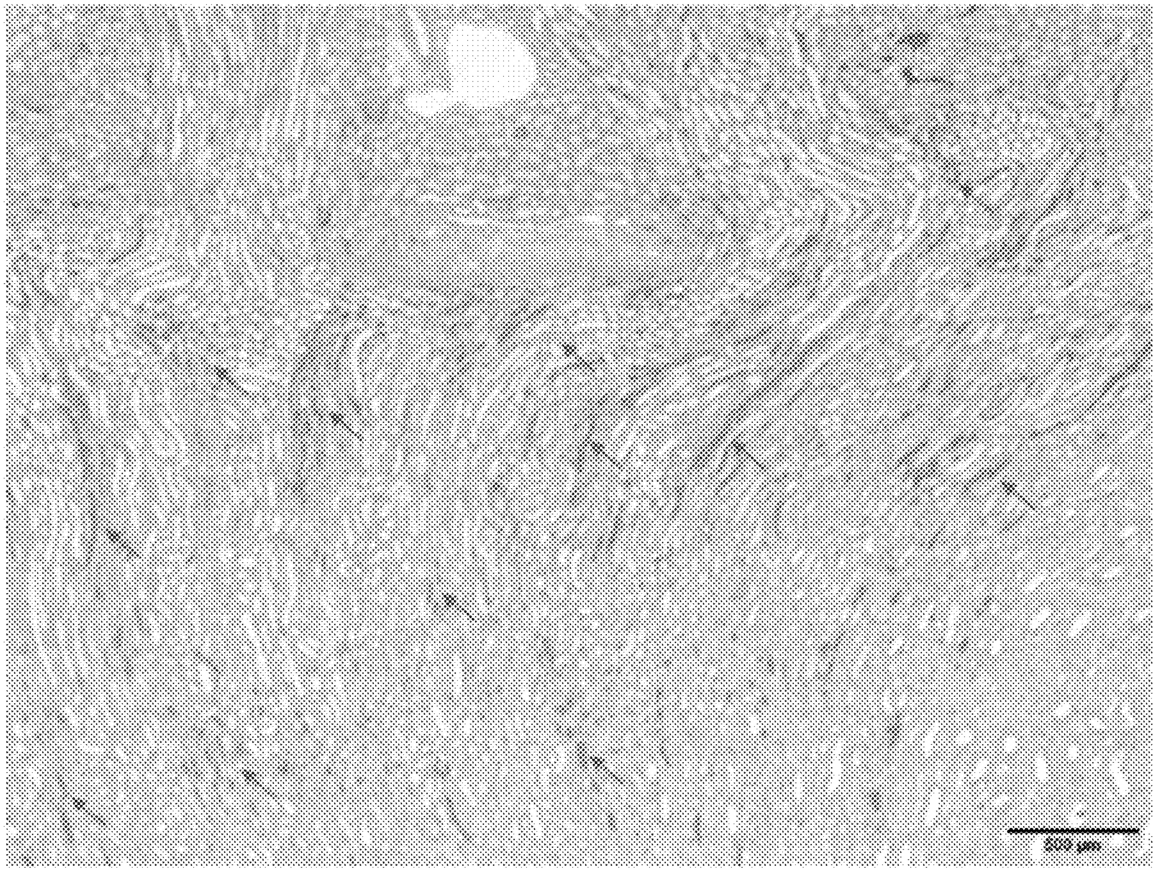
FIG. 24C is a low magnification photomicrograph of kidney tissue from a congested and untreated (e.g., control) kidney.
Figure 24D:
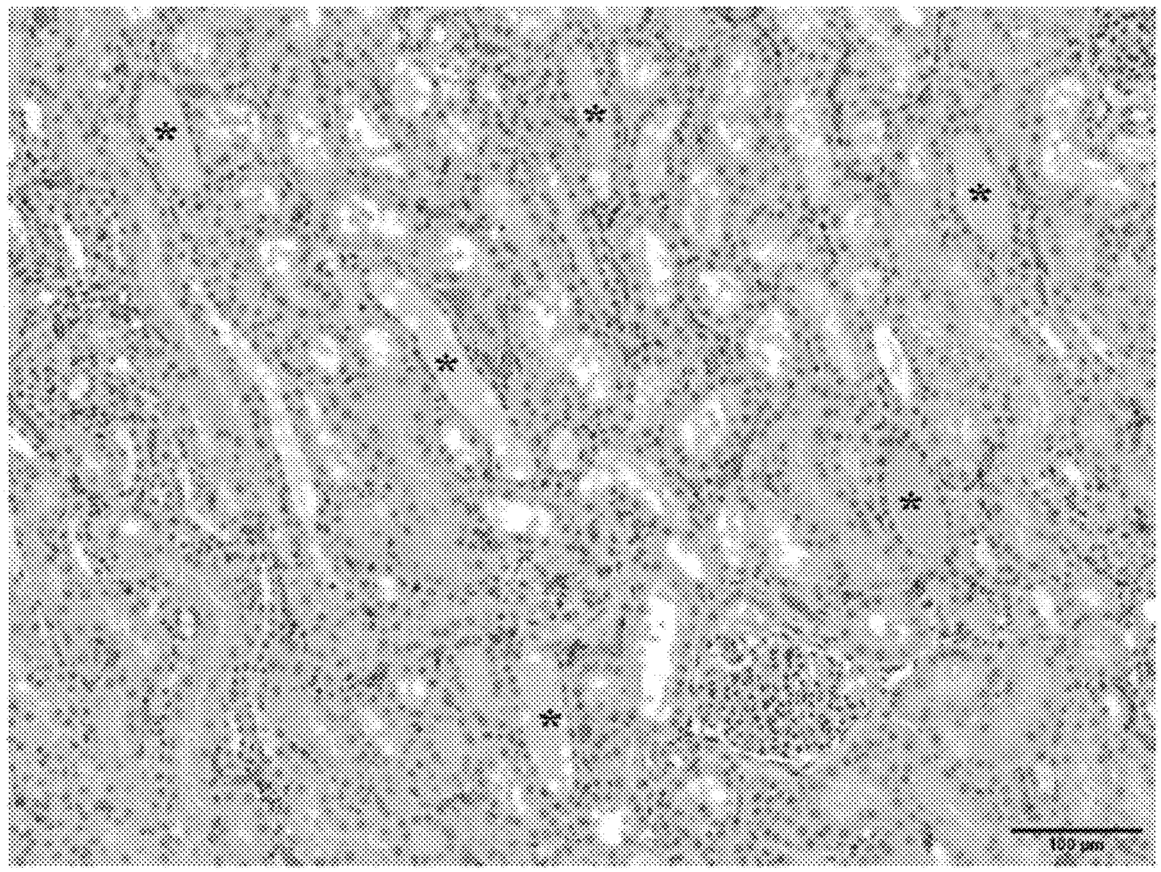
FIG. 24D is a high magnification photomicrograph of the kidney tissue shown in FIG. 24C.

FIGS. 24C and 24D are low and high resolution photomicrographs of the control kidney (right kidney). Based on the histological review, moderate congestion in the blood vessel at the corticomedullary junction was identified, as shown by the arrows in FIG. 24C. As shown in FIG. 24D, several tubules with hyaline casts were present in the tissue sample (as identified by asterisks in the image). Presence of a substantial number of hyaline casts is evidence of hypoxia.

Surface mapping analysis provided the following results. The treated kidney was determined to have 1.5 times greater fluid volume in Bowman's space and 2 times greater fluid volume in tubule lumen. Increased fluid volume in Bowman's space and the tubule lumen corresponds to increased urine output. In addition, the treated kidney was determined to have 5 times less blood volume in capillaries compared to the control kidney. The increased volume in the treated kidney appears to be a result of (1) a decrease in individual capillary size compared to the control and (2) an increase in the number of capillaries without visible red blood cells in the treated kidney compared to the control kidney, an indicator of less congestion in the treated organ.

SUMMARY

These results indicate that the control kidney had more congestion and more tubules with intraluminal hyaline casts, which represent protein-rich intraluminal material, compared to the treated kidney. Accordingly, the treated kidney exhibits a lower degree of loss of renal function. While not intending to be bound by theory, it is believed that as severe congestion develops in the kidney, hypoxemia of the organ follows. Hypoxemia interferes with oxidative phosphorylation within the organ (e.g., ATP production). Loss of ATP and/or a decrease in ATP production inhibits the active transport of proteins causing intraluminal protein content to increase, which manifests as hyaline casts. The number of renal tubules with intraluminal hyaline casts correlates with the degree of loss of renal function. Accordingly, the reduced number of tubules in the treated left kidney is believed to be physiologically significant. While not intending to be bound by theory, it is believed that these results show that damage to the kidney can be prevented or inhibited by applying negative pressure to a ureteral catheter inserted into the renal pelvis to facilitate urine output.

Example 2

Method

Four (4) farm swine (A, B, C, D) were sedated and anesthetized. Vitals for each of the swine were monitored throughout the experiment and cardiac output was measured at the end of each 30-minute phase of the study. Ureteral catheters, such as the ureteral catheter 112 shown in FIGS. 2A and 2B of the '331 patent, were deployed in the renal pelvis region of the kidneys of each of the swine. The deployed catheters were a 6 Fr catheter having an outer diameter of 2.0±0.1 mm. The catheters were 54±2 cm in length, not including the distal retention portion. The retention portion was 16±2 mm in length. As shown in the ureteral catheter 112 shown in FIGS. 2A and 2B of the '331 patent, the retention portion included two full coils and one proximal half coil. The outer diameter of the full coils was 18±2 mm. The half coil diameter was about 14 mm. The retention portion of the deployed ureteral catheters included six drainage openings, plus an additional opening at the distal end of the catheter tube. The diameter of each of the drainage openings was 0.83±0.01 mm. The distance between adjacent drainage openings 1232, specifically the linear distance between drainage openings when the coils were straightened, was 22.5±2.5 mm.

The ureteral catheters were positioned to extend from the renal pelvis of the swine, through the bladder, and urethra, and to fluid collection containers external to each swine. Following placement of the ureteral catheters, pressure sensors for measuring IVC pressure were placed in the IVC at a position distal to the renal veins. An inflatable balloon catheter, specifically a PTS® percutaneous balloon catheter (30 mm diameter by 5 cm length), manufactured by NuMED Inc. of Hopkinton, NY, was expanded in the IVC at a position proximal to the renal veins. A thermodilution catheter, specifically a Swan-Ganz thermodilution pulmonary artery catheter manufactured by Edwards Lifesciences Corp. of Irvine, CA, was then placed in the pulmonary artery for the purpose of measuring cardiac output.

Initially, baseline urine output was measured for 30 minutes, and blood and urine samples were collected for biochemical analysis. Following the 30-minute baseline period, the balloon catheter was inflated to increase IVC pressure from a baseline pressure of 1-4 mm Hg to an elevated congested pressure of about 20 mm Hg (+/−5 mm Hg). A congestion baseline was then collected for 30 minutes with corresponding blood and urine analysis.

At the end of the congestion period, the elevated congested IVC pressure was maintained and negative pressure diuresis treatment was provided for swine A and swine C. Specifically, the swine (A, C) were treated by applying a negative pressure of −25 mm Hg through the ureteral catheters with a pump. As in previously-discussed examples, the pump was an Air Cadet Vacuum Pump from Cole-Parmer Instrument Company (Model No. EW-07530-85). The pump was connected in series to a regulator. The regulator was a V-800 Series Miniature Precision Vacuum Regulator—⅛ NPT Ports (Model No. V-800-10-W/K), manufactured by Airtrol Components Inc. The swine were observed for 120 minutes, as treatment was provided. Blood and urine collection were performed every 30 minutes, during the treatment period. Two of the swine (B, D) were treated as congested controls (e.g., negative pressure was not applied to the renal pelvis through the ureteral catheters), meaning that the two swine (B, D) did not receive negative pressure diuresis therapy.

Following collection of urine output and creatinine clearance data for the 120-minute treatment period, the animals were sacrificed and kidneys from each animal were subjected to gross examination. Following gross examination, histological sections were obtained and examined, and magnified images of the sections were captured.

Results

Measurements collected during the Baseline, Congestion, and Treatment periods are provided in Table 2. Specifically, urine output, serum creatinine, and urinary creatinine measurements were obtained for each time period. These values allow for the calculation of a measured creatinine clearance as follows:

$$\text{Creatinine Clearance: } CrCl = \text{Urine Output (ml/min)} * \frac{\text{Urinary Creatinine }(\text{mg}/dl)}{\text{Serum Creatinine }(\text{mg}/dl)}$$

In addition, Neutrophil gelatinase-associated lipocalin (NAL) values were measured from serum samples obtained for each time period and Kidney Injury Molecule 1 (KIM-1) values were measured from the urine samples obtained for each time period. Qualitative histological findings determined from review of the obtained histological sections are also included in Table 2.

TABLE 2

| | Animal | | | |
|---|---|---|---|---|
| Treatment assignment | A Treatment | B Control | C Treatment | D Control |
| Baseline: | | | | |
| Urine output (ml/min) | 3.01 | 2.63 | 0.47 | 0.98 |
| Serum creatinine (mg/dl) | 0.8 | 0.9 | 3.2 | 1.0 |
| Creatinine clearance (ml/min) | 261 | 172 | 5.4 | 46.8 |
| Serum NGAL (ng/ml) | 169 | * | 963 | 99 |
| Urinary KIM-1 (ng/ml) | 4.11 | * | 3.59 | 1.16 |
| Congestion: | | | | |
| Urine output (ml/min) | 0.06 (2%) | 0.53 (20%) | 0.12 (25%) | 0.24 (25%) |
| Serum creatinine (mg/dl) | 1.2 (150%) | 1.1 (122%) | 3.1 (97%) | 1.2 (120%) |
| Creatinine clearance (ml/min) | 1.0 (0.4%) | 30.8 (18%) | 1.6 (21%) | 16.2 (35%) |
| Serum NGAL (ng/ml) | 102 (60%) | * | 809 (84%) | 126 (127%) |
| Urinary KIM-1 (ng/ml) | 24.3 (591%) | * | 2.2 (61%) | 1.39 (120%) |
| Treatment: | | | | |
| Urine output (ml/min) | 0.54 (17%) | | 0.47 (101%) | 0.35 (36%) |
| Serum creatinine (mg/dl) | 1.3 (163%) | | 3.1 (97%) | 1.7 (170%) |
| Creatinine clearance (ml/min) | 30.6 (12%) | ** | 18.3 (341%) | 13.6 (29%) |

TABLE 2-continued

| | Animal | | | |
|---|---|---|---|---|
| Treatment assignment | A Treatment | B Control | C Treatment | D Control |
| Serum NGAL (ng/ml) | 197 (117%) | | 1104 (115%) | 208 (209%) |
| Urinary KIM-1 (ng/ml) | 260 (6326%) | | 28.7 (799%) | 233 (20000%) |
| Histological findings: | | | | |
| Blood volume in capillary space | 2.4% | | 0.9% | 4.0% |
| Hyaline casts | Mild/Mod | ** | None | Mod |
| Degranulation | Mild/Mod | | None | Mod |

Data are raw values (% baseline)
* not measured
** confounded by phenylephrine

Animal A: The animal weighed 50.6 kg and had a baseline urine output rate of 3.01 ml/min, a baseline serum creatinine of 0.8 mg/dl, and a measured CrCl of 261 ml/min. It is noted that these measurements, aside from serum creatinine, were uncharacteristically high relative to other animals studied. Congestion was associated with a 98% reduction in urine output rate (0.06 ml/min) and a >99% reduction in CrCl (1.0 ml/min). Treatment with negative pressure applied through the ureteral catheters was associated with urine output and CrCl of 17% and 12%, respectively, of baseline values, and 9× and >10×, respectively, of congestion values. Levels of NGAL changed throughout the experiment, ranging from 68% of baseline during congestion to 258% of baseline after 1 minutes of therapy. The final value was 130% of baseline. Levels of KIM-1 were 6 times and 4 times of baseline for the first two 30-minute windows after baseline assessment, before increasing to 68×, 52×, and 63× of baseline values, respectively, for the last three collection periods. The 2-hour serum creatinine was 1.3 mg/dl. Histological examination revealed an overall congestion level, measured by blood volume in capillary space, of 2.4%. Histological examination also noted several tubules with intraluminal hyaline casts and some degree of tubular epithelial degeneration, a finding consistent with cellular damage.

Animal B: The animal weighed 50.2 kg and had a baseline urine output rate of 2.62 ml/min and a measured CrCl of 172 ml/min (also higher than anticipated). Congestion was associated with an 80% reduction in urine output rate (0.5 ml/min) and an 83% reduction in CrCl (30 ml/min). At 50 minutes into the congestion (20 minutes after the congestion baseline period), the animal experienced an abrupt drop in mean arterial pressure and respiration rate, followed by tachycardia. The anesthesiologist administered a dose of phenylephrine (75 mg) to avert cardiogenic shock. Phenylephrine is indicated for intravenous administration when blood pressure drops below safe levels during anesthesia. However, since the experiment was testing the impact of congestion on renal physiology, administration of phenylephrine confounded the remainder of the experiment.

Animal C: The animal weighed 39.8 kg and had a baseline urine output rate of 0.47 ml/min, a baseline serum creatinine of 3.2 mg/dl, and a measured CrCl of 5.4 ml/min. Congestion was associated with a 75% reduction in urine output (0.12 ml/min) and a 79% reduction in CrCl (1.6 ml/min). It was determined that baseline NGAL levels were >5× the upper limit of normal (ULN). Treatment with negative pressure applied to the renal pelvis through the ureteral catheters was associated with a normalization of urine output (101% of baseline) and a 341% improvement in CrCl (18.2 ml/min). Levels of NGAL changed throughout the experiment, ranging from 84% of baseline during congestion to 47% to 84% of baseline between 30 and 1 minutes. The final value was 115% of baseline. Levels of KIM-1 decreased 40% from baseline within the first 30 minutes of congestion, before increasing to 8.7×, 6.7×, 6.6×, and 8× of baseline values, respectively, for the remaining 30-minute windows. Serum creatinine level at 2 hours was 3.1 mg/dl. Histological examination revealed an overall congestion level, measured by blood volume in capillary space, of 0.9%. The tubules were noted to be histologically normal.

Animal D: The animal weighed 38.2 kg and had a baseline urine output of 0.98 ml/min, a baseline serum creatinine of 1.0 mg/dl, and a measured CrCl of 46.8 ml/min. Congestion was associated with a 75% reduction in urine output rate (0.24 ml/min) and a 65% reduction in Cr Cl (16.2 ml/min). Continued congestion was associated with a 66% to 91% reduction of urine output and 89% to 71% reduction in CrCl. Levels of NGAL changed throughout the experiment, ranging from 127% of baseline during congestion to a final value of 209% of baseline. Levels of KIM-1 remained between 1× and 2× of baseline for the first two 30-minute windows after baseline assessment, before increasing to 190×, 219×, and 201× of baseline values for the last three 30-minute periods. The 2-hour serum creatinine level was 1.7 mg/dl. Histological examination revealed an overall congestion level 2.44× greater than that observed in tissue samples for the treated animals (A, C) with an average capillary size 2.33 times greater than that observed in either of the treated animals. The histological evaluation also noted several tubules with intraluminal hyaline casts as well as tubular epithelial degeneration, indicating substantial cellular damage.

Summary

While not intending to be bound by theory, it is believed that the collected data supports the hypothesis that venous congestion creates a physiologically significant impact on renal function. In particular, it was observed that elevation of the renal vein pressure reduced urine output by 75% to 98% within seconds. The association between elevations in biomarkers of tubular injury and histological damage is consistent with the degree of venous congestion generated, both in terms of magnitude and duration of the injury.

The data also appears to support the hypothesis that venous congestion decreases the filtration gradients in the medullary nephrons by altering the interstitial pressures. The change appears to directly contribute to the hypoxia and cellular injury within medullary nephrons. While this model does not mimic the clinical condition of AKI, it does provide insight into the mechanical sustaining injury.

The data also appears to support the hypothesis that applying negative pressure to the renal pelvis through ureteral catheters can increase urine output in a venous congestion model. In particular, negative pressure treatment was associated with increases in urine output and creatinine clearance that would be clinically significant. Physiologically meaningful decreases in medullary capillary volume and smaller elevations in biomarkers of tubular injury were also observed. Thus, it appears that by increasing urine output rate and decreasing interstitial pressures in medullary nephrons, negative pressure therapy may directly decrease congestion. While not intending to be bound by theory, by decreasing congestion, it may be concluded that negative pressure therapy reduces hypoxia and its downstream effects within the kidney in a venous congestion mediated AKI.

The experimental results appear to support the hypothesis that the degree of congestion, both in terms of the magnitude of pressure and duration, is associated with the degree of cellular injury observed. Specifically, an association between the degree of urine output reduction and the histological damage was observed. For example, treated Swine A, which had a 98% reduction in urine output, experienced more damage than treated Swine C, which had a 75% reduction in urine output. As would be expected, control Swine D, which was subjected to a 75% reduction in urine output without benefit of therapy for two and a half hours, exhibited the most histological damage. These findings are broadly consistent with human data demonstrating an increased risk for AKI onset with greater venous congestion. See e.g., Legrand, M. et al., *Association between systemic hemodynamics and septic acute kidney injury in critically ill patients: a retrospective observational study. Critical Care* 17:R278-86, 2013.

Example 3: Renal Negative Pressure Treatment with Furosemide

Example 3 evaluates use of Negative Pressure Treatment (rNPT) for improvement of diuresis, natriuresis, and renal function in a congestion heart failure (HF) model.

Method

Ten Yorkshire farm pigs that were from 18-20 weeks of age (~80 kg) were used to investigate effects of renal Negative Pressure Treatment (rNPT) using the JuxtaFlow® catheter and pump system. As previously discussed, the JuxtaFlow® catheter is a memory polymer catheter which deploys into a 3-dimensional helix when placed in the renal pelvis allowing application of negative pressure to the kidney without causing tissue collapse or obstruction. The JuxtaFlow® catheter is similar or identical to the ureteral catheter 112 shown in FIGS. 2A and 2B of the '331 patent. The JuxtaFlow® pump is a tightly controlled, self-regulating negative pressure pump system designed for use with the JuxtaFlow® catheter and rNPT. The JuxtaFlow® pump includes features of the external pumps shown in FIGS. 1A and 4A.

In order to deploy the JuxtaFlow® catheters, after an overnight fast, pigs were anesthetized with a combination of intramuscular ketamine and tiletamine/zolazepam (Telazol), intubated, and maintained on inhaled isoflurane. An intrapericardial catheter was placed via a left lateral thoracotomy. A Swan-Ganz catheter was placed via a right internal jugular vein cutdown. An arterial line for continuous hemodynamic monitoring was placed in the carotid or femoral artery by either Seldinger technique or arterial cutdown. Large bore central venous access was similarly placed in either the contralateral jugular or a femoral vein for fluid and tracer infusions. To catheterize the ureters, the bladder was retracted caudally through a small suprapubic incision and each ureter was isolated and directly cannulated through a small incision. The JuxtaFlow® catheters were then advanced into the renal pelvis under fluoroscopic guidance. Each kidney was drained through the JuxtaFlow® catheters either passively or under negative pressure provided by the JuxtaFlow® pump for applying rNPT.

Given that the human heart failure use-case for the JuxtaFlow® catheter and system may be in conjunction with intravenous loop diuretic use, two experimental phases were conducted to investigate the effect of rNPT: 1) during maximal furosemide diuresis without heart failure (HF); and 2) in a state of HF characterized by venous congestion and concurrent furosemide diuresis. During the two phases, each animal served as its own control with randomization of either the left or right kidney to rNPT versus No-rNPT. The experiment was started with an equilibration period where intravenous (IV) boluses and continuous infusion of the following agents were initiated and maintained for a period of 2.5 hours: iothalamate ("IOT", 120 mg bolus with 0.3 mg/min infusion, Guerbet, USA); para-aminohippurate ("PAH", 800 mg bolus with 8.4 mg/min infusion, MilliporeSigma, USAsupplier); and furosemide (400 mg bolus with infusion at 80 mg/hr). To avoid volume depletion, a 4 Liter IV infusion of normal saline followed by a maintenance IV infusion titrated to match urine output 1:1 (mL) occurred during this equilibrium period.

Experimental Periods

After equilibration of tracers, the right and left kidneys were randomized (−30 mmHg rNPT was applied to one kidney, while the other kidney drained by passive drainage) and the rNPT therapy was started. In order to ensure that the pre-tamponade and tamponade experimental periods had similar background fluid status, a rapid, large-volume, normal saline infusion of 20% to 25% body weight occurred at this point. After 10 minutes of equilibration, the animals underwent two 15 minute "post fluid" clearance periods. Next, cardiac tamponade was induced by pericardial instillation of approximately 200 mL of 6% hydroxyethyl starch. Pericardial hydroxyethyl starch and additional IV normal saline infusion were titrated to maintain a hemodynamic profile sufficient for relative preservation of cardiac output and mean arterial pressure (compared to the baseline pre-fluid readings), while maintaining a central venous pressure of less than 20 mmHg. After stabilization and a 10 minute equilibration, two 15 minute study periods were repeated.

Assays and Calculations

A Randox Imola automated clinical chemistry analyzer was used to measure concentration of urine or serum chemistry parameters. The calibrators, reagents, and urine Level 2 and Level 3 controls were purchased from Randox Laboratories. All assay measurements were carried out in accordance with the manufacturer's instructions (Randox Laboratories, UK). Creatinine measurements were standardized to Isotope Dilution Mass Spectrometry (IDMS) traceable National Institute of Standards and Technology reference material (SRM 967). Urine and plasma iothalamate were measured using Agilent 6490 QTOF equipped with Agilent 1290 UHPLC.

A stock solution of iothalamate was serially diluted in 0.1% formic acid containing deuterated iothalamate to create the calibration curve (1-2000 ng/ml). Plasma samples (100 μL) were deproteinized by adding 300 μL of 100% methanol containing deuterated iothalamate (1000 ng/ml) (Cambridge Isotope Laboratories, Inc), vortexed, and centrifuged at 12,000 rpm for 10 minutes. 200 μL of the supernatant was then transferred to glass sampler vials, and 10 μL of the sample was injected to the UHPLC-MS/MS system. The urine samples were diluted 10-fold with 0.1% formic acid containing the internal standard. 10 μL of the diluted urine sample was injected into the UHPLC-MS/MS system. Separation was achieved using Agilent Zorbax Eclipse plus RP 2.1×50 mm 1.8 μm column with a constant flow rate of 400 μL/min. An instrument-controlled gradient of 0.1% formic acid and 100% methanol were used as Buffer A and Buffer B, respectively. Quantitation was carried out using the Agilent MassHunter Quantitative analysis software. Urine and plasma PAH were measured using the PAH colorimetric assay kit from Abcam, according to manufacturer's recommendation. Urine neutrophil gelatinase-associated lipocalin (NGAL) was measured with porcine NGAL kit from Alpco (Alpco, Salem, NH). Urine cGMP concentrations were assayed using a comlrniercially available competitive enzyme-linked immunosorbent assay kit according the manufacturer's guidelines (Parameter cGM P Assay, R&D Systems Inc, Minneapolis, MN, USA).

Measured creatinine clearance was calculated as Urine creatinine×Volume of urine per minute/Plasma creatinine. Measured GFR was calculated as Urine iothalamate×Volume of urine per minute/Plasma iothalamate. Renal plasma flow was calculated as Urine PAH×Volume of urine per minute/Plasma PAH. Filtration fraction was calculated as GFR/(renal plasma flow/0.9). Fractional excretion of sodium (FENa) was calculated as was calculated as (Naurine/Nasemm)×(Crseum/Crurine)×100%.

Statistical Analysis

Continuous data is shown as mean±standard deviation or median (quartile 1-quartile 3) according to observed distribution. Categorical data is shown as frequency (percentage). Variables with skewed distribution were log transformed to approximate normal distribution. Changes in continuous variables from baseline to post-fluid (No HF) or to HF model of venous congestion were compared with the paired t test. Changes in continuous variables during the experiments were analyzed via linear mixed models accounting for correlations within animals. rNPT and HF models of venous congestion were included as main factors (binary variables) in a full factorial model. Statistical significance was defined as 2-tailed $P<0.05$. Statistical analysis was performed with IBM SPSS Statistics version 26 (IBM Corp, Armonk, NY) and Stata SE version 16.0 (StataCorp, College Station, TX).

Figure 25A:
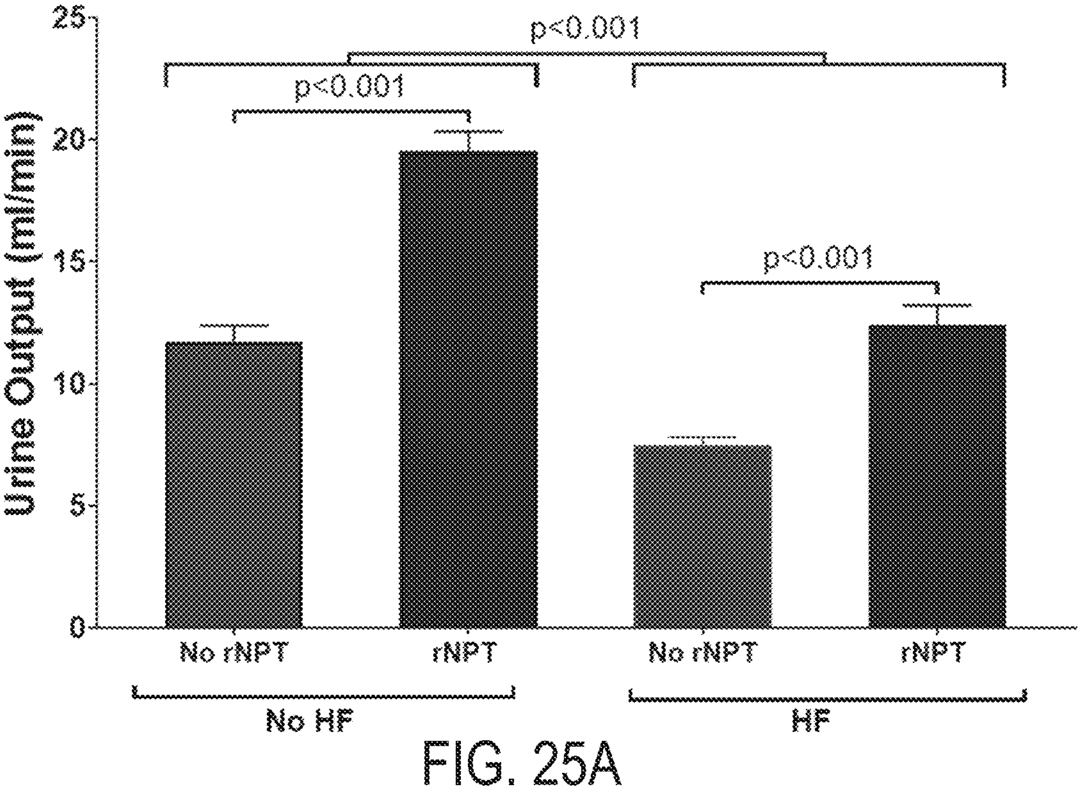
FIGS. 25A-25F are graphs showing measured hemodynamic variables for a 15-minute baseline period without renal negative pressure therapy and a 15-minute period of renal negative pressure therapy in a no heart failure (No-HF) state, as described in Example 3.
Figure 25B:
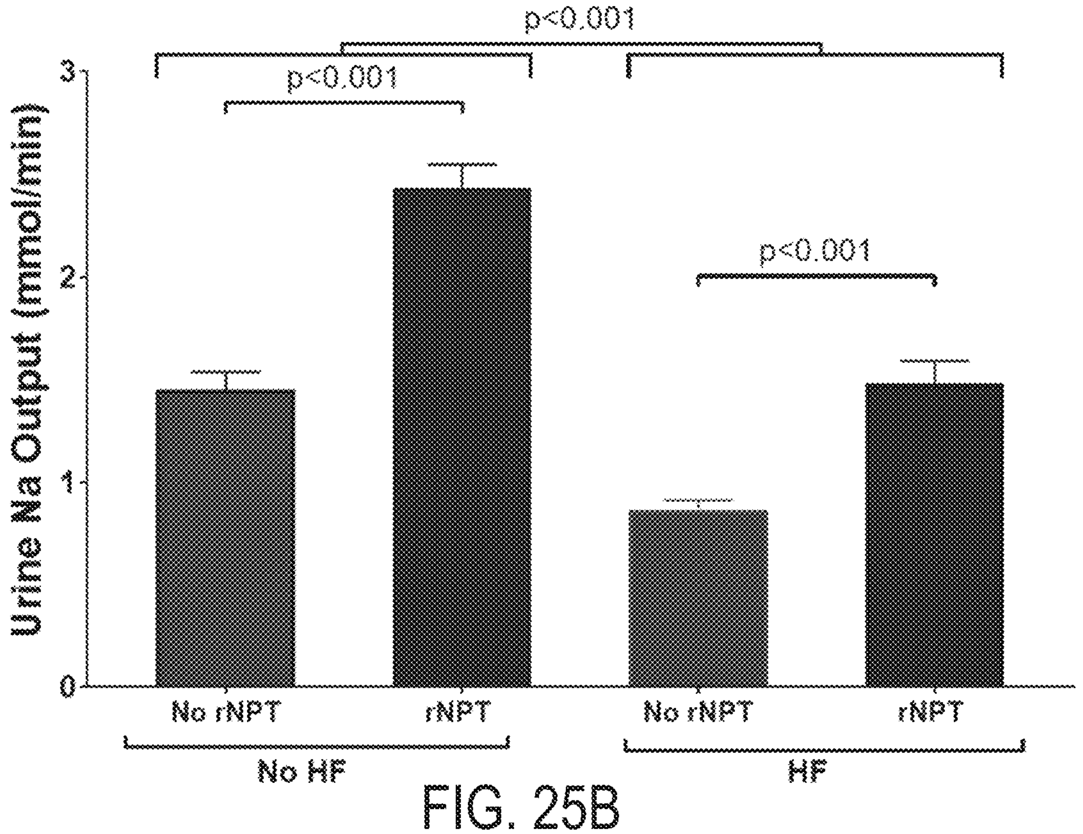
Figure 25C:
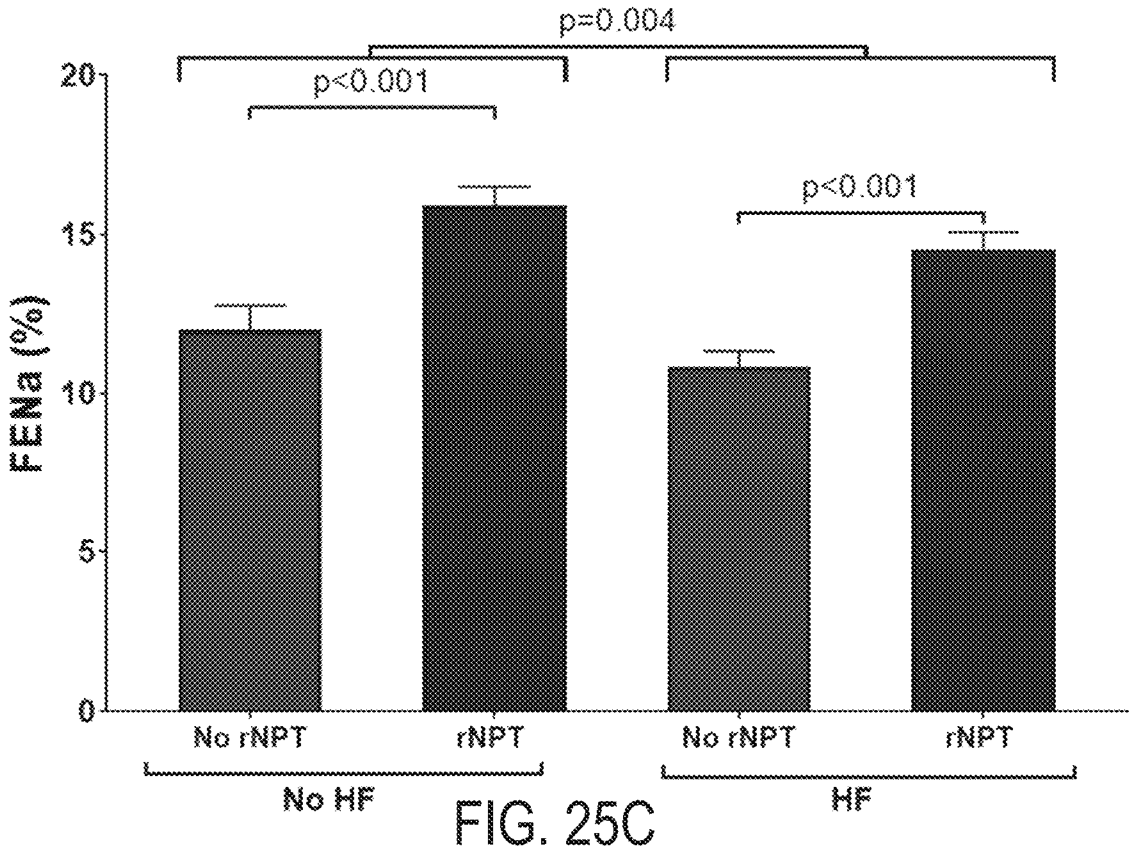
Figure 25D:
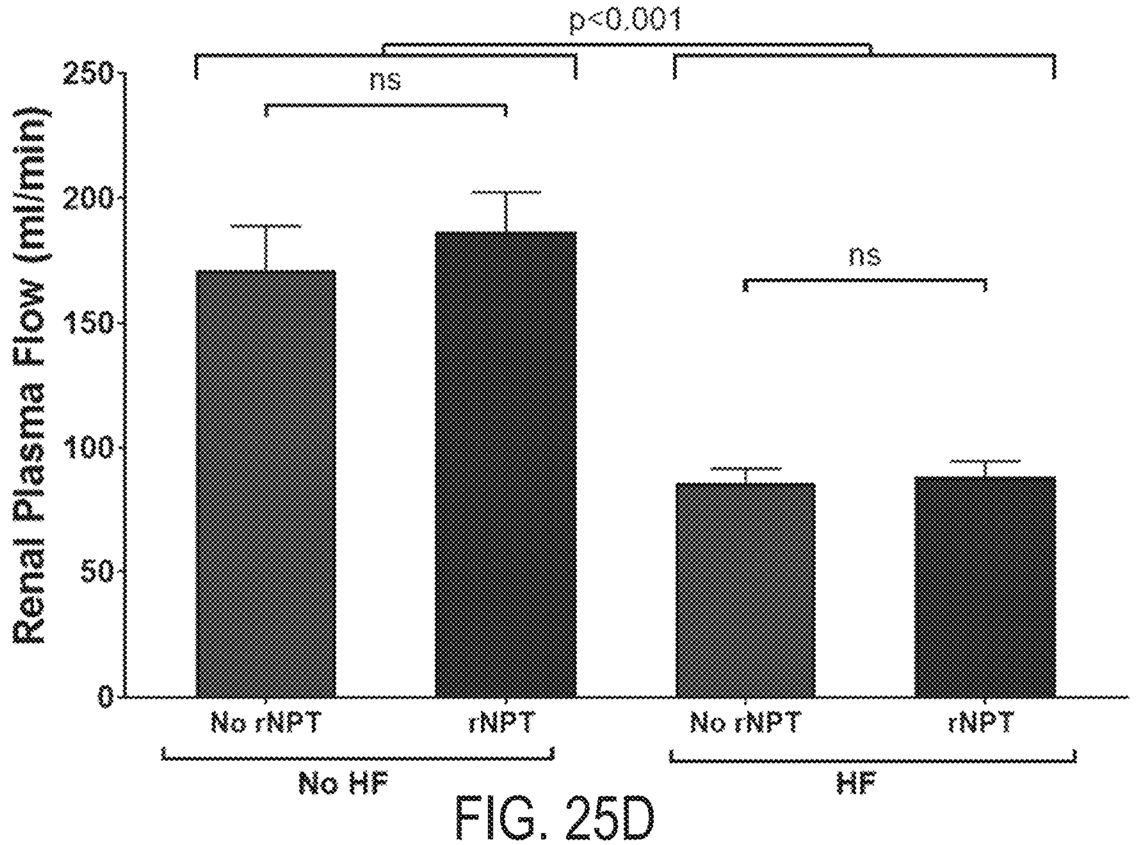
Figure 25E:
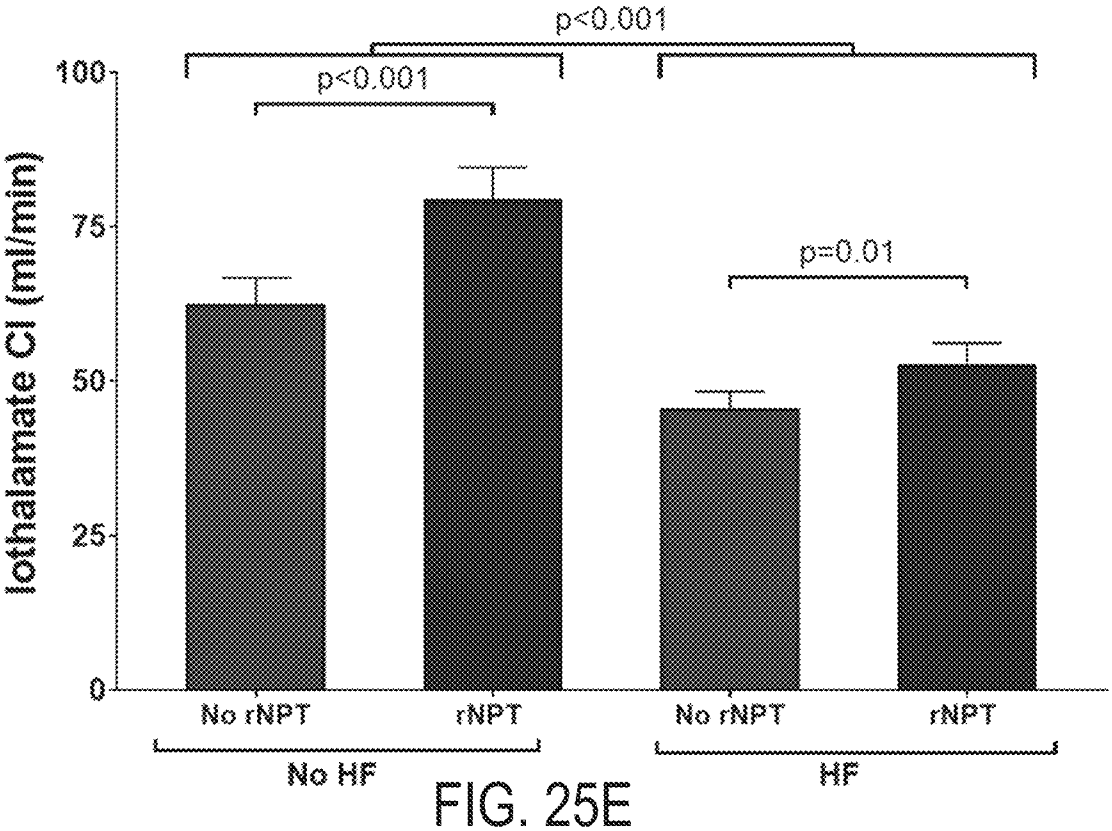
Figure 25F:
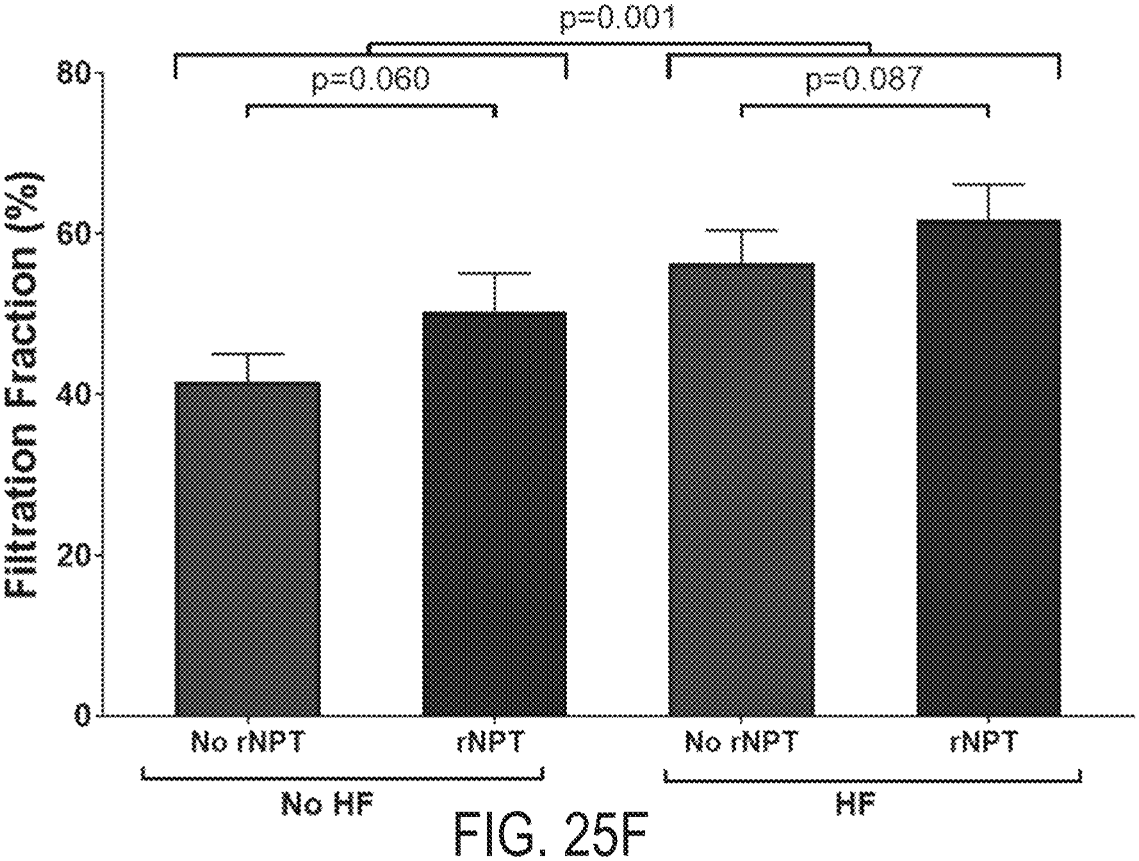

FIGS. 25A-25F are graphs illustrating results for urine output (FIG. 25A), cumulative urine sodium excretion (FIG. 25B), fractional excretion of sodium (FIG. 25C), renal plasma flow (FIG. 25D), glomerular filtration rate measured by iothalamate (IOH) (FIG. 25E), and filtration fraction (FIG. 25F). The graphs are presented as mean±standard error of the mean. Each graph compares a 15-minute baseline period without renal negative pressure therapy to a 15-minute period of renal negative pressure therapy in a non-HF state and in a HF model.

Figure 26A:
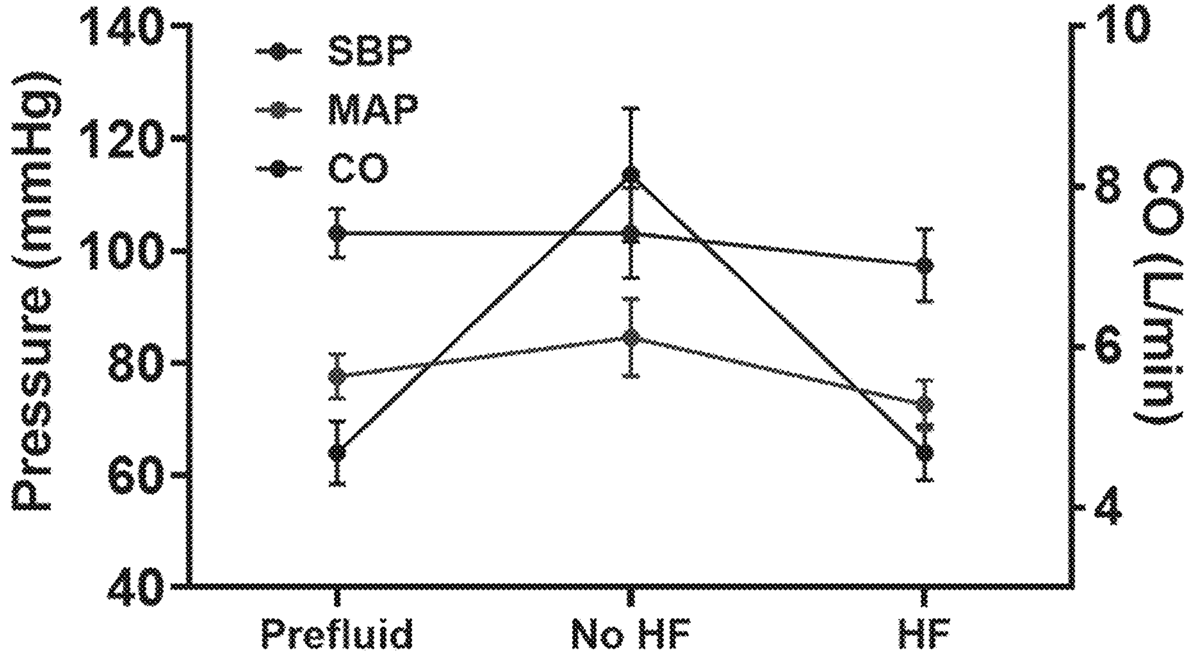
FIGS. 26A-26D are graphs showing measured hemodynamic variables measured in Example 3 for a pre-fluid state, a No-HF state, and an HF state.
Figure 26B:
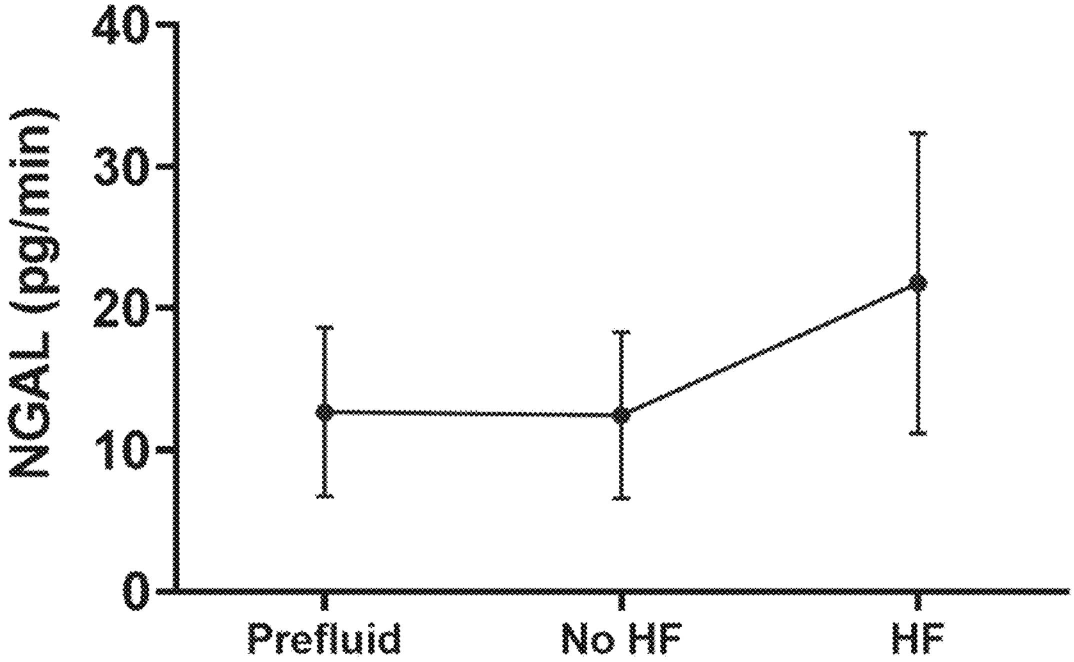
Figure 26C:
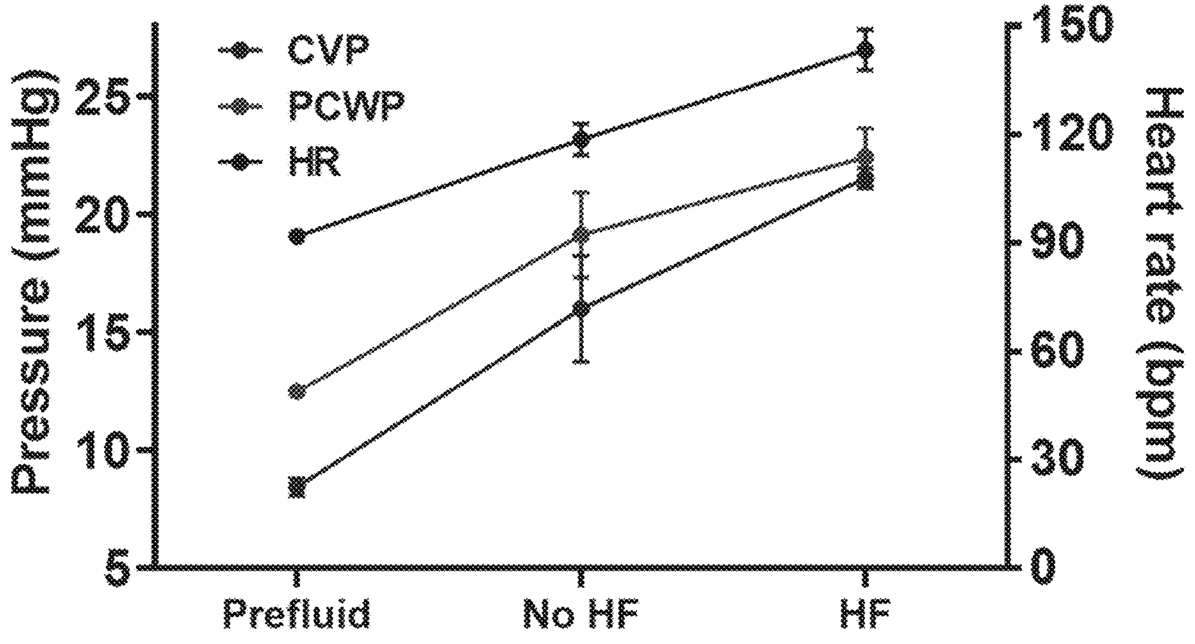
Figure 26D:
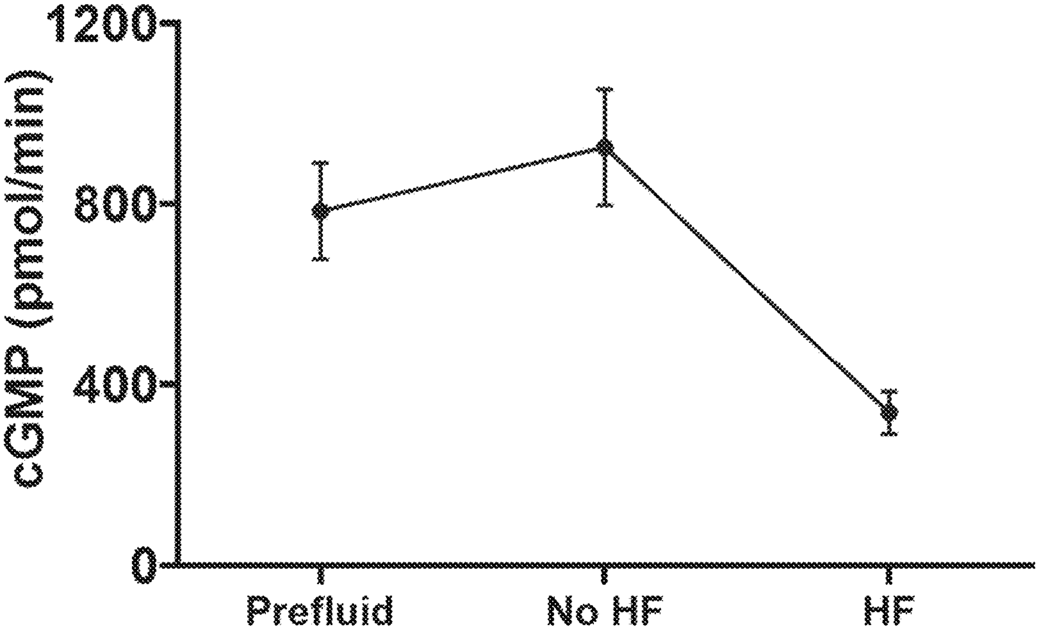

FIGS. 26A-26D are line graphs for hemodynamic variables collected during the experiments of Example 3. The hemodynamic variables are presented as mean±standard error of the mean across the three study periods: 1) before intravenous (IV) fluid administration (Prefluid), 2) after IV fluid administration with no heart failure (No HF), and 3) after induction of a HF model from cardiac tamponade. As shown in FIG. 26A, SBP and MAP (FIG. 26A) were not statistically different among the three periods ($p>0.12$ for each comparison), while CO increased from the prefluid to the No-HF period ($p<0.01$). CO was not statistically different in the HF model compared to the Prefluid period ($p=0.90$).

CVP, PCWP, and HR (FIG. 26C) increased significantly from the Prefluid to the No-HF period, and from the No-HF period to the HF model ($p<0.05$ for all comparisons). Neutrophil Gelatinase-Associated Lipocalin (NGAL) (FIG. 26B) did not change from the Prefluid to the No-HF period, but tended to increase from the No-HF to the HF period ($p=0.053$). Cyclic GMP (cGMP) (FIG. 26D) did not change from the Prefluid to the No-HF period, but decreased significantly from the No-HF to the HF period ($p<0.001$).

As illustrated by these figures, during furosemide diuresis, rNPT substantially increased natriuresis (2.4±0.6 mmol/min vs 1.5±0.5 mmol/min; $p<0.001$) and diuresis (19.7±4.5 ml/min vs 11.8±3.7 ml/min; $p<0.001$) compared to control. See FIGS. 25A and 25B. rNPT also increased iothalamate clearance (79±28 ml/min vs 62±23 ml/min; $p<0.001$) and creatinine clearance (105±38 vs. 85±30, $p=0.001$). See FIG. 46E. Renal plasma flow ($p=0.13$) did not differ significantly between rNPT and control. See FIG. 25D. The increased natriuresis with rNPT was not solely driven by increased sodium filtration, because the fractional excretion of sodium (FENa) was also higher with rNPT (15.9%±3.3% vs 12.0%±4.2%, $p<0.001$). See FIG. 25C.

The figures also show that induction of cardiac tamponade was successful in producing a "warm and wet" HF phenotype with preserved cardiac output and blood pressure, but with severely elevated right sided filling pressures. See FIGS. 26A and 26C. A cardio-renal phenotype also emerged as urine output (37%), renal sodium excretion (40%), measured GFR (27%), and renal plasma flow (50%) all decreased substantially with induction of HF ($p<0.001$). Furthermore, urine cyclic GMP decreased substantially ($p<0.001$) and NGAL tended to increase with induction of HF ($p=0.053$). Filtration fraction increased during induction of HF (42±18% vs 56±21%, $p=0.001$).

The effect of rNPT on GFR was similar between HF and No-HF periods (i.e., similar increments in GFR with rNPT; p interaction=0.23 for a different effect of rNPT in HF and no HF). rNPT did not significantly change renal plasma flow in either the HF or no HF periods ($p=0.47$ for the interaction). During HF, rNPT yielded greater urine output (276 ml±113 ml vs 167 ml±55 ml $p<0.001$) and urine sodium excretion (33.0±14.5 mmol vs 19.5±6.8 mmol; $p<0.001$) compared to the control kidney. See FIGS. 46A and 46B. FENa was also higher with rNPT (14.5%±3.0% vs 10.9%±2.7%, $p<0.001$). See FIG. 46C. Renal plasma flow did not change significantly with rNPT in HF ($p=0.58$). See FIG. 46D. Filtration fraction increased during rNPT (55.6±24.8% vs 49.0±20.8%; $p=0.034$) with a similar effect between HF and no HF periods ($p=0.70$ for the interaction). See FIG. 46F. Urine NGAL was similar with and without rNPT ($p=0.70$). Importantly, during HF, the rNPT kidney had similar urine output ($p=0.52$) and sodium excretion ($p=0.87$), and higher FENa (14.5±3.0% vs 12.0±4.2%; $p=0.001$) compared to the non-rNPT kidney without HF.

DISCUSSION

The foregoing test results of Example 3 demonstrate that negative pressure applied to the renal pelvis during high dose furosemide therapy significantly improves a wide range of cardio-renal parameters, such as increased GFR, increased urine output, and increased sodium output. The mechanism of the increase in cumulative urine sodium excretion was not due purely to an increase in GFR, because both total and fractional sodium excretion increased. Importantly, the benefit appears to be of a clinically significant magnitude as urine output and sodium excretion with rNPT during experimental heart failure was similar to the non-rNPT kidney during the control period, i.e., after the heart failure model was shown to significantly decrease renal function, application of rNPT during heart failure appeared to restore renal function back to substantially normal levels.

As known to those skilled in the art, in ADHF, elevated central venous pressure is transmitted to renal veins. The transmission of central venous pressure to the renal veins increases renal venous pressure and decreases venous compliance, without changing renal arterial resistance or compliance. Renal venous congestion raises intrarenal and tubular pressure in the fixed space of the encapsulated kidney. While not intending to be bound by any theory, since alterations in renal venous blood flow normalize with decongestion, the inventors theorized that interventions to reduce intrarenal pressure may improve diuretic response and, potentially, ADHF outcomes. The experiments of Example 3 show that an intervention with renal negative pressure therapy increased urine output and urine sodium excretion. These findings are consistent with observations in humans with ADHF, where abnormal measurements of renal venous impedance and flow have been shown to be associated with higher sodium avidity, diminished diuretic response, and worsening HF outcomes independent of central venous pressure. In patients with ADHF, the inverse relationship between diuretic response and elevated renal venous impedance is independent of GFR.

In addition to the beneficial effects in a HF model, renal negative pressure therapy appears to improve natriuresis and GFR during high dose furosemide therapy. This is an unexpected result because one might hypothesize that, in the normal state, increased filtration from rNPT would activate tubular glomerular feedback (TGF), which reduces filtration and brings GFR back to baseline. However, it is known that furosemide can reduce GFR. For example, it has been reported that furosemide administration can acutely increase proximal tubular pressure by −10 mmHg to −15 mmHg and increase renal interstitial pressure by −7 mmHg, both of which are likely contributors to the fall in GFR observed with loop diuretic administration. Thus, even in the absence of HF, furosemide would be expected to reduce GFR and elevate tubular and interstitial pressures, which could theoretically be improved with rNPT. This observation may be expected to have clinical relevance as the therapeutic value of rNPT may extend beyond the often-brief period when patients have intravascular congestion severe enough to negatively impact kidney function.

While not intending to be bound by theory, it is believed that the current observations from the congestion predominate HF model of Example 3 may shed light on the human literature on kidney dysfunction in human HF. The majority of contemporary human studies have not found a meaningful association between cardiac output and kidney function. Thus, the finding of Example 3 showing substantial deterioration in kidney function in an HF model with normal "forward flow" is congruent with conditions described in relevant literature. See e.g., Damman K, Navis G, Smilde T D et al., *Decreased cardiac output, venous congestion and the association with renal impairment in patients with cardiac dysfunction, European journal of heart failure* (2007) 9:872-878; Uthoff H, Breidthardt T, Klima T et al., Central venous pressure and impaired renal function in patients with acute heart failure, *European journal of heart failure* (2011) 13:432-9; and Nohria A, Hasselblad V, Stebbins A et al., *Cardiorenal interactions: insights from the ESCAPE trial, Journal of the American College of Cardiology* (2008) 51:1268-74. Further, these several human studies have noted an association between central venous pressure and renal function. However, it appears that these findings are heterogeneous with studies reporting that decongestion of patients with high CVP is associated with worsening kidney function in some individuals and improved kidney function for others. In Example 3, a large volume of intravenous normal saline substantially increased cardiac filling pressures, but available metrics of renal function were either unaffected or even improved. Upon induction of cardiac tamponade, a substantial reduction in natriuresis, renal plasma flow, GFR, and urinary cGMP was observed. Much like the human literature showing sometimes opposite effects of congestion on renal function and diuresis, the experiments of Example 3 appear to illustrate that the overall balance of natriuretic and anti-natriuretic factors ultimately determine the impact of volume expansion on kidney function.

While interpreting the results in Example 3, it should be considered that although the acute cardiac tamponade model employed sought to provide a relatively stable, predictable, and titratable "warm and wet" HF phenotype, acute tamponade is a rare human HF presentation. Thus, the findings of Example 3 may not extrapolate to acute or chronic decompensated human HF. Although the human-use case for the Juxtaflow® catheter and system may involve high dose loop diuretics, the lack of data in humans on the effect of rNPT in the absence of diuretics is a consideration. While the presumed mechanism underlying the improved renal function with rNPT is reduction of intra-tubular and interstitial pressure, this was not directly measured. Although utilizing the JuxtaFlow® catheter for both negative and atmospheric pressure provided a control for any mechanical effects of instrumenting the renal pelvis, the experiments of Example 3 did not measure delivered pressure at the level of the renal pelvis through the single lumen of the Juxtaflow® catheter. Thus, it was not determined if the actual delivered pressure deviated from −30 mmHg in the rNPT group and 0 mmHg in the non-rNPT group. However, Example 3 provides proof of concept results showing the benefits of rNPT to improve renal function in an acute cardiac tamponade model in pigs.

Example 3 shows that in the setting of high dose loop diuretic therapy in pigs, rNPT with the JuxtaFlow® catheter and pump system resulted in significantly increased diuresis, natriuresis, and mGFR. Importantly, the benefit appeared to be of clinically significant magnitude as urine output and sodium excretion with rNPT during experimental heart failure was similar to the non-rNPT kidney during the control period.

The preceding examples and embodiments of the invention have been described with reference to various examples. Modifications and alterations will occur to others upon reading and understanding the foregoing examples. Accordingly, the foregoing examples are not to be construed as limiting the disclosure.

What is claimed is:

1. A method for deploying a negative pressure therapy system within a urinary tract, the method comprising:

implanting a negative pressure source within a body outside of the urinary tract;

inserting an inflow member of a urinary catheter through a kidney to a renal pelvis of the urinary tract, wherein the inflow member comprises at least one inflow lumen fluidly connected to the implanted negative pressure source, the inflow member further comprising (i) a proximal portion fluidly connected to the negative pressure source, (ii) a retention portion configured to be deployed within the renal pelvis, the retention portion comprising at least one drainage hole leading to the at least one inflow lumen, and (iii) at least one intermediate portion between the proximal portion and the retention portion;

deploying the retention portion of the inflow member within the renal pelvis to maintain patency of fluid flow from the kidney through at least a portion of the at least one inflow lumen; and inserting an outflow member of the urinary catheter through the kidney, the renal pelvis, a ureter, and to a bladder of the urinary tract, wherein the outflow member comprises at least one outflow lumen configured to be in fluid communication with the negative pressure source, the outflow member further comprising (i) a proximal portion, (ii) a distal end configured to be positioned in the bladder, and (iii) at least one intermediate portion extending from the proximal portion to the distal end, wherein the intermediate portion of the outflow member passes through the kidney, renal pelvis and/or ureter.

2. The method of claim 1, further comprising deploying a retention portion of the outflow member in the bladder to retain the distal end of the outflow member in the bladder, such that fluid expelled from the negative pressure source passes through the at least one outflow lumen to the bladder.

3. The method of claim 2, wherein deploying the retention portion of the outflow member causes the retention portion of the outflow member to adopt a three-dimensional shape sized to restrict a distal end of the outflow member from being pulled out of the bladder into the ureter of the urinary tract.

4. The method of claim 2, wherein deploying the retention portion of the outflow member causes the retention portion of the outflow member to form at least one of a pigtail coil, a helical coil, a funnel, or any combination thereof.

5. The method of claim 1, wherein the negative pressure source comprises a pump.

6. The method of claim 1, wherein the pump is implanted at a position posterolateral to the kidney or proximate to an abdominal wall of the body.

7. The method of claim 1, wherein inserting the inflow member of the urinary catheter comprises: inserting a needle into a portion of a patient's body to create a percutaneous opening; inserting the needle into the kidney and advancing the needle through the kidney to the renal pelvis; and inserting the inflow member over the needle, such that a distal end of the inflow member advances from the kidney into the renal pelvis.

8. The method of claim 7, wherein inserting the needle comprises inserting the needle into an abdominal region of the body.

9. The method of claim 1, wherein deploying the retention portion of the inflow member causes the retention portion of the inflow member to adapt a three-dimensional shape sized and positioned to maintain patency of fluid flow between the kidney and/or renal pelvis and a proximal end of the at least one inflow lumen by inhibiting mucosal tissue from appreciably occluding the at least one drainage hole when negative pressure is applied through the inflow member.

10. The method of claim 9, wherein inserting the outflow member comprises inserting the outflow member through the three-dimensional shape defined by the retention portion of the inflow member.

11. The method of any of claim 1, wherein deploying the retention portion of the inflow member causes the retention portion to form a plurality of coils, and wherein a distal-most coil of the plurality of coils has a smaller diameter than other coils of the plurality of coils.

12. The method of claim 11, wherein inserting the outflow member comprises inserting the outflow member through one or more of the plurality of coils of the retention portion of the inflow member.

13. The method of claim 12, wherein inserting the outflow member comprises inserting the outflow member through the distal-most coil of the plurality of coils of the retention portion of the inflow member.

14. The method of claim 1, further comprising activating the negative pressure source to draw fluid from the renal pelvis and/or kidney through the at least one inflow lumen to the negative pressure source and to expel fluid to the bladder through the at least one outflow lumen.

15. The method of claim 14, further comprising regulating positive and/or negative pressure provided by the negative pressure source within a pressure range that facilitates increased urine production from the kidney.

* * * * *